(12) United States Patent
Babich et al.

(10) Patent No.: US 9,433,594 B2
(45) Date of Patent: *Sep. 6, 2016

(54) TECHNETIUM- AND RHENIUM-BIS(HETEROARYL) COMPLEXES AND METHODS OF USE THEREOF

(71) Applicant: Molecular Insight Pharmaceuticals, Inc., Tarrytown, NY (US)

(72) Inventors: John W. Babich, Tarrytown, NY (US); Craig Zimmerman, Topsfield, MA (US); John Joyal, Melrose, MA (US); Kevin P. Maresca, Tewksbury, MA (US); John Marquis, Nashua, NH (US); Genliang Lu, Winchester, MA (US); Jian-cheng Wang, Revere, MA (US); Shawn Hillier, Danvers, MA (US)

(73) Assignee: Molecular Insight Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/610,417

(22) Filed: Jan. 30, 2015

(65) Prior Publication Data

US 2016/0222036 A1 Aug. 4, 2016

Related U.S. Application Data

(63) Continuation of application No. 14/446,220, filed on Jul. 29, 2014, now Pat. No. 8,962,799, which is a continuation of application No. 14/041,643, filed on Sep. 30, 2013, now Pat. No. 8,840,865, which is a continuation of application No. 12/631,312, filed on Dec. 4, 2009, now Pat. No. 8,562,945, and a continuation-in-part of application No. 12/350,894, filed on Jan. 8, 2009, now Pat. No. 8,877,970.

(60) Provisional application No. 61/120,226, filed on Dec. 5, 2008, provisional application No. 61/180,341, filed on May 21, 2009, provisional application No. 61/020,043, filed on Jan. 9, 2008, provisional application No. 61/088,980, filed on Aug. 14, 2008, provisional application No. 61/142,002, filed on Dec. 31, 2008.

(51) Int. Cl.
| | |
|---|---|
| *A61K 31/18* | (2006.01) |
| *A61K 31/4192* | (2006.01) |
| *A61K 31/444* | (2006.01) |
| *A61K 31/555* | (2006.01) |
| *A61K 51/04* | (2006.01) |
| *A61K 47/22* | (2006.01) |
| *A61K 49/00* | (2006.01) |
| *C07D 213/38* | (2006.01) |
| *C07D 403/12* | (2006.01) |
| *C07D 403/06* | (2006.01) |
| *C07C 275/16* | (2006.01) |
| *C07C 311/16* | (2006.01) |

(52) U.S. Cl.
CPC .................................. *A61K 31/18* (2013.01)

(58) Field of Classification Search
CPC ............ A61K 31/18; A61K 31/4192; A61K 31/444; A61K 51/04; A61K 47/22; A61K 49/00; C07D 213/38; C07D 403/12; C07D 403/06; C07C 275/16; C07C 311/16
See application file for complete search history.

(56) References Cited

U.S. PATENT DOCUMENTS

| | | | |
|---|---|---|---|
| 2,730,456 | A | 1/1956 | Green et al. |
| 2,730,457 | A | 1/1956 | Green et al. |
| 2,800,457 | A | 7/1957 | Green et al. |
| 3,527,789 | A | 9/1970 | Payne |
| 3,625,214 | A | 12/1971 | Higuchi |
| 4,272,398 | A | 6/1981 | Jaffe |
| 4,798,734 | A | 1/1989 | Kaneda |
| 4,885,136 | A | 12/1989 | Katayama et al. |
| 4,888,136 | A | 12/1989 | Chellapa et al. |
| 4,906,474 | A | 3/1990 | Langer et al. |
| 4,925,673 | A | 5/1990 | Steiner et al. |
| 5,442,088 | A | 8/1995 | Hoffmann |
| 5,672,592 | A | 9/1997 | Jackson et al. |
| 5,739,123 | A | 4/1998 | Norcini et al. |
| 5,795,877 | A | 8/1998 | Jackson et al. |
| 5,824,662 | A | 10/1998 | Slusher et al. |
| 5,880,112 | A | 3/1999 | Jackson et al. |
| 6,071,965 | A | 6/2000 | Jackson et al. |
| 6,479,470 | B1 | 11/2002 | Kozikowski et al. |
| 6,528,499 | B1 | 3/2003 | Kozikowski et al. |
| 7,381,745 | B2 | 6/2008 | Kozikowski et al. |
| 8,211,402 | B2 | 7/2012 | Babich et al. |

(Continued)

FOREIGN PATENT DOCUMENTS

| | | |
|---|---|---|
| CN | 102272102 | 12/2011 |
| EP | 0 544 412 A2 | 6/1993 |

(Continued)

OTHER PUBLICATIONS

Dischino et al., caplus an 1991:177144.*

(Continued)

*Primary Examiner* — Sun Jae Yoo

(74) *Attorney, Agent, or Firm* — Gilberto M. Villacorta; Jeffrey R. Lomprey; Foley & Lardner LLP

(57) ABSTRACT

A method of imaging a region in a subject includes administering to the subject a complex of a metal chelated to a compound, and obtaining an image of the region in the subject.

5 Claims, 8 Drawing Sheets

(56) References Cited

U.S. PATENT DOCUMENTS

| | | | |
|---|---|---|---|
| 8,926,944 B2 * | 1/2015 | Babich et al. | 424/1.65 |
| 2003/0100594 A1 | 5/2003 | Masferrer et al. | |
| 2003/0235843 A1 | 12/2003 | Babich et al. | |
| 2004/0002478 A1 | 1/2004 | Kozikowski et al. | |
| 2004/0054190 A1 | 3/2004 | Pomper et al. | |
| 2004/0191174 A1 | 9/2004 | Linder et al. | |
| 2004/0209921 A1 | 10/2004 | Bridger et al. | |
| 2005/0038258 A1 | 2/2005 | Koike et al. | |
| 2006/0057068 A1 | 3/2006 | Supuran et al. | |
| 2006/0155021 A1 | 7/2006 | Lenges et al. | |
| 2006/0155146 A1 | 7/2006 | Lenges et al. | |
| 2006/0198785 A1 | 9/2006 | Santos et al. | |
| 2008/0176821 A1 | 7/2008 | Kozikowski et al. | |
| 2008/0227962 A1 | 9/2008 | Mazzanti | |
| 2009/0175794 A1 | 7/2009 | Zimmerman et al. | |
| 2009/0192182 A1 | 7/2009 | Kusumi et al. | |
| 2010/0140483 A1 | 6/2010 | Rousso et al. | |
| 2010/0178246 A1 | 7/2010 | Babich et al. | |
| 2010/0178247 A1 | 7/2010 | Babich et al. | |
| 2010/0183509 A1 | 7/2010 | Babich et al. | |

FOREIGN PATENT DOCUMENTS

| | | |
|---|---|---|
| EP | 0 878 463 B1 | 11/1998 |
| EP | 1 389 460 A1 | 2/2004 |
| EP | 1 550 657 A1 | 7/2005 |
| EP | 1 961 744 A1 | 8/2008 |
| JP | 04-342560 A | 11/1992 |
| JP | 4342560 | 11/1992 |
| JP | 05-239046 | 9/1993 |
| JP | 08-282117 | 10/1996 |
| JP | 2002-506858 | 3/2002 |
| JP | 2005-519957 | 7/2005 |
| JP | 2005-539023 | 12/2005 |
| JP | 2006-509844 | 3/2006 |
| JP | 2007-523902 | 8/2007 |
| JP | 2007-524685 | 8/2007 |
| JP | 2010-523599 | 7/2010 |
| JP | 5220203 B2 | 6/2013 |
| WO | WO-97/48399 A1 | 12/1997 |
| WO | WO-97/48400 A1 | 12/1997 |
| WO | WO-97/48409 A1 | 12/1997 |
| WO | WO-98/13046 A1 | 4/1998 |
| WO | WO-98/45256 A1 | 10/1998 |
| WO | WO-98/45257 A1 | 10/1998 |
| WO | WO-99/33847 A1 | 7/1999 |
| WO | WO-99/47507 | 9/1999 |
| WO | WO-00/64911 A1 | 11/2000 |
| WO | WO-01/01974 A2 | 1/2001 |
| WO | WO-02/22627 A2 | 3/2002 |
| WO | WO-03/013617 A2 | 2/2003 |
| WO | WO-03/060523 A1 | 7/2003 |
| WO | WO-03/077727 A | 9/2003 |
| WO | WO-03/077727 A2 | 9/2003 |
| WO | WO-2004/014352 A2 | 2/2004 |
| WO | WO-2004/048544 A2 | 6/2004 |
| WO | WO-2005/056520 A1 | 6/2005 |
| WO | WO-2005/079865 A1 | 9/2005 |
| WO | WO-2006/032911 A2 | 3/2006 |
| WO | WO-2006/080993 A2 | 8/2006 |
| WO | WO-2006/093991 A1 | 9/2006 |
| WO | WO-2006/116736 | 11/2006 |
| WO | WO-2007/008848 A2 | 1/2007 |
| WO | WO-2007/031640 | 3/2007 |
| WO | WO-2007/042504 | 4/2007 |
| WO | WO-2007/090461 A1 | 8/2007 |
| WO | WO-2007/148738 A1 | 12/2007 |
| WO | WO-2008/016006 A1 | 2/2008 |
| WO | WO-2008/028000 A2 | 3/2008 |
| WO | WO-2008/058192 A2 | 5/2008 |
| WO | WO-2008/124703 A2 | 10/2008 |
| WO | WO-2009/076434 A1 | 6/2009 |
| WO | WO-2009/089383 A2 | 7/2009 |
| WO | WO-2010/036814 A1 | 4/2010 |
| WO | WO-2010/065899 A2 | 6/2010 |
| WO | WO-2010/065902 A2 | 6/2010 |
| WO | WO-2010/065906 A2 | 6/2010 |
| WO | WO-2013/022797 A2 | 2/2013 |
| WO | WO-2013/166110 | 11/2013 |

OTHER PUBLICATIONS

AminoAcid, 2015, https://en.wikipedia.org/wiki/Amino_acid.*

Radical, 2015, https://www.google.com/search?q=definition+of+radical&sourceid=ie7&rls=com.microsoft:en-us:IE-Address&ie=&oe=&gws$_{13}$ rd=ssl.*

Tweedle et al., 1989, caplus an 1989:173270.*

Tweedle et al., caplus an 1989:173270, 1989.*

Pomper et al., 2009, caplus an 2009:1755.*

Alberto et al., "A Novel Organometallic Aqua Complex of Technetium for the Labeling of Biomolecules: Synthesis of [99mTc(OH2)3(CO3]+ from [99mTc04]-in Aqueous Solution and Its Reaction with a Bifunctional Ligand", Journal of American Chemical Society, American Chemical Society, vol. 120, No. 31, 1998, pp. 7987-7988.

Banerjee et al., "{Re(III)Cl3} Core Complexes with Bifunctional Single Amino Acid Chelates", Inorganic Chemistry, American Chemical Society, vol. 41, No. 22, 2002, pp. 5795-5802.

Banerjee et al., Bifunctional Single Amino Acid Chelates for Labeling of Biomolecules with the {Tc(CO)3} and {Re(CO)3} Cores. Crystal and Molecular Structures of [ReBr(CO)3(H2NCH2C5H4N)], [Re(CO)3{C5H4NCH2}2NH}Br, [Re(CO)3{C5H4NCH2}2NCH2CO2H}Br, [Re(CO)3{X(Y)NCH2CO2CH2CH3}Br(X=Y=2-pyridylmethyl; X=2-pyridylmethyl, Y=2-(1-methylimidazolyl)methyl,[ReBr(CO)3{C5H4NCH2}NH(CH2C4H3S)}], and [Re(CO)3{C5H4NCH2}N(CH2C4H3S)(CH2CO2)}], Inorganic Chemistry, vol. 41, No. 24, 2002, pp. 6417-6425.

Banerjee et al., "Synthesis and Evaluation of Technetium-99m- and Rhenium-Labeled Inhibitors of the Prostate-Specific Membrane Antigen (PSMA)", Journal of Medicinal Chemistry, vol. 15, pp. 4504-4517, 2008.

Banerjee, A. et al "Inhibition of matrix metalloproteinase-9 by "multi-prong" surface binding groups", Chem. Commun., 2005, No. 20, pp. 2549-2551.

Benita, S. et al., "Characterization of Drug-Loaded Poly(d,l-lactide) Microspheres," Journal of Pharmaceutical Sciences, vol. 73, No. 12, Dec. 1984, pp. 1721-1724.

Berge, et al., "Pharmaceutical Salts," Journal of Pharmaceutical Sciences, vol. 66, No. 1, Jan. 1977, pp. 1-19.

Bonomi et al., "Phosphate Diester and DNA Hydrolysis by a Multivalent, Nanoparticle-Based Catalyst", Journal of the American Chemical Society, vol. 130, 2008, pp. 15744-15745.

Casini, et al., "Carbonic Anhydrase Inhibitors: Synthesis of Water Soluble Sulfonamides Incorporating a 4-sulfamoylphenylmethylthiourea Scaffold, with Potent Intraocular Pressure Lowering Properties," Journal of Enzyme Inhibition and Medicinal Chemistry, 2002, vol. 17, No. 5, pp. 333-343.

Cecchi et al., Alessandro, "Carbonic Anhydrase Inhibitors. Design of Fluorescent Sulfonamides as Probes of Tumor-assoicated Carbonic Anhydrase IX that Inhibit Isozyme IX-Mediated Acidification of Hypoxic Tumores," Journal of Medicinal Cheimistry, vol. 48, No. 15, Jul. 2005, pp. 4834-4841.

Database Beilstein [Online]; Beilstein Institute for Organic Chemistry, 1958, Database Accession No. Citation No. 990210, XP002577062.

Database CAPLUS, [Online] Nov. 30, 1992, Karube Yoshiharu et al: "Preparation of sulfanilamide derivatives and their technetium complexes as radiodiagnostic agents", XP002577771, retrieved from CAPLUS Database accession No. 1993-427837.

Database WPI, Week 199302, Thomas Scientific, London, GB; AN 1993-014070 & JP4342560 A (Daiichi Radioisotope Kenkyusho) Nov. 30, 1992.

De Leval, et al. "Carbonic Anhydrase Inhibitors: Synthesis and Topical Intraocular Pressure Lowering Effects of Fluorine-Containing Inhibitors Devoid of Enhanced Reactivity", Journal of Medicinal Chemistry, 2004, vol. 47, No. 11, pp. 2796-2804.

(56) References Cited

OTHER PUBLICATIONS

Deasy, Patrick et al., "Microencapsulation and Related Drug Processes", 1984, School of Pharmacy, University of Dublin, Marcel Dekker, Inc. (TOC).
Dubenko, et al. "Thiocarbanilide Derivatives. IV. Synthesis of unsymmetrical monohalothiocarbanilides", Zhurnal Obshchei Khimii, 1962, vol. 32, pp. 626-628.
Dubois, L., et al., "Imaging the hypoxia surrogate marker CA IX requires expression and catalytic activity for binding fluorescent sulfonamide inhibitors," 2007, Radiotherapy and Oncology, vol. 83, pp. 367-373.
EPA, Commonly Encountered Radionuclides, 2011, 2 pages.
Feng et al., "Comparing a mononuclear Zn(II)complex with hydrogen bond donors with a dinuclear Zn(II) complex for catalysing phosphate ester cleavage", Chem. Commun., 2006, pp. 1845-1847.
Gallagher, J. et al. "Protease Activity of 1,10-Phenanthroline-Copper(I). Targeted Scission of the Catalytic Site of Carbonic Anhydrase", Biochemistry, 1998, vol. 37, pp. 2096-2104.
Gracheva, et al. "Chemical changes during beta-decay of bismuth-210 (RaE) entering into the composition of tris(p-sulfamoylphenyl)bismuth", STN on the Web, File CAPLUS, 1968, vol. 83, p. 305.
Greene, T. W. et al., "Protection for the Hydroxyl Group, Including 1,2- and 1,3-Diols," Protective Groups in Organic Synthesis, Third Edition, 1999, pp. 113-148.
Greene, T. W. et al., Protective Groups in Organic Synthesis, Second Edition, Wiley, New York, 1991.
Gregoriadis, G., et al., Drug Carriers in Biology and Medicine, Chapter 14: Liposomes, 1979, Academic Press, pp. 287-341.
Hanada et al., "Preparation of 2,8-diazaspiro[4.5]decane containing bis(imidazol-2-ylmethyl_amines as CXCR4 antagonists for treatment of inflammation and immune disease", caplus an 2008:159048, 5 pages.
Henson et al., "Resonance Raman Investigation of Equatorial Ligand Donor Effects on the Cu2O22 Core in End-On and Side-On u-Perozo-Dicopper(II) and Bis-u-oxo-Dicopper(III) Complexes", Journal of American Chemical Society, vol. 125, 2003, pp. 5186-5192.
Jalil, R. et al., "Biodegradable poly(lactic acid) and poly(lactide-co-glycolide) microcapsules: problems associated with preparative techniques and release properties", J. Microencapsulation, 1990, vol. 7, No. 3, pp. 297-325.
Kojima et al., "Synthesis and Characterization of Mononuclear Ruthenium (III) Pyridylamine Complexes and Mechanistic Insights into Their Catalytic Alkane Functionalization with m-Chloroperbenzoic Acid", Chemistry, vol. 13, 2007, pp. 8212-8222.
Kojima, "Synthesis and Characterization of Mononuclear Ruthenium(III) Pyridylamine Complexes and Mechanistic Insights into Their Catalytic Alkane Functionalization with m-Chloroperbenzoic Acid", Chemistry, 2007, vol. 13, No. 29, pp. 8212-8222.
Krebs, H.A., "Inhibition of Carbonic Anhydrase by Sulphonamides," The Biochemical Journal, vol. 43, 1948, pp. 525-528.
Kularatne, S.A. et al., "Design, Synthesis, and Preclinical Evaluation of Prostate-Specific Membrane Antigen Targeted 99mTc-Radioimaging Agents," Molecular Pharmaceutics, 2009, vol. 6, No. 3, pp. 790-800.
Kusumi et al., "Preparation of heterocycle compounds having (un)protected acidic group as CXCR4 antagonists", caplus an 2007:1332283, 8 pages.
Lewis et al., "Maleimidocysteineamido-DOTA Derivatives: New Reagents for Radiometal Chelate Conjugation to Antibody Sulfhydryl Groups Undergo pH-Dependent Cleavage Reactions", Bioconjugate Chemistry, American Chemical Society, vol. 9, No. 1, 1998, pp. 72-86.
Lim, et al. "Microencapsulation of Living Cells and Tissues," Journal of Pharmaceutical Sciences, Apr. 1981, vol. 70, No. 4, pp. 351-354.
Mathiowitz, E. et al., "Morphology of Polyanhydride Miscrosphere Delivery Systems," Scanning Microscopy, 1990, vol. 4, No. 2, pp. 329-340.
Mathiowitz, E. et al., "Polyanhydride Microspheres as Drug Carriers. II. Microencapsulation by Solvent Removal," Journal of Applied Polymer Science, 1988, vol. 35, pp. 755-774.
Nakano, M. et al., "Sustained Urinary Excretion of Sulfamethizole Following Oral Administration of Enteric Coated Microcapsules in Humans," International Journal of Pharmaceutics, 1980, vol. 4, pp. 291-298.
Nonat et al., "Structure, Stability, Dynamics, High-Field Relaxivity and Ternary-Complex Formation of a New Tris(aquo) Gadolinium Complex", Chemistry, vol. 13, 2007, pp. 8489-8506.
Pastorekov, S., et ai., "Carbonic anhydrase IX (CA IX) as potential target for cancer therapy," 2004, Cancer Therapy, vol. 2. (19 pages).
Rami, M. et al. "Carbonic Anhydrase Inhibitors: Design of Membrane-Impermeant Copper(II) Complexes of DTPA-, DOTA-, and TETA-Tailed Sulfonamides Targeting the Tumor-Associated Transmembrane Isoform IX", CHEMMEDCHEM, 2008, vol. 3, pp. 1780-1788.
Roy, B. et al., "Two-Prong Inhibitors for Human Carbonic Anhydrase II", Journal of American Chemical Society, vol. 126, 2004, pp. 13206-13207.
Saitou et al., "Preparation of N-arylmethyl or N-hererocyclylmethyl-N-(imidazol-2-ymethyl)amines as antagonists of chemokine receptor CXCR4", caplus an 2005:1004718, 6 pages.
Salib, N. et al., "Utilization of Sodium Alginate in Drug Microencapsulation," Pharm. Ind., vol. 40, No. 11a, 1978, pp. 1230-1234.
Sawhney, A. et al., "Bioerodible Hydrogels Based on Photopolymerized Poly(ethylene glycol)-co-poly(a-hydroxy acid) Diacrylate Macromers," Macromolucules, vol. 26, 1993, pp. 581-587.
Shah, et al. "Benzylthioureas, Part III", Journal of Indian Chemical Society, 1959, vol. 36, No. 7, pp. 507-508.
Singh, et al. "The Enzyme-Inhibitor Approach to Cell-Selective Labelling—II. In Vivo Studies with pIBS in Small Animals and Man", Applied Radiation and Isotopes, 1991, vol. 42, No. 3, pp. 261-267.
Steffens MG, et al., Targeting of renal cell carcinoma with iodine-131-labeled chimeric monoclonal antibody G250, 1997, J. Clin. Oncol., 15(4) 1529-37 (1 page abstract).
Thallaj, et al. "A Ferrous Center as Reaction Site for Hydration of a Nitrile Group into a Carboxamide in Mild Conditions", Journal of American Chemical Society, vol. 130, 2007, pp. 2414-2415.
Thiry et al., "Targeting Tumor-Associated Carbonic Anhydrase IX in Cancer Therapy," Trends in Pharmacological Sciences, vol. 27, No. 11, Nov. 2006, pp. 566-573.
Thiry, et al. "Indanesulfonamides as Carbonic Anhydrase Inhibitors. Toward Structure-Based Design of Selective Inhibitors of the Tumor-Associated Isozyme CA IX", Journal of Medicinial Chemistry, 2006, vol. 49, No. 9, pp. 2743-2749.
Viswanathan, et al. "Metanilamide-Substituted Thiourea Derivatives", Current Science, 1952, No. 12, pp. 342-343.
Yao, Zhen et al., Synthesis of Porphyrins Bearing 1-4 hydroxymethyl Groups and other One-carbon oxygenic Substituents in Distinct Patterns, Tetrahedron, vol. 63, 2007, pp. 10657-10670.
Examination Report mailed Aug. 28, 2014 in Australia Application No. 2009322164.
Examination Report mailed Jul. 22, 2014 in Australia Application No. 2009322171.
Examination Report mailed Jul. 29, 2014 in Australia Application No. 2009322167.
Office Action mailed Sep. 2, 2014 in Japan Application No. 2010-542351 (Translation).
Babich, et al., "Applications of Nuclear Imaging in Drug Discovery and Development," Drug Discovery Dev., 2006, vol. 1, pp. 365-381.
Berthommier, E., et al., "New preparation of [123I]PE2I: investigation of the oxidation and purification steps," J. Label Compd Radiopharm, 2002, vol. 45, No. 12, pp. 1019-1028.

(56) References Cited

OTHER PUBLICATIONS

Carter et al., "Prostate-Specific Membrane Antigen is a Hydrolase with Substrate and Pharacologic Characteristics of a Neuropeptidase," Proc. Nat. Acad. Sci., USA, 93:749-753, Jan. 1996.
Chen et al., "Radiohalogenated Prostate-Specific Membrane Antigen (PSMA)-Based Ureas as Imaging Agents for Prostate Cancer," *Journal of Medicinal Chemistry*, 2008, vol. 51, pp. 7933-7943.
Chen, et al., "Age-related decrease in cardiopulomnary andrenergic neuronal function in children as assessed by I-123 metaiodobenzylgucanidine imaging," *J. Nucl. Cardiol.*, 2008, vol. 15, No. 1, pp. 73-79.
Communication—EP Search Report in EP Appln No. 13195617.9 dated Jan. 31, 2014.
Communication pursuant to Article 94(3) EPC in EP Appln No. 09 775 430.3 dated Aug. 8, 2013.
Communication received in EP Appln. No. 09701293.4 dated May 3, 2012.
Decision of Rejection in CN Appln No. 200980107793.4 dated Feb. 12, 2014.
Decision of Rejection mailed Sep. 11, 2014 in China Appln. No. 200980153878.6.
Donovan et al., XP002614474 "Fluorous Isocyanates: Convenient Synthons for the Preparation of Radioiodinated Compounds in High Effective Specific Activity," *Journal of Organic Chemistry*, Oct. 2, 2009, vol. 74, pp. 8133-8138.
European Search Report in Application No. 07844938.6 mailed Jun. 13, 2012.
Final Office Action received for U.S. Appl. No. 12/631,312 dated Sep. 6, 2012.
First Examination Report in Au Appln No. 2010260195 issued Jul. 30, 2014.
Flux, et al., "Absorbed Dose Ratios for Repeated Therapy of Neuroblastoma with I-131 mIBG," Cancer Biother., *Radiopharm.*, 2003, vol. 18, No. 1, pp. 81-87.
Foss et al., "Radiolabeled Small-Molecule Ligands for Prostate-Specific Membrane Antigen: In Vivo Imaging in Experimental Models of Prostate Cancer," *Clin. Cancer Res.*, 11(11):4022-4028 (2005).
Fullerton, et al., "Comparison of Radiohaloanalogues of Meta-Iodobenzylguanidine (MIBG) for a Combined Gene-and Targeted Radiotherapy Approach to Bladder Carcinoma," *Med. Chem.*, 2005, vol. 1, pp. 611-618.
Gasparini et al., "(R,S)-4-Phosphononphenylglycine, a Potent and Selective Group III Metabotropic Glutamate Receptor Agonist, is Anticonvulsive and Neuroprotective in Vivo," *J. Pharm. Exper. Ther.*, 1999, vol. 290, No. 3, pp. 1678-1687.
Genis et al., Design of a Carbonic Anhydrase IX Active-Site Mimic to Screen Inhibitors for Possible Anti-Cancer Properties, *Biochemistry*, 2009, vol. 48, No. 6, pp. 1-20 [pp. 1322-1331].
Hayakawa et al., XP-002614476 "Second-Generation Total Synthesis of Haterumalide NA Using B-Alkyl Suzuki-Miyaura Coupling", *Organic Letters*, 2008, vol. 10, No. 9, pp. 1859-1862.
Heidenreich et al., EAU guidelines on prostate cancer, *European Urology*, 2008, vol. 53, pp. 68-80.
International Preliminary Examination Report and Written Opinion mailed Jul. 17, 2014 in International Application No. PCT/US2013/020283.
International Search Report mailed Mar. 13, 2013 in International Application No. PCT/US2013/020283 (WO2013/103813).
International Search Report and Written Opinion in PCT/US2009/030487 dated Jun. 26, 2009.
International Search Report and Written Opinion in PCT/US2009/066836 dated Dec. 28, 2010.
International Search Report and Written Opinion in PCT/US2009/066832 dated Oct. 14, 2010.
International Search Report and Written Opinion mailed Mar. 30, 2011 in International Application No. PCT/US2009/066842.
International Search Report and Written Opinion of the International Searching Authority issued in International Application No. PCT/US2014/061249 mailed Apr. 3, 2015.
International Search Report in International Application No. PCT/US00/11262, mailed Sep. 12, 2000.
International Search Report in International Application No. PCT/US07/83934, mailed Mar. 13, 2008.
Invitation to Pay Additional Fees mailed May 17, 2010 in International Application No. PCT/US2009/066832.
Invitation to Pay Additional Fees mailed May 17, 2010 in International Application No. PCT/US2009/066836.
Invitation to Pay Additional Fees mailed May 17, 2010 in International Application No. PCT/US2009/066842.
Izdebski et al., "Synthesis of N,N'-Carbonyl-bis-amino Acids and N,N'-Carbonyl-bis-peptides," *Polish J. Chem.*, 1997, vol. 71, No. 8, pp. 1066-1074.
Jackson et al., "Design, Synthesis, and Biological Activity of a Potent Inhibitor of the Neuropeptidase N-Acetylated alpha-Linked Acidic Dipeptidase," *J. Med. Chem.*, 1996, vol. 39, No. 2, pp. 619-622.
K.P.Maresca et al. A series of Halogneated heterodimeric Inhibitors of Prostate Specific Membrane Antigen (PSMA) as Radiolabeled Probes for Targeting Prostate Cancer, *J. Med. Chem.*, 2009, vol. 52, 347-357.
Kozikowski et al., "Design of Remarkably Simple, Yet Potent Urea-Based Inhibitors of Glutamate Carboxypeptidase II (NAALADase)," *J. Med. Chem.*, 2001, vol. 44, No. 3, pp. 298-301.
Kozikowski et al., "Synthesis of Urea-Based Inhibitors as Active Site Probes of Glutamate Carboxypeptidase II: Efficacy as Analgesic Agents," *J. Med. Chem.*, 2004, vol. 47, pp. 1729-1738.
Lewis, Hawley's Condensed Chemical Dictionary, 12 Ed., Van Nostrand Reinhold Co., New York, Ny, pp. 9, 420, 421, and 881, 1993.
Liu et al., Preparation and Properties of 99mTc(Co)3-Labeled N,N-Bis(2-pyridylmethyl)-4-aminobutyric Acid, *Bioconjug Chem.*, 2004, vol. 15, No. 6, pp. 1-14 [pp. 1441-1446].
McIntee, et al., "A Convenient Method for the Preparation of Fluorous Tin Derivatives for the Fluorous Labeling Strategy" *J. Org. Chem.*, 2008, vol. 73, pp. 8236-8243.
Moyer et al., "Screening for prostate cancer: U.S. preventive services task force recommendation statement," *Ann Intern Med*, May 22, 2012, vol. 157, No. 2, pp. 120-134.
Nan et al., "Dual Function Glutamate-Related Ligands: Discovery of a Novel, Potent Inhibitor of Glutamate Carboxypeptidase II Possessing mGluR3 Agonist Activity," *J. Med. Chem.*, 2000, vol. 43, No. 5, pp. 772-774.
Non-Final Office Action in U.S. Appl. No. 12/631,312 dated Dec. 27, 2012.
Non-final Office Action received for U.S. Appl. No. 12/631,312 dated Mar. 6, 2012.
Notice of Allowance issued in U.S. Appl. No. 13/734,534 mailed Apr. 23, 2015.
Notice of Allowance issued in U.S. Appl. No. 13/734,534 mailed Jan. 2, 2015.
Notice of Allowance received for U.S. Appl. No. 12/631,337 dated Mar. 15, 2012.
Notice of Allowance received for U.S. Appl. No. 12/631,343 dated Mar. 12, 2012.
Notice of Reasons for Rejection in JP Appln. No. JP 2011-539752 dated Mar. 25, 2014.
Office Action—Final—Reasons for Rejection in JP Appln. No: 2010-542351 dated Apr. 1, 2014.
Office Action cited in U.S. Appl. No. 12/029,367 mailed Oct. 19, 2010.
Office Action for JP 2011-539755, mailed Oct. 30, 2012.
Office Action for JP 2011-539755, mailed Oct. 30, 2012—English Translation.
Office Action in CN Appln. No. 200980153722.8 dated Oct. 30, 2012.
Office Action in CN Appln. No. 200980153877.1 dated Apr. 8, 2014.
Office Action in CN Appln. No. 200980153877.1 dated Sep. 17, 2013.

(56) References Cited

OTHER PUBLICATIONS

Office Action in CN Appln. No. 200980153878.6 dated Jan. 14, 2013.
Office Action in CN Appln. No. 200980153878.6 dated Mar. 7, 2014.
Office Action in CN Appln. No. 200980153877.1 dated Oct. 30, 2012.
Office Action in EP Appln. No. 09 701 293.4 dated Dec. 20, 2012.
Office Action in Japan Application No. 2011-539757 mailed Jun. 17, 2014.
Office Action in JP Appln. No. 2010-542351 dated Aug. 20, 2013.
Office Action in JP Appln. No. 2011-539757 dated Dec. 24, 2013.
Office Action in RU Appln. No. 2011127467 dated Apr. 20, 2013.
Office Action in RU Appln. No. 2011127468 dated Jul. 17, 2013.
Official Action RU Appln. No. 2011127462, dated May 22, 2013.
Partial International Search document received in connection with the Invitation to pay Additional Fees for PCT/US2010-038645; mailed Mar. 21, 2011.
Remington's: the Science and Practice of Pharmacy, 17th Edition, p. 1795, 1985.
Restriction Requirement received for U.S. Appl. No. 12/350,894 dated Jun. 10, 2011.
Second Office Action in CN Appln. No. 200980107793.4 dated Feb. 5, 2013.
Sempuku, K., "Sulfur Compounds," 6001 Chemical Abstracts, Columbus Ohio, US, 101(27). XP 002196919, 1984.
Slusher, et al., "Immunocytochemical Localization of the N-Acetyl-Aspartyl-Glutamate (NAAG) Hydrolyzing Enzyme N-Acetylated alpha-Linked Acidic Dipeptidase (NAALADase)," *J. Compar. Neurol.*, 1992, vol. 315, No. 2, pp. 217-229.
Slusher, et al., "Rat Brain N-Acetylated alpha-Linked Acidic Dipeptidase Activity," *J. Biolog. Chem.*, 1990, vol. 265, No. 34, pp. 21297-21301.
Uddin et al., XP-002614475 "Synthesis and evaluation of [123I]-indomethacin derivatives as COX-2 targeted imaging agents", Journal of Labelled Compounds and Radiopharmaceuticals, May 2009, vol. 52, No. 2, pp. 387-393.
US Notice of Allowance on DTD Jun. 25, 2014.
US Notice of Allowance on DTD Jun. 19, 2013.
US Notice of Allowance on DTD May 1, 2014.
US Notice of Allowance on DTD Oct. 17, 2014.
US Notice of Allowance on DTD Feb. 11, 2013.
US Notice of Allowance on DTD Dec. 9, 2014.
US Office Action on DTD May 16, 2014.
US Office Action on DTD Sep. 8, 2011.
US Office Action on DTD Feb. 27, 2013.
US Office Action on DTD Sep. 16, 2014.
US Office Action on DTD Aug. 15, 2012.
US Office Action on DTD Jun. 24, 2014.
Notice of Allowance issued in co-pending U.S. Appl. No. 13/890,912 dated Jun. 4, 2015.
Office Action issued in co-pending Chinese Application No. 200980153722.8 dated Jun. 5, 2015.
Office Action issued in co-pending Chinese application No. 200980153878.6 dated Jul. 30, 2015.
Office Action issued in co-pending Japanese Application No. 2014-145241 dated Jul. 28, 2015 (with English translation).
Office Action issued in co-pending U.S. Appl. No. 14/152,864 dated Nov. 9, 2015.
Office Action issued in corresponding Chinese application No. 200980153722.8 dated Dec. 15, 2015.
Office Action issued in co-pending U.S. Appl. No. 14/820,953 dated Oct. 27, 2015.
Notice of Allowance issued in co-pending U.S. Appl. No. 14/820,953 dated Apr. 14, 2016.
Office Action issued in co-pending U.S. Appl. No. 14/152,864 dated Mar. 7, 2016.
Office Action issued in co-pending U.S. Appl. No. 14/820,953 dated Mar. 4, 2016.
Office Action issued in corresponding Chinese application No. 200980153722.8 dated Feb. 26, 2016.
Notice of Allowance issued in co-pending U.S. Appl. No. 14/152,864 dated May 12, 2016.
Extended European Search Report mailed Apr. 28, 2016 in related EP Appl. 14738117.2 (5 pgs.).

\* cited by examiner

Example 80 Saturation Binding

Example 48 Saturation Binding

TECHNETIUM- AND RHENIUM-BIS(HETEROARYL) COMPLEXES AND METHODS OF USE THEREOF

CROSS-REFERENCE TO RELATED APPLICATIONS

This application is a continuation of U.S. patent application Ser. No. 14/446,220, filed on Jul. 29, 2014, which in turn is a continuation of U.S. patent application Ser. No. 14/041,643, filed on Sep. 30, 2013, now U.S. Pat. No. 8,840,865, which in turn is a continuation of U.S. patent application Ser. No. 12/631,312, filed on Dec. 4, 2009, now U.S. Pat. No. 8,562,945, which in turn is a continuation-in-part of U.S. patent application Ser. No. 12/350,894, filed on Jan. 8, 2009, now U.S. Pat. No. 8,877,970, all of which claim the benefit of U.S. Provisional Application Nos. 61/020,043, filed on Jan. 9, 2008; 61/088,980, filed on Aug. 14, 2008; and 61/142,002, filed on Dec. 31, 2008. This application also claims the benefit of U.S. Provisional Patent Application Nos. 61/120,226, filed on Dec. 5, 2008, and 61/180,341, filed on May 21, 2009, all applications and patents of which are incorporated herein by reference in their entirety, for any and all purposes.

FIELD

The present technology is generally related to radiopharmaceutical agents.

BACKGROUND

Radiopharmaceuticals may be used as diagnostic or therapeutic agents by virtue of the physical properties of their constituent radionuclides. Thus, their utility is not based on any pharmacologic action per se. Most clinical drugs of this class are diagnostic agents incorporating a gamma-emitting nuclide which, because of physical, metabolic or biochemical properties of its coordinated ligands, localizes in a specific organ after intravenous injection. The resultant images can reflect organ structure or function. These images are obtained by means of a gamma camera that detects the distribution of ionizing radiation emitted by the radioactive molecules.

In radioimaging, the radiolabel is a gamma-radiation emitting radionuclide and the radiotracer is located using a gamma-radiation detecting camera (this process is often referred to as gamma scintigraphy). The imaged site is detectable because the radiotracer is chosen either to localize at a pathological site (termed positive contrast) or, alternatively, the radiotracer is chosen specifically not to localize at such pathological sites (termed negative contrast).

Many of the procedures presently conducted in the field of nuclear medicine involve radiopharmaceuticals which provide diagnostic images of blood flow (perfusion) in the major organs and in tumors. The regional uptake of these radiopharmaceuticals within the organ of interest is proportional to flow; high flow regions will display the highest concentration of radiopharmaceutical, while regions of little or no flow have relatively low concentrations. Diagnostic images showing these regional differences are useful in identifying areas of poor perfusion, but do not provide biochemical or metabolic information of the state of the tissue within the region of apparently low perfusion.

It is well known that tumors may express unique proteins associated with their malignant phenotype or may over-express normal constituent proteins in greater number than normal cells. The expression of distinct proteins on the surface of tumor cells offers the opportunity to diagnose and characterize disease by probing the phenotypic identity and biochemical composition and activity of the tumor. Radioactive molecules that selectively bind to specific tumor cell surface proteins allow the use of noninvasive imaging techniques, such as molecular imaging or nuclear medicine, for detecting the presence and quantity of tumor associated proteins, thereby providing vital information related to the diagnosis and extent of disease, prognosis and therapeutic management options. In addition, as radiopharmaceuticals can be prepared that are not only capable of imaging disease but also delivering a therapeutic radionuclide to the diseased tissue, therapy, in particular cancer therapy, can be realized. The expression of peptide receptors and other ligand receptors on tumors makes them attractive targets to exploit for noninvasive imaging as well as targeted radiotherapy.

A variety of radionuclides are known to be useful for radioimaging, including Ga-67, Tc-99m, In-111, I-123, and I-131. Perhaps the most widely use radioisotope for medical imaging is Tc-99m. Its 140 keV gamma-photon is ideal for use with widely-available gamma cameras. It has a short (6 hour) half life, which is desirable when considering patient dosimetry. Tc-99m is readily available at relatively low cost through commercially-produced $^{99}$Mo/Tc-99m generator systems.

The combination of the medically useful radionuclides, technetium-99m ($^{99m}$Tc) and rhenium-186/188 ($^{186/188}$Re), is attractive for developing molecular imaging and molecular radiotherapeutics due to the similarities in their coordination chemistry and their excellent physical decay characteristics which enable imaging and therapy, respectively. The coordination chemistries of $^{99m}$Tc and $^{186/188}$Re are remarkably similar in regards to the $M(CO)_3L_3$ core, where the coordination complexes of $^{99m}$Tc and $^{186/188}$Re are isostructural. The resulting complexes show robust stability even in the presence of 1000-fold excess of competing chelates and ligands, under extreme conditions of pH and for prolonged periods of time.

SUMMARY

Generally, ligands are provided having heterocyclic groups such as pyridyl and imidazoloyl, and technetium (Tc) and rhenium (Re) complexes of the ligand. The heterocyclic ligands are hydrophilic, allowing for enhanced renal excretion as compared to more lipophilic analogs. Also provided is the use of the ligands and their metal complexes in radioimaging for a variety of clinical diagnostic applications, as well as radiopharmaceuticals for therapeutic applications. The ligands may also be used to attach metals such as Tc and Re to biomolecules such as peptides, that include somatostatins, and small molecule antagonists, that include PSMA, CA-IX or Seprase for use in imaging and therapeutic applications. Methods for the preparation of the ligands, the technetium and rhenium complexes, and the labeled biomolecules are also described. Additionally, methods are provided for imaging regions of a mammal using the complexes.

DETAILED DESCRIPTION

Figure 1:
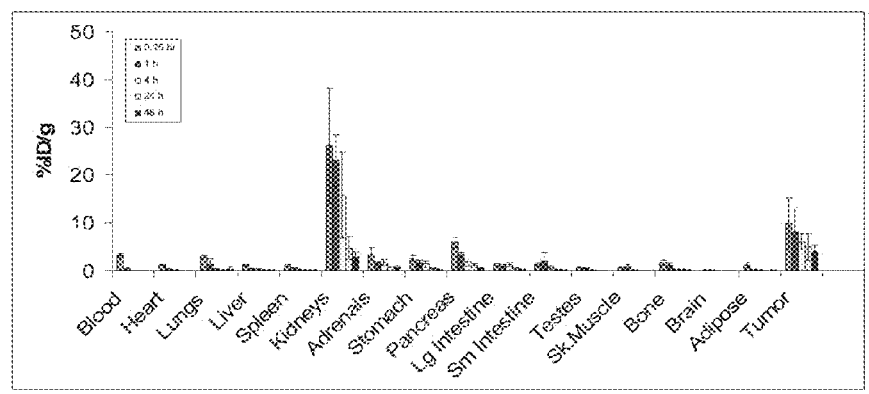
FIG. 1 is a graph of the tissue biodistribution of SSRT2 receptor mediated $^{111}$In-DOTA-Edotreotide (top) verses $^{99m}$Tc-DpK-Edotreotide (middle) and $^{99m}$Tc—COOH-imidazole (Compound 2)-Edotreotide (bottom) in AR42J mouse tumor model.
Figure 1:
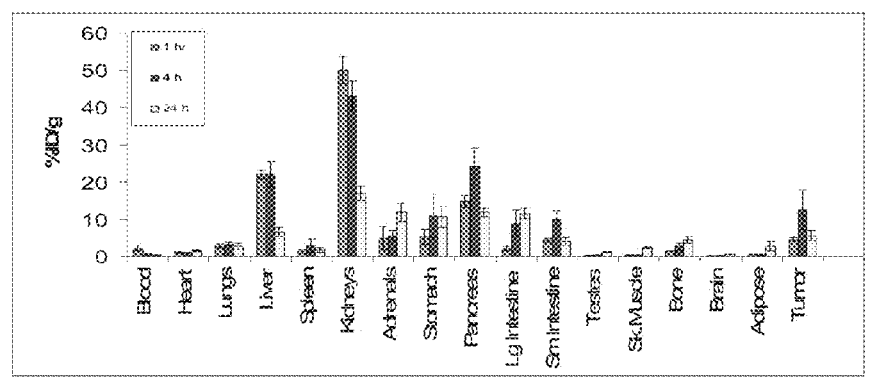
Figure 1:
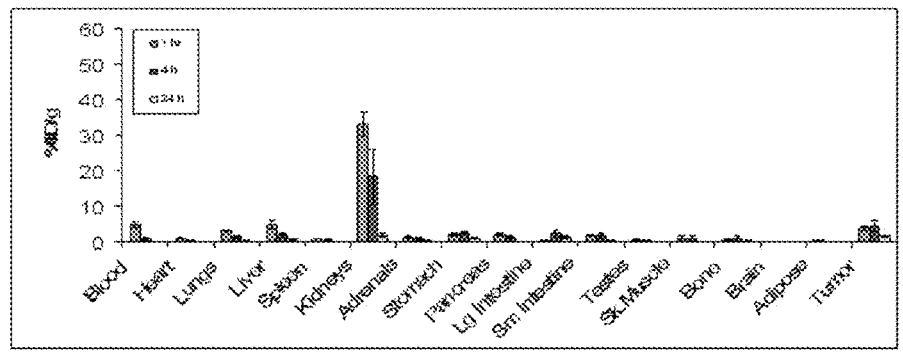

In one aspect, compounds are provided that are tridentate single amino acid chelator (SAAC) ligands. According to some embodiments, such ligands may be used in positron emission tomography (PET) and single photon emission computed tomography (SPECT). The compounds provide for imaging with improved kinetic properties, and decreased lipophilicity, which will allow for rapid and robust chelation of a metal center. For example, in some embodiments the metal center is a M(CO)$_3$ group. In other embodiments, the chelation occurs under mild conditions, for example at room temperature, neutral pH, and/or in aqueous based solvents.

Generally, the SAAC compounds contain containing functionalized, polar, heterocyclic rings as chelating groups to reduce the overall lipophilicity of the chelators when either coupled to small molecules or incorporated into peptides (including SSTR2 peptides). Such compounds localize to tumor xenografts and dramatically enhance renal clearance and diminish hepatobiliary uptake. SAAC compounds demonstrate facile labeling with radioactive metals, and exhibit robust complex stability. The SAAC compounds, as they are amino acid analogs, can be incorporated directly into peptide sequences.

In another aspect, the use of such SAAC ligands is provided to derivatize, and alter the pharmacokinetic profile of $^{99m}$Tc radiolabeled compounds to which they are attached. Such derivatized compounds may form the basis for $^{99m}$Tc-labeled radiopharmaceuticals. In one embodiment, lysine will be modified at the epsilon amine with two distinct sets of donor atom functionalities, having one or more ring groups, to create tridentate chelators with reduced lipophilicity as a result of oxygen and nitrogen substituents attached to the ring groups. For example, in some embodiments, the ring groups are imidazolyl and/or pyridyl derivatives. Such derivatized compounds may exhibit enhanced renal clearance and rapid background clearance.

DEFINITIONS

For convenience, certain terms employed herein and within the appended claims are collected here.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The use of the terms "a" and "an" and "the" and similar referents in the context of describing the elements (especially in the context of the following claims) are to be construed to cover both the singular and the plural, unless otherwise indicated herein or clearly contradicted by context.

The terms "lipophilic group" and "lipophilic moiety" as used herein refer to a group, moiety or substituent that has a greater affinity for non-polar or non-aqueous environments versus polar or aqueous environments. For example, Merriam Webster's online dictionary defines "lipophilic" as "having an affinity for lipids (as fats)." Exemplary lipophilic moieties include aliphatic hydrocarbon radicals, e.g., alkyl radicals, aromatic hydrocarbon radicals, and long-chain acyl radicals; all of them have increasing lipophilicity as the number of constituent carbons increases. In general, addition of a lipophilic moiety to a particular compound will increase the compound's affinity for octanol in the standard octanol/water partition-coefficient-determination protocol; this protocol may be used to gauge a compound's relative hydrophobicity (lipophilicity) and hydrophilicity.

The terms "Lewis base" and "Lewis basic" refer to a chemical moiety capable of donating a pair of electrons under certain reaction conditions. It may be possible to characterize a Lewis base as donating a single electron in certain complexes, depending on the identity of the Lewis base and the metal ion, but for most purposes, however, a Lewis base is best understood as a two electron donor. Examples of Lewis basic moieties include uncharged compounds such as alcohols, thiols, and amines, and charged moieties such as alkoxides, thiolates, carbanions, and a variety of other organic anions. In certain examples, a Lewis base may consist of a single atom, such as oxide (O$_2^-$). In certain, less common circumstances, a Lewis base or ligand may be positively charged. A Lewis base, when coordinated to a metal ion, is often referred to as a ligand.

The term "ligand" refers to a species that interacts in some fashion with another species. In one example, a ligand may be a Lewis base that is capable of forming a coordinate bond with a Lewis Acid. In other examples, a ligand is a species, often organic, that forms a coordinate bond with a metal ion. Ligands, when coordinated to a metal ion, may have a variety of binding modes know to those of skill in the art, which include, for example, terminal (i.e., bound to a single metal ion) and bridging (i.e., one atom of the Lewis base bound to more than one metal ion).

The term "chelating agent" refers to a molecule, often an organic one, and often a Lewis base, having two or more unshared electron pairs available for donation to a metal ion. The metal ion is usually coordinated by two or more electron pairs to the chelating agent. The terms, "bidentate chelating agent", "tridentate chelating agent", and "tetradentate chelating agent" refer to chelating agents having, respectively, two, three, and four electron pairs readily available for simultaneous donation to a metal ion coordinated by the chelating agent. Usually, the electron pairs of a chelating agent forms coordinate bonds with a single metal ion; however, in certain examples, a chelating agent may form coordinate bonds with more than one metal ion, with a variety of binding modes being possible.

The term "coordination" refers to an interaction in which one multi-electron pair donor coordinatively bonds (is "coordinated") to one metal ion.

The term "complex" refers to a compound formed by the union of one or more electron-rich and electron-poor molecules or atoms capable of independent existence with one or more electronically poor molecules or atoms, each of which is also capable of independent existence.

The phrase "therapeutically-effective amount" as used herein means that amount of a compound, material, or composition comprising a compound which is effective for producing some desired therapeutic effect in at least a sub-population of cells in an animal at a reasonable benefit/risk ratio applicable to any medical treatment.

As used herein, the terms "treating" or "treatment" is intended to encompass also diagnosis, prophylaxis, therapy and cure. The patient receiving this treatment is any animal in need, including primates, in particular humans, and other mammals such as equines, cattle, swine and sheep; and poultry and pets in general.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The term "amino acid" refers to all compounds, whether natural or synthetic, which include both an amino functionality and an acid functionality, including amino acid analogs and derivatives.

The term "heteroatom" refers to an atom of any element other than carbon or hydrogen. Illustrative heteroatoms include boron, nitrogen, oxygen, phosphorus, sulfur and selenium.

In general, "substituted" refers to an alkyl or alkenyl group, as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Alkyl groups may be substituted or unsubstituted. Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The terms "cyclic alkyl" or "cycloalkyl" refers to a saturated or partially saturated non-aromatic cyclic alkyl groups of from 3 to 14 carbon atoms and no ring heteroatoms and having a single ring or multiple rings including fused and bridged ring systems. Cycloalkyl groups may be substituted or unsubstituted. Cycloalkyl or cyclic alkyl groups include mono-, bi- or tricyclic alkyl groups having from 3 to 14 carbon atoms in the ring(s), or, in some embodiments, 3 to 12, 3 to 10, 3 to 8, or 3 to 4, 5, 6 or 7 carbon atoms. Exemplary monocyclic cycloalkyl groups include, but not limited to, cyclopropyl, cyclobutyl, cyclopentyl, cyclohexyl, cycloheptyl, and cyclooctyl groups. Bi- and tricyclic ring systems include both bridged cycloalkyl groups and fused rings, such as, but not limited to, bicyclo [2.1.1]hexane, adamantyl, decalinyl, and the like.

Alkenyl groups include straight and branched chain and cycloalkyl groups as defined above, except that at least one double bond exists between two carbon atoms. Thus, alkenyl groups have from 2 to about 12 carbon atoms in some embodiments, from 2 to 10 carbon atoms in other embodiments, and from 2 to 8 carbon atoms in other embodiments. Examples include, but are not limited to vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, cyclohexenyl, cyclopentenyl, cyclohexadienyl, butadienyl, pentadienyl, and hexadienyl, among others. Alkenyl groups may be substituted or unsubstituted. Representative substituted alkenyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Aryl group includes both substituted and unsubstituted aryl groups. Substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 20 carbon atoms, 7 to 14 carbon atoms or 7 to 10 carbon atoms.

Heterocyclyl groups includes non-aromatic ring compounds containing 3 or more ring members, of which one or more is a heteroatom such as, but not limited to, N, O, and S. In some embodiments, heterocyclyl groups include 3 to 20 ring members, whereas other such groups have 3 to 6, 3 to 10, 3 to 12, or 3 to 15 ring members. Heterocyclyl groups encompass unsaturated, partially saturated and saturated ring systems, such as, for example, imidazolyl, imidazolinyl and imidazolidinyl groups. Heterocyclyl groups may be substituted or unsubstituted. Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Heterocyclyl groups may be substituted or unsubstituted. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups may be substituted or unsubstituted. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Alkoxy groups may be substituted or unsubstituted. Representative substituted alkoxy groups may be substituted one or more times with substituents such as those listed above.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, monoalkylamino, dialkylamino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "carbocycle" refers to an aromatic or non-aromatic ring in which each atom of the ring is carbon.

The term "nitro" refers to —NO$_2$; the term "halogen" refers to —F, —Cl, —Br or —I; the term "sulfhydryl" refers to —SH; the term "hydroxyl" means —OH; and the term "sulfonyl" refers to —SO$_2^-$. "Halide" designates the corresponding anion of the halogens, and "pseudohalide" has the definition set forth on 560 of "*Advanced Inorganic Chemistry*" by Cotton and Wilkinson.

The terms "amine" and "amino" refer to both unsubstituted and substituted amines, e.g., a moiety that may be represented by the general formulas, —NR$^\alpha$R$^\beta$ and —[NR$^\alpha$R$^\beta$R$^\gamma$]$^+$, wherein R$^\alpha$, R$^\beta$ and R$^\gamma$ each independently represent a hydrogen, an alkyl, an alkenyl, —(CH$_2$)$_m$—R$^\delta$, or R$^\alpha$ and R$^\beta$, taken together with the N atom to which they are attached complete a heterocycle having from 4 to 8 atoms in the ring structure; R$^\delta$ represents an aryl, a cycloalkyl, a cycloalkenyl, a heterocycle or a polycycle; and m is zero or an integer in the range of 1 to 8. In other embodiments, R$^\alpha$ and R$^\beta$ (and optionally R$^\gamma$) each independently represent a hydrogen, an alkyl, an alkenyl, or —(CH$_2$)$_m$—R$^\delta$. Thus, the term "alkylamine" includes an amine group, as defined above, having a substituted or unsubstituted alkyl attached thereto, i.e., at least one of R$^\alpha$ and R$^\beta$ is an alkyl group.

The term "acylamino" refers to a moiety that may be represented by the general formula, —N(R$^\alpha$)C(O)R$^\beta$, wherein R$^\alpha$ and R$^\beta$ are as defined above.

The term "amido" as an amino-substituted carbonyl and includes a moiety that may be represented by the general formula, —C(O)NR$^\alpha$R$^\beta$, wherein R$^\alpha$, Rβ, and m are as defined above. According to some embodiments, the amide does not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R$^\delta$, wherein m and R$^\delta$ are defined above. Representative alkylthio groups include methylthio, ethyl thio, and the like.

The terms "carboxyl" and "carboxylate" include such moieties as may be represented by the general formulas:

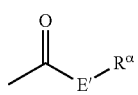

or

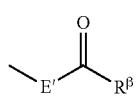

wherein E' is a bond, O, or S; and R$^\alpha$ and R$^\beta$ are as defined above. Where E' is O and R$^\alpha$ and R$^\beta$ are not hydrogen, the formula represents an ester. Where E' is O, and R$^\alpha$ is as defined above, the moiety is referred to herein as a carboxyl group, and particularly when R$^\alpha$ is a hydrogen, the formula represents a carboxylic acid. Where E' is O, and R$^\beta$ is hydrogen, the formula represents a formate. In general, where the O of the above formula is replaced by S, the formula represents a thiolcarbonyl group. Where E' is S and R$^\alpha$ and R$^\beta$ are not hydrogen, the formula represents a thiolester. Where E' is S and R$^\alpha$ is hydrogen, the formula represents a thiolcarboxylic acid. Where E' is S and R$^\beta$ is hydrogen, the formula represents a thiolformate. On the other hand, where E' is a bond, and R$^\alpha$ is not hydrogen, the above formula represents a ketone. Where E' is a bond, and R$^\alpha$ is hydrogen, the above formula represents an aldehyde group.

The term "carbamoyl" refers to —O(C=O)NR$^\epsilon$R$^\kappa$, where R$^\epsilon$ and R$^\kappa$ are independently H, aliphatic groups, aryl groups or heteroaryl groups. The term "oxo" refers to a carbonyl oxygen (=O).

The terms "oxime" and "oxime ether" refer to moieties that may be represented by the general formula:

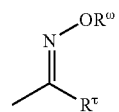

wherein R$^\tau$ is hydrogen, alkyl, cycloalkyl, alkenyl, alkynyl, aryl, aralkyl, or —(CH$_2$)$_m$—R$^\delta$, and R$^\delta$ is as defined above. The moiety is an "oxime" when R is H; and it is an "oxime ether" when R$^\omega$ is alkyl, cycloalkyl, alkenyl, alkynyl, aryl, aralkyl, or —(CH$_2$)$_m$—R$^\delta$.

The terms "alkoxyl" or "alkoxy" refer to an alkyl group, as defined above, having an oxygen radical attached thereto. Representative alkoxyl groups include methoxy, ethoxy, propoxy, butyoxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, or —(CH$_2$)$_m$—R$^\delta$, where m and R$^\delta$ are described above. "Ether" also encompasses polyethers where more than one ether group, or linkage, may be present in a given group. "Ether" also encompasses cyclic ethers, and crown ethers, where the ether linkage is within a cyclic group.

The term "sulfonate" refers to a moiety that may be represented by the general formula, —S(O)$_2$OR$^\pi$, in which R$^\pi$ is an electron pair, bond, hydrogen, alkyl, cycloalkyl, or aryl. The term "sulfate" includes a moiety that may be represented by the general formula, —OS(O)$_2$OR$^\pi$. The term "sulfonamido" includes a moiety that may be represented by the general formula: —N(R$^\alpha$)S(O)$_2$OR$^\delta$, in which R$^\alpha$ and R$^\beta$ are as defined above. The term "sulfamoyl" refers to a moiety that may be represented by the general formula, —S(O)$_2$NR$^\alpha$R$^\beta$, in which R$^\alpha$ and R$^\delta$ and R$^\beta$ are as defined above. The term "sulfonyl" refers to a moiety that may be represented by the general formula: —S(O)$_2$R$^\eta$, in which R$^\eta$ is hydrogen, alkyl, alkenyl, alkynyl, cycloalkyl, heterocyclyl, aryl or heteroaryl. The term "sulfoxido" refers to a moiety that may be represented by the general formula, —S(O)R$^\eta$, in which R$^\eta$ is defined above.

The term "phosphoryl" may in general be represented by the formula:

wherein E' is S or O, and R$^\phi$ represents hydrogen, a lower alkyl or an aryl. When used to substitute, e.g., an alkyl, the phosphoryl group of the phosphorylalkyl may be represented by the general formulas:

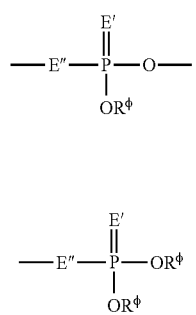

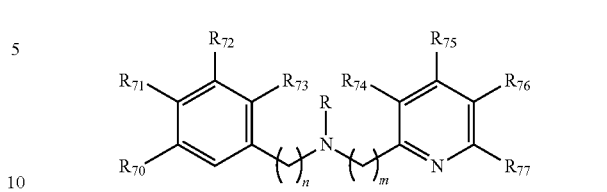

wherein E' and $R^\Phi$, each independently, are defined above, and E" represents O, S or N. When E' is S, the phosphoryl moiety is a "phosphorothioate".

The definition of each expression, e.g. alkyl, m, n, and the like, when it occurs more than once in any structure, is intended to be independent of its definition elsewhere in the same structure.

The terms triflyl, tosyl, mesyl, and nonaflyl refer to trifluoromethanesulfonyl, p-toluenesulfonyl, methanesulfonyl, and nonafluorobutanesulfonyl groups, respectively. The terms triflate, tosylate, mesylate, and nonaflate refer to trifluoromethanesulfonate ester, p-toluenesulfonate ester, methanesulfonate ester, and nonafluorobutanesulfonate ester functional groups and molecules that contain said groups, respectively. The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain compounds contained in the compositions may exist in particular geometric or stereoisomeric forms. In addition, compounds may also be optically active. The compounds may also include cis- and trans-isomers, R- and S-enantiomers, diastereomers, (D)-isomers, (L)-isomers, the racemic mixtures thereof, and other mixtures thereof. Additional asymmetric carbon atoms may be present in a substituent such as an alkyl group. If, for instance, a particular enantiomer of compound is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T.W.; Wuts, P.G.M. *Protective Groups in Organic Synthesis*, 3$^{rd}$ ed.; Wiley: New York, 1999).

In one aspect, a compound of Formula I is provided:

where, R is H, alkyl, hydroxyalkyl, alkoxyalkyl, aminoalkyl, thioalkyl, alkenyl, alkynyl, aryl, heteroaryl, aralkyl, heteroaralkyl, acyl, aminoacyl, hydroxyacyl, thioacyl, —CO$_2$H, —(CH$_2$)$_d$—R$_{80}$, or an amino acid radical; R$_{80}$ is independently for each occurrence carboxaldehyde, carboxylate, carboxamido, alkoxycarbonyl, aryloxycarbonyl, ammonium, aryl, heteroaryl, cycloalkyl, cycloalkenyl, heterocyclyl, polycyclyl, amino acid, peptide, saccharide, ribonucleic acid, (deoxy)ribonucleic acid, or a ligand for a G-protein-coupled receptor, a oxoreductase, a transferase, a hydrolase, a ligase, a osomerase, a ligase, a GPCR, a direct ligand-gated channel receptor, a cytokine receptor, a integrin receptor, a tyrosine kinase associated receptor, a nuclear receptor, a peptide receptor, a transmembrane receptor, a transcription factor, a cytoskeletal protein, a structural protein, or a signaling protein; d is an integer in the range 0 to 12; m is an integer in the range 0 to 6; n is an integer in the range 0 to 6; and R$_{70}$, R$_{71}$, R$_{72}$, R$_{73}$, R$_{74}$, R$_{75}$, R$_{76}$, and R$_{77}$ are each independently hydrogen, halogen, alkyl, alkenyl, alkynyl, hydroxyl, alkoxyl, acyl, acyloxy, acylamino, silyloxy, amino, monoalkylamino, dialkylamino, nitro, sulfhydryl, alkylthio, imino, amido, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, cyano, guanidine, amidine, acetal, ketal, amine oxide, aryl, heteroaryl, aralkyl, heteroaralkyl, azido, aziridine, carbamoyl, epoxide, hydroxamic acid, imide, oxime, sulfonamide, thioamide, thiocarbamate, urea, thiourea, or —(CH$_2$)$_d$—R$_{80}$. Alternatively, R$_{70}$ and R$_{71}$; R$_{71}$ and R$_{72}$; or R$_{72}$ and R$_{73}$ may join to form a ring; and R$_{74}$ and R$_{75}$; R$_{75}$ and R$_{76}$; or R$_{76}$ and R$_{77}$ may join to form a ring. In some embodiments, the compound of formula I is subject to the proviso that at least one of R$_{70}$, R$_{71}$, R$_{72}$, or R$_{73}$ is other than hydrogen and at least one of R$_{74}$, R$_{75}$, R$_{76}$, or R$_{77}$ is other than hydrogen.

In some embodiments, the compound of Formula I has a general structure according to any one of the following:

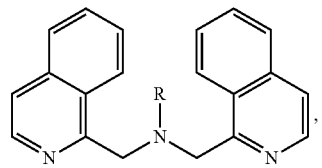

or

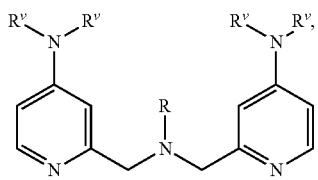

where, $R^v$ is alkyl. According to some embodiments, $R^v$ is methyl, ethyl, n-propyl, iso-propyl, n-butyl, iso-butyl, or tert-butyl. In other embodiments, $R^v$ is methyl. In some embodiments, R is hydroxyalkyl, alkoxyalkyl, aminoalkyl, thioalkyl, aralkyl, heteroaralkyl, acyl, aminoacyl, hydroxyacyl, thioacyl, —$CO_2H$, —$(CH_2)_d$—$R_{80}$, or an amino acid radical; $R_{80}$ is independently for each occurrence carboxaldehyde, carboxylate, carboxamido, alkoxycarbonyl, aryloxycarbonyl, ammonium, aryl, heteroaryl, cycloalkyl, cycloalkenyl, heterocyclyl, polycyclyl, amino acid, peptide, saccharide, ribonucleic acid, (deoxy)ribonucleic acid, or a ligand for a G-protein-coupled receptor, a oxoreductase, a transferase, a hydrolase, a ligase, a osomerase, a ligase, a GPCR, a direct ligand-gated channel receptor, a cytokine receptor, a integrin receptor, a tyrosine kinase associated receptor, a nuclear receptor, a peptide receptor, a transmembrane receptor, a transcription factor, a cytoskeletal protein, a structural protein, or a signaling protein; d is an integer in the range 0 to 12; m is an integer in the range 0 to 6; n is an integer in the range 0 to 6.

In another aspect, a compound of Formula II is provided:

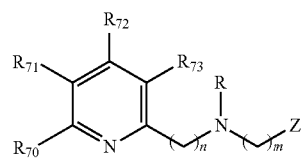

where R, m, and n are as defined above with respect to the compound of Formula I. In Formula II, Z is thioalkyl, carboxylate, 2-(carboxy)aryl, 2-(carboxy)heteroaryl, 2-(hydroxy)aryl, 2-(hydroxy)heteroaryl, 2-(thiol)aryl, or 2-(thiol)heteroaryl; and $R_{70}$, $R_{71}$, $R_{72}$, and $R_{73}$ are each independently hydrogen, halogen, alkyl, alkenyl, alkynyl, hydroxyl, alkoxyl, acyl, acyloxy, acylamino, silyloxy, amino, monoalkylamino, dialkylamino, nitro, sulfhydryl, alkylthio, imino, amido, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, cyano, guanidine, amidine, acetal, ketal, amine oxide, aryl, heteroaryl, aralkyl, heteroaralkyl, azido, aziridine, carbamoyl, epoxide, hydroxamic acid, imide, oxime, sulfonamide, thioamide, thiocarbamate, urea, thiourea, or —$(CH_2)_d$—$R_{80}$. Alternatively, $R_{70}$ and $R_{71}$; $R_{71}$ and $R_{72}$, or $R_{72}$ and $R_{73}$ may join to form a ring. In some embodiments, the compound of Formula II is subjection to the proviso that at least one of $R_{70}$, $R_{71}$, $R_{72}$, and $R_{73}$ is other than hydrogen and at least one of $R_{74}$, $R_{75}$, $R_{76}$, and $R_{77}$ is other than hydrogen.

In some embodiments, the compound of Formula II has a general structure of

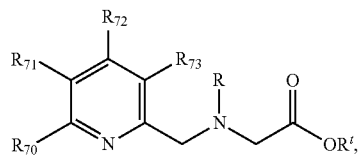

or

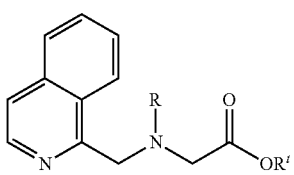

where, $R^t$ is H, a $C_1$-$C_8$ alkyl group, an ammonium ion, or an alkali or alkaline earth metal ion. According to some embodiments, $R^t$ is H or tert-butyl. In yet other embodiments, $R^t$ is H.

In some embodiments, the compound of Formula I or II is complexed with a radionuclide. In some embodiments, the compound of Formula I or II is complexed a radionuclide, where the radionuclide is technetium or rhenium.

In some embodiments, in the compound of Formula I or II, m is 1. In some embodiments, in the compound of Formula I or II, n is 1. In some embodiments, in the compound of Formula I or II, m is 1; and n is 1.

In some embodiments, in the compound of Formula I or II, at least one of $R_{70}$, $R_{71}$, $R_{72}$, or $R_{73}$ is amino. In some embodiments, in the compound of Formula I or II, at least one of $R_{74}$, $R_{75}$, $R_{76}$, or $R_{77}$ is amino. In some embodiments, in the compound of Formula I or II, at least one of $R_{70}$, $R_{71}$, $R_{72}$, or $R_{73}$ is amino and at least one of $R_{74}$, $R_{75}$, $R_{76}$, or $R_{77}$ is amino. In some embodiments, in the compound of Formula I or II, $R_{71}$ is amino. In some embodiments, in the compound of Formula I or II, $R_{72}$ is amino. In some embodiments, in the compound of Formula I or II, $R_{75}$ is amino. In some embodiments, in the compound of Formula I or II, $R_{76}$ is amino. In some embodiments, in the compound of Formula I or II, $R_{72}$ is —$N(CH_3)_2$. In some embodiments, in the compound of Formula I or II, $R_{75}$ is —$N(CH_3)_2$. In some embodiments, in the compound of Formula I or II, $R_{71}$ is —$N(R_{90})_2$. In some embodiments, in the compound of Formula I or II, $R_{76}$ is —$N(R_{90})_2$. In some embodiments, —$N(R_{90})_2$ is:

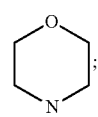

;

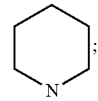

;

or

In some embodiments, in the compound of Formula I or II, R is —$(CH_2)_d$—$R_{80}$. In some embodiments, in the compound of Formula I or II, m is 1; n is 1; and R is —$(CH_2)_d$—$R_{80}$. In some embodiments, in the compound of Formula I or II, R is an amino acid radical. In some embodiments, the amino acid radical is —$CH_2CH_2CH_2CH_2CH(NH_2)CO_2H$, —$CH(CO_2H)CH_2CH_2CH_2CH_2NH_2$, —$CH_2CH_2CO_2H$, —$CH_2CH_2CH_2CO_2H$, —$CH_2(CH_2)_xCO_2H$, —$CH_2(CH_2)_xCH(NH_2)CO_2H$, or —$CH(CO_2H)(CH_2)_xCH(NH_2)CO_2H$, where x is an integer from 3 to 9.

In some embodiments, in the compound of Formula II, Z is a carboxylate. In some embodiments, in the compound of Formula II, Z is carboxylate; m is 1; and n is 1.

In another aspect, a formulation is provided including a compound of Formula I or II, and a pharmaceutically acceptable excipient.

In another aspect, a method of imaging a region in a patient includes the step of administering to a patient a diagnostically effective amount of a compound of Formula I or II. In some embodiments, the method further includes the step of obtaining an image of said region of said patient.

In another aspect, a method of preparing a peptide conjugate incorporating a compound of Formula I or II includes the step of synthesizing a peptide conjugate using solid-phase peptide-synthesis techniques.

In another aspect, a compound of Formula III is provided:

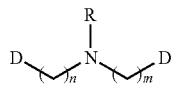

III wherein R is H, alkyl, hydroxyalkyl, alkoxyalkyl, aminoalkyl, thioalkyl, alkenyl, alkynyl, aryl, heteroaryl, aralkyl, heteroaralkyl, acyl, aminoacyl, hydroxyacyl, thioacyl, —$CO_2H$, —$(CH_2)_d$—$R_{80}$, or an amino acid radical; $R_{80}$ is independently for each occurrence carboxaldehyde, carboxylate, carboxamido, alkoxycarbonyl, aryloxycarbonyl, ammonium, aryl, heteroaryl, cycloalkyl, cycloalkenyl, heterocyclyl, polycyclyl, amino acid, peptide, saccharide, ribonucleic acid, (deoxy)ribonucleic acid, or a ligand for a G-protein-coupled receptor, a oxoreductase, a transferase, a hydrolase, a ligase, a osomerase, a ligase, a GPCR, a direct ligand-gated channel receptor, a cytokine receptor, a integrin receptor, a tyrosine kinase associated receptor, a nuclear receptor, a peptide receptor, a transmembrane receptor, a transcription factor, a cytoskeletal protein, a structural protein, or a signaling protein; d is an integer in the range 0 to 12; m is an integer in the range 0 to 6; n is an integer in the range 0 to 6; D is

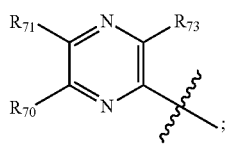

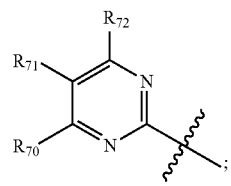

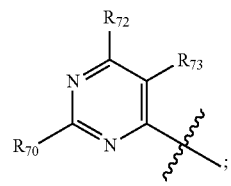

or

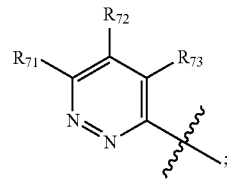

and
$R_{70}$, $R_{71}$, $R_{72}$, $R_{73}$, $R_{74}$, $R_{75}$, $R_{76}$, and $R_{77}$ at each individual occurrence are independently hydrogen, halogen, alkyl, alkenyl, alkynyl, hydroxyl, alkoxyl, acyl, acyloxy, acylamino, silyloxy, amino, monoalkylamino, dialkylamino, nitro, sulfhydryl, alkylthio, imino, amido, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, cyano, guanidine, amidine, acetal, ketal, amine oxide, aryl, heteroaryl, aralkyl, heteroaralkyl, azido, aziridine, carbamoyl, epoxide, hydroxamic acid, imide, oxime, sulfonamide, thioamide, thiocarbamate, urea, thiourea, or —$(CH_2)_d$—$R_{80}$.

In another aspect, a compound of Formula IV is provided:

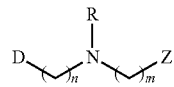

IV wherein R is H, alkyl, hydroxyalkyl, alkoxyalkyl, aminoalkyl, thioalkyl, alkenyl, alkynyl, aryl, heteroaryl, aralkyl, heteroaralkyl, acyl, aminoacyl, hydroxyacyl, thioacyl, —$CO_2H$, —$(CH_2)_d$—$R_{80}$, or an amino acid radical; $R_{80}$ is independently for each occurrence carboxaldehyde, carboxylate, carboxamido, alkoxycarbonyl, aryloxycarbonyl, ammonium, aryl, heteroaryl, cycloalkyl, cycloalkenyl, heterocyclyl, polycyclyl, amino acid, peptide, saccharide, ribonucleic acid, (deoxy)ribonucleic acid, or a ligand for a G-protein-coupled receptor, a oxoreductase, a transferase, a hydrolase, a ligase, a osomerase, a ligase, a GPCR, a direct ligand-gated channel receptor, a cytokine receptor, a integrin receptor, a tyrosine kinase associated receptor, a nuclear receptor, a peptide receptor, a transmembrane receptor, a transcription factor, a cytoskeletal protein, a structural protein, or a signaling protein; d is an integer in the range 0 to 12; m is an integer in the range 0 to 6; n is an integer in the range 0 to 6; Z is thioalkyl, carboxylate, 2-(carboxy)aryl, 2-(carboxy)heteroaryl, 2-(hydroxy)aryl, 2-(hydroxy)heteroaryl, 2-(thiol)aryl, or 2-(thiol)heteroaryl; D is

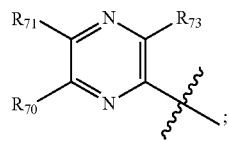

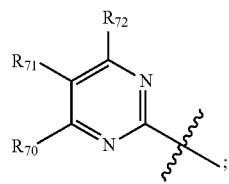

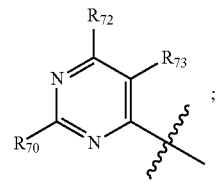

or

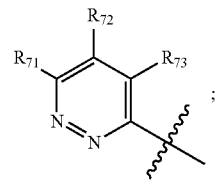

and
$R_{70}$, $R_{71}$, $R_{72}$, $R_{73}$, $R_{74}$, $R_{75}$, $R_{76}$, and $R_{77}$ at each individual occurrence are independently hydrogen, halogen, alkyl, alkenyl, alkynyl, hydroxyl, alkoxyl, acyl, acyloxy, acylamino, silyloxy, amino, monoalkylamino, dialkylamino, nitro, sulfhydryl, alkylthio, imino, amido, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, cyano, guanidine, amidine, acetal, ketal, amine oxide, aryl, heteroaryl, aralkyl, heteroaralkyl, azido, aziridine, carbamoyl, epoxide, hydroxamic acid, imide, oxime, sulfonamide, thioamide, thiocarbamate, urea, thiourea, or —$(CH_2)_d$—$R_{80}$.

In some embodiments, the compound of Formula III or IV is complexed with a radionuclide. In some embodiments, the compound of Formula III or IV is complexed a radionuclide, where the radionuclide is technetium or rhenium.

In some embodiments, in the compound of Formula III or IV, m is 1. In some embodiments, in the compound of Formula III or IV, n is 1. In some embodiments, in the compound of Formula III or IV, m is 1; and n is 1.

In some embodiments, in the compound of Formula III or IV, at least one of $R_{70}$, $R_{71}$, $R_{72}$, or $R_{73}$ is amino. In some embodiments, in the compound of Formula III or IV, at least one of $R_{74}$, $R_{75}$, $R_{76}$, or $R_{77}$ is amino. In some embodiments, in the compound of Formula III or IV, at least one of $R_{70}$, $R_{71}$, $R_{72}$, or $R_{73}$ is amino and at least one of $R_{74}$, $R_{75}$, $R_{76}$, or $R_{77}$ is amino. In some embodiments, in the compound of Formula III or IV, $R_{71}$ is amino. In some embodiments, in the compound of Formula III or IV, $R_{72}$ is amino. In some embodiments, in the compound of Formula III or IV, $R_{75}$ is amino. In some embodiments, in the compound of Formula III or IV, $R_{76}$ is amino. In some embodiments, in the compound of Formula III or IV, $R_{72}$ is —$N(CH_3)_2$. In some embodiments, in the compound of Formula III or IV, $R_{75}$ is —$N(CH_3)_2$. In some embodiments, in the compound of Formula III or IV, $R_{71}$ is —$N(R_{90})_2$. In some embodiments, in the compound of Formula III or IV, $R_{76}$ is —$N(R_{90})_2$. In some embodiments, —$N(R_{90})_2$ is:

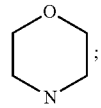

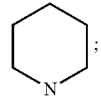

or

In some embodiments, in the compound of Formula III or IV, R is —$(CH_2)_d$—$R_{80}$. In some embodiments, in the compound of Formula III or IV, m is 1; n is 1; and R is –$(CH_2)_d$—$R_{80}$. In some embodiments, in the compound of Formula III or IV, R is an amino acid radical. In some embodiments, the amino acid radical is —$CH_2CH_2CH_2CH_2CH(NH_2)CO_2H$, —$CH(CO_2H)CH_2CH_2CH_2CH_2NH_2$, —$CH_2CH_2CO_2H$, —$CH_2CH_2CH_2CO_2H$, —$CH_2(CH_2)_xCO_2H$, —$CH_2(CH_2)_xCH(NH_2)CO_2H$, or —$CH(CO_2H)(CH_2)_xCH(NH_2)CO_2H$, where x is an integer from 3 to 9.

In some embodiments, in the compound of Formula IV, Z is carboxylate. In some embodiments, in the compound of Formula IV, Z is carboxylate; m is 1; and n is 1.

In another aspect, a formulation is provided including a compound of Formula III or IV, and a pharmaceutically acceptable excipient.

In another aspect, a method of imaging a region in a patient includes the step of administering to a patient a diagnostically effective amount of a compound of Formula III or IV. In some embodiments, the method further includes the step of obtaining an image of said region of said patient.

In another aspect, a method of preparing a peptide conjugate incorporating a compound of Formula III or IV includes the step of synthesizing a peptide conjugate using solid-phase peptide-synthesis techniques.

In another aspect, a compound of Formula V is provided:

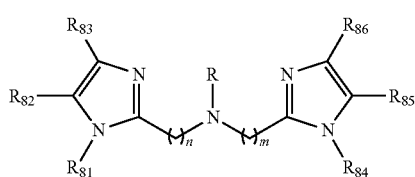

where, R is H, or a substituted or unsubstituted alkyl, hydroxyalkyl, alkoxyalkyl, aminoalkyl, thioalkyl, alkenyl, alkynyl, aryl, heteroaryl, aralkyl, heteroaralkyl, acyl, aminoacyl, hydroxyacyl, thioacyl, alkylketo, aminoalkoxylalkyl, boratoalkyl, phosphonatoalkyl, phosphinatoalkyl, $(CH_2)_4CH(NH_2)CO_2H$, $(CH_2)_3CH(NH_2)CO_2H$, $(CH_2)_2CH(NH_2)CO_2H$, $C(O)CH_2(CH)NH_2CO_2H$, $C(O)(CH_2)_2(CH)NH_2CO_2H$, $(CC)(CH_2)_2CH(NH_2)CO_2H$, $(CHCH)(CH_2)_2CHNH_2CO_2H$, $(CH_2)_2(CHOH)(CH_2)CHNH_2CO_2H$ or $(CH_2)(CHOH)(CH_2)_2CHNH_2CO_2H$, $(CO_2H)_2$, $—CO_2H$, $—(CH_2)_d—R_{80}$, $—C(O)(CH_2)_d—R_{80}$, or an amino acid radical; $R_{80}$ is independently for each occurrence carboxaldehyde, carboxylate, carboxamido, alkoxycarbonyl, aryloxycarbonyl, ammonium, aryl, heteroaryl, cycloalkyl, cycloalkenyl, heterocyclyl, polycyclyl, amino acid, $CH_2CH_2OCH_2CH_3$, $CH_2C(OCH_3)_2$, $(CH_2CH_2O)_dCH_2CH_3$, $(CH_2)_dNH_2$, $(CH_2)_dC(O)NH_2$, $(CH_2)_dN(CH_3)_2$, $CH_2CH_2OH$, $(CH_2)_dC(CO_2H)_2$, $(CH_2)_dP(O)(OH)_2$, $(CH_2)_dB(OH)_2$, peptide, saccharide, ribonucleic acid, (deoxy)ribonucleic acid, or a ligand for a G-protein-coupled receptor, a oxoreductase, a transferase, a hydrolase, a ligase, a osomerase, a ligase, a GPCR, a direct ligand-gated channel receptor, a cytokine receptor, a integrin receptor, a tyrosine kinase associated receptor, a nuclear receptor, a peptide receptor, a transmembrane receptor, a transcription factor, a cytoskeletal protein, a structural protein, or a signaling protein; d is an integer in the range 0 to 12; m is an integer in the range 0 to 6; n is an integer in the range 0 to 6; $R_{81}$, $R_{82}$, $R_{83}$, $R_{84}$, $R_{85}$, and $R_{86}$ are each independently hydrogen, halogen, or a substituted or unsubstituted alkyl, alkenyl, alkynyl, hydroxyl, alkoxyl, acyl, acyloxy, acylamino, silyloxy, amino, monoalkylamino, dialkylamino, nitro, sulfhydryl, alkylthio, imino, amido, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ether, ester, heteroalkyl, cyano, guanidine, amidine, acetal, ketal, amine oxide, aryl, heteroaryl, aralkyl, arylether, heteroaralkyl, azido, aziridine, carbamoyl, epoxide, hydroxamic acid, imide, oxime, sulfonamide, thioamide, thiocarbamate, urea, thiourea, $—(CH_2)_d—R_{80}$, $(CH_2)_d(CO_2H)_2$, $CH_2CH_2OCH_2CH_3$, $CH_2C(OCH_3)_2$, $(CH_2CH_2O)_d$ $CH_2CH_3$, $(CH_2)_dNH_2$, $(CH_2)_dC(O)NH_2$, $(CH_2)_dN(CH_3)_2$, $CH_2CH_2OH$, $(CH_2)—C(CO_2H)_2$, $(CH_2)_dP(O)(OH)_2$, $(CH_2)_dB(OH)_2$, $—(CH_2)_d—R_{80}$, $(CH_2)_dR_{87}$, or $—(CH_2)_d—R_{88}$; and $R_{87}$ and $R_{88}$ are each independently 15-Crown-5, 18-Crown-6, tetrazole, oxazole, aziridine, triazole, imidazole, pyrazole, thiazole, hydroxamic acid, phosphonate, phosphinate, thiol, thioether, polysacharride, sacharride, nucleotide or oligonucleotide. In some embodiments, the compound of formula V is subject to the proviso that at least one of $R_{81}$, $R_{82}$, or $R_{83}$, is a hydrophilic group. In some embodiments, the compound of formula V is subject to the proviso that at least one of $R_{84}$, $R_{85}$, or $R_{86}$ is a hydrophilic group. In some embodiments, the compound of formula V is subject to the proviso that at least one of $R_{81}$, $R_{82}$, or $R_{83}$ is a hydrophilic group, and at least one of $R_{84}$, $R_{85}$, or is a hydrophilic group. In some embodiments, the compound of formula V is subject to the proviso that at least one of $R_{81}$ and $R_{84}$ is a hydrophilic group. In some embodiments, a hydrophilic group is an ether, an alkoxyaralkyl, a carboxylate, an alcohol, or an amide. In some embodiments, the compound of formula V is subject to the proviso that at least one of $R_{81}$, $R_{82}$, or $R_{83}$, is a hydrophilic group.

In some embodiments, R is H, $CH_3$, $(CH_2)_dCH_3$, $CH_2CH_2OCH_2CH_3$, $(CH_2)_dC(O)NH_2$, $CH_2C(OCH_3)_2$, $CH_2$(18-Crown-6), $CH_2$(15-Crown-5), $C(O)(CH_2)_d(CH)(NH_2)CO_2H$, $(CH_2CH_2O)_dCH_2CH_3$, $(CH_2)_dPh(SO_2NH_2)$, $(CH_2)_dP(O)OH_2$, $(CH_2)_dOCH_2NH_2$, $(CH_2)_dNHCH_2NH_2$, $(CH_2)_dNHCH_2CO_2H$, $(CH_2)_dNH_2$, $(CH_2)_dN(CH_3)_2$, $(CH_2)_dCO_2H$, $(CH_2)_dCO_2H$, $(CH_2)_dCH(CO_2H)(NHC(S)NH)Ph(SO_2NH_2)$, $(CH_2)_dC(CO_2H)_2$, $(CH_2)_dB(OH)_3$, $(CH_2)_d$(triazole), $(CH_2)_d$(thiol), $(CH_2)_d$(thioether), $(CH_2)_d$(thiazole), $(CH_2)_d$(tetrazole), $(CH_2)_d$(sacharride), $(CH_2)_d$(pyrazole), $(CH_2)_d$(polysacharride), $(CH_2)_d$(phosphonate), $(CH_2)_d$(phosphinate), $(CH_2)_d$(oxazole), $(CH_2)_d$(oligonucleotide), $(CH_2)_d$(nucleotide), $(CH_2)_d$(imidazole), $(CH_2)_d$(hydroxamic acid), $(CH_2)_d(CO_2H)_2$, $(CH_2)_d(CHOH)(CH_2)_dCH(NH_2)CO_2H$, $(CH_2)_d$(aziridine), $(CH_2)_dOH$, $(CH_2)_dOCH_2CO_2H$, $(CH_2)_dO(CH_2)—CH_3$, $(CH_2)_dNH_2$, $(CH_2)_dCH(NH_2)CO_2H$, $(CH_2)(CHOH)(CH_2)_dCH(NH_2)CO_2H$, $(CH=CH)(CH_2)_dCH(NH_2)CO_2H$, $(C≡C)(CH_2)_dCH(NH_2)CO_2H$; and $R_{81}$, $R_{82}$, $R_{83}$, $R_{84}$, $R_{85}$, and $R_{86}$ are each independently H, F, Cl, Br, I, $NO_2$, $CH_3$, $(CH_2)_dCH_3$, $CH_2CH_2OCH_2CH_3$, $(CH_2)_dC(O)NH_2$, $CH_2C(OCH_3)_2$, $CH_2$(18-Crown-6), $CH_2$(15-Crown-5), $C(O)(CH_2)_d(CH)(NH_2)CO_2H$, $(CH_2CH_2O)_dCH_2CH_3$, $(CH_2)_dPh(SO_2NH_2)$, $(CH_2)_dP(O)OH_2$, $(CH_2)_dOCH_2NH_2$, $(CH_2)_dNHCH_2NH_2$, $(CH_2)_dNHCH_2CO_2H$, $(CH_2)_dNH_2$, $(CH_2)_dN(CH_3)_2$, $(CH_2)_dCO_2H$, $(CH_2)_dCO_2H$, $(CH_2)_dCH(CO_2H)(NHC(S)NH)Ph(SO_2NH_2)$, $(CH_2)_dC(CO_2H)_2$, $(CH_2)_dB(OH)_3$, $(CH_2)_d$(triazole), $(CH_2)_d$(thiol), $(CH_2)_d$(thioether), $(CH_2)_d$(thiazole), $(CH_2)_d$(tetrazole), $(CH_2)_d$(sacharride), $(CH_2)_d$(pyrazole), $(CH_2)_d$(polysacharride), $(CH_2)_d$(phosphonate), $(CH_2)_d$(phosphinate), $(CH_2)_d$(oxazole), $(CH_2)_d$(oligonucleotide), $(CH_2)_d$(nucleotide), $(CH_2)_d$(imidazole), $(CH_2)_d$(hydroxamic acid), $(CH_2)_d(CO_2H)_2$, $(CH_2)_d(CHOH)(CH_2)_dCH(NH_2)CO_2H$, $(CH_2)_d$(aziridine), $(CH_2)_dOH$, $(CH_2)_dOCH_2CO_2H$, $(CH_2)_dO(CH_2)—CH_3$, $(CH_2)_dNH_2$, $(CH_2)_dCH(NH_2)CO_2H$, $(CH_2)(CHOH)(CH_2)_dCH(NH_2)CO_2H$, $(CH=CH)(CH_2)_dCH(NH_2)CO_2H$, $(C≡C)(CH_2)_dCH(NH_2)CO_2H$; each d is independently an integer in the range 0 to 6.

In another aspect, a compound of Formula VI is provided:

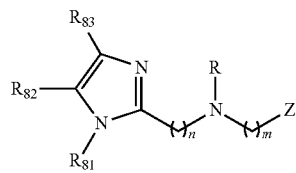

where R is H, alkyl, hydroxyalkyl, alkoxyalkyl, aminoalkyl, thioalkyl, alkenyl, alkynyl, aryl, heteroaryl, aralkyl, heteroaralkyl, acyl, aminoacyl, hydroxyacyl, thioacyl, $(CH_2)_4CH(NH_2)CO_2H$, $(CH_2)_3CH(NH_2)CO_2H$, $(CH_2)_2CH(NH_2)CO_2H$, $C(O)CH_2(CH)NH_2CO_2H$, $C(O)(CH_2)_2(CH)NH_2CO_2H$, $(CC)(CH_2)_2CH(NH_2)CO_2H$, $(CHCH)(CH_2)_2CHNH_2CO_2H$, $(CH_2)_2(CHOH)(CH_2)CHNH_2CO_2H$ or $(CH_2)(CHOH)(CH_2)_2CHNH_2CO_2H$, $(CO_2H)_2$, $—CO_2H$, —(CH$_2$)$_d$—R$_{80}$, or an amino acid radical; R$_{80}$ is independently for each occurrence carboxaldehyde, carboxylate, carboxamido, alkoxycarbonyl, aryloxycarbonyl, ammonium, aryl, heteroaryl, cycloalkyl, cycloalkenyl, heterocyclyl, polycyclyl, amino acid, CH$_2$CH$_2$OCH$_2$CH$_3$, CH$_2$C (OCH$_3$)$_2$, (CH$_2$CH$_2$O)$_d$CH$_2$CH$_3$, (CH$_2$)$_d$NH$_2$, (CH$_2$)$_d$C(O)NH$_2$, (CH$_2$)$_d$N(CH$_3$)$_2$, CH$_2$CH$_2$OH, (CH$_2$)$_d$C(CO$_2$H)$_2$, (CH$_2$)$_d$P(O)(OH)$_2$, (CH$_2$)$_d$B(OH)$_2$, peptide, saccharide, ribonucleic acid, (deoxy)ribonucleic acid, or a ligand for a G-protein-coupled receptor, a oxoreductase, a transferase, a hydrolase, a ligase, a osomerase, a ligase, a GPCR, a direct ligand-gated channel receptor, a cytokine receptor, a integrin receptor, a tyrosine kinase associated receptor, a nuclear receptor, a peptide receptor, a transmembrane receptor, a transcription factor, a cytoskeletal protein, a structural protein, or a signaling protein; d is an integer in the range 0 to 12; m is an integer in the range 0 to 6; n is an integer in the range 0 to 6; and Z is a substituted or unsubstituted thioalkyl, carboxylate, 2-(carboxy)aryl, 2-(carboxy)heteroaryl, 2-(hydroxy)aryl, 2-(hydroxy)heteroaryl, 2-(thiol)aryl, 2-pyrrolidine boronic acid, or 2-(thiol)heteroaryl; R$_{81}$, R$_{82}$, and R$_{83}$ are each independently hydrogen, halogen, alkyl, alkenyl, alkynyl, hydroxyl, alkoxyl, acyl, acyloxy, acylamino, silyloxy, amino, monoalkylamino, dialkylamino, nitro, sulfhydryl, alkylthio, imino, amido, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ether, ester, heteroalkyl, cyano, guanidine, amidine, acetal, ketal, amine oxide, aryl, heteroaryl, aralkyl, arylether, heteroaralkyl, azido, aziridine, carbamoyl, epoxide, hydroxamic acid, imide, oxime, sulfonamide, thioamide, thiocarbamate, urea, thiourea, —(CH$_2$)$_d$—R$_{80}$, (CH$_2$)$_d$ (CO$_2$H)$_2$, CH$_2$CH$_2$OCH$_2$CH$_3$, CH$_2$C(OCH$_3$)$_2$, (CH$_2$CH$_2$O)$_d$ CH$_2$CH$_3$, (CH$_2$)$_d$NH$_2$, (CH$_2$)$_d$C(O)NH$_2$, (CH$_2$)$_d$N(CH$_3$)$_2$, CH$_2$CH$_2$OH, (CH$_2$)$_d$C(CO$_2$H)$_2$, (CH$_2$)$_d$P (O)(OH)$_2$, (CH$_2$)$_d$B(OH)$_2$, —(CH$_2$)$_d$—R$_{80}$, (CH$_2$)$_d$R$_{87}$, or —(CH$_2$)$_d$—R$_{88}$; and R$_{87}$ and R$_{88}$ are each independently 15-Crown-5, 18-Crown-6, tetrazole, oxazole, aziridine, triazole, imidazole, pyrazole, thiazole, hydroxamic acid, phosphonate, phosphinate, thiol, thioether, polysacharride, sacharride, nucleotide or oligonucleotide. In some embodiments, the compound of formula VI is subject to the proviso that at least one of R$_{81}$, R$_{82}$, or R$_{83}$, is a hydrophilic group. In some embodiments, the compound of formula VI is subject to the proviso that R$_{81}$ is a hydrophilic group. In some embodiments, a hydrophilic group is an ether, an alkoxyaralkyl, a carboxylate, an alcohol, or an amide.

In some embodiments, R is H, CH$_3$, (CH$_2$)$_d$CH$_3$, CH$_2$CH$_2$OCH$_2$CH$_3$, (CH$_2$)$_d$C(O)NH$_2$, CH$_2$C(OCH$_3$)$_2$, CH$_2$ (18-Crown-6), CH$_2$(15-Crown-5), C(O)(CH$_2$)$_d$(CH)(NH$_2$) CO$_2$H, (CH$_2$CH$_2$O)$_d$CH$_2$CH$_3$, (CH$_2$)$_d$Ph(SO$_2$NH$_2$), (CH$_2$)$_d$ P(O)OH$_2$, (CH$_2$)$_d$OCH$_2$NH$_2$, (CH$_2$)$_d$NHCH$_2$NH$_2$, (CH$_2$)$_d$ NHCH$_2$CO$_2$H, (CH$_2$)$_d$NH$_2$, (CH$_2$)$_d$N(CH$_3$)$_2$, (CH$_2$)$_d$CO$_2$H, (CH$_2$)$_d$CO$_2$H, (CH$_2$)$_d$CH(CO$_2$H)(NHC(S)NH)Ph (SO$_2$NH$_2$), (CH$_2$)$_d$C(CO$_2$H)$_2$, (CH$_2$)$_d$B(OH)$_3$, (CH$_2$)$_d$(triazole), (CH$_2$)$_d$(thiol), (CH$_2$)$_d$(thioether), (CH$_2$)$_d$(thiazole), (CH$_2$)$_d$(tetrazole), (CH$_2$)$_d$(sacharride), (CH$_2$)$_d$(pyrazole), (CH$_2$)$_d$(polysacharride), (CH$_2$)$_d$(phosphonate), (CH$_2$)$_d$ (phosphinate), (CH$_2$)$_d$(oxazole), (CH$_2$)$_d$(oligonucleotide), (CH$_2$)$_d$(nucleotide), (CH$_2$)$_d$(imidazole), (CH$_2$)$_d$(hydroxamic acid), (CH$_2$)$_d$(CO$_2$H)$_2$, (CH$_2$)$_d$(CHOH)(CH$_2$)$_d$CH(NH$_2$) CO$_2$H, (CH$_2$)$_d$(aziridine), (CH$_2$)$_d$OH, (CH$_2$)$_d$OCH$_2$CO$_2$H, (CH$_2$)$_d$O(CH$_2$)—CH$_3$, (CH$_2$)$_d$NH$_2$, (CH$_2$)$_d$CH(NH$_2$)CO$_2$H, (CH$_2$)(CHOH)(CH$_2$)$_d$CH(NH$_2$)CO$_2$H, (CH=CH)(CH$_2$)$_d$ CH(NH$_2$)CO$_2$H, (C≡C)(CH$_2$)$_d$CH(NH$_2$)CO$_2$H; R$_{81}$, R$_{82}$, and R$_{83}$ are each independently H, F, Cl, Br, I, NO$_2$, CH$_3$, (CH$_2$)$_d$CH$_3$, CH$_2$CH$_2$OCH$_2$CH$_3$, (CH$_2$)$_d$C(O)NH$_2$, CH$_2$C (OCH$_3$)$_2$, CH$_2$(18-Crown-6), CH$_2$(15-Crown-5), C(O) (CH$_2$)$_d$(CH)(NH$_2$)CO$_2$H, (CH$_2$CH$_2$O)$_d$CH$_2$CH$_3$, (CH$_2$)$_d$Ph (SO$_2$NH$_2$), (CH$_2$)$_d$P(O)OH$_2$, (CH$_2$)$_d$OCH$_2$NH$_2$, (CH$_2$)$_d$ NHCH$_2$NH$_2$, (CH$_2$)$_d$NHCH$_2$CO$_2$H, (CH$_2$)$_d$NH$_2$, (CH$_2$)$_d$N (CH$_3$)$_2$, (CH$_2$)$_d$CO$_2$H, (CH$_2$)$_d$CO$_2$H, (CH$_2$)$_d$CH(CO$_2$H) (NHC(S)NH)Ph(SO$_2$NH$_2$), (CH$_2$)$_d$C(CO$_2$H)$_2$, (CH$_2$)$_d$B (OH)$_3$, (CH$_2$)$_d$(triazole), (CH$_2$)$_d$(thiol), (CH$_2$)$_d$(thioether), (CH$_2$)$_d$(thiazole), (CH$_2$)$_d$(tetrazole), (CH$_2$)$_d$(sacharride), (CH$_2$)$_d$(pyrazole), (CH$_2$)$_d$(polysacharride), (CH$_2$)$_d$(phosphonate), (CH$_2$)$_d$(phosphinate), (CH$_2$)$_d$(oxazole), (CH$_2$)$_d$ (oligonucleotide), (CH$_2$)$_d$(nucleotide), (CH$_2$)$_d$(imidazole), (CH$_2$)$_d$(hydroxamic acid), (CH$_2$)$_d$(CO$_2$H)$_2$, (CH$_2$)$_d$(CHOH) (CH$_2$)$_d$CH(NH$_2$)CO$_2$H, (CH$_2$)$_d$(aziridine), (CH$_2$)$_d$OH, (CH$_2$)$_d$OCH$_2$CO$_2$H, (CH$_2$)$_d$O(CH$_2$)—CH$_3$, (CH$_2$)$_d$NH$_2$, (CH$_2$)$_d$CH(NH$_2$)CO$_2$H, (CH$_2$)(CHOH)(CH$_2$)$_d$CH(NH$_2$) CO$_2$H, (CH=CH)(CH$_2$)$_d$CH(NH$_2$)CO$_2$H, (C≡C)(CH$_2$)$_d$ CH(NH$_2$)CO$_2$H; and each d is independently an integer in the range 0 to 6.

In some embodiments, the compound of Formula V has a general structure according to any one of the following:

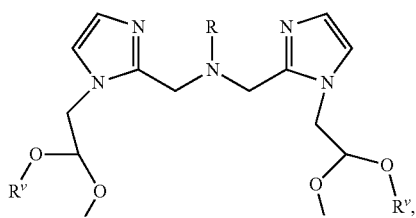

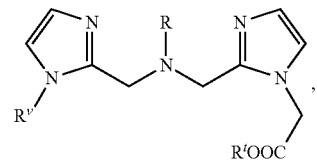

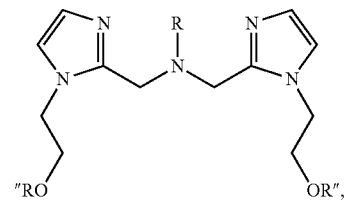

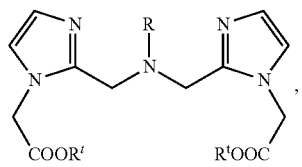

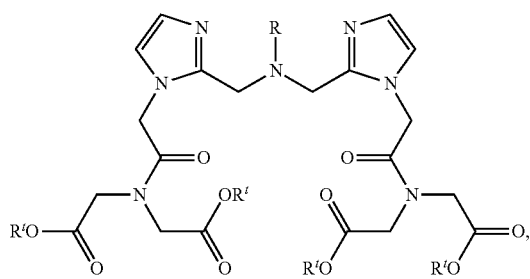

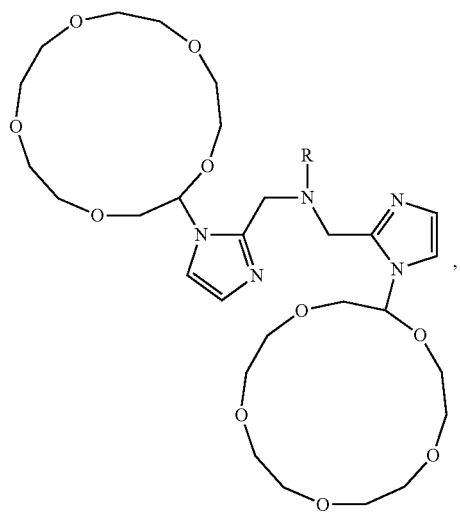

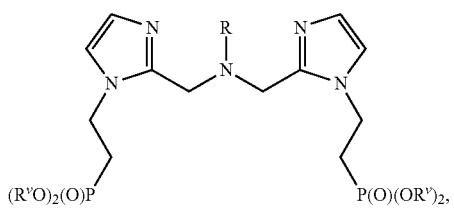

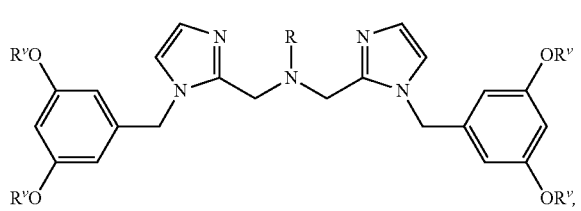

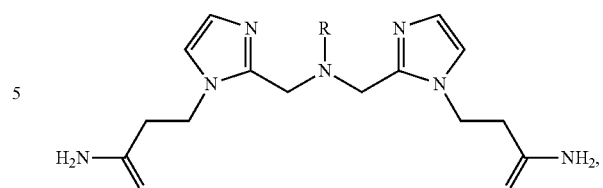

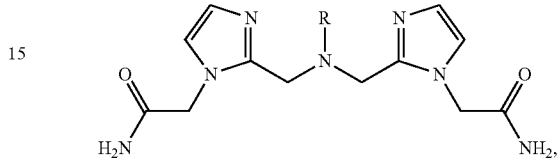

or

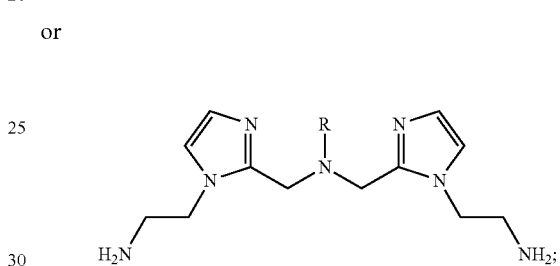

where, $R^t$ is H, a $C_1$-$C_8$ alkyl group, an ammonium ion, or an alkali or alkaline earth metal ion; and $R^v$ is alkyl. According to some embodiments, $R^v$ is methyl, ethyl, n-propyl, iso-propyl, n-butyl, iso-butyl, or tert-butyl. In other embodiments, $R^v$ is methyl. In some embodiments, each $R^t$ is independently H or tert-butyl. In yet other embodiments, $R^t$ is H. In some embodiments, R is hydroxyalkyl, alkoxyalkyl, aminoalkyl, thioalkyl, aralkyl, heteroaralkyl, hydroxyacyl, $CH_2)_d R_{80}$, or an amino acid radical; $R_{80}$ is independently for each occurrence carboxylate, carboxamido, alkoxycarbonyl, aryloxycarbonyl, amino, amino acid, peptide, saccharide, ribonucleic acid, (deoxy)ribonucleic acid, or a ligand for a G-protein-coupled receptor, or ligands for a oxoreductase, a transferase, a hydrolase, a ligase, a osomerase, a ligase, a direct ligand-gated channel receptor, a cytokine receptor, a integrin receptor, a tyrosine kinase associated receptor, a nuclear receptor, a peptide receptor, a transmembrane receptor, a transcription factor, a cytoskeletal protein, a structural protein, or a signaling protein; d is an integer in the range 0 to 12; m is an integer in the range 0 to 6; n is an integer in the range 0 to 6.

In some embodiments, the compound of Formula VI has a general structure according to any one of the following:

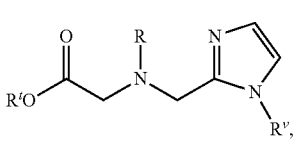

or

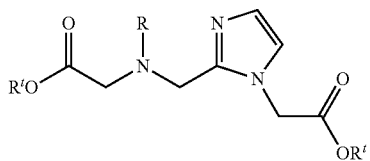

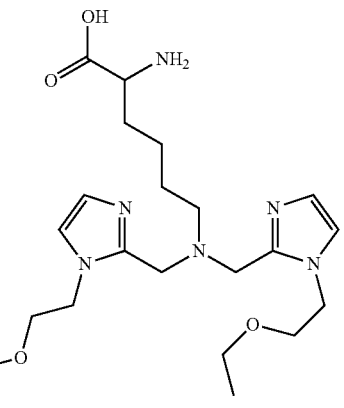

where, $R^t$ is H, a $C_1$-$C_8$ alkyl group, an ammonium ion, or an alkali or alkaline earth metal ion; and $R^v$ is H or alkyl. According to some embodiments, $R^v$ is H, methyl, ethyl, n-propyl, iso-propyl, n-butyl, iso-butyl, or tert-butyl. In other embodiments, $R^v$ is methyl. In other embodiments, $R^v$ is H. In some embodiments, each $R^t$ is independently H or tert-butyl. In yet other embodiments, $R^t$ is H. In some embodiments, R is hydroxyalkyl, alkoxyalkyl, aminoalkyl, thioalkyl, aralkyl, heteroaralkyl, hydroxyacyl, $(CH_2)_d$—$R_{80}$, or an amino acid radical; $R_{80}$ is independently for each occurrence carboxylate, carboxamido, alkoxycarbonyl, aryloxycarbonyl, amino, amino acid, peptide, saccharide, ribonucleic acid, (deoxy)ribonucleic acid, or a ligand for a G-protein-coupled receptor, or ligands for a oxoreductase, a transferase, a hydrolase, a ligase, a osomerase, a ligase, a direct ligand-gated channel receptor, a cytokine receptor, a integrin receptor, a tyrosine kinase associated receptor, a nuclear receptor, a peptide receptor, a transmembrane receptor, a transcription factor, a cytoskeletal protein, a structural protein, or a signaling protein; d is an integer in the range 0 to 12; m is an integer in the range 0 to 6; n is an integer in the range 0 to 6.

In some embodiments, the compound of Formula V or VI is complexed with a radionuclide. In some embodiments, the compound of Formula V or VI is complexed a radionuclide, where the radionuclide is technetium or rhenium.

In some embodiments, in the compound of Formula V or VI, m is 1. In some embodiments, in the compound of Formula V or VI, n is 1. In some embodiments, in the compound of Formula V or VI, m is 1; and n is 1.

In some embodiments, in the compound of Formula V or VI at least one of $R_{81}$, $R_{82}$, or $R_{83}$ is an ether, an alkoxyaralkyl, a carboxylate, an alcohol, or an amide. In some embodiments, in the compound of Formula V, at least one of $R_{84}$, $R_{85}$, or $R_{86}$ is an ether, an alkoxyaralkyl, a carboxylate, an alcohol, or an amide. In some embodiments, in the compound of Formula V, at least one of $R_{81}$, $R_{82}$, or $R_{83}$ and at least one of $R_{84}$, $R_{85}$, or $R_{86}$ is an ether, an alkoxyaralkyl, a carboxylate, an alcohol, or an amide. In some embodiments, in the compound of Formula V or VI, $R_{81}$ is an ether, an alkoxyaralkyl, a carboxylate, an alcohol, or an amide. In some embodiments, in the compound of Formula V $R_{84}$ is an ether, an alkoxyaralkyl, a carboxylate, an alcohol, or an amide. In some embodiments, $R_{81}$ and/or $R_{84}$ are individually a 2-ethoxyethyl group, a 2-(ethoxymethoxymethoxy)ethyl group, a 2,2-dimethoxyethyl group, a dimethoxyphenylmethyl group, a 2-hydroxyethanol group, 3-propanoic acid group, a 3-propoxyamide group, or a 15-crown-5-ether group. Exemplary compounds of base formula V having a lysine residue are shown below:

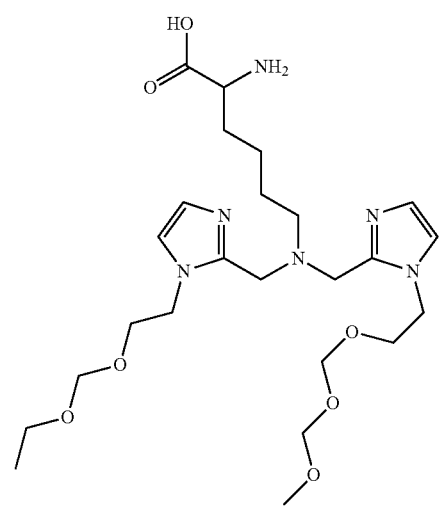 [SMILES: CCOCOCCn1ccnc1CN(CCCCC(N)C(=O)O)Cc1nccn1CCOCOCOC]

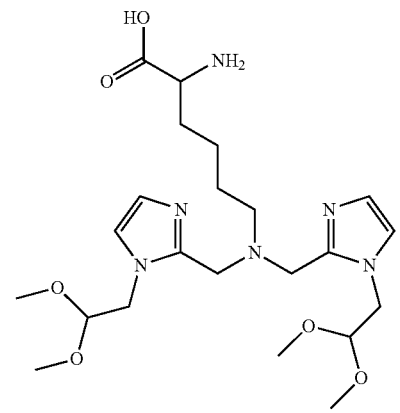 [SMILES: COC(Cn1ccnc1CN(CCCCC(N)C(=O)O)Cc1nccn1CC(OC)OC)OC]

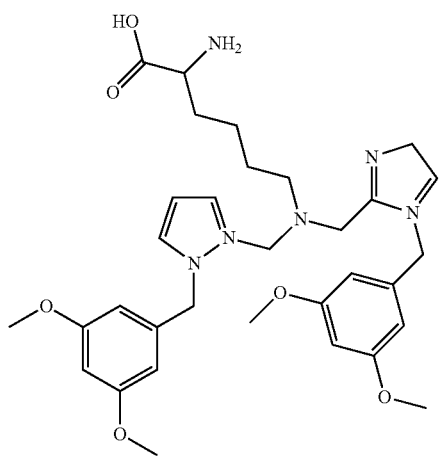

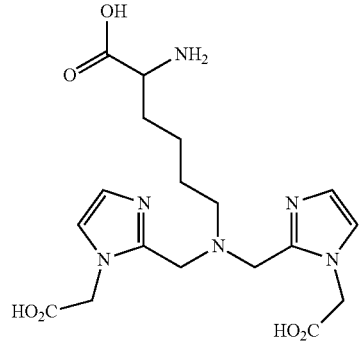

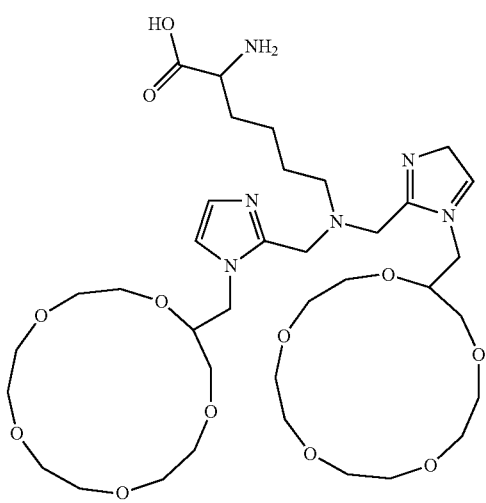

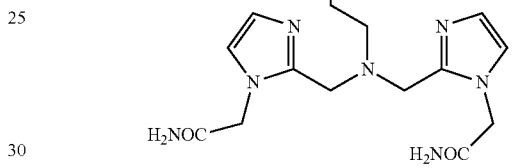

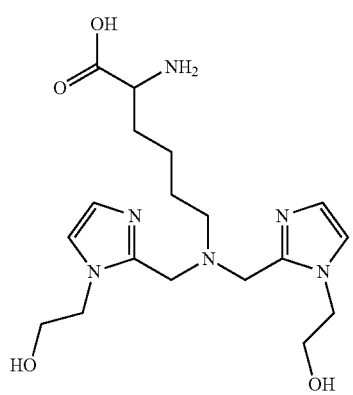 [SMILES: NC(CCCCN(Cc1nccn1CCO)Cc1nccn1CCO)C(=O)O]

In some embodiments, in the compound of Formula V or VI, R is $-(CH_2)_d-R_{80}$. In some embodiments, in the compound of Formula V or VI, m is 1; n is 1; and R is $-(CH_2)_d-R_{80}$. In some embodiments, in the compound of Formula V or VI, R is an amino acid radical. In some embodiments, the amino acid radical is $-CH_2CH_2CH_2CH_2CH(NH_2)CO_2H$, $-CH(CO_2H)CH_2CH_2CH_2CH_2NH_2$, $-CH_2CH_2CO_2H$, $-CH_2CH_2CH_2CO_2H$, $-CH_2(CH_2)_xCO_2H$, $-CH_2(CH_2)_xCH(NH_2)CO_2H$, or $-CH(CO_2H)(CH_2)_xCH(NH_2)CO_2H$, where x is an integer from 3 to 9.

In some embodiments, in the compound of Formula VI, Z is carboxylate. In some embodiments, in the compound of Formula VI, Z is carboxylate; m is 1; and n is 1.

In another aspect, a formulation is provided including a compound of Formula V or VI, and a pharmaceutically acceptable excipient.

In another aspect, a method of imaging tissue in a mammal is provided including administering to the mammal an imaging agent comprising a radionuclide chelated with a compound comprising a substituted or unsubstituted di(imidazolylalkyl)amine, having at least one hydrophilic substituent; and detecting the spatial distribution of the imaging agent in the mammal.

In another aspect, a method of imaging a region in a patient includes the step of administering to a patient a diagnostically effective amount of a compound of Formula V or VI. In some embodiments, the method further includes the step of obtaining an image of said region of said patient.

In another aspect, a method of preparing a peptide conjugate incorporating a compound of Formula V or VI includes the step of synthesizing a peptide conjugate using solid-phase peptide-synthesis techniques.

In another aspect, a compound of Formula VII, is provided, which incorporates a chelator based upon 1,4,7,10-tetraazacyclododecane-1,4,7,10-tetraacetic acid (DOTA).

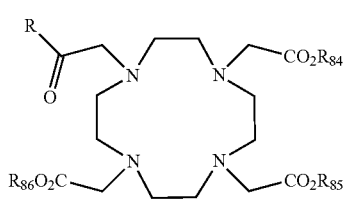

VII

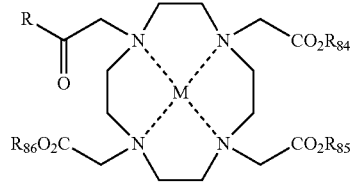

VII-M

In the compound of represented by VII, R is alkoxyalkyl, aminoalkyl, thioalkyl, alkenyl, alkynyl, aryl, heteroaryl, aralkyl, heteroaralkyl, acyl, aminoacyl, hydroxyacyl, thioacyl, $(CH_2)_4CH(NH_2)CO_2H$, $(CH_2)_3CH(NH_2)CO_2H$, $(CH_2)_2CH(NH_2)CO_2H$, $C(O)CH_2(CH)NH_2CO_2H$, $C(O)(CH_2)_2(CH)NH_2CO_2H$, $(CC)(CH_2)_2CH(NH_2)CO_2H$, $(CHCH)(CH_2)_2CHNH_2CO_2H$, $(CH_2)_2(CHOH)(CH_2)CHNH_2CO_2H$ or $(CH_2)(CHOH)(CH_2)_2CHNH_2CO_2H$, $(CO_2H)_2$, $—CO_2H$, $—(CH_2)_d—R_{80}$, or an amino acid radical; $R_{80}$ is independently for each occurrence carboxaldehyde, carboxylate, carboxamido, alkoxycarbonyl, aryloxycarbonyl, ammonium, aryl, heteroaryl, cycloalkyl, cycloalkenyl, heterocyclyl, polycyclyl, amino acid, $CH_2CH_2OCH_2CH_3$, $CH_2C(OCH_3)_2$, $(CH_2CH_2O)_dCH_2CH_3$, $(CH_2)_dNH_2$, $(CH_2)_dC(O)NH_2$, $(CH_2)_dN(CH_3)_2$, $CH_2CH_2OH$, $(CH_2)_dC(CO_2H)_2$, $(CH_2)_dP(O)(OH)_2$, $(CH_2)_dB(OH)_2$, peptide, saccharide, ribonucleic acid, (deoxy)ribonucleic acid, or a ligand for a G-protein-coupled receptor, a oxoreductase, a transferase, a hydrolase, a ligase, a osomerase, a ligase, a GPCR, a direct ligand-gated channel receptor, a cytokine receptor, a integrin receptor, a tyrosine kinase associated receptor, a nuclear receptor, a peptide receptor, a transmembrane receptor, a transcription factor, a cytoskeletal protein, a structural protein, or a signaling protein; d is an integer in the range 0 to 12; and $R_{84}$, $R_{85}$, and $R_{86}$ are independently H or alkyl.

In some embodiments, R is $CH_2CH_2OCH_2CH_3$, $(CH_2)_dC(O)NH_2$, $CH_2C(OCH_3)_2$, $CH_2(18-Crown-6)$, $CH_2(15-Crown-5)$, $C(O)(CH_2)_d(CH)(NH_2)CO_2H$, $(CH_2CH_2O)_dCH_2CH_3$, $(CH_2)_dPh(SO_2NH_2)$, $(CH_2)_dP(O)OH_2$, $(CH_2)_dOCH_2NH_2$, $(CH_2)_dNHCH_2NH_2$, $(CH_2)_dNHCH_2CO_2H$, $(CH_2)_dNH_2$, $(CH_2)_dN(CH_3)_2$, $(CH_2)_dCO_2H$, $(CH_2)_dCO_2H$, $(CH_2)_dCH(CO_2H)(NHC(S)NH)Ph(SO_2NH_2)$, $(CH_2)_dC(CO_2H)_2$, $(CH_2)_dB(OH)_3$, $(CH_2)_d(triazole)$, $(CH_2)_d(thiol)$, $(CH_2)_d(thioether)$, $(CH_2)_d(thiazole)$, $(CH_2)_d(tetrazole)$, $(CH_2)_d(sacharride)$, $(CH_2)_d(pyrazole)$, $(CH_2)_d(polysacharride)$, $(CH_2)_d(phosphonate)$, $(CH_2)_d(phosphinate)$, $(CH_2)_d(oxazole)$, $(CH_2)_d(oligonucleotide)$, $(CH_2)_d(nucleotide)$, $(CH_2)_d(imidazole)$, $(CH_2)_d(hydroxamic acid)$, $(CH_2)_d(CO_2H)_2$, $(CH_2)_d(CHOH)(CH_2)_dCH(NH_2)CO_2H$, $(CH_2)_d(aziridine)$, $(CH_2)_dOH$, $(CH_2)_dOCH_2CO_2H$, $(CH_2)_dO(CH_2)—CH_3$, $(CH_2)_dNH_2$, $(CH_2)_dCH(NH_2)CO_2H$, $(CH_2)(CHOH)(CH_2)_dCH(NH_2)CO_2H$, and $(CH=CH)(CH_2)_dCH(NH_2)CO_2H$, $(C≡C)(CH_2)_dCH(NH_2)CO_2H$. In some embodiments, $R_{84}$, $R_{85}$, and $R_{86}$ are H.

In some embodiments, such DOTA-based chelators may be used for the cheation of a metal including, but not limited to, yttrium, lutetium, gallium, and indium. Such metal-chelated compounds may have the general formula VII-M, where M is Y, Lu, Ga, or In:

In another aspect, a formulation is provided including a compound of Formula VII or VII-M, and a pharmaceutically acceptable excipient.

In another aspect, a method of imaging a region in a patient includes the step of administering to a patient a diagnostically effective amount of a compound of Formula VII or VII-M. In some embodiments, the method further includes the step of obtaining an image of said region of said patient.

In another aspect, a method of preparing a peptide conjugate incorporating a compound of Formula VII or VII-M includes the step of synthesizing a peptide conjugate using solid-phase peptide-synthesis techniques.

The ligands/chelators described above, may be incorporated into radionuclide complexes used as radiographic imaging agents. Further, these ligands or complexes can be covalently or non-covalently attached to biologically active carrier molecules, such as, antibodies, enzymes, peptides peptidomimetics, hormones, and the like. The complexes prepared by reacting one of the aforementioned ligands with a radionuclide containing solution under radionuclide complex forming reaction conditions. In particular, if a technetium agent is desired, the reaction is carried out with a pertechnetate solution under technetium-99m complex forming reaction conditions. The solvent may then be removed by any appropriate means, such as evaporation. The complexes are then prepared for administration to the patient by dissolution or suspension in a pharmaceutically acceptable vehicle.

In another aspect, imaging agents are provided containing a radionuclide complex as described above, in an amount sufficient for imaging, together with a pharmaceutically acceptable radiological vehicle. The radiological vehicle should be suitable for injection or aspiration, such as human serum albumin; aqueous buffer solutions, e.g., tris(hydromethyl) aminomethane (and its salts), phosphate, citrate, bicarbonate, etc.; sterile water; physiological saline; and balanced ionic solutions containing chloride and or dicarbonate salts or normal blood plasma cations such as calcium, potassium, sodium, and magnesium.

The concentration of the imaging agent in the radiological vehicle should be sufficient to provide satisfactory imaging. For example, when using an aqueous solution, the dosage is about 1.0 to 50 millicuries. The imaging agent should be administered so as to remain in the patient for about 1 to 3 hours, although both longer and shorter time periods are acceptable. Therefore, convenient ampoules containing 1 to 10 mL of aqueous solution may be prepared.

Imaging may be carried out in the normal manner, for example by injecting a sufficient amount of the imaging composition to provide adequate imaging and then scanning with a suitable machine, such as a gamma camera. In certain embodiments, a method of imaging a region in a patient includes the steps of: administering to a patient a diagnostically effective amount of a compound complexed with a radionuclide; exposing a region of said patient to radiation;

and obtaining an image of said region of said patient. In certain embodiments of the method of imaging a region in a patient, said region of said patient is the head or thorax.

In another aspect, a method of improving the renal clearance of a radiopharmaceutical compound from a patient includes administering a complex of Formula I, II, III, IV, VI, or VII to a subject. In some embodiments, the compound is of Formula V or VI. In other embodiments, R is a hydrophilic group. In some embodiments, the compound has the following formula:

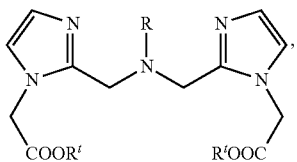

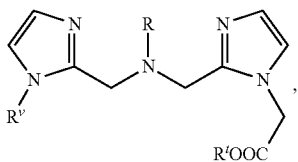

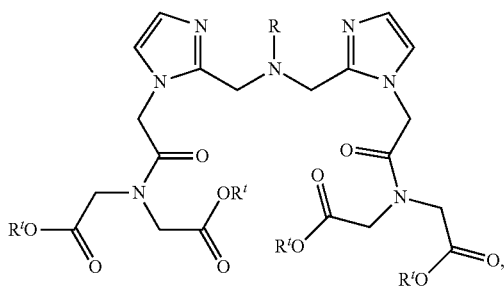

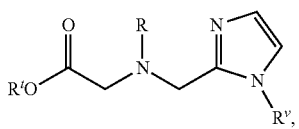

or

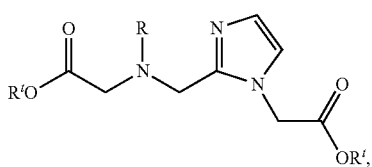

In another aspect, a compound of formula Y-Target is provided, where Y is derived from the compounds represented by formulas I, II, III, IV, V, VI and VII, the Target is a drug target of interest including but not limited to the following: oxoreductases exemplified but not limited to cyclooxygenases, aromatases, dihydrofolate reductase, xanthine oxidase, and 5-alphatestosterone reductase; transferases exemplified but not limited to protein kinase C, DNA and RNA polymerases, and tyrosine kinases; hydrolases exemplified but not limited to aspartyl proteases, serine proteases (e.g. plasminogen, thrombin), metalloproteases (e.g. ACE, Seprase, PSMA, DPPIV), cysteine proteases (caspase), gelatinase (MMP-9), lipases, phosphatases, phosphorylases, and GTPases; lyases exemplified but not limited to carbonic anhydrase especially CA-IX, and guanylyl clyclase; osomerases exemplified but not limited to DNA gyrases, and topoisomerases; ligases also known as synthases exemplified but not limited to thymidylate synthase and mTOR; GPCRs exemplified but not limited to peptide receptors exemplified by somatostatin receptor and GRP/bombesin receptor, angiotensin receptors, cannabinoid receptors, adenosine receptors, GLP-1 receptors, opioid receptors, adrenoceptors, prostanoid receptors, serotonin receptors, dopamine receptors, and vasopressin receptors; direct ligand-gated channel receptors exemplified but not limited to GABA receptors and glutamate receptors; cytokine receptors exemplified but not limited to TNF-alpha receptor; integrin receptors exemplified but not limited to VLA-4, glycoprotein IIb/IIIa, $\alpha v \beta 3$ and $\alpha v \beta 6$; tyrosine Kinase associated receptors exemplified but not limited to insulin receptor; nuclear receptors (steroid hormone receptors) exemplified but not limited to progesterone receptors, estrogen receptors, and androgen receptors; peptide receptors exemplified but not limited to somatostatin receptors, GRP/bombesin receptors, adhesion proteins; transmembrane receptors such as Notch; transcription factors; cytoskeletal proteins; structural proteins; and signaling proteins.

In another aspect, compounds of formula Y-Target, are provided. In some embodiments, the Target is a somatostatin, such that Y-Target is a compound of formula Y-Somatostatin. In such embodiments, Y is derived from the compounds represented by formulas I, II, III, IV, V, VI and VII. In some embodiments, the Somatostatin is octreotide or 3-tyr-octreotide. In some embodiments, R in each of the derived formulas of I, II, III, IV, V, VI and VII is derived from —CH$_2$CH$_2$CH$_2$CH$_2$CH(NH$_2$)CO$_2$H. As one example, the derivatized Tyr-3-octreotide (Edotreotide) may have the formula DpK-Edotreotide:

DpK-Edotreotide

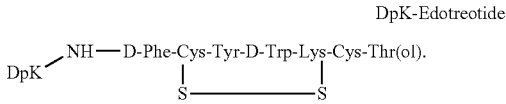

In this example, DpK is an abbreviation for [ε-{N,N-di(pyridyl-2-methyl)}α-lysine], however other SAAC derivatives, such as di(pyridinemethyl)amine (DPMA), and di(imidazolylmethyl)amine (DIMA) derivatives. Additional SAAC derivatives of somatostatins such as edotreotide and octreotide, include those of DOTA,

33

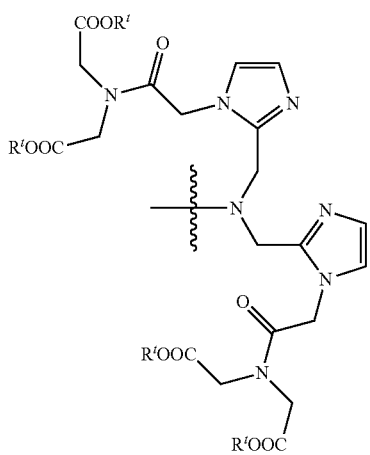

and

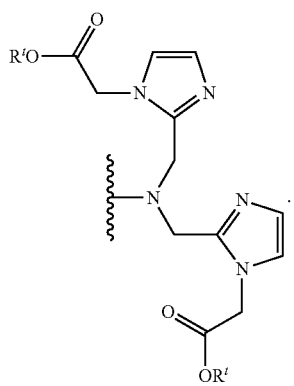

Such compounds may have the general structure SAAC-Edotreotide:

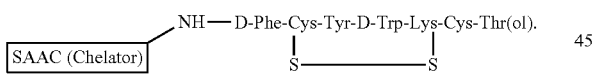

In some embodiments, a chelated-Tc-99m labeled pharmaceutical, or bio-molecule, is provided in which the biological behavior of the pharmaceutical, or bio-molecule, is not altered. In these labeling approaches, the chelated radionuclide is bound to the bio-molecule via a pendant chain distant to the receptor-binding site. Advantages of this design include the ability to change the length and location of the pendant chain, as well as the ability to vary chelating moieties.

In some aspects, the compounds are configured to provide for renal clearance from a patient. According to some embodiments, compounds where are reduced in lipophilicity are provided. In some embodiments, the reduction in lipophilicity is accomplished via the incorporation of various ethers, amines, acids and other water soluble functionalities, into the ring systems of SAAC ligands. By the incorporation of water soluble functionality, the pharmacokinetic properties of the SAAC ligands, and the biological relevant molecules to which SAAC ligands are attached, may be realized.

34

In some embodiments of the compound of formula Y-Somatostatin, the compound has the following formula:

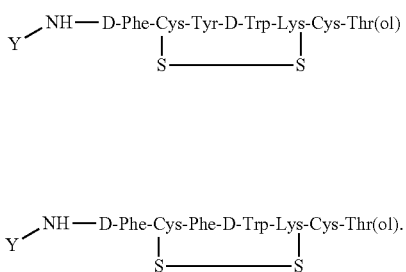

or

In such embodiments, Y is:

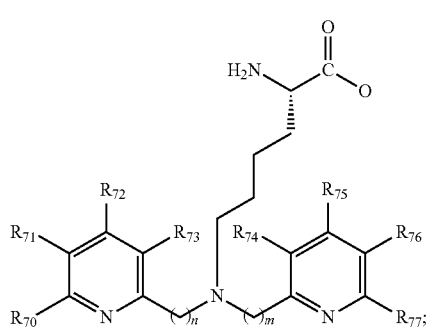

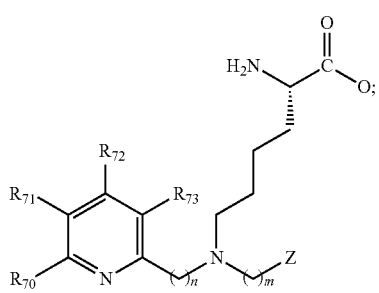

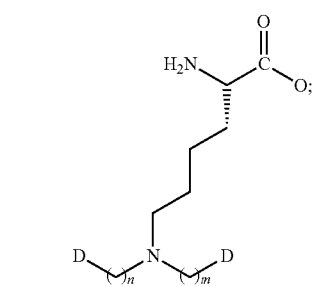

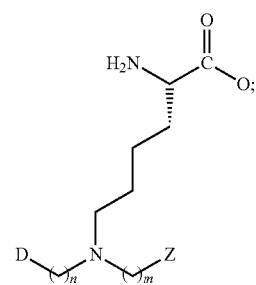

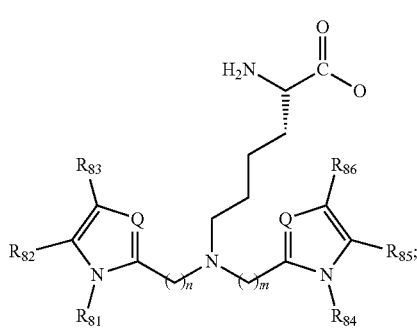

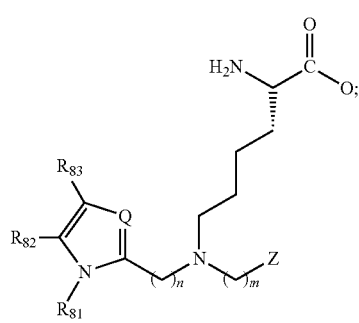

or

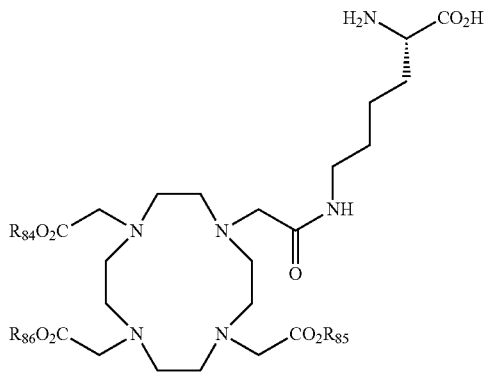

Those of skill in the art will realize that the attachment of the above complexes through the carboxylic group is but one means of attachment, as the lysine or other amino acid residue has, or may have, an amino functionality that may be accessed for attachment. Analogously to those complexes shown above that attach to the somatostatin through the carboxylic group, other attachments to a peptide or somatostatin may be achieved through the amino group.

In another aspect, a formulation of the compound Y-Somatostatin is provided including a pharmaceutically acceptable excipient.

In another aspect, a method of imaging a region in a patient is provided including the steps of: administering to a patient a diagnostically effective amount of a compound of formula Y-Somatostatin, and obtaining an image of said region of said patient.

In one non-limiting example of preparing compounds of formula I or II, the synthesis may be initiated through the preparation of a pyridyl aldehyde, as shown in Scheme 1:

Scheme 1: Reactants/Conditions: (i) Reaction with Dimethylamine at 110° C.; (ii) Manganese Dioxide

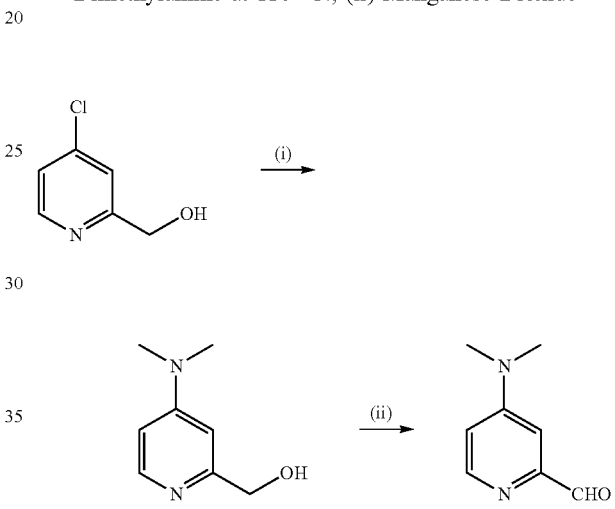

As shown by Scheme 2, the product of Scheme 1 may then be further functionalized to form a SAAC ligand.

Scheme 2: Synthesis of a DPMA analog from two equivalents of 4-dimethylaminopyridine-2-carboxaldehyde via reductive alkylation of a protected lysine residue

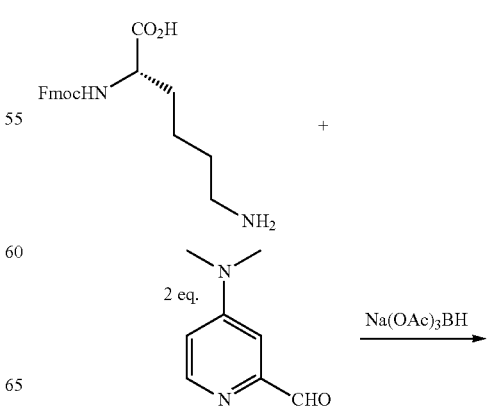

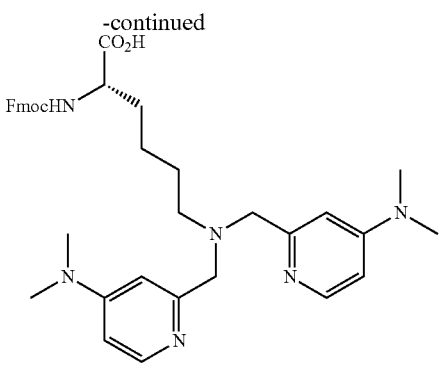

Other DPMA analogs may synthesized according to various embodiments. For example, halogenated pyridyl analogs may also be prepared. For example, 4-bromo-3-chloro-1-hydroxymethanolpyridine, 4-fluoro-3-chloro-1-hydroxymethanolpyridine, 3,4-dichloro-1-hydroxymethanolpyridine, and 3-chloro-2-fluoro-1-hydroxymethanolpyridine may be used as starting materials for the aldehyde preparation exemplified in Scheme 1. Scheme 3 illustrates an alternative route to DPMA analogs via a Buchwald-Hartwig amination.

Scheme 3. Reactants/Conditions: (iii) Pd(0), $NH(R_{90})_2$

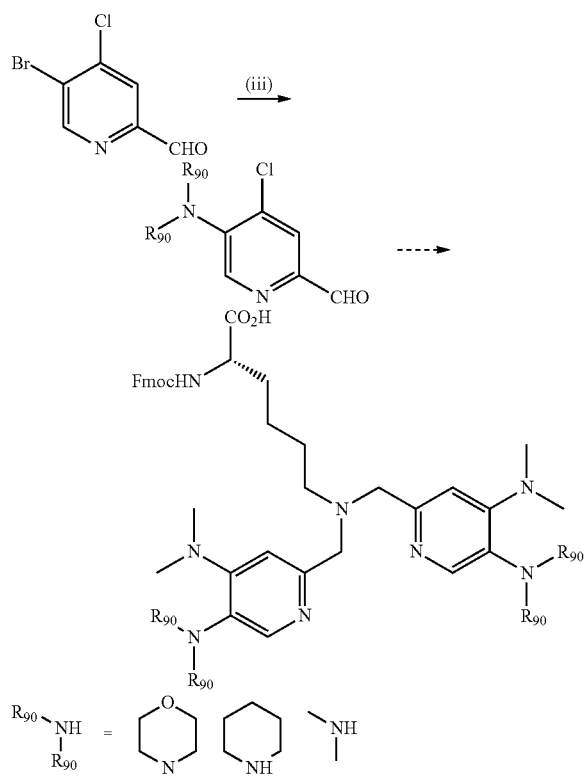

As is known to those of skill in the art, the pyridine groups illustrated in Schemes 1, 2, and 3, are more electron rich than an unsubstituted pyridine group due to the amino group substitutions. Polarity of the pyridyl group resulting from such substitution also increases the aqueous solubility of the compounds. The compounds also exhibit increased metal chelation.

The ability of the nitrogen atoms to complex technetium may be related to the pKa of the donor nitrogen involved in the complexation. Heterocycles with ring systems that are more electron rich than unsubstituted 2-pyridine ring systems would likely have a larger pKa and therefore they will be weaker acids and consequently stronger bases (Scheme 4). The additional donating capabilities should improve $^{99m}$Tc and/or Re binding, resulting in higher specific activity compounds with the same robust stability.

Scheme 4: Effect of Additional Ring Nitrogens and Nitrogen Substitution on the pKa of the Pyridine Ring System

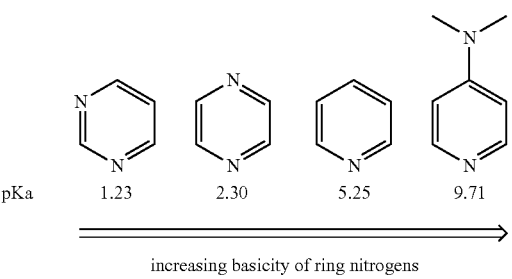

increasing basicity of ring nitrogens

Analogously to those compounds illustrated in Schemes 2 and 3, where dipyridyl compounds represented by I are incorporated into the DPMA analogs, so too may the compounds represented by II. Such corresponding compounds, where R is lysinyl, may be represented by VIII:

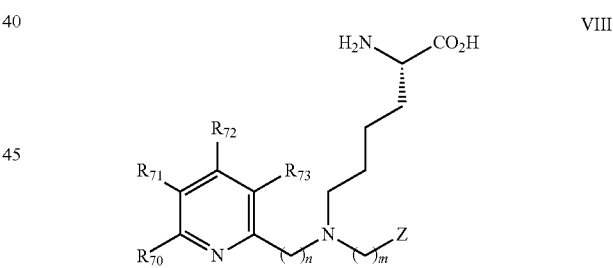

where $R_{70}$, $R_{71}$, $R_{72}$, $R_{73}$, m, n, and Z are as defined above and where the $NH_2$ group may be as shown or may be protected. In some embodiments, Z is a carboxylic acid group. Due to the smaller steric profile of the Z group, as compared to the pyridyl group, such SAAC ligands are smaller and less hindered at the metal center.

Alternative synthetic schemes for the compounds of Formulas II, IV, or VI, may also be used. For example, where R is lysine, such compounds may be prepared by a double reductive alkylation sequence on a protected lysine. Addition of a first aldehyde, followed by reduction may afford a compound of Formula II, IV, or VI to form a compound of Formula IX. Subsequent treatment of IX with an oxalate followed by deprotection results in the compounds of formula II, IV, or VI, where R is a lysine group. This is illustrated in Scheme 5, below:

Scheme 5: X' Represents an Imidazolyl or Pyridyl Group as Indicated in the Compounds Represented by II, IV, or VI

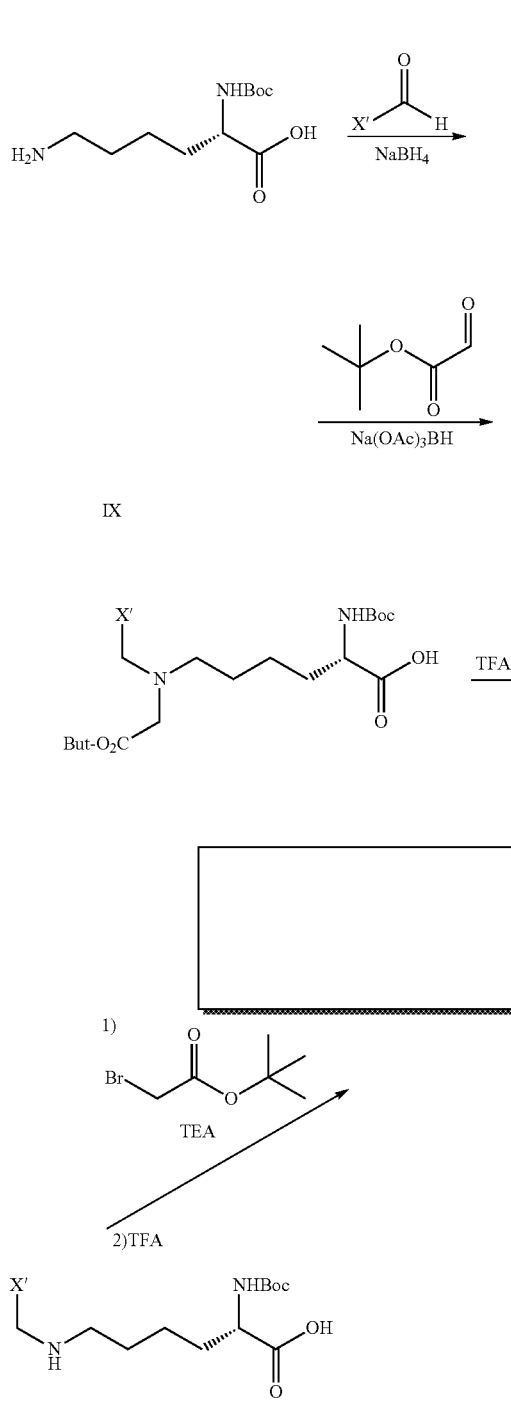

Scheme 6: Preparation of LIMES Compounds

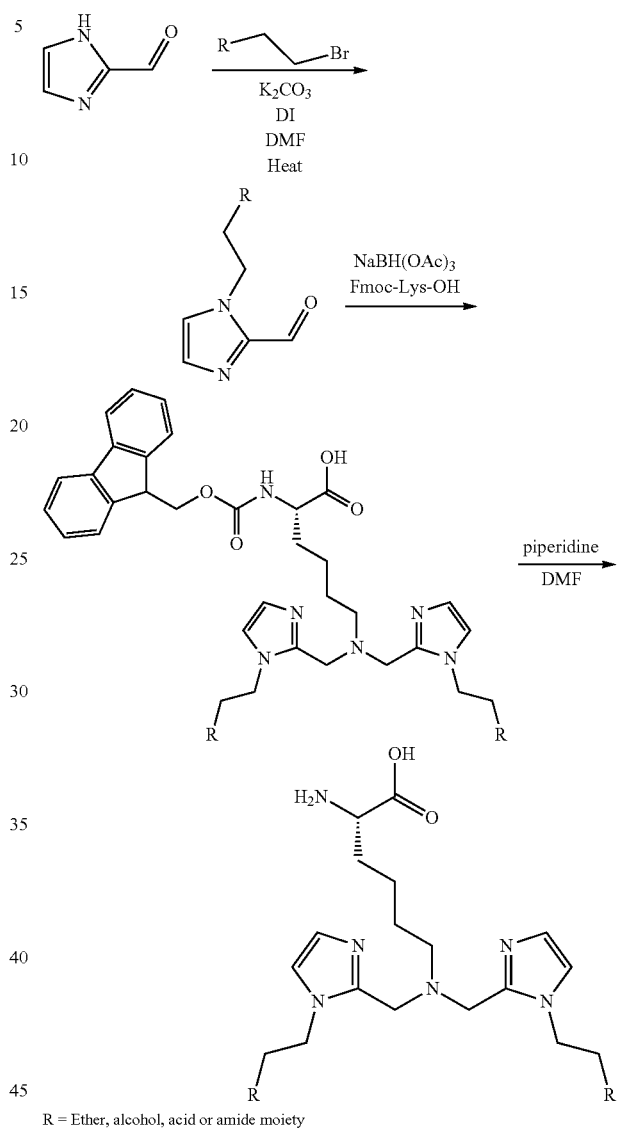

R = Ether, alcohol, acid or amide moiety

In one embodiment, imidazole ethers are derivatized to form lysine imidazole ethers (LIMES). One exemplary synthetic scheme is set forth in Scheme 6. The LIMES compounds described above and as represented as an embodiment of the compounds represented by V and VI, may be prepared along with the specific compounds illustrated as exemplary of V, where $R_{81}$ and $R_{84}$ are groups in which an ethylenic group links an alcohol, ether, acid, or amide group to the imidazolyl rings.

In another aspect, a compound is provided having a substituted or unsubstituted di(imidazolylalkyl)amine having at least one hydrophilic substituent, or a pharmaceutically acceptable salt thereof, and a physiologically acceptable carrier.

In another aspect, pharmaceutically acceptable compositions are provided which include a therapeutically-effective amount of one or more of the compounds described above, formulated together with one or more pharmaceutically acceptable carriers (additives) and/or diluents. As described in detail below, the pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

Formulations of the compounds may be based in part on liposomes. Liposomes consist of a phospholipid bilayer which forms a shell around an aqueous core. Methods for preparing liposomes for administration to a patient are known to those skilled in the art; for example, U.S. Pat. No. 4,798,734 describes methods for encapsulation of biological materials in liposomes. The biological material is dissolved in a aqueous solution, and the appropriate phospholipids and lipids are added, along with surfactants if required. The material is then dialyzed or sonicated, as necessary. A review of known methods is presented by G. Gregoriadis, Chapter 14 ("Liposomes"), in Drug Carriers in Biology and Medicine, pp. 287-341 (Academic Press, 1979).

Formulations of the compounds may be based in part on polymeric microparticles. Microspheres formed of polymers or proteins are also well known to those skilled in the art, and can be tailored for passage through the gastrointestinal tract, as described in U.S. Pat. Nos. 4,906,474, 4,925,673, and 3,625,214, for example. There are a number of well-known methods, including solvent evaporation and coacervation/phase separation, for preparing microspheres. Bioerodible microspheres can be prepared using any of the methods developed for making microspheres for drug delivery, as described, for example, by Mathiowitz et al., J. Appl. Polymer Sci. 35, 755-774 (1988), and P. Deasy, in Microencapsulation and Related Drug Processes, pp. 61-193, (Dekker, 1984), the teachings of which are incorporated herein. The selection of a method depends on the drug properties and choice of polymer, as well as the size, external morphology, and degree of crystallinity desired, as discussed, for example, by Benita et al., J. Pharm. Sci. 73, 1721-1724 (1984), Jalil and Nixon, J. Microencapsulation, 7, 297-325 (1990), and Mathiowitz et al., Scanning Microscopy 4, 329-340 (1990), the teachings of which are incorporated herein.

In solvent evaporation, described, for example, in Mathiowitz et al., (1990), Benita, and U.S. Pat. No. 4,272,398 to Jaffe, the polymer is dissolved in a volatile organic solvent. The drug, either in soluble or particulate form, is added to the polymer solution and the mixture is suspended in an aqueous phase containing a surface active agent such as poly(vinyl alcohol). The resulting emulsion is stirred until most of the organic solvent evaporates, leaving solid microspheres. Microspheres of various sizes (1-1000 microns) and morphologies may be obtained by this method, which is useful for non-labile polymers.

Coacervation/phase separation techniques have been used to encapsulate both solid and liquid core materials with various polymer coatings. U.S. Pat. Nos. 2,730,456, 2,730, 457, and 2,800,457 to Green and Schleichter, describe gelatin and gelatin-acacia (gum arabic) coating systems, for example. Simple coacervation employs a single colloid (e.g. gelatin in water) and involves the removal of the associated water from around the dispersed colloid by agents with a higher affinity for water, such as alcohols and salts. Complex coacervation employs more than one colloid, and the separation proceeds mainly by charge neutralization of the colloids carrying opposite charges rather than by dehydration. Coacervation may also be induced using non-aqueous vehicles, as described in Nakano et al., Int. J. Pharm, 4, 29-298 (1980), for example.

Hydrogel microspheres made of gel-type polymers such as alginate or polyphosphazenes or other dicarboxylic polymers can be prepared by dissolving the polymer in an aqueous solution, suspending the material to be incorporated into the mixture, and extruding the polymer mixture through a microdroplet forming device, equipped with a nitrogen gas jet. The resulting microspheres fall into a slowly stirring, ionic hardening bath, as illustrated, for example, by Salib, et al., Pharmazeutische Industrie 40-11A, 1230 (1978), the teachings of which are incorporated herein. The advantage of this system is the ability to further modify the surface of the microspheres by coating them with polycationic polymers (such as polylysine) after fabrication, as described, for example, by Lim et al, J. Pharm Sci. 70, 351-354 (1981). The microsphere particle size depends upon the extruder size as well as the polymer and gas flow rates.

Examples of polymers that can be used include polyamides, polycarbonates, polyalkylenes and derivatives thereof including, polyalkylene glycols, polyalkylene oxides, polyalkylene terepthalates, polymers of acrylic and methacrylic esters, including poly(methyl methacrylate), poly(ethyl methacrylate), poly(butylmethacrylate), poly (isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly (ethylene oxide), and poly(ethylene terephthalate), and polystyrene.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

A diluent used in the compositions can be one or more compounds which are capable of densifying the active principle to give the desired mass. The preferred diluents are mineral phosphates such as calcium phosphates; sugars such as hydrated or anhydrous lactose, or mannitol; and cellulose or cellulose derivatives, for example microcrystalline cellulose, starch, corn starch or pregelatinized starch. Very particularly preferred diluents are lactose monohydrate, mannitol, microcrystalline cellulose and corn starch, used by themselves or in a mixture, for example a mixture of lactose monohydrate and corn starch or a mixture of lactose monohydrate, corn starch and microcrystalline cellulose.

A binder employed in the compositions can be one or more compounds which are capable of densifying a compound of formula (I), converting it to coarser and denser particles with better flow properties. The preferred binders are alginic acid or sodium alginate; cellulose and cellulose derivatives such as sodium carboxymethyl cellulose, ethyl cellulose, hydroxyethyl cellulose, hydroxypropyl cellulose, hydroxypropyl methyl cellulose or methyl cellulose, gelatin; acrylic acid polymers; and povidone, for example povidone K-30; hydroxypropyl methyl cellulose and povidone K-30 are very particularly preferred binders.

A disintegrating agent may be included in the compositions and include one or more compounds which facilitate the disintegration of the prepared formulation when it is placed in an aqueous medium. The preferred disintegrating agents are cellulose or cellulose derivatives such as sodium carboxymethyl cellulose, crosslinked sodium carboxymethyl cellulose, microcrystalline cellulose, cellulose powder, crospovidone; pregelatinized starch, sodium starch glyconate, sodium carboxymethyl starch, or starch. Crospovidone, crosslinked sodium carboxymethyl cellulose and sodium carboxymethyl starch are preferred disintegrating agents.

An anti-adhesive employed in the compositions may be one or more compounds which are capable of reducing the sticky character of the formulation, for example of preventing adhesion to metal surfaces. Suitable anti-adhesives include compounds containing silicon, for example silica or talcum.

A flow promoter may be included in the compositions, according to some embodiments. The flow promoter may be one or more compounds which are capable of facilitating the flow of the prepared formulation. Suitable promoters include compounds containing silicon, for example anhydrous colloidal silica or precipitated silica.

A lubricant may be included in the compositions, according to some embodiments. The lubricant may be one or more compounds which are capable of preventing the problems associated with the preparation of dry forms, such as the sticking and/or seizing problems which occur in the machines during compression or filling. Suitable lubricants include fatty acids or fatty acid derivatives such as calcium stearate, glyceryl monostearate, glyceryl palmitostearate, magnesium stearate, sodium laurylsulfate, sodium stearylfumarate, zinc stearate or stearic acid; hydrogenated vegetable oils, for example hydrogenated castor oil; polyalkylene glycols or polyethylene glycol; sodium benzoate; or talcum. In some embodiments, the lubricant is magnesium stearate or sodium stearylfumarate.

A color employed may be included in the compositions, according to some embodiments. The color may be one or more compounds which are capable of imparting the desired color to the prepared formulation. The addition of a color can serve, for example, to differentiate between formulations containing different doses of active principle. The preferred colors are iron oxides.

As set out above, certain embodiments of the present compounds may contain a basic functional group, such as amino or alkylamino, and are, thus, capable of forming pharmaceutically-acceptable salts with pharmaceutically-acceptable acids. The salts may be prepared in situ in the administration vehicle or the dosage form manufacturing process, or by separately reacting a purified compound in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

Pharmaceutically acceptable salts include the nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In some embodiments, the compounds contain one or more acidic functional groups and, thus, are capable of forming pharmaceutically-acceptable salts with pharmaceutically-acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. See Berge et al., supra.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the compounds include those suitable for oral, nasal, topical (including buccal and sublingual), rectal, vaginal and/or parenteral administration. The formulations may be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, from about 5 percent to about 70 percent, or from about 10 percent to about 30 percent.

In certain embodiments, a formulation of the compounds includes an excipient selected from cyclodextrins, liposomes, micelle forming agents, e.g., bile acids, and polymeric carriers, e.g., polyesters, or polyanhydrides. In certain embodiments, an aforementioned formulation renders orally bioavailable on of the compounds.

Methods of preparing these formulations or compositions include the step of bringing into association a compound with the carrier and, optionally, one or more accessory ingredients. In general, the formulations are prepared by uniformly and intimately bringing into association a compound with liquid carriers, or finely divided solid carriers, or both, and then, if necessary, shaping the product.

Pharmaceutical compositions suitable for parenteral administration, may include one or more the compounds in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microcapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The pharmaceutical formulations may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. In some embodiments, the formulation is administered orally.

Regardless of the route of administration selected, the compounds may be used in a suitable hydrated form, and/or the pharmaceutical compositions are formulated into pharmaceutically-acceptable dosage forms by conventional methods known to those of skill in the art.

Actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of factors including the activity of the particular compound employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts. In general, a suitable daily dose of the compounds may be that amount of the compound which is the lowest dose effective to produce a therapeutic effect. Such an effective dose will generally depend upon the factors described above. Generally, intravenous, intracerebroventricular and subcutaneous doses of the compounds for a patient, when used for the indicated analgesic effects, will range from about 0.0001 to about 100 mg per kilogram of body weight per day. If desired, the effective daily dose of the active compound may be administered as two, three, four, five, six or more sub-doses administered separately at appropriate intervals throughout the day, optionally, in unit dosage forms.

In another aspect, pharmaceutically acceptable compositions are provided. According to some embodiments, the pharmaceutically acceptable compositions include a therapeutically-effective amount of one or more of the compounds of Formulas I, II, III, IV, V, VI, VII, or VIII, formulated together with one or more pharmaceutically acceptable carriers (additives) and/or diluents. As described in detail below, the pharmaceutical compositions may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or oral cavity; or (4) intravaginally or intravectally, for example, as a pessary, cream or foam; (5) sublingually; (6) ocularly; (7) transdermally; or (8) nasally.

The compounds of Formulas I, II, III, IV, V, VI, VII, or VIII may be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutic effects of the first administered one has not entirely disappeared when the subsequent is administered.

In one aspect, a method of therapeutic treatment is provided including administering to a mammal in need thereof, a therapeutic agent comprising a substituted or unsubstituted di(imidazolylalkyl)amine, having at least one hydrophilic substituent in a pharmaceutically acceptable carrier.

The present invention, thus generally described, will be understood more readily by reference to the following examples, which are provided by way of illustration and are not intended to be limiting of the present invention.

EXAMPLES

The present disclosure is further illustrated by the following examples and example compounds, which should not be construed as limiting in any way.

General Methods.

All reactions were carried out in dry glassware under an atmosphere of argon unless otherwise noted. Reactions were purified by column chromatography, under medium pressure using a Biotage SP4 or by preparative high pressure liquid chromatography using a Varian Prostar 210 preparative HPLC system equipped with a semi-preparative Vydac C18 reverse-phase column (250 mm×10 mm×5 μm) connected to a Varian Prostar model 320 UV-visible detector and monitored at a wavelength of 254 nm. The final technetium complex purifications were achieved using a binary solvent gradient of 5-50% B over 21 minutes (A=triethyl ammonium phosphate (TEAP) pH 3, B=methanol). Analytical HPLC of the radio-iodinated compounds was performed using the same method with an analytical Vydac C18 reverse-phase column (250 mm×4.6 mm×5 μm). $^1$H NMR spectra were obtained on a Bruker 400 MHz instrument. Spectra are reported as ppm and are referenced to the solvent resonances in CDCl$_3$, DMSO-d$_6$ or methanol-d$_4$. Elemental analysis was performed by Prevalere Life Sciences, Inc. $^{99m}$Tc was used as a Na$^{99m}$TcO$_4$ solution in saline, as a commercial $^{99}$Mo/$^{99m}$Tc generator eluant (Cardinal Health). The $^{99m}$Tc-containing solutions were always kept behind sufficient lead shielding. The use of [$^{99m}$Tc(CO)$_3$(H$_2$O)$_3$]$^+$ was prepared from commercially available Isolink™ kits (Mallinckrodt). All solvents were purchased from Sigma Aldrich. Reagents were purchased from Sigma Aldrich (St. Louis, Mo.), Bachem (Switzerland), Akaal (Long Beach, Calif.), or Anaspec (San Jose, Calif.). The following abbreviations are used: Fmoc=Fluorenylmethyloxycarbonyl, DPMA=N,N-dimethylaminopyridine, DMF=N,N-dimethylformamide, DCM=dichloromethane, NaOH=sodium hydroxide, ID/g=injected dose per gram, PBS=phosphate buffered saline, RCP=radiochemical purity, RCY=radiochemical yield.

Scheme 6, above, illustrates a general procedure that has been, and may be used to prepare SAAC analogs. In the scheme, the base may be a base known to those of skill in the art such as an amine base. Exemplary amine bases include ammonia; a trialkylamine such as trimethyl amine, triethylamine, tri(n- or iso-)propylamine, tri(n-, iso- or tert-)butylamine; mixed trialkylamines such as diethylmethylamine; heterocyclic amines such as substituted or unsubstituted pyridines and piperadines, or diazabicycloundecene. R is a hydrophilic group.

To a solution of 2-imidazole carboxaldehyde in DMF (1 mL) is added 1 eq each of alkyl bromide and potassium carbonate, and a catalytic amount of potassium iodide. The reactions are heated at approximately 110° C. for 18 hrs followed by evaporation to dryness. The crude R-alkylimidazol carboxyaldehyde product may then purified utilizing the Biotage SP4 with a gradient method of 5-50% methanol in DCM.

To a solution of L-Fmoc-Lysine-OH HCl (90 mg, 0.185 mmol) in dichloroethane (DCE) (2 mL) is added 2.1 eq. of the R-alkylimidazol carboxyaldehyde. The reaction is heated at approximately 50° C. for 1 h, followed by addition of sodium triacetoxyborohydride (36 mg, 0.185 mmol). The reaction mixture is then stirred at room temperature for 12 hours, and then evaporated to dryness. The fmoc-protected compound may then be purified utilizing a Biotage SP4 with a gradient method of 5-50% methanol in DCM. The purified fmoc-protected compound (24 mg, 0.034 mmol) is then deprotected by treatment with piperidine in DMF ("base", 1:1, 1 mL) and the reaction stirred at room temperature for 2 hours. Following evaporation of the volatile components, the residue is subjected to aqueous extraction and washing with excess methylene chloride to afford the desired compounds as an off-white solid.

Compound 1: tert-Butyl
2-(2-formyl-1H-imidazol-1-yl)acetate

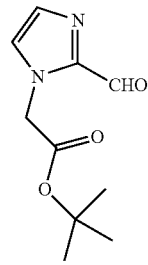

To a solution of 2-imidazole carboxaldehyde (1.00 g, 10.4 mmol) in DMF (1 mL) was added 1 eq. tert-butylbromoacetate, potassium carbonate and a catalytic amount of potassium iodide. The reactions were heated at 110° C. for 18 hrs followed by evaporation to dryness and purified utilizing a Biotage SP4 with a gradient method of 5-50% methanol in DCM to yield the desired compound (850 mg, 4.03 mmol, 39% yield). $^1$H NMR (400 MHz, DMSO-d$_6$) δ 7.6 (s, H), 7.23 (s, H), 5.15 (s, 2H), 1.40 (s, 9H).

Compound 2: 2,2'-(2,2'(5-amino-5-carboxypentylazanediyl)bis(methylene) bis(1H-imidazole-2,1-diyl))diacetic acid

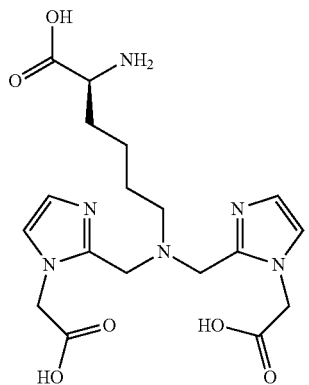 [SMILES: N[C@@H](CCCCN(Cc1nccn1CC(=O)O)Cc1nccn1CC(=O)O)C(=O)O]

To a solution of L-Fmoc-Lysine-OH HCl (200 mg, 0.494 mmol) in DCE (20 mL) was added tert-butyl 2-(2-formyl-1H-imidazol-1-yl)acetate (219 mg, 1.04 mmol). The reaction was heated at 50° C. for one hour, and then sodium triacetoxyborohydride (219 mg, 1.04 mmol) was added. The reaction stirred at room temperature for 12 hours and was subsequently evaporated to dryness and purified as the Fmoc-protected product utilizing a Biotage SP4 with a gradient method of 5-50% methanol in DCM (155 mg, 0.205 mmol, 42% yield). $^1$H NMR (400 MHz, DMSO-$d_6$) δ 7.67 (d, 2H), 7.35 (m, 4H), 7.30 (m, 2H), 7.05 (s, H), 6.7 (s, H), 4.70 (s, 4H), 4.2 (m, 4H), 3.4 (d, 2H), 2.4 (m, 2H), 1.8 (s, 2H), 1.39 (s, 18H). 1.2 (m, 2H). ESMS m/z: 758 (M+H)$^+$. The purified compound was deprotected by treatment with piperidine/DMF 1:1 (1 mL) and the reaction stirred at room temperature for 18 hours. Following evaporation to a residue, aqueous extraction from methylene chloride afforded the desired product (25 mg, 0.047 mmol, 25% yield) as an off-white solid. $^1$H NMR (400 MHz, DMSO-$d_6$) δ 7.0 (s, 2H), 6.65 (s, H), 4.70 (s, 4H), 4.2 (m, 4H), 3.2 (d, 2H), 2.4 (m, 2H), 1.8 (s, 2H), 1.39 (s, 18H). 1.15 (m, 2H). ESMS m/z: 535 (M+H)$^+$.

Compound 3:
1-(2-ethoxyethyl)-1H-imidazole-2-carbaldehyde

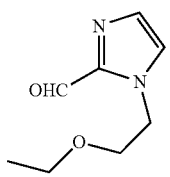

To a solution of imidazole-2-carboxaldehyde (2.00 g, 21 mmol) in DMF (1 mL) was added 1.1 eq. of 1-bromo-2-ethoxyethane (3.51 g, 22 mmol), potassium carbonate and a catalytic amount of potassium iodide. The reactions were heated at 110° C. for 18 hrs followed by evaporation to dryness and purified utilizing a Biotage SP4 with a gradient method of 5-50% methanol in DCM to yield the desired compound (580 mg, 3.56 mmol, 17% yield). $^1$H NMR (400 MHz, DMSO-$d_6$) δ 9.63 (s, H), 7.6 (s, H), 7.21 (s, H), 4.45 (dd, 2H), 3.62 (dd, 2H), 3.38 (m, 2H), 1.05 (t, 3H).

Compound 4: 2-amino-6-(bis((1-(2-ethoxyethyl)-1H-imidazol-2-yl)methyl)amino)hexanoic acid

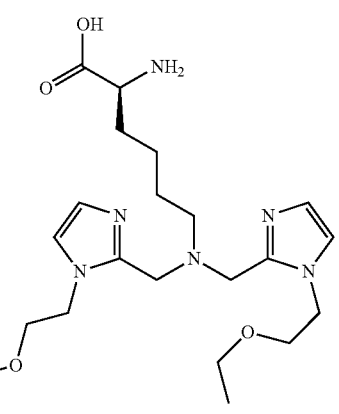

To a solution of L-Fmoc-Lysine-OH HCl (200 mg, 0.494 mmol) in DCE (20 mL) was added 1-(2-ethoxyethyl)-1H-imidazole-2-carbaldehyde (169 mg, 1.04 mmol). The reaction was heated at 50° C. for one hour whereupon sodium triacetoxyborohydride (219 mg, 1.04 mmol) was added. The reaction stirred at room temperature for 12 hours and was subsequently evaporated to dryness and purified as the Fmoc-protected product utilizing a Biotage SP4 with a gradient method of 5-50% methanol in DCM (141 mg, 0.210 mmol, 44% yield). $^1$H NMR (400 MHz, DMSO-$d_6$) δ 7.67 (d, 2H), 7.35 (m, 4H), 7.30 (m, 2H), 7.05 (s, H), 6.75 (s, H), 3.95 (m, 4H), 3.58 (d, 4H), 3.55 (s, 4H), 3.3 (s, 4H), 2.30 (m, 2H), 2.15 (m, 2H), 1.50 (m, 2H). 1.15 (s, 2H), 1.05 (t, 6H). ESMS m/z: 674 (M+H)$^+$. The purified compound was deprotected by treatment with piperidine/DMF 1:1 (1 mL) and the reaction stirred at room temperature for 18 hours. Following evaporation to residue, aqueous extraction from methylene chloride afforded the desired product (31 mg, 0.069 mmol, 91% yield) as an off-white solid. $^1$H NMR (400 MHz, DMSO-$d_6$) δ 8.35 (s, H), 7.98 (s, H), 7.05 (s, H), 6.75 (s, H), 3.95 (m, 4H), 3.58 (d, 4H), 3.55 (s, 4H), 3.3 (s, 4H), 2.30 (m, 2H), 2.15 (m, 2H), 1.50 (m, 2H). 1.15 (s, 2H), 1.05 (t, 6H). ESMS m/z: 451 (M+H)$^+$.

Compound 5:
1-(2,2-dimethoxyethyl)-1H-imidazole-2-carbaldehyde

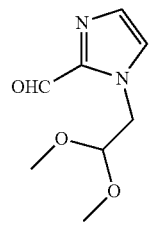

To a solution of the imidazole-2-carboxaldehyde (0.41 g, 4.27 mmol) in DMF (1 mL) was added 1.1 eq. of 2-bromo-1,1-dimethoxyethane (0.79 g, 4.69 mmol), potassium carbonate and a catalytic amount of potassium iodide. The reactions were heated at 110° C. for 18 hrs followed by evaporation to dryness and purified utilizing a Biotage SP4 with a gradient method of 5-50% methanol in DCM to yield the desired compound (248 mg, 1.35 mmol, 32% yield). $^1$H NMR (400 MHz, DMSO-$d_6$) δ 9.9 (s, H), 7.85 (s, H), 7.55 (s, H), 5.82 (m, H), 4.75 (d, 2H), 3.45 (s, 6H).

Compound 6: 2-amino-6-(bis((1-(2,2-dimethoxyethyl)-1H-imidazol-2-yl)methyl)amino)hexanoic acid

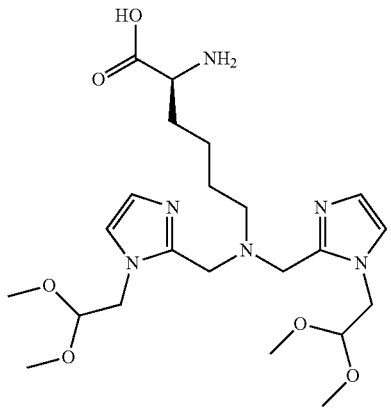 [SMILES: COC(Cn1ccnc1CN(CCCC[C@H](N)C(=O)O)Cc1nccn1CC(OC)OC)OC]

To a solution of L-Fmoc-Lysine-OH HCl (100 mg, 0.250 mmol) dissolved in DCE (20 mL) was added 1-(2,2-dimethoxyethyl)-1H-imidazole-2-carbaldehyde (95 mg, 0.52 mmol). The reaction was heated at 50° C. for one hour whereupon sodium triacetoxyborohydride (110 mg, 0.52 mmol) was added. The reaction stirred at room temperature for 12 hours and was subsequently evaporated to dryness and purified as the Fmoc-protected product utilizing a Biotage SP4 with a gradient method of 5-50% methanol in DCM (93 mg, 0.132 mmol, 54% yield). $^1$H NMR (400 MHz, DMSO-$d_6$) δ 7.90 (d, 2H), 7.72 (d, 2H), 7.41 (m, 2H), 7.30 (m, 2H), 7.05 (s, H), 6.75 (s, H), 4.45 (m, 3H), 4.2 (m, 4H), 3.95 (d, 2H), 3.80 (m, H), 3.55 (s, 2H), 3.2 (s, 6H), 2.3 (m, 2H), 1.60 (m, H), 1.35 (m, H) 1.15 (m, 2H). ESMS m/z: 705 (M+H)$^+$. The purified compound was deprotected by treatment with piperidine/DMF 1:1 (1 mL) and the reaction stirred at room temperature for 18 hours. Following evaporation to residue, aqueous extraction from methylene chloride afforded the desired product (44 mg, 0.093 mmol, 76% yield) as an off-white solid. $^1$H NMR (400 MHz, DMSO-$d_6$) δ 7.98 (s, H), 7.05 (s, H), 6.85 (s, H), 4.45 (s, 2H), 3.95 (m, 4H), 3.55 (s, 2H), 3.2 (s, 6H), 2.85 (m, 2H), 2.15 (m, 2H), 1.40 (m, 2H). 1.15 (m, 2H). ESMS m/z: 483 (M+H)$^+$.

Compound 7: 2,2'-(5-amino-5-carboxypentylazanediyl)diacetic acid

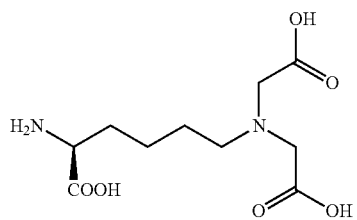 [SMILES: N[C@@H](CCCCN(CC(=O)O)CC(=O)O)C(=O)O]

To a solution of L-Fmoc-Lysine-OH HCl (200 mg, 0.494 mmol) in DCE (20 mL) was added tert-butyl 2-oxoacetate (134 mg, 1.04 mmol). The reaction was heated at 50° C. for one hour whereupon sodium triacetoxyborohydride (219 mg, 1.04 mmol) was added. The reaction stirred at room temperature for 12 hours and was subsequently evaporated to dryness and purified as the Fmoc-protected product utilizing a Biotage SP4 with a gradient method of 5-50% methanol in DCM (100 mg, 0.168 mmol, 34% yield). $^1$H NMR (400 MHz, DMSO-$d_6$) δ 7.67 (d, 2H), 7.35 (m, 4H), 7.30 (m, 2H), 4.70 (m, 2H), 4.55 (m, 2H), 3.3 (d, 2H), 2.4 (m, 2H), 1.8 (s, 2H), 1.45 (m, 2H). ESMS m/z: 484 (M+H)$^+$. The purified compound was deprotected by treatment with piperidine/DMF 1:1 (1 mL) and the reaction was stirred at room temperature for 18 hours. Following evaporation to residue, aqueous extraction from methylene chloride afforded the desired product (3 mg, 0.11 mmol, 55% yield) as an off-white solid. $^1$H NMR (400 MHz, DMSO-$d_6$) δ 7.9 (s, 2H), 3.5 (m, H), 3.3 (d, 2H), 2.4 (m, 2H), 1.8 (s, 2H), 1.45 (m, 2H). 1.15 (m, 2H). ESMS m/z: 263 (M+H)$^+$.

Compound 8: (S)-1-(9H-fluoren-9-yl)-14,14-dimethyl-3,12-dioxo-10-(pyridin-2-ylmethyl)-2,13-dioxa-4,10-diazapentadecane-5-carboxylic acid (PAMA-K)

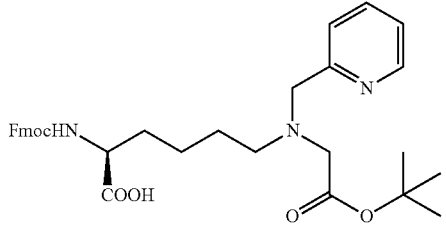

A suspension of Fmoc-Lys-OH.HCl (4.859 g, 12 mmol) and 2-pyridinecarboxaldehyde (1.285 g, 12 mmol) in DCE (100 mL) was refluxed for 30 min under nitrogen. The reaction mixture was cooled to 0° C., and treated sequentially with NaBH(OAc)$_3$ (6.36 g, 30 mmol) and crude tert-butyl glyoxalate (2.34 g, 18 mmol) The reaction mixture was stirred at room temperature for overnight and decomposed with water. The reaction mixture was extracted with DCM. The organic layer was dried and concentrated under reduced pressure. The residue was purified by flash chromatography over silica gel to afford ((S)-1-(9H-fluoren-9-yl)-14,14-dimethyl-3,12-dioxo-10-(pyridin-2-ylmethyl)-2, 13-dioxa-4,10-diazapentadecane-5-carboxylic acid (1.924 g, 28%). $^1$H NMR (400 MHz, CDCl$_3$) 8.89 (d, J=4.4 Hz, 1H), 8.06 (d, J=8.0 Hz, 1H), 8.02 (d, J=7.6 Hz, 2H), 7.88 (t, J=5.8 Hz, 2H), 7.81 (d, J=7.6 Hz, 1H), 7.66 (t, J=7.4 Hz, 2H), 7.60-7.53 (m, 4H), 6.03 (d, J=7.2 Hz, 1H), 4.67-4.22 (m, 8H), 3.64-3.53 (m, 2H), 3.12 (t, J=6.8 Hz, 2H), 2.19-2.08 (m, 2H), 1.92-1.79 (m, 2H), 1.73 (s, 9H); MS (ESI), 564 (M+H)$^+$.

Compound 9: (S)-10-(2-tert-butoxy-2-oxoethyl)-1-(9H-fluoren-9-yl)-14,14-dimethyl-3,12-dioxo-2,13-dioxa-4,10-diazapentadecane-5-carboxylic acid

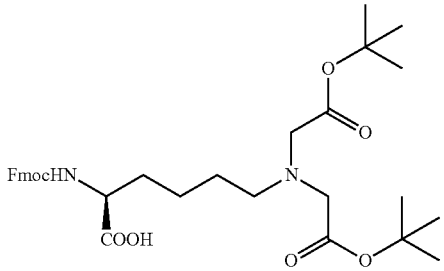

A solution of Fmoc-Lys-OH (1.47 g, 4.0 mmol) and crude tert-butyl glyoxalate (3.60 g) in DCE (50 mL) was stirred at 75° C. for 30 min under nitrogen. The reaction mixture was cooled to 0° C., and treated with NaBH(OAc)$_3$ (2.12 g, 10 mmol). The reaction mixture was stirred at room temperature for 3 hrs and decomposed with water. The reaction mixture was extracted with DCM, the organic layer dried, and concentrated under reduced pressure. The residue was purified by flash chromatography over silica gel to afford (S)-10-(2-tert-butoxy-2-oxoethyl)-1-(9H-fluoren-9-yl)-14,14-dimethyl-3,12-dioxo-2,13-dioxa-4,10-diazapentadecane-5-carboxylic acid (1.70 g, 71%). $^1$H NMR (400 MHz, CDCl$_3$) 7.76 (d, J=7.2 Hz, 2H), 7.60 (d, J=7.2 Hz, 2H), 7.40 (t, J=7.2 Hz, 2H), 7.30 (t, J=7.2 Hz, 2H), 6.63 (d, J=7.6 Hz, 1H), 4.40-4.34 (m, 3H), 4.22 (t, J=7.2 Hz, 1H), 3.49 (s, 4H), 2.83-2.64 (m, 4H), 1.96-1.77 (m, 4H), 1.40 (s, 18H); MS (ESI), 564 (M+H)$^+$.

Compound 10: (S)-1-(9H-fluoren-9-yl)-14,14-dimethyl-3,12-dioxo-10-(thiazol-2-ylmethyl)-2,13-dioxa-4,10-diazapentadecane-5-carboxylic acid (MTMA-K)

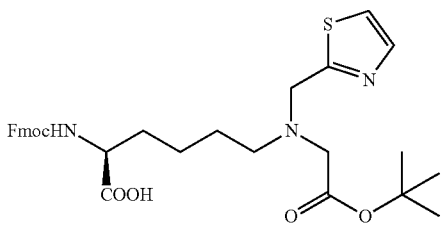

A suspension of Fmoc-Lys-OH.HCl (6.07 g, 15 mmol) and thiazole-2-carbaldehyde (1.697 g, 15 mmol) in DCE (100 mL) was refluxed for 30 min under nitrogen. The reaction mixture was cooled to 0° C., and treated sequentially with NaBH(OAc)$_3$ (7.95 g, 37.5 mmol) and crude tert-butyl glyoxalate (3.53 g). The reaction mixture was stirred at room temperature for overnight and decomposed with water. The reaction mixture was extracted with DCM. The organic layer was dried and concentrated under reduced pressure. The residue was purified by flash chromatography over silica gel to afford (S)-1-(9H-fluoren-9-yl)-14,14-dimethyl-3,12-dioxo-10-(thiazol-2-ylmethyl)-2,13-dioxa-4,10-diazapentadecane-5-carboxylic acid (1.85 g, 21%). MS (ESI), 580 (M+H)$^+$.

Compound 11: (S)-2-amino-6-((2-tert-butoxy-2-oxoethyl)(thiazol-2-ylmethyl)amino)hexanoic acid

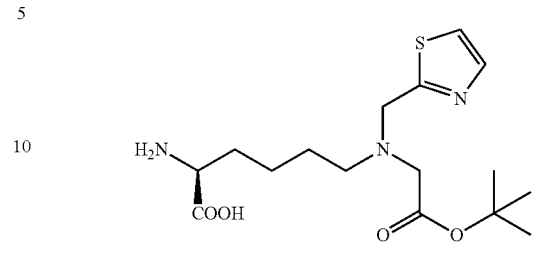

Piperidine (0.20 mL) was added to a solution of (S)-1-(9H-fluoren-9-yl)-14,14-dimethyl-3,12-dioxo-10-(thiazol-2-ylmethyl)-2,13-dioxa-4,10-diazapentadecane-5-carboxylic acid (72.5 mg, 0.125 mmol) in DMF (1.0 mL). The mixture was stirred at room temperature for 2 hrs. Solvent was evaporated under reduce pressure to afford a residue, which was purified by flash chromatography over silica gel to afford (S)-2-amino-6-((2-tert-butoxy-2-oxoethyl)(thiazol-2-ylmethyl)amino)hexanoic acid (25 mg, 35%). $^1$H NMR (400 MHz, CD$_3$OD) 7.70 (d, J=3.6 Hz, 1H), 7.53 (d, J=3.2 Hz, 1H), 4.15 (s, 2H), 3.52 (dd, J=7.2, 5.2 Hz, 1H), 3.38 (s, 2H), 2.73 (t, J=7.2 Hz, 2H), 1.91-1.76 (m, 2H), 1.60-1.44 (m, 13H); MS (ESI), 358 (M+H)$^+$.

Compound 12: (S)-2-(((9H-fluoren-9-yl)methoxy)carbonylamino)-6-(bis((1-methyl-1H-imidazol-2-yl)methyl)amino)hexanoic acid

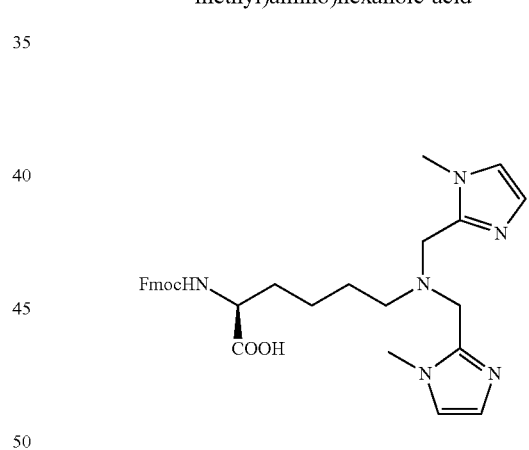

A solution of Fmoc-Lys-OH.HCl (1.822 g, 4.5 mmol) and 1-methyl-1H-imidazole-2-carbaldehyde (1.10 g, 10 mmol) in DCE (50 mL) was stirred at 75° C. for 30 min under nitrogen. The reaction mixture was cooled to 0° C., and treated with NaBH(OAc)$_3$ (3.165 g, 15 mmol). The reaction mixture was stirred at room temperature for overnight and decomposed with water. The reaction mixture was extracted with DCM, the organic layer dried and concentrated under reduced pressure. The residue was purified by flash chromatography over silica gel to afford (S)-2-(((9H-fluoren-9-yl)methoxy)carbonylamino)-6-(bis((1-methyl-1H-imidazol-2-yl)methyl)amino)hexanoic acid (2.30 g, 92%). MS (ESI), 557 (M+H)$^+$.

Compound 13: (S)-2-amino-6-(bis((1-methyl-1H-imidazol-2-yl)methyl)amino)hexanoic acid

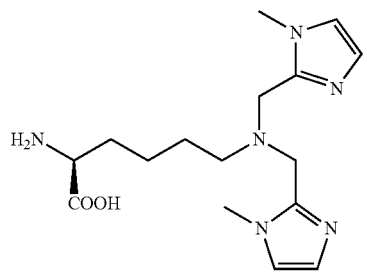 [SMILES: Cn1ccnc1CN(CCCC[C@H](N)C(=O)O)Cc1nccn1C]

Piperidine (0.80 mL) was added to a solution of (S)-2-(((9H-fluoren-9-yl)methoxy)carbonylamino)-6-(bis((1-methyl-1H-imidazol-2-yl)methyl)amino)hexanoic acid (556 mg, 1.00 mmol) in DMF (4.0 mL). The mixture was stirred at room temperature for 2 hrs. Solvent was evaporated under reduce pressure to afford a residue, which was purified by Amberchrom to afford (S)-2-amino-6-(bis((1-methyl-1H-imidazol-2-yl)methyl)amino) hexanoic acid (330 mg, 99%). $^1$H NMR (400 MHz, DMSO-$d_6$) 7.94 (s, 1H), 7.04 (d, J=1.2 Hz, 2H), 6.74 (d, J=1.2 Hz, 2H), 3.54 (s, 4H), 3.98 (brs, 1H), 2.88 (s, 3H), 2.72 (s, 3H), 2.35 (t, J=6.8 Hz, 2H), 1.60-1.54 (m, 1H), 1.43-1.29 (m, 3H), 1.16-1.11 (m, 2H); MS (ESI), 335 (M+H)$^+$.

Compound 14: (S)-1-(9H-fluoren-9-yl)-14,14-dimethyl-10-((1-methyl-1H-imidazol-2-yl)methyl)-3,12-dioxo-2,13-dioxa-4,10-diazapentadecane-5-carboxylic acid

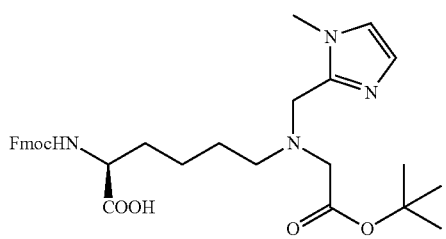

The title compound was prepared by following the same procedure as described in the preparation of Compound 1, except 1-methyl-1H-imidazole-2-carbaldehyde was used in place of 2-pyridinecarboxaldehyde. $^1$H NMR (400 MHz, CDCl$_3$) 7.88 (d, J=7.2 Hz, 2H), 7.71 (dd, J=7.2, 2.4 Hz, 2H), 7.55 (d, J=8.0 Hz, 1H), 7.40 (t, J=7.6 Hz, 2H), 7.31 (t, J=7.6 Hz, 4H), 7.01 (s, 1H), 6.71 (s, 1H), 4.27-4.18 (m, 3H), 3.88-3.83 (m, 1H), 3.72 (s, 2H), 3.14 (s, 2H), 1.62-1.50 (m, 2H), 1.38 (s, 9H), 1.33-1.21 (m, 4H); MS (ESI), 577 (M+H)$^+$.

Compound 15: (S)-2-amino-6-((2-tert-butoxy-2-oxoethyl)((1-methyl-1H-imidazol-2-yl)methyl)amino)hexanoic acid

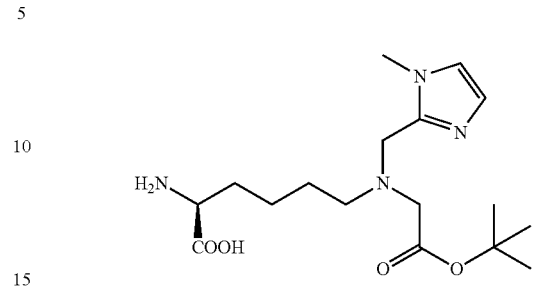

Piperidine (0.40 mL) was added to a solution of (S)-1-(9H-fluoren-9-yl)-14,14-dimethyl-10-((1-methyl-1H-imidazol-2-yl)methyl)-3,12-dioxo-2,13-dioxa-4,10-diazapentadecane-5-carboxylic acid (190 mg, 0.33 mmol) in DMF (2.0 mL). The mixture was stirred at room temperature for 2 hrs. The solvent was evaporated under reduce pressure to afford a residue, which was purified by Amberchrom to afford (S)-2-amino-6-((2-tert-butoxy-2-oxoethyl)((1-methyl-1H-imidazol-2-yl)methyl)amino)hexanoic acid (115 mg, 100%). $^1$H NMR (400 MHz, DMSO) 7.27 (brs, 1H), 7.04 (s, 1H), 6.72 (s, 1H), 3.73 (s, 2H), 3.64 (s, 3H), 3.15 (s, 2H), 3.04 (dd, J=6.8, 5.2 Hz, 1H), 2.47 (t, J=7.2 Hz, 2H), 1.65-1.46 (m, 2H), 1.39 (s, 9H), 1.30-1.21 (m, 4H); MS (ESI), 355 (M+H)$^+$.

Compound 16 (Protected): 2,2'-(2,2'-(4-sulfamoylphenethylazanediyl)-bis(methylene) bis(1H-imidazole-2,1-diyl))diacetic acid

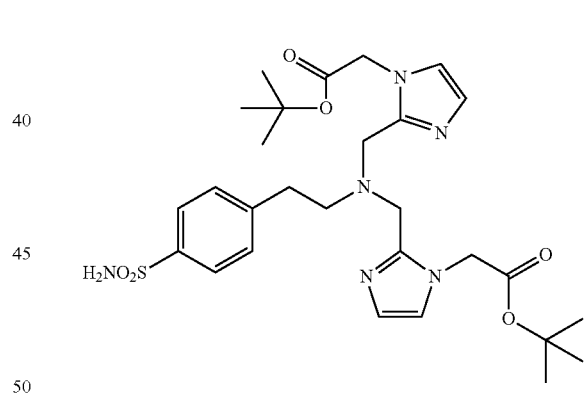

A solution of 4-(2-aminoethyl)benzenesulfonamide (110 mg, 0.55 mmol), AcOH (0.10 mL) and tert-butyl 2-(2-formyl-1H-imidazol-1-yl)acetate (250 mg, 1.19 mmol) in DCE (20 mL) was stirred at 80° C. for 30 min under nitrogen. The reaction mixture was cooled to 0° C., and treated with NaBH(OAc)$_3$ (3.165 g, 15 mmol). The reaction mixture was stirred at room temperature for overnight and decomposed with water. The reaction mixture was extracted with DCM. The organic layer was dried and concentrated under reduced pressure. The residue was purified by flash chromatography over silica gel to afford tert-butyl 2,2'-(2,2'-(4-sulfamoylphenethylazanediyl)bis(methylene)bis(1H-imidazole-2,1-diyl))diacetate (132 mg, 41%). $^1$H NMR (400 MHz, CD$_3$OD) 7.75 (d, J=8.4 Hz, 2H), 7.18 (d, J=8.4 Hz, 2H), 7.07 (s, 2H), 6.93 (s, 2H), 4.58 (s, 4H), 3.68 (s, 4H), 2.84-2.74 (m, 4H), 1.44 (s, 18H); MS (ESI), 589.4 (M+H)$^+$.

Compound 17 (protected, prior to metal complexation): 2-(2-(((carboxymethyl)(4-sulfamoyl phenethyl)amino)methyl)-1H-imidazol-1-yl)acetic acid

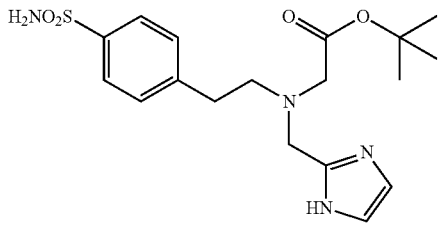 [SMILES: CC(C)(C)OC(=O)CN(CCc1ccc(S(N)(=O)=O)cc1)Cc1ncc[nH]1]

A solution of 4-(2-aminoethyl)benzenesulfonamide (0.70 g, 3.5 mmol), AcOH (0.20 mL) and tert-butyl 2-(2-formyl-1H-imidazol-1-yl)acetate (0.735 g, 3.5 mmol) in DCE (20 mL) was heated at 80° C. for 30 min under nitrogen. The reaction mixture was cooled to 0° C., and treated sequentially with NaBH(OAc)$_3$ (2.25 g, 10.5 mmol) and crude tert-butyl glyoxalate (1.80 g)[1]. The reaction mixture was stirred at room temperature for overnight and decomposed with water. The reaction mixture was extracted with DCM. The organic layer was dried and concentrated under reduced pressure. The residue was purified by flash chromatography over silica gel to tert-butyl 2-(((1-methyl-1H-imidazol-2-yl)methyl)(4-sulfamoylphenethyl)amino)acetate (0.63 g, 35%). %). $^1$H NMR (400 MHz, DMSO-d$_6$) 7.67 (d, J=8.4 Hz, 2H), 7.25 (s, 2H), 7.23 (d, J=8.4 Hz, 2H), 7.04 (d, J=1.2 Hz, 1H), 6.76 (d, J=1.2 Hz, 1H), 4.82 (s, 2H), 3.74 (s, 2H), 3.24 (s, 2H), 2.69-2.66 (m, 4H), 1.41 (s, 9H), 1.40 (s, 9H); MS (ESI), 509 (M+H)$^+$.

As described above, and as evident from the protected examples 16 and 17, above, the compounds of Table 1, below, may or may not be isolated. Rather, the acid, or other groups may be protected.

Compound 24: 4-(2-(bis(isoquinolin-1-ylmethyl)amino)ethyl)benzenesulfonamide

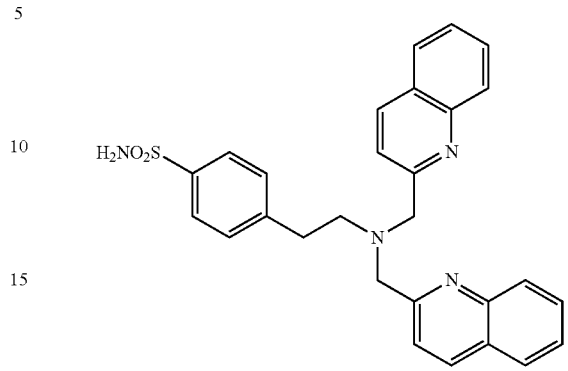

A solution of 4-(2-aminoethyl)benzenesulfonamide (1.0 g, 5.0 mmol), AcOH (1.0 mL) and isoquinoline-1-carbaldehyde (2.09 g, 13.3 mmol) in DCE (50 mL) was stirred at 75° C. for 30 min under nitrogen. The reaction mixture was cooled to 0° C., and treated with NaBH(OAc)$_3$ (3.165 g, 15 mmol). The reaction mixture was stirred at room temperature for overnight and decomposed with water. The reaction mixture was extracted with DCM. The organic layer was dried and concentrated under reduced pressure. The residue was purified by flash chromatography over silica gel to afford 4-(2-(bis(isoquinolin-1-ylmethyl)amino)ethyl)benzenesulfonamide (1.86 g, 77%). $^1$H NMR (400 MHz, DMSO-d$_6$) 8.24 (d, J=8.8 Hz, 2H), 7.96 (d, J=8.4 Hz, 2H), 7.91 (d, J=8.0 Hz, 2H), 7.72 (t, J=7.8 Hz, 2H), 7.65 (d, J=8.4 Hz, 2H), 7.55 (t, J=7.6 Hz, 2H), 7.50 (d, J=8.4 Hz, 2H), 7.30 (d, J=6.0 Hz, 2H), 7.29 (s, 2H), 4.01 (s, 4H), 2.94 (t, J=7.0 Hz, 2H), 2.78 (t, J=7.0 Hz, 2H); MS (ESI), 483.3 (M+H)$^+$.

The following examples were, or are, prepared by the above methods, either isolated, or in situ as described above with respect to protected groups:

TABLE 1

Compounds Prepared By The Methods Exemplified In Compounds 1-15, By Appropriate Reagent Selection.

| Ex. Cmpd. | Compound Name | E | L | γ | G |
|---|---|---|---|---|---|
| 2 | 2-Amino-6-[bis-(1-carboxymethyl-1H-imidazol-2-ylmethyl)-amino]-hexanoic acid | | | 4 | |
| 4 | 2-amino-6-(bis(1-(2-(ethoxyethyl)-1H-imidazol-2-yl)methyl)amino)hexanoic acid | | | 4 | |
| 7 | 2-Amino-6-(bis-carboxymethyl-amino)-hexanoic acid | | | 4 | |
| 13 | 2-Amino-6-[bis-(1-methyl-1H-imidazol-2-ylmethyl)-amino]-hexanoic acid | | | 4 | |

TABLE 1-continued

Compounds Prepared By The Methods Exemplified In Compounds 1-15, By Appropriate Reagent Selection.

| Ex. Cmpd. | Compound Name | E | L | Y | G |
|---|---|---|---|---|---|
| 16 | t-butyl protected-2,2'-(2,2'-(4-sulfamoyl phenethylazanediyl)-bis(methylene) bis(1H-imidazole-2,1-diyl))diacetic acid | 2-(t-butoxycarbonylmethyl)imidazole | 2-(t-butoxycarbonylmethyl)imidazole | 2 | 4-sulfamoylphenyl |
| 16A | 2,2'-(2,2'-(4-sulfamoylphenethylazanediyl)-bis(methylene) bis(1H-imidazole-2,1-diyl))diacetic acid | 2-(carboxymethyl)imidazole | 2-(carboxymethyl)imidazole | 2 | 4-sulfamoylphenyl |
| 17 | 2-(2-(((carboxymethyl)(4-sulfamoylphenethyl)amino)methyl)-1H-imidazol-1-yl)acetic acid | 2-(carboxymethyl)imidazole | carboxymethyl | 2 | 4-sulfamoylphenyl |
| 18 | (S)-2-amino-6-(((carboxymethyl)(1-methyl-1H-imidazol-2-yl)methyl)amino)hexanoic acid | 1-methylimidazole | carboxymethyl | 4 | (S)-2-amino-carboxyl |

TABLE 1-continued

Compounds Prepared By The Methods Exemplified In Compounds 1-15, By Appropriate Reagent Selection.

| Ex. Cmpd. | Compound Name | E | L | Y | G |
|---|---|---|---|---|---|
| 19 | 2-amino-6-(bis((1-((1,4,7,10,13-pentaoxacyclopentadecan-2-yl)methyl)-1H-imidazol-2-yl)methyl)amino) hexanoic acid | ((CH₂CH₂O)₄ CH₂C(H)O) | | 4 | (α-methyl amino acid with OH, C=O, NH₂) |
| 20 | 2-amino-6-(bis((1-(3-(diethoxyphosphoryl)propyl)-1H-imidazol-2-yl)methyl)amino) hexanoic acid | (imidazole with diethoxyphosphorylpropyl) | ((CH₂CH₂O)₄ CH₂C(H)O) | 4 | (α-methyl amino acid with OH, C=O, NH₂) |
| 21 | 4-(2-(bis(pyridin-2-ylmethyl)amino)ethyl)benzenesulfonamide | (pyridin-2-yl) | (pyridin-2-yl) | 2 | (4-SO₂NH₂-phenyl) |
| 22 | 2-((pyridin-2-ylmethyl)(4-sulfamoylphenethyl)amino)acetic acid | (pyridin-2-yl) | (CH₂COOH) | 2 | (4-SO₂NH₂-phenyl) |

TABLE 1-continued

Compounds Prepared By The Methods Exemplified In Compounds 1-15, By Appropriate Reagent Selection.

| Ex. Cmpd. | Compound Name | E | L | Y | G |
|---|---|---|---|---|---|
| 23 | 4-(2-(bis((1-methyl-1H-imidazol-2-yl)methyl)amino)ethyl)benzenesulfonamide | 1-methyl-1H-imidazol-2-yl | 1-methyl-1H-imidazol-2-yl | 2 | 4-sulfamoylphenyl |
| 24 | Compound 24: 4-(2-(bis(quinolin-2-ylmethyl)amino)ethyl)benzenesulfonamide | quinolin-2-yl | quinolin-2-yl | 2 | 4-sulfamoylphenyl |
| 25 | 2-(((1-methyl-1H-imidazol-2-yl)methyl)(4-sulfamoylphenethyl)amino)acetic acid | 1-methyl-1H-imidazol-2-yl | carboxymethyl | 2 | 4-sulfamoylphenyl |
| 26 | 2,2'-(4-sulfamoylphenethylazanediyl)diacetic acid | carboxymethyl | carboxymethyl | 2 | 4-sulfamoylphenyl |

TABLE 1-continued

Compounds Prepared By The Methods Exemplified In Compounds 1-15, By Appropriate Reagent Selection.

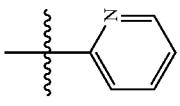

| Ex. Cmpd. | Compound Name | E | L | Y | G |
|---|---|---|---|---|---|
| 27 | 4-(3-(8-(bis(pyridin-2-ylmethyl)amino)octyl)thioureido)benzenesulfonamide | 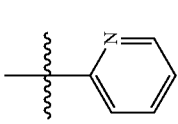 | 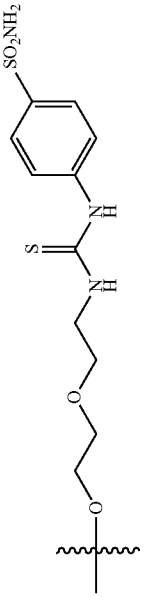 | 8 | 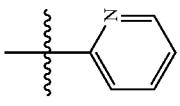 |
| 28 | 4-(3-(2-(2-(bis(pyridin-2-ylmethyl)amino)ethoxy)ethoxy)thioureido)benzenesulfonamide | 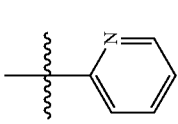 | 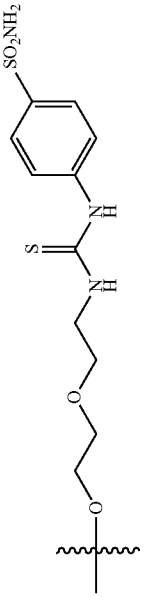 | 2 | 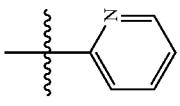 |
| 29 | 4-(3-(5-(bis(pyridin-2-ylmethyl)amino)pentyl)thioureido)benzenesulfonamide | 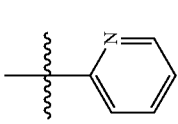 | 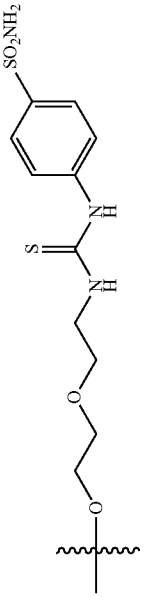 | 5 | 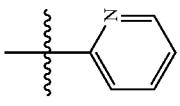 |
| 30 | 2-((pyridin-2-ylmethyl)(8-(3-(4-sulfamoylphenyl)thioureido)octyl)amino)acetic acid | 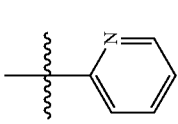 | 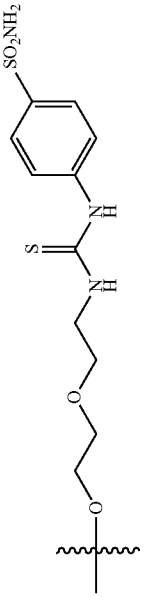 | 8 | |

TABLE 1-continued

Compounds Prepared By The Methods Exemplified In Compounds 1-15, By Appropriate Reagent Selection.

| Ex. Cmpd. | Compound Name | E | L | γ | G |
|---|---|---|---|---|---|
| 31 | 4-(3-((10-(bis((1-methyl-1H-imidazol-2-yl)methyl)amino)decyl)thioureido)benzenesulfonamide | 1-methyl-imidazol-2-yl | 1-methyl-imidazol-2-yl | 10 | 4-(thioureido)benzenesulfonamide |
| 37 | 1-(2-(5-(bis(pyridin-2-yl)methyl)amino)pentanamido)acetyl)pyrrolidin-2-ylboronic acid | pyridin-2-yl | pyridin-2-yl | 4 | glycyl-pyrrolidin-2-ylboronic acid |
| 38 | 2-((6-(2-(2-boronopyrrolidin-1-yl)-2-oxoethyl)amino)-6-oxohexyl)amino)(pyridin-2-ylmethyl)amino)acetic acid | pyridin-2-yl | carboxymethyl | 5 | glycyl-pyrrolidin-2-ylboronic acid |
| 39 | 1-(2-(6-(bis((1-methyl-1H-imidazol-2-yl)methyl)amino)hexanamido)acetyl)pyrrolidin-2-ylboronic acid | 1-methyl-imidazol-2-yl | 1-methyl-imidazol-2-yl | 5 | glycyl-pyrrolidin-2-ylboronic acid |

TABLE 1-continued

Compounds Prepared By The Methods Exemplified In Compounds 1-15, By Appropriate Reagent Selection.

| Ex. Cmpd. | Compound Name | E | L | Y | G |
|---|---|---|---|---|---|
| 40 | 2,2'-(2,2'-(6-(2-(2-boronopyrrolidin-1-yl)-2-oxoethylamino)-6-oxohexylazanediyl)bis(methylene)bis(1H-imidazole-2,1-diyl))diacetic acid | imidazole-CH$_2$COOH | imidazole-CH$_2$COOH | 5 | pyrrolidinyl boronic acid with glycinamide linker |
| 42 | 2-Amino-6-(carboxymethyl-thiazol-2-ylmethyl-amino)-hexanoic acid | thiazole | CH(CH$_3$)COOH | 4 | alanine (amino acid) |
| 44 | 2,2'-(2,2'-(2-(2-boronopyrrolidin-1-yl)-2-oxoethylazanediyl) bis(methylene) bis(1H-imidazole-2,1-diyl))diacetic acid | imidazole-CH$_2$COOH | imidazole-CH$_2$COOH | 1 | pyrrolidinyl boronic acid |
| 45 | 1-(2-(bis(pyridin-2-ylmethyl)amino)acetyl) pyrrolidin-2-ylboronic acid | pyridine | pyridine | 1 | pyrrolidinyl boronic acid |

TABLE 1-continued

Compounds Prepared By The Methods Exemplified In Compounds 1-15, By Appropriate Reagent Selection.

| Ex. Cmpd. | Compound Name | E | L | Y | G |
|---|---|---|---|---|---|
| 48 | 2-((6-(2-(2-boronopyrrolidin-1-yl)-2-oxoethylamino)-6-oxohexyl)(pyridin-2-ylmethyl)amino)acetic acid | pyridin-2-yl | pyridin-2-yl | 5 | 2-(2-boronopyrrolidin-1-yl)-2-oxoethylcarbamoyl group |
| 49 | 2-amino-6-(bis((1-(2-tert-butoxy-2-oxoethyl)-1H-imidazol-2-yl)methyl)amino)hexanoic acid | 1-(2-tert-butoxy-2-oxoethyl)-1H-imidazol-2-yl | 1-(2-tert-butoxy-2-oxoethyl)-1H-imidazol-2-yl | 4 | 2-amino-carboxylic acid |
| 79 | 2-Amino-6-[bis(4-dimethylamino-pyridin-2-ylmethyl)-amino]-hexanoic acid | 4-dimethylamino-pyridin-2-yl | 4-dimethylamino-pyridin-2-yl | 4 | 2-amino-carboxylic acid |
| 200 | 11-(Bis(pyridin-2-ylmethyl)amino)-N-(4-sulfamoylphenyl)undecanamide | pyridin-2-yl | pyridin-2-yl | 10 | N-(4-sulfamoylphenyl)carbamoyl |

TABLE 1-continued

Compounds Prepared By The Methods Exemplified In Compounds 1-15, By Appropriate Reagent Selection.

| Ex. Cmpd. | Compound Name | E | L | γ | G |
|---|---|---|---|---|---|
| 201 | 11-(bis(pyridin-2-ylmethyl)amino)-N-(4-sulfamoylbenzyl)undecanamide | pyridin-2-yl | pyridin-2-yl | 10 | 4-sulfamoylbenzyl amide |
| 202 | 11-(Bis(pyridin-2-ylmethyl)amino)-N-(4-sulfamoylphenethyl)undecanamide | pyridin-2-yl | pyridin-2-yl | 10 | 4-sulfamoylphenethyl amide |
| 203 | 2-((6-oxo-6-(4-sulfamoylphenylamino)hexyl)(pyridin-2-ylmethyl)amino)acetic acid | pyridin-2-yl | carboxymethyl | 5 | 4-sulfamoylphenyl amide |
| 204 | [[[5-(Bis-pyridin-2-ylmethyl-amino)-pentylcarbamoyl]-methyl]-(2-{carboxymethyl-[(4-sulfamoyl-phenylcarbamoyl)-methyl]-amino}-ethyl)-amino]-acetic acid | pyridin-2-yl | pyridin-2-yl | 4 | bis-carboxymethyl ethylenediamine with 4-sulfamoylphenyl amide |

TABLE 1-continued

Compounds Prepared By The Methods Exemplified In Compounds 1-15, By Appropriate Reagent Selection.

| Ex. Cmpd. | Compound Name | E | L | Y | G |
|---|---|---|---|---|---|
| 205 | [{[8-(Bis-pyridin-2-ylmethyl-amino)-octylcarbamoyl]-methyl}-(2-{carboxymethyl-[((4-sulfamoyl-phenyl)carbamoyl)-methyl]-amino}-ethyl)-amino]-acetic acid | 2-pyridyl | 2-pyridyl | 8 | bis-amide branched structure with $CO_2H$ groups and 4-sulfamoylphenyl |
| 206 | tert-butyl 2-(2-(((2-tert-butoxy-2-oxoethyl)(4-sulfamoylphenethyl)amino)methyl)-1H-imidazol-1-yl)acetate | imidazole with tert-butyl acetate | imidazole with tert-butyl acetate | 2 | 4-($SO_2NH_2$)phenyl |
| 207 | 2,2'-(2,2'-(4-sulfamoylphenethylazanediyl)bis(methylene)bis(1H-imidazole-2,1-diyl)azanediyl))-diacetic acid | imidazole with N,N-diacetic acid | imidazole with N,N-diacetic acid | 2 | 4-($SO_2NH_2$)phenyl |

TABLE 1-continued

Compounds Prepared By The Methods Exemplified In Compounds 1-15, By Appropriate Reagent Selection.

| Ex. Cmpd. | Compound Name | E | L | Y | G |
|---|---|---|---|---|---|
| 208 | 2,2'-(2,2'-(8-(3-(4-sulfamoylphenyl)thioureido)octylazanediyl)bis(methylene)bis(1H-imidazole-2,1-diyl))diacetic acid | 2-(imidazol-1-yl)acetic acid | 2-(imidazol-1-yl)acetic acid | 8 | 4-sulfamoylphenyl thiourea |
| 209 | 3-(2-(2-(bis(pyridin-2-ylmethyl)amino)ethoxy)ethoxy)-N-(4-sulfamoylphenethyl)propanamide | pyridin-2-yl | pyridin-2-yl | 2 | N-(4-sulfamoylphenethyl) ethoxyethoxy propanamide |
| 210 | 3-(2-(2-(bis(pyridin-2-ylmethyl)amino)ethoxy)ethoxy)-N-(4-sulfamoylbenzyl)propanamide | pyridin-2-yl | pyridin-2-yl | 2 | N-(4-sulfamoylbenzyl) ethoxyethoxy propanamide |
| 211 | 3-(2-(2-(bis(pyridin-2-ylmethyl)amino)ethoxy)ethoxy)-N-(4-sulfamoylbenzyl)propanamide | pyridin-2-yl | pyridin-2-yl | 2 | N-(4-sulfamoylphenyl) ethoxyethoxy propanamide |

TABLE 1-continued

Compounds Prepared By The Methods Exemplified In Compounds 1-15, By Appropriate Reagent Selection.

| Ex. Cmpd. | Compound Name | E | L | γ | G |
|---|---|---|---|---|---|
| 212 | 11-(bis((1-methyl-1H-imidazol-2-yl)methyl)amino)-N-(4-sulfamoylphenyl)undecanamide | 1-methyl-1H-imidazol-2-yl | 1-methyl-1H-imidazol-2-yl | 10 | -C(O)-CH2-C6H4-SO2NH2 (4-sulfamoylphenyl ketone) |
| 213 | 6-(bis(pyridin-2-ylmethyl)amino)-N-(4-sulfamoylphenyl)hexanamide | pyridin-2-yl | pyridin-2-yl | 5 | -C(O)-NH-C6H4-SO2NH2 (4-sulfamoylphenyl amide) |

Compound 214: [Re(CO)₃][(S)-6-(bis((1-(carboxymethyl)-1H-imidazol-2-yl)methyl)amino)-2-(3-((S)-1-carboxy-4-oxo-4-(4-sulfamoylphenethylamino)butyl) ureido)hexanoic acid] (214-Re)

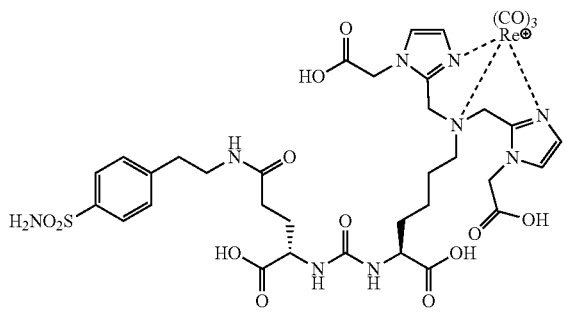

Step 1. (9S,13S)-15-benzyl 13,9-di-tert-butyl 3,11-dioxo-1-phenyl-2-oxa-4,10,12-triazapentadecane-9,13,15-tricarboxylate

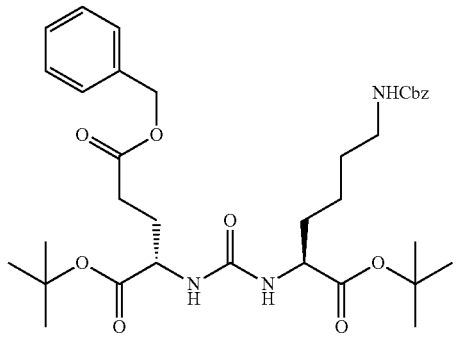 [SMILES: CC(C)(C)OC(=O)[C@H](CCCCNC(=O)OCc1ccccc1)NC(=O)N[C@@H](CCC(=O)OCc1ccccc1)C(=O)OC(C)(C)C]

To a solution of L-Glu(OBn)-OtBu hydrochloride (3.13 mg, 9.49 mmol) and triphosgene (923 mg, 3.13 mmol) in DCE (70 mL) cooled to −78° C. was added triethylamine (2.80 mL) under nitrogen. After stirring at −78° C. for 2 h, a solution of L-Lys(Z)-OtBu (3.88 g, 10.40 mmol) and TEA (1.5 mL) in DCE (10 mL) was added. The mixture was allowed to come to room temperature over a period of 1 h and stirred at room temperature overnight. The reaction was quenched with 1N HCl, and extracted with DCM. The organic layer was dried and concentrated under reduced pressure and the residue was purified utilizing a Biotage SP4 to afford (9S,13S)-15-benzyl 13,9-di-tert-butyl 3,11-dioxo-1-phenyl-2-oxa-4,10,12-triazapentadecane-9,13,15-tricarboxylate as a colorless oil (4.71 g, 76%). $^1$H NMR (400 MHz, CDCl₃) δ 7.34-7.29 (m, 10H), 5.13-5.04 (m, 6H), 4.97 (brs, 1H), 4.38-4.28 (m, 2H), 3.18-3.14 (m, 2H), 2.50-2.35 (m, 2H), 2.19-2.10 (m, 1H), 1.94-1.85 (m, 1H), 1.79-1.72 (m, 1H), 1.58-1.33 (m, 21H).

Step 2. (S)-4-(3-((S)-6-amino-1-tert-butoxy-1-oxohexan-2-yl)ureido)-5-tert-butoxy-5-oxopentanoic acid

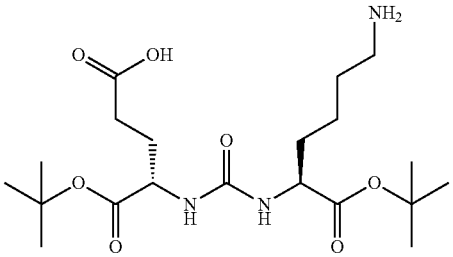 [SMILES: CC(C)(C)OC(=O)[C@H](CCCCN)NC(=O)N[C@@H](CCC(=O)O)C(=O)OC(C)(C)C]

A suspension of (9S,13S)-15-benzyl 13,9-di-tert-butyl 3,11-dioxo-1-phenyl-2-oxa-4,10,12-triazapentadecane-9,13,15-tricarboxylate (4.30 g, 6.64 mmol), 10% Pd/C (1.0 g) and ammonium formate (4.0 g) in EtOH (70 mL) under a empty balloon was stirred at room temperature overnight. The reaction mixture was filtered through a pad of celite and washed with EtOAc. The solvent was evaporated to give (S)-4-(3-((S)-6-amino-1-tert-butoxy-1-oxohexan-2-yl)ureido)-5-tert-butoxy-5-oxopentanoic acid (4.07 g, 70%) which was used without further purification. ESMS m/z: 432.3 (M/2+H)⁺.

Step 3. (S)-4-(3-((S)-6-(bis((1-(2-tert-butoxy-2-oxoethyl)-1H-imidazol-2-yl)methyl)amino)-1-tert-butoxy-1-oxohexan-2-yl)ureido)-5-tert-butoxy-5-oxopentanoic acid

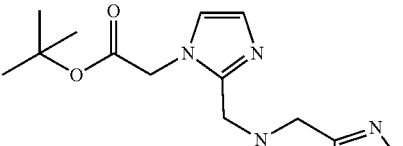

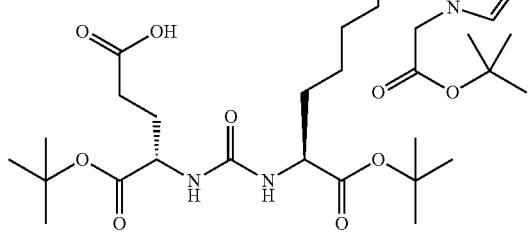

A solution of (S)-4-(3-((S)-6-amino-1-tert-butoxy-1-oxohexan-2-yl)ureido)-5-tert-butoxy-5-oxopentanoic acid (432 mg, 70% pure, 0.70 mmol), AcOH (0.10 mL) and tert-butyl 2-(2-formyl-1H-imidazol-1-yl)acetate (470 mg, 2.0 mmol) in DCE (20 mL) was stirred at 75° C. for 30 min under nitrogen. The reaction mixture was cooled to 0° C., and treated with NaBH(OAc)₃ (0.633 g, 3.0 mmol). The reaction was allowed to proceed overnight with stirring at room temperature. The reaction mixture was quenched with water and concentrated under reduced pressure to afford a residue which was purified by on a Biotage SP4 utilizing a gradient of 5-50% MeOH in DCM to afford (S)-4-(3-((S)-6-(bis((1-(2-tert-butoxy-2-oxoethyl)-1H-imidazol-2-yl)methyl)amino)-1-tert-butoxy-1-oxohexan-2-yl)ureido)-5-tert-butoxy-5-oxopentanoic acid (300 mg, 52%) as a colorless oil. ¹H NMR (400 MHz, CDCl₃) δ 6.99 (s, 2H), 6.84 (s, 2H), 4.57 (s, 4H), 4.29-4.19 (m, 2H), 3.66-3.56 (m, 4H), 2.98-2.90 (m, 2H), 2.49-2.37 (m, 4H), 1.95-1.41 (m, 42H); ESMS m/z: 410.8 (M/2+H)⁺.

Step 4. (S)-tert-butyl 6-(bis((1-(2-tert-butoxy-2-oxoethyl)-1H-imidazol-2-yl)methyl)amino)-2-(3-((S)-1-tert-butoxy-1,5-dioxo-5-(4-sulfamoylphenethylamino)pentan-2-yl)ureido)hexanoate

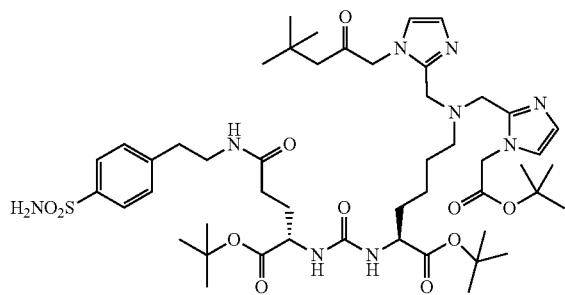 [SMILES: CC(C)(C)CC(=O)Cn1ccnc1CN(CCCC[C@H](NC(=O)N[C@@H](CCC(=O)NCCc1ccc(S(N)(=O)=O)cc1)C(=O)OC(C)(C)C)C(=O)OC(C)(C)C)Cc1nccn1CC(=O)OC(C)(C)C]

A solution of (S)-4-(3-((S)-6-(bis((1-(2-tert-butoxy-2-oxoethyl)-1H-imidazol-2-yl)methyl)amino)-1-tert-butoxy-1-oxohexan-2-yl)ureido)-5-tert-butoxy-5-oxopentanoic acid (80 mg, 0.098 mmol), 4-(2-aminoethyl)benzenesulfonamide (30 mg, 0.15 mmol), 2-(1-H-7-azabenzotriazol-1-yl)-1,1,3,3-tetramethyl uronium hexafluorophosphate methanaminium (HATU, 50 mg, 0.17 mmol), and DIPEA (0.50 mL) in DMF (5 mL) was stirred at 40° C. overnight. The solvents were evaporated under reduced pressure to give a residue, which was purified by Biotage SP4 using a gradient of 0-20% MeOH in DCM to give (S)-tert-butyl 6-(bis((1-(2-tert-butoxy-2-oxoethyl)-1H-imidazol-2-yl)methyl)amino)-2-(3-((S)-1-tert-butoxy-1,5-dioxo-5-(4-sulfamoylphenethylamino)pentan-2-yl)ureido)hexanoate (100 mg, 100%). ESMS m/z: 501.9 (M/2+H)⁺.

Step 5. [Re(CO)₃][(S)-6-(bis((1-(carboxymethyl)-1H-imidazol-2-yl)methyl)amino)-2-(3-((S)-1-carboxy-4-oxo-4-(4-sulfamoylphenethylamino)butyl)ureido)hexanoic acid] (214)

A solution of (S)-tert-butyl 6-(bis((1-(2-tert-butoxy-2-oxoethyl)-1H-imidazol-2-yl)methyl)amino)-2-(3-((S)-1-tert-butoxy-1,5-dioxo-5-(4-sulfamoylphenethylamino)pentan-2-yl)ureido)hexanoate (60 mg, 0.060 mmol) and [NEt₄]₂[ReBr₃(CO)₃] (60 mg, 0.077 mmol) in MeOH (4.0 mL) was stirred at 80° C. overnight in a sealed pressure tube. The solvent was evaporated under reduced pressure to give a residue. A solution of the above isolated residue was dissolved in DCM (2.0 mL) and trifluoroacetic acid (TFA) (2.0 mL) was added and the reaction mixture was stirred at room temperature for 2 h. The solvent was removed under reduced pressure to afford a residue, which was purified by HPLC to give [Re(CO)₃][(S)-6-(bis((1-(carboxymethyl)-1H-imida- zol-2-yl)methyl)amino)-2-(3-((S)-1-carboxy-4-oxo-4-(4-sulfamoylphenethylamino)butyl)ureido)hexanoic acid] (16 mg, 25% over 2 steps) as a white solid. ¹H NMR (400 MHz, DMSO-d₆) δ 7.94 (brs, 1H), 7.71 (d, J=8.4 Hz, 2H), 7.35 (d, J=8.4 Hz, 2H), 7.26 (s, 2H), 7.17 (s, 2H), 7.03 (s, 2H), 6.37-6.33 (m, 2H), 4.83 (s, 4H), 4.55 (d, J=16.4 Hz, 2H), 4.39 (d, J=16.4 Hz, 2H), 4.14-4.02 (m, 2H), 3.65-3.61 (m, 2H), 3.25-3.22 (m, 2H), 2.74 (t, J=7.0 Hz, 2H), 2.05-1.30 (m, 10H); ESMS m/z: 524.8 (M/2+H)⁺.

Compounds 217-220, 230 and 231a, b, and c were all prepared in overall yields ranging from 20-40% following the route depicted in Scheme 7. The first step, performed at 0° C. under inert conditions used the di-t-butyl ester of Glutamic acid with CDI in the presence of base to form the intermediate Glu-urea-imidazole derivative 2. This intermediate was activated with MeOTf under basic conditions to afford the methylated imidazole 3, which under inert conditions reacted readily with amines. The tert-butyl ester protecting groups were removed using 20% TFA in DCM for 1 to 4 hour at room temperature. Upon completion of the deprotection, the reactions were concentrated on a rotary evaporator or blown dry with nitrogen and purified on a silica column or recrystallized. The final products were tested in vitro and in vivo.

Scheme 7

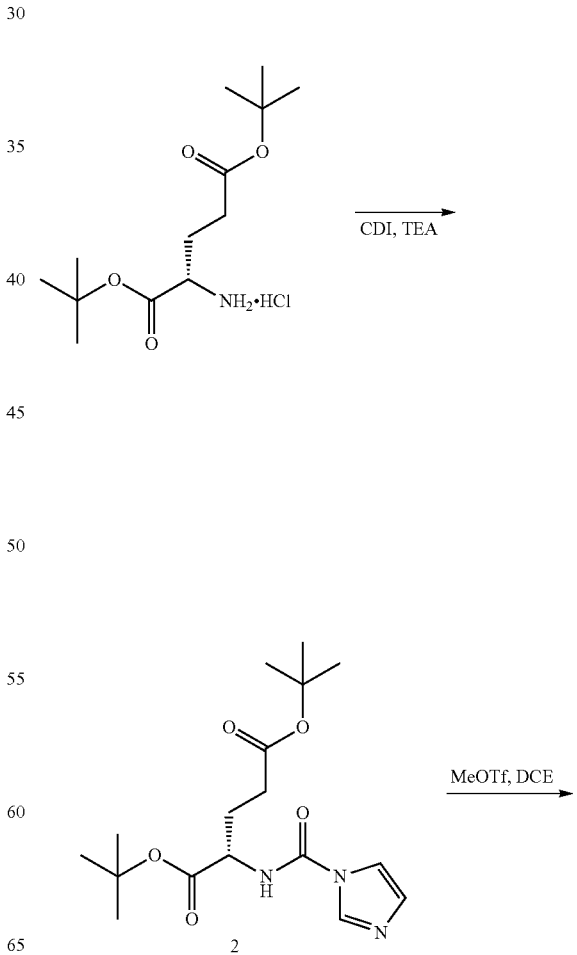

-continued

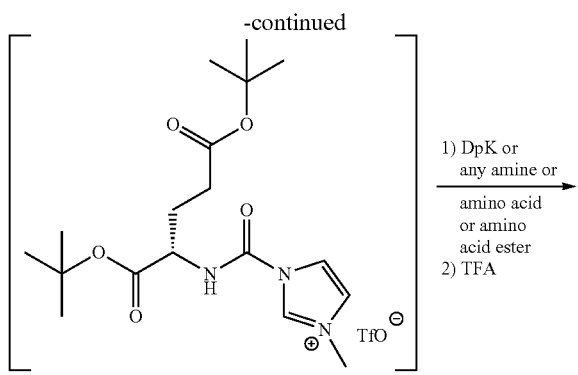

1) DpK or any amine or amino acid or amino acid ester
2) TFA ester complex was prepared employing the same procedure as described in the general rhenium experimental. The compound was deprotected using the previously described methods employing TFA to yield the desired product (4.0 mg, 29%) as an off-white solid. $^1$H NMR (400 MHz, DMSO-$d_6$) δ 7.2 (s, 2H), 7.0 (s, 2H), 6.3 (s, 2H), 4.85 (s, 4H), 4.55 (d, 2H), 4.4 (d, 2H), 4.10 (s, 2H), 3.5 (s, 2H), 2.2 (m, 2H), 1.7 (m, 6H), 1.25 (m, 2H). ESMS m/z: 866 (M+H)$^+$.

Compound 218: [Re(CO)$_3${(14R,18S)-1-(1-(carboxymethyl)-1H-imidazol-2-yl)-2-((1-(carboxymethyl)-1H-imidazol-2-yl)methyl)-8,16-dioxo-2,9,15,17-tetraazaicosane-14,18,20-tricarboxylic acid}]

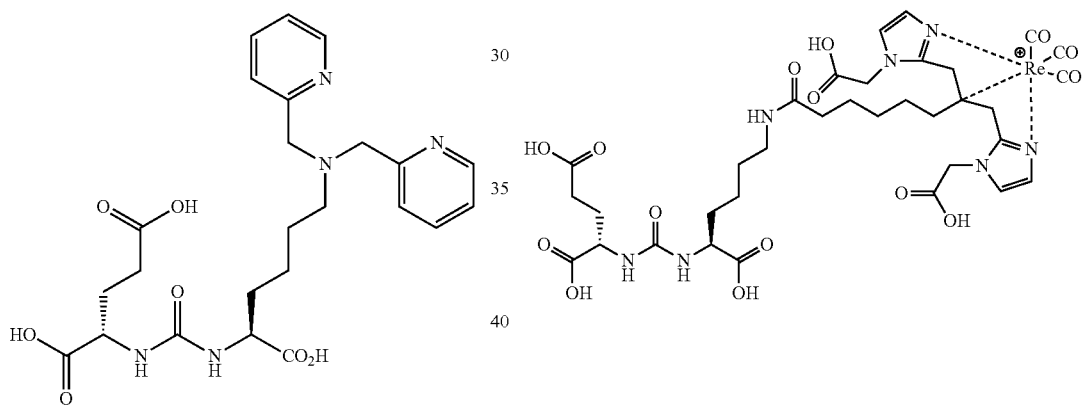

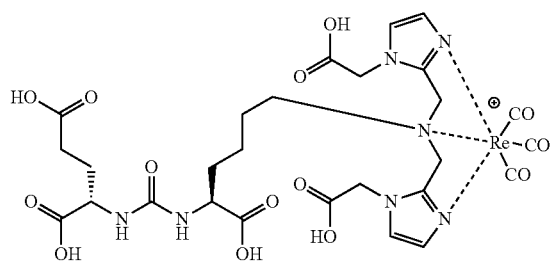

Compound 217: [Re(CO)$_3${(S)-2-(3-((R)-5-(bis((1-(carboxymethyl)-1H-imidazol-2-yl)methyl)amino)-1-carboxypentyl)ureido)pentanedioic acid}]

(S)-2-(3-((R)-5-(bis((1-(carboxymethyl)-1H-imidazol-2-yl)methyl)amino)-1-carboxypentyl)ureido) pentanedioic acid was prepared employing the same general procedure as shown in Scheme 7, using 2-[3-(5-Amino-1-carboxy-pentyl)-ureido]-pentanedioic acid di t-butyl ester. The rhenium (14R,18S)-1-(1-(carboxymethyl)-1H-imidazol-2-yl)-2-((1-(carboxymethyl)-1H-imidazol-2-yl)methyl)-8,16-dioxo-2,9,15,17-tetraazaicosane-14,18,20-tricarboxylic acid was prepared employing the same general procedure as shown in Scheme 7, using previously prepared and protected 2-[3-(5-Amino-1-carboxy-pentyl)-ureido]-pentanedioic acid di t-butyl ester. The rhenium ester complex was prepared employing the same procedure as described in the general rhenium experimental. The compound was deprotected using the previously described methods employing TFA to yield the desired product (8.0 mg, 13%) as an off-white solid. $^1$H NMR (400 MHz, DMSO-$d_6$) δ 7.9 (s, H), 7.2 (s, 2H), 7.0 (2, 2H), 6.3 (s, 2H), 4.85 (s, 4H), 4.55 (d, 2H), 4.4 (d, 2H), 4.1 (m, 2H), 3.5 (s, 2H), 2.9 (s, 4H), 2.2 (m, 2H), 2.05 (m, 2H), 1.85 (m, 2H), 1.6 (m, 6H), 1.3 (m, 4H). ESMS m/z: 979 (M+H)$^+$.

Compound 219: [Re(CO)$_3$\{(19R,23S)-1-(1-(carboxymethyl)-1H-imidazol-2-yl)-2-((1-(carboxymethyl)-1H-imidazol-2-yl)methyl)-13,21-dioxo-2,14,20,22-tetraazapentacosane-19,23,25-tricarboxylic acid\}]

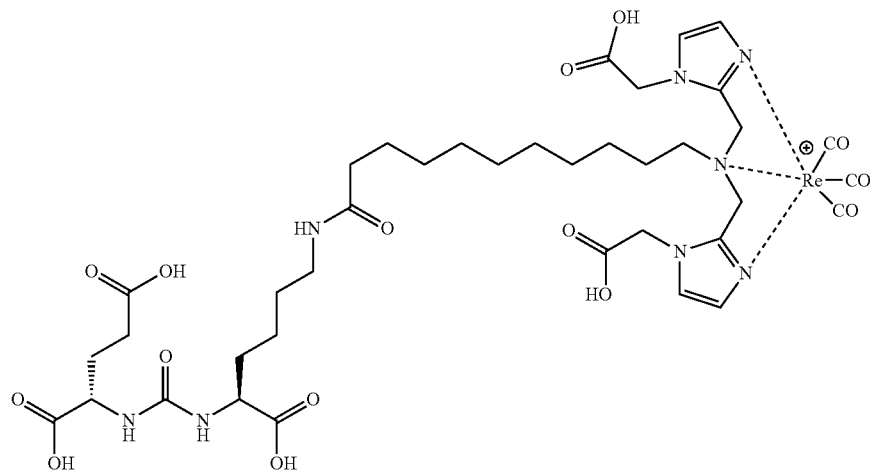

(19R,23S)-1-(1-(carboxymethyl)-1H-imidazol-2-yl)-2-((1-(carboxymethyl)-1H-imidazol-2-yl)methyl)-13,21-dioxo-2,14,20,22-tetraazapentacosane-19,23,25-tricarboxylic acid was prepared employing the same general procedure as shown in Scheme 7, using previously prepared and protected 2-[3-(5-Amino-1-carboxy-pentyl)-ureido]-pentanedioic acid di t-butyl ester. The rhenium ester complex was prepared employing the same procedure as described in the general rhenium experimental. The compound was deprotected using the previously described methods employing TFA to yield the desired product (7.0 mg, 24%) as an off-white solid. $^1$H NMR (400 MHz, DMSO-d$_6$) δ 7.8 (s, H), 7.2 (s, 2H), 7.0 (2, 2H), 6.3 (s, 2H), 4.8 (s, 4H), 4.55 (d, 2H), 4.4 (d, 2H), 4.1 (m, 2H), 3.5 (m, 2H), 2.9 (m, 2H), 2.2 (m, 2H), 2.05 (m, 4H), 1.9 (m, 4H), 1.6 (m, 4H), 1.4 (m, 2H) 1.3 (m, 16H). ESMS m/z: 525 (M/2).

Compound 230: [Re(CO)$_3$\{(19R,23S)-13,21-dioxo-2-(pyridin-2-ylmethyl)-2,14,20,22-tetraazapentacosane-1,19,23,25-tetracarboxylic acid\}]

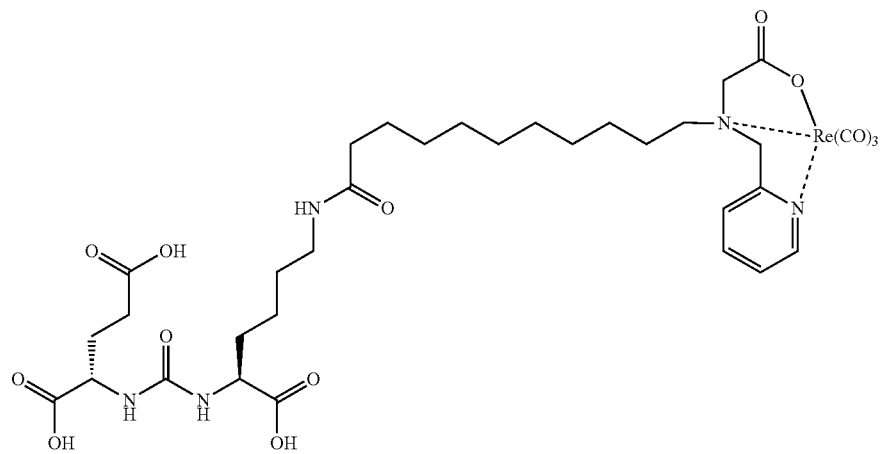

The C11-PAMA compound, (19R,23S)-13,21-dioxo-2-(pyridin-2-ylmethyl)-2,14,20,22-tetraazapentacosane-1,19,23,25-tetracarboxylic acid was prepared employing the same general procedure as the general procedure outlined in Scheme 7, using previously prepared and protected 2-[3-(5-Amino-1-carboxy-pentyl)-ureido]-pentanedioic acid di t-butyl ester. The rhenium ester complex was prepared employing the same procedure as described in the general rhenium experimental. The compound was deprotected using the previously described methods to yield the desired product (3.0 mg, 75%) as an off-white solid. ESMS m/z: 922 (M+H)$^+$.

Compound 220: [Re(CO)$_3${(17R,21S)-1-(1-(carboxymethyl)-1H-imidazol-2-yl)-2-((1-(carboxymethyl)-1H-imidazol-2-yl)methyl)-11,19-dioxo-5,8-dioxa-2,12,18,20-tetraazatricosane-17,21,23-tricarboxylic acid}]

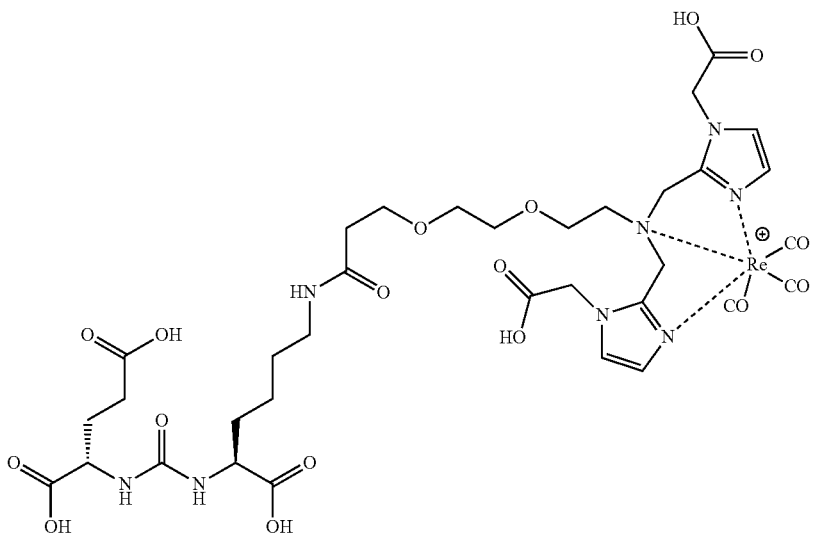

(17R,21S)-1-(1-(carboxymethyl)-1H-imidazol-2-yl)-2-((1-(carboxymethyl)-1H-imidazol-2-yl)methyl)-11,19-dioxo-5,8-dioxa-2,12,18,20-tetraazatricosane-17,21,23-tricarboxylic acid was prepared employing the same general procedure as shown in Scheme 7, using previously prepared and protected 2-[3-(5-Amino-1-carboxy-pentyl)-ureido]-pentanedioic acid di t-butyl ester. The rhenium ester complex was prepared employing the same procedure as described in the general rhenium experimental. The compound was deprotected using the previously described methods employing TFA to yield the desired product (6.0 mg, 38%) as an off-white solid. $^1$H NMR (400 MHz, DMSO-d$_6$) δ 7.9 (s, H), 7.2 (s, 2H), 7.0 (s, 2H), 6.3 (s, 2H), 4.85 (s, 4H), 4.6 (d, 2H), 4.5 (d, 2H), 3.80 (m, 12H), 3.5 (m, 10H), 2.4 (m, 4H). ESMS m/z: 738 (M+H)$^+$.

Compounds 231a, b, and c

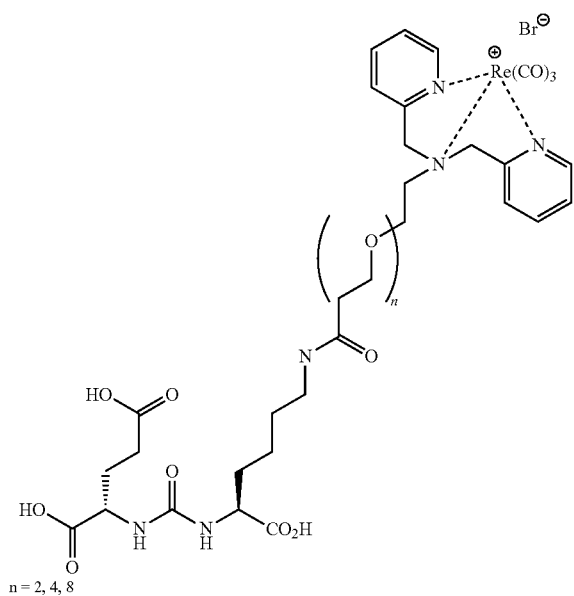

n = 2, 4, 8

Compound 231a (n=2): Glu-urea-Lys-PEG2-ReDP: [Re(CO)₃{(17R,21S)-11,19-dioxo-1-(pyridin-2-yl)-2-(pyridin-2-ylmethyl)-5,8-dioxa-2,12,18,20-tetraazatricosane-17,21,23-tricarboxylic acid}][Br]

The PEG2 dipyridyl compound, (17R,21S)-11,19-dioxo-1-(pyridin-2-yl)-2-(pyridin-2-ylmethyl)-5,8-dioxa-2,12,18,20-tetraazatricosane-17,21,23-tricarboxylic acid was prepared employing the same general procedure as that of Compound 220, using previously prepared and protected 2-[3-(5-Amino-1-carboxy-pentyl)-ureido]-pentanedioic acid di t-butyl ester. The rhenium ester complex was prepared employing the same procedure as described in the general rhenium experimental. The compound was deprotected using the previously described methods to yield the desired product (2 mg, 20%) as an off-white solid. $^1$H NMR (400 MHz, DMSO-$d_6$) δ 8.8 (d), 8.00 (dd), 7.55 (d), 7.42 (dd), 6.45 (s), 3.95 (m), 3.4-3.6 (m), 2.45 (m), 1.25 (m), 1.1 (m), 0.8 (m). ESMS m/z: 931 (M+H)$^+$.

Compound 231b (n=4): Glu-urea-Lys-PEG4-ReDP: [Re(CO)₃{(23R,27S)-17,25-dioxo-1-(pyridin-2-yl)-2-(pyridin-2-ylmethyl)-5,8,11,14-tetraoxa-2,18,24,26-tetraazanonacosane-23,27,29-tricarboxylic acid}][Br]

The PEG4 dipyridyl compound (23R,27S)-17,25-dioxo-1-(pyridin-2-yl)-2-(pyridin-2-ylmethyl)-5,8,11,14-tetraoxa-2,18,24,26-tetraazanonacosane-23,27,29-tricarboxylic acid was prepared employing the same general procedure that for Compound 231a, using previously prepared and protected 2-[3-(5-Amino-1-carboxy-pentyl)-ureido]-pentanedioic acid di t-butyl ester. The rhenium ester complex was prepared employing the same procedure as described in the general rhenium experimental. The compound was deprotected using the previously described methods to yield the desired product. (5.1 mg, 29.6%) as a white solid. ESMS m/z: 1019 (M+H)$^+$.

Compound 231c (n=8): Glu-urea-Lys-PEG8-ReDP: [Re(CO)₃{(35R,39S)-29,37-dioxo-1-(pyridin-2-yl)-2-(pyridin-2-ylmethyl)-5,8,11,14,17,20,23,26-octaoxa-2,30,36,38-tetraazahentetracontane-35,39,41-tricarboxylic acid}][Br]

The PEG8 dipyridyl compound, (35R,39S)-29,37-dioxo-1-(pyridin-2-yl)-2-(pyridin-2-ylmethyl)-5,8,11,14,17,20,23,26-octaoxa-2,30,36,38-tetraazahentetracontane-35,39,41-tricarboxylic acid was prepared employing the same general procedure as for Compound 231a, using previously prepared and protected 2-[3-(5-Amino-1-carboxy-pentyl)-ureido]-pentanedioic acid di t-butyl ester. The rhenium ester complex was prepared employing the same procedure as described in the general rhenium experimental. The compound was deprotected using the previously described methods to yield the desired product (8.0 mg, 30.4%) as a white solid. ESMS m/z: 1195 (M+H)$^+$.

Compound 221: [Re(CO)₃][(19S,23S)-2-((1-(carboxymethyl)-1H-imidazol-2-yl)methyl)-13,21-dioxo-2,14,20,22-tetraazapentacosane-1,19,23,25-tetracarboxylic acid]

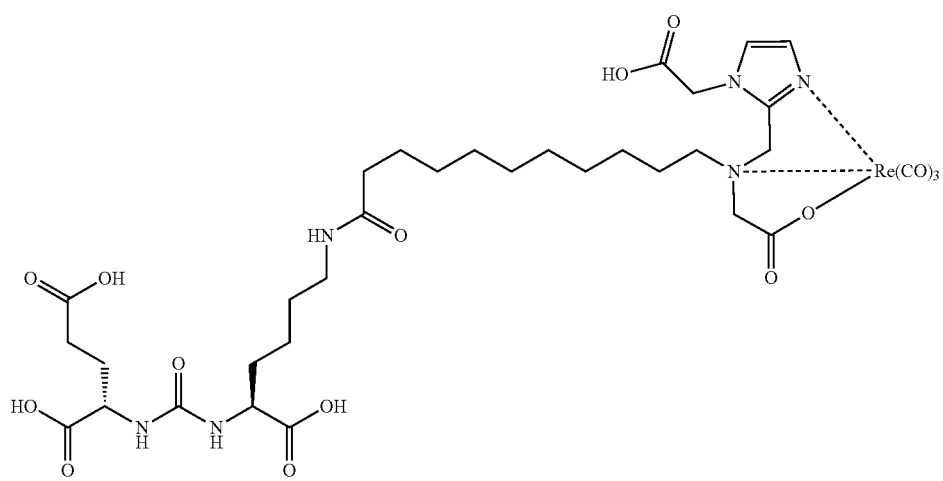

Step 1. 11-((2-tert-butoxy-2-oxoethyl)((1-(2-tert-butoxy-2-oxoethyl)-1H-imidazol-2-yl)-methyl)amino)undecanoic acid

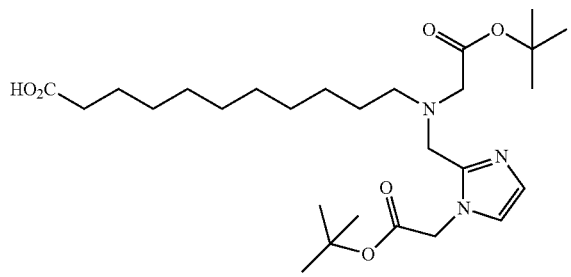 [SMILES: CC(C)(C)OC(=O)CN(CCCCCCCCCCC(=O)O)Cc1nccn1CC(=O)OC(C)(C)C]

A suspension of 11-aminoundecanoic acid (603 mg, 3.0 mmol), 2-pyridinecarboxaldehyde (630 mg, 3.0 mmol) and AcOH (0.20 mL) in DCE (20 mL) was refluxed for 30 min under nitrogen. The reaction mixture was cooled to 0° C., and treated sequentially with NaBH(OAc)$_3$ (1.908 g, 9.0 mmol) and crude tert-butyl glyoxalate (1.50 g, 11.5 mmol). The reaction mixture was stirred at room temperature for overnight and decomposed with water. The reaction mixture was extracted with DCM. The organic layer was dried and concentrated under reduced pressure. The residue was purified by biotage over silica gel column to afford 11-((2-tert-butoxy-2-oxoethyl)((1-(2-tert-butoxy-2-oxoethyl)-1H-imidazol-2-yl)methyl)amino)undecanoic acid (343 mg, 22%) as a yellow oil. $^1$H NMR (400 MHz, CDCl$_3$) 7.01 (d, J=1.2 Hz, 0.46H), 6.99 (d, J=1.2 Hz, 0.54H), 6.88 (d, J=1.2 Hz, 0.54H), 6.86 (d, J=1.2 Hz, 0.46H), 5.30 (s, 1.08H), 5.07 (s, 0.92H), 4.67 (s, 2H), 4.66 (s, 2H), 3.83 (s, 0.92H), 3.17 (s, 1.08H), 2.41-2.32 (m, 2H), 1.66-1.63 (m, 2H), 1.47 (s, 9H), 1.45 (s, 9H), 1.42-1.10 (m, 14H); MS (ESI), 510 (M+H)$^+$.

Step 2. (19S,23S)-tetra-tert-butyl 2-((1-(2-tert-butoxy-2-oxoethyl)-1H-imidazol-2-yl)-methyl)-13,21-dioxo-2,14,20,22-tetraazapentacosane-1,19,23,25-tetracarboxylate A solution of (S)-di-tert-butyl 2-(3-((S)-6-amino-1-tert-butoxy-1-oxohexan-2-yl)ureido)pentanedioate (85 mg, 0.175 mmol), 11-((2-tert-butoxy-2-oxoethyl)((1-(2-tert-butoxy-2-oxoethyl)-1H-imidazol-2-yl)methyl)amino)undecanoic acid (89 mg, 0.175 mmol), EDCI (38 mg, 0.20 mmol), HOBt (26 mg, 0.20) and DIPEA (0.30 mL) in DCM (5.0 mL) was stirred at rt for 3 days. The reaction mixture was purified by biotage eluting with 1% to 10% MeOH in DCM to afford (19S,23S)-tetra-tert-butyl 2-((1-(2-tert-butoxy-2-oxoethyl)-1H-imidazol-2-yl)methyl)-13,21-dioxo-2,14,20,22-tetraazapentacosane-1,19,23,25-tetracarboxylate (111 mg, 65%) as a yellow oil. MS (ESI), 490.5 (M/2+H)$^+$.

Step 3. [Re(CO)$_3$][(19S,23S)-2-((1-(carboxymethyl)-1H-imidazol-2-yl)methyl)-13,21-dioxo-2,14,20,22-tetraazapentacosane-1,19,23,25-tetracarboxylic acid] (221)

A solution of (19S,23S)-tetra-tert-butyl 2-((1-(2-tert-butoxy-2-oxoethyl)-1H-imidazol-2-yl)methyl)-13,21-dioxo-2,14,20,22-tetraazapentacosane-1,19,23,25-tetracarboxylate (18.8 mg, 0.019 mmol) in TFA (1.0 mL)/DCM (1.0 mL) was stirred at room temperature for overnight. The solvent was evaporated to give 19S,23S)-2-((1-(carboxymethyl)-1H-imidazol-2-yl)methyl)-13,21-dioxo-2,14,20,22-tetraazapentacosane-1,19,23,25-tetracarboxylic acid as a colorless oil. To a solution of the above deprotected product in water (1.0 mL) that was adjusted to pH=9 by 2 N NaOH was added Re(CO)$_3$(H2O)OTf (0.50 mL, 0.10 mL/mmol). The reaction mixtures were stirred at room temperature for overnight and purified by HPLC to afford the title compound (4.0 mg, 19%) as a white solid. $^1$H NMR (400 MHz, DMSO-d$_6$) 7.70 (t, J=5.6 Hz, 1H), 7.33 (s, 1H), 7.13 (s, 2H), 6.29 (d, J=8.4 Hz, 1H), 6.26 (d, J=8.4 Hz, 1H), 4.96 (d, J=4.8 Hz, 2H), 4.56 (d, J=16.4 Hz, 1H), 4.12 (d, J=16.8 Hz, 1H), 4.07-3.90 (m, 2H), 3.70 (d, J=17.2 Hz, 1H), 3.40 (d, J=17.2 Hz, 1H), 2.98-2.94 (m, 4H), 2.21 (q, J=7.73, 2 H), 1.99 (t, J=7.6 Hz, 2H), 1.70-1.22 (m, 24H); MS (ESI), 485.2 (M/2+H)$^+$.

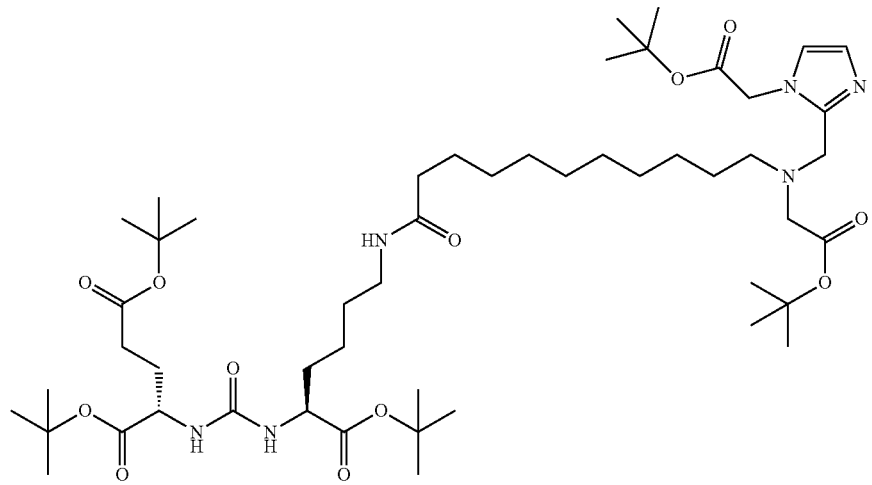 [SMILES: CC(C)(C)OC(=O)CC[C@H](NC(=O)N[C@@H](CCCCNC(=O)CCCCCCCCCCN(CC(=O)OC(C)(C)C)Cc1nccn1CC(=O)OC(C)(C)C)C(=O)OC(C)(C)C)C(=O)OC(C)(C)C]

Compound 222: [Re(CO)₃][(7S,14S,18S)-7-amino-1-(1-(carboxymethyl)-1H-imidazol-2-yl)-2-((1-(carboxymethyl)-1H-imidazol-2-yl)methyl)-8,16-dioxo-2,9,15,17-tetraazaicosane-14,18,20-tricarboxylic acid]

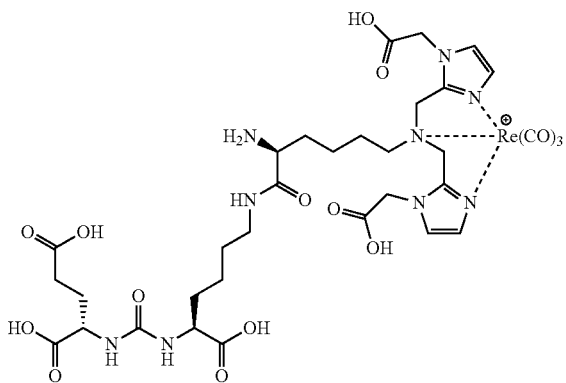

Step 1. (5S,12S,16S)-tri-tert-butyl 5-(4-(bis((1-(2-tert-butoxy-2-oxoethyl)-1H-imidazol-2-yl)methyl)amino)butyl)-1-(9H-fluoren-9-yl)-3,6,14-trioxo-2-oxa-4,7,13,15-tetraazaoctadecane-12,16,18-tricarboxylate

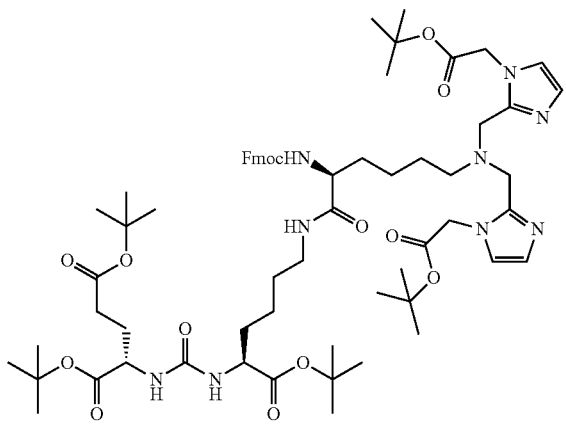

A solution of (S)-di-tert-butyl 2-(3-((S)-6-amino-1-tert-butoxy-1-oxohexan-2-yl)ureido)pentanedioate (97 mg, 0.20 mmol), Compound 2 (151 mg, 0.20 mmol), EDCI (38 mg, 0.20 mmol), HOBt (26 mg, 0.20) and DIPEA (0.30 mL) in DCM (5.0 mL) was stirred at rt for overnight. The reaction mixture was purified by biotage eluting with 1% to 10% MeOH in DCM to afford (5S,12S,16S)-tri-tert-butyl 5-(4-(bis((1-(2-tert-butoxy-2-oxoethyl)-1H-imidazol-2-yl)methyl)amino)butyl)-1-(9H-fluoren-9-yl)-3,6,14-trioxo-2-oxa-4,7,13,15-tetraazaoctadecane-12,16,18-tricarboxylate (85.7 mg, 35%) as a white solid. ¹H NMR (400 MHz, CDCl₃) 7.75 (d, J=7.6 Hz, 2H), 7.64 (d, J=7.6 Hz, 2H), 7.38 (t, J=7.4 Hz, 2H), 7.29 (dd, J=7.6, 4.4 Hz, 2H), 7.02 (brs, 1H), 6.93 (s, 2H), 6.80 (s, 2H), 6.08 (d, J=8.0 Hz, 1H), 5.75 (d, J=8.8 Hz, 1H), 5.67 (d, J=7.6 Hz, 1H), 4.58 (s, 2H), 4.56 (s, 2H), 4.55-4.52 (m, 1H), 4.36-4.29 (m, 3H), 4.21 (d, J=7.0 Hz, 1H), 4.13 (t, J=6.8 Hz, 1H), 3.63 (s, 4H), 3.48-3.46 (m, 1H), 3.05-3.01 (m, 1H), 2.53 (t, J=7.2 Hz, 2H), 2.33-2.26 (m, 2H), 2.07-2.00 (m, 2H), 1.77-1.26 (m, 55H); MS (ESI), 614.0 (M/2+H)⁺.

Step 2. (7S,14S,18S)-tri-tert-butyl 7-amino-1-(1-(2-tert-butoxy-2-oxoethyl)-1H-imidazol-2-yl)-2-((1-(2-tert-butoxy-2-oxoethyl)-1H-imidazol-2-yl)methyl)-8,16-dioxo-2,9,15,17-tetraazaicosane-14,18,20-tricarboxylate

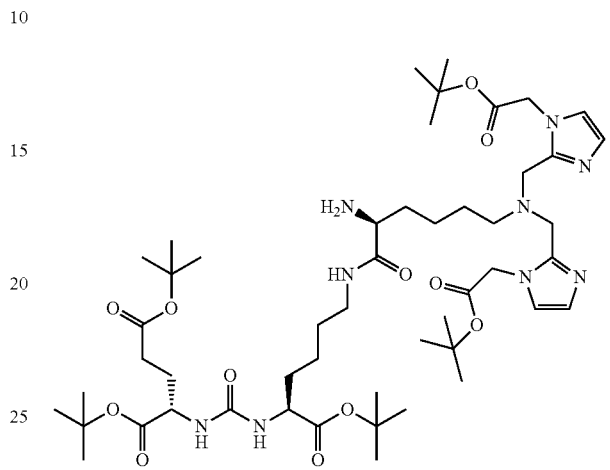

To a solution of (5S,12S,16S)-tri-tert-butyl 5-(4-(bis((1-(2-tert-butoxy-2-oxoethyl)-1H-imidazol-2-yl)methyl)amino)butyl)-1-(9H-fluoren-9-yl)-3,6,14-trioxo-2-oxa-4,7,13,15-tetraazaoctadecane-12,16,18-tricarboxylate (84 mg, 0.069 mmol) in DMF (0.50 mL) was added piperidine (0.50 mL). The mixture was stirred at room temperature for 2 hrs. Solvent was evaporated under reduce pressure to afford a residue, which was purified by biotage eluting with 5% MeOH to 25% MeOH in DCM to afford (7S,14S,18S)-tri-tert-butyl 7-amino-1-(1-(2-tert-butoxy-2-oxoethyl)-1H-imidazol-2-yl)-2-((1-(2-tert-butoxy-2-oxoethyl)-1H-imidazol-2-yl)methyl)-8,16-dioxo-2,9,15,17-tetraazaicosane-14,18,20-tricarboxylate (59 mg, 86%). ¹H NMR (400 MHz, CDCl₃) 6.96 (d, J=0.8 Hz, 2H), 6.85 (d, J=0.8 Hz, 2H), 5.55 (brs, 1H), 5.43 (brs, 1H), 4.59 (s, 4H), 4.37-4.28 (m, 2H), 3.61 (s, 4H), 3.35-3.27 (m, 2H), 3.18-3.12 (m, 1H), 2.53 (t, J=7.4 Hz, 2H), 2.34-2.28 (m, 2H), 2.10-2.00 (m, 2H), 1.85-1.26 (m, 55H); MS (ESI), 503.0 (M/2+H)⁺.

Step 3. [Re(CO)₃][(7S,14S,18S)-7-amino-1-(1-(carboxymethyl)-1H-imidazol-2-yl)-2-((1-(carboxymethyl)-1H-imidazol-2-yl)methyl)-8,16-dioxo-2,9,15,17-tetraazaicosane-14,18,20-tricarboxylic acid]

A solution of (7S,14S,18S)-tri-tert-butyl 7-amino-1-(1-(2-tert-butoxy-2-oxoethyl)-1H-imidazol-2-yl)-2-((1-(2-tert-butoxy-2-oxoethyl)-1H-imidazol-2-yl)methyl)-8,16-dioxo-2,9,15,17-tetraazaicosane-14,18,20-tricarboxylate (42 mg, 0.042 mmol) and [NEt₄]₂[Re(CO)₃Br₃] (42 mg, 0.055 mmol) in MeOH (5 mL) at a pressure tube was stirred at 90° C. for 4 hrs. The solvent was evaporated to give a residue, which was directly used for next step. A solution of the above product in TFA (3.0 mL)/DCM (3.0 mL) was stirred at room temperature for overnight. The solvent was evaporated to give a crude product, which was purified by HPLC to give the tile compound (27.9 mg, 67% over 2 steps) as a white solid. ¹H NMR (400 MHz, DMSO-d₆) 8.42 (brs, 1H), 8.10 (brs, 2H), 7.18 (s, 2H), 7.04 (s, 2H), 6.32 (d, J=8.4 Hz, 1H), 6.29 (d, J=8.0 Hz, 1H), 4.02 (s, 4H), 4.56-4.37 (m, 4H), 4.08-4.01 (m, 2H), 3.68-3.61 (m, 3H), 3.11-3.08 (m, 2H), 2.23-1.29 (m, 16H); MS (ESI), 497.7 (M/2+H)⁺.

Compound 223: [Re(CO)₃][(19S,23S)-1-(1-(2-(bis(carboxymethyl)amino)-2-oxoethyl)-1H-imidazol-2-yl)-2-((1-(2-(bis(carboxymethyl)amino)-2-oxoethyl)-1H-imidazol-2-yl)methyl)-13,21-dioxo-2,14,20,22-tetraazapentacosane-19,23,25-tricarboxylic acid]

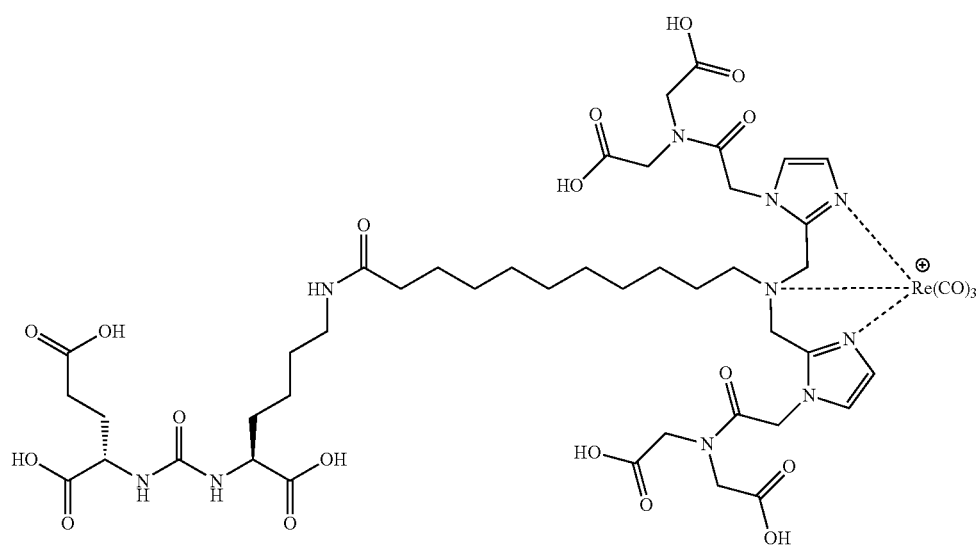

Step 1. tert-butyl 2,2'-(2-bromoacetylazanediyl)diacetate

To a solution of tert-butyl 2,2'-azanediyldiacetate (3.00 g, 12.24 mmol) and 2-bromoacetyl bromide (1.39 mL, 3.23 g, 16.00 mmol) in DCM (100 mL) was added Et₃N (2.0 mL) at room temperature. The reaction mixtures were stirred at room temperature for 2 hrs. The reaction mixtures were diluted with DCM (300 mL), washed with water, abd dried over Na₂SO₄. Solvent was evaporated under reduce pressure to afford a residue, which was purified by biotage eluting with 10% hexanes in EtOAc to 50% hexanes in EtOAc to tert-butyl 2,2'-(2-bromoacetylazanediyl)diacetate (4.68 g, 100%). ¹H NMR (400 MHz, CDCl₃) 4.09 (s, 2H), 4.07 (s, 2H), 3.86 (s, 2H), 1.49 (s, 9H), 1.46 (s, 9H); MS (ESI), 388, 390 (M+Na)⁺.

Step 2. tert-butyl 2,2'-(2-(2-formyl-1H-imidazol-1-yl)acetylazanediyl)diacetate

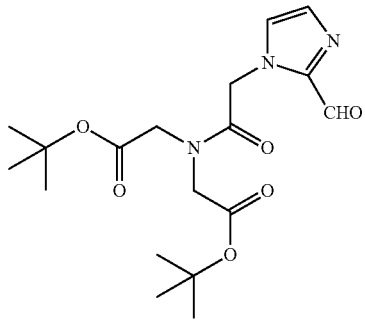 [SMILES: CC(C)(C)OC(=O)CN(CC(=O)OC(C)(C)C)C(=O)Cn1ccnc1C=O]

A solution of tert-butyl 2,2'-(2-bromoacetylazanediyl)diacetate (4.55 g, 12.43 mmol), 1H-imidazole-2-carbaldehyde (1.536 g, 16.0 mmol), DIPEA (5.0 mL), and KI (0.64 g, 4.0 mmol) was stirred at 80° C. for overnight. After the solvent was evaporated under reduced pressure, the reaction mixture was diluted with DCM, washed with water and dried. Solvent was evaporated under reduce pressure to afford a residue, which was purified by biotage eluting with DCM to 3% MeOH in DCM to tert-butyl 2,2'-(2-(2-formyl-1H-imidazol-1-yl)acetylazanediyl)diacetate (3.96 g, 84%). $^1$H NMR (400 MHz, CDCl$_3$) 9.76 (s, 1H), 7.31 (s, 1H), 7.25 (s, 1H), 5.30 (s, 2H), 4.14 (s, 2H), 4.07 (s, 2H), 1.51 (s, 9H), 1.43 (s, 9H); MS (ESI), 382 (M+H)$^+$.

Step 3. 11-(bis((1-(2-(bis(2-tert-butoxy-2-oxoethyl)amino)-2-oxoethyl)-1H-imidazol-2-yl)methyl)amino)undecanoic acid A solution of 11-aminoundecanoic acid (100 mg, 0.50 mmol), tert-butyl 2,2'-(2-(2-formyl-1H-imidazol-1-yl)acetylazanediyl)diacetate (381 mg, 1.0 mmol) and AcOH (0.02 mL) in DCE (30 mL) was stirred at 75° C. for 30 min under nitrogen. The reaction mixture was cooled to 0° C., and treated with NaBH(OAc)$_3$ (0.3165 g, 1.5 mmol). The reaction mixture was stirred at room temperature for overnight and decomposed with water. Solvent was evaporated under reduce pressure to afford a residue, which was purified by biotage eluting with 1-10% MeOH in DCM 11-(bis((1-(2-(bis(2-tert-butoxy-2-oxoethyl)amino)-2-oxoethyl)-1H-imidazol-2-yl)methyl)amino)undecanoic acid (368 mg, 79%). $^1$H NMR (400 MHz, DMSO-d$_6$) 6.93 (s, 2H), 6.76 (s, 2H), 5.02 (s, 4H), 4.29 (s, 4H), 3.93 (s, 4H), 3.44 (s, 4H), 2.30 (t, J=7.6 Hz, 2H), 2.09 (t, J=7.6 Hz, 2H), 1.43 (s, 18H), 1.35 (s, 18H), 1.29-1.00 (m, 16H); MS (ESI), 466.9 (M/2+H)$^+$.

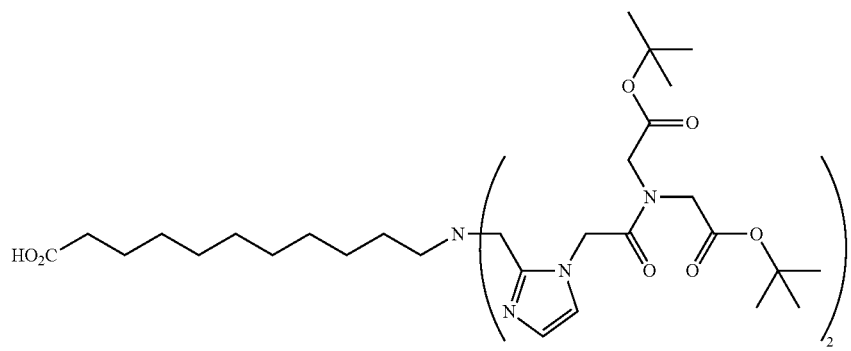

Step 4. (19S,23S)-tri-tert-butyl 1-(1-(2-(bis(2-tert-butoxy-2-oxoethyl)amino)-2-oxoethyl)-1H-imidazol-2-yl)-2-((1-(2-(bis(2-tert-butoxy-2-oxoethyl)amino)-2-oxoethyl)-1H-imidazol-2-yl)methyl)-13,21-dioxo-2,14,20,22-tetraazapentacosane-19,23,25-tricarboxylate

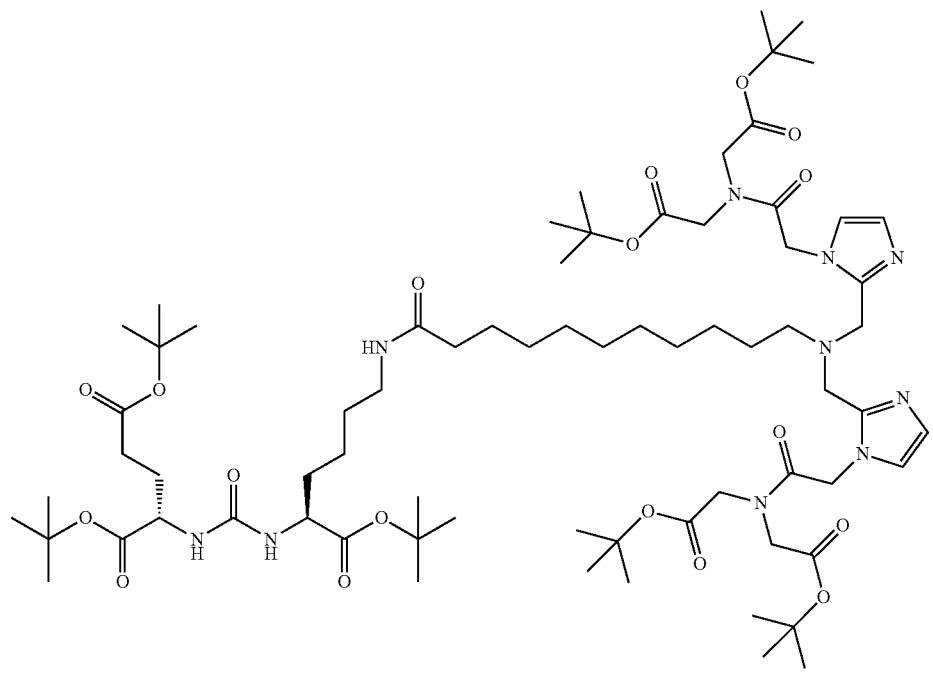 [SMILES: CC(C)(C)OC(=O)CC[C@H](NC(=O)N[C@@H](CCCCNC(=O)CCCCCCCCCCN(Cc1nccn1CC(=O)N(CC(=O)OC(C)(C)C)CC(=O)OC(C)(C)C)Cc1nccn1CC(=O)N(CC(=O)OC(C)(C)C)CC(=O)OC(C)(C)C)C(=O)OC(C)(C)C)C(=O)OC(C)(C)C]

A solution of (S)-di-tert-butyl 2-(3-((S)-6-amino-1-tert-butoxy-1-oxohexan-2-yl)ureido)pentanedioate (85 mg, 0.174 mmol), 11-(bis((1-(2-(bis(2-tert-butoxy-2-oxoethyl)amino)-2-oxoethyl)-1H-imidazol-2-yl)methyl)amino)undecanoic acid (118 mg, 0.127 mmol), EDCI (38 mg, 0.20 mmol), HOBt (26 mg, 0.20) and DIPEA (0.30 mL) in DCM (5.0 mL) was stirred at rt for overnight. The reaction mixture was purified by biotage eluting with 1% to 10% MeOH in DCM to afford (19S,23S)-tri-tert-butyl 1-(1-(2-(bis(2-tert-butoxy-2-oxoethyl)amino)-2-oxoethyl)-1H-imidazol-2-yl)-2-((1-(2-(bis(2-tert-butoxy-2-oxoethyl)amino)-2-oxoethyl)-1H-imidazol-2-yl)methyl)-13,21-dioxo-2,14,20,22-tetraazapentacosane-19,23,25-tricarboxylate (38 mg, 21%) as a colorless oil. $^1$H NMR (400 MHz, CDCl$_3$) 6.95 (d, J=1.2 Hz, 2H), 6.83 (d, J=0.80 Hz, 2H), 5.97 (s, 1H), 5.28 (d, J=7.6 Hz, 1H), 5.23 (d, J=8.4 Hz, 1H), 4.94 (s, 4H), 4.33-4.25 (m, 2H), 4.12 (s, 4H), 4.03 (s, 4H), 3.63 (s, 4H), 3.25-3.16 (m, 2H), 2.53 (t, J=7.4 Hz, 2H), 2.33-2.24 (m, 2H), 2.15 (t, J=7.6 Hz, 2H), 2.08-2.03 (m, 2H), 2.02-1.20 (m, 85H); MS (ESI), 701.6 (M/2+H)$^+$.

Step 5. [Re(CO)$_3$][(19S,23S)-1-(1-(2-(bis(carboxymethyl)amino)-2-oxoethyl)-1H-imidazol-2-yl)-2-((1-(2-(bis(carboxymethyl)amino)-2-oxoethyl)-1H-imidazol-2-yl)methyl)-13,21-dioxo-2,14,20,22-tetraazapentacosane-19,23,25-tricarboxylic acid] (223)

A solution of (19S,23S)-tri-tert-butyl 1-(1-(2-(bis(2-tert-butoxy-2-oxoethyl)amino)-2-oxoethyl)-1H-imidazol-2-yl)-2-((1-(2-(bis(2-tert-butoxy-2-oxoethyl)amino)-2-oxoethyl)-1H-imidazol-2-yl)methyl)-13,21-dioxo-2,14,20,22-tetraazapentacosane-19,23,25-tricarboxylate (28 mg, 0.02 mmol) and [NEt$_4$]$_2$[Re(CO)$_3$Br$_3$] (30 mg, 0.039 mmol) in MeOH (5 mL) at a pressure tube was stirred at 90° C. for overnight. The solvent was evaporated to give a residue, which was directly used for next step. A solution of the above product in TFA (3.0 mL)/DCM (3.0 mL) was stirred at room temperature for 3 hrs. The solvent was evaporated to give a crude product, which was purified by HPLC to give the title compound (17.6 mg, 69% over 2 steps) as a white solid. $^1$H NMR (400 MHz, DMSO-d$_6$) 7.70 (t, J=4.8 Hz, 1H), 7.10 (s, 2H), 7.03 (s, 2H), 6.29 (d, J=8.4 Hz, 1H), 6.26 (d, J=8.4 Hz, 1H), 5.02 (s, 4H), 4.37-3.97 (m, 14H), 3.60-3.57 (m, 2H), 3.01-2.94 (m, 2H), 2.24-1.22 (m, 28H); MS (ESI), 640.3 (M/2+H)$^+$.

Compound 224: [Re(CO)$_3$][(7S,14S,18S)-7-amino-1-(1-(2-(bis(carboxymethyl) amino)-2-oxoethyl)-1H-imidazol-2-yl)-2-((1-(2-(bis(carboxymethyl) amino)-2-oxoethyl)-1H-imidazol-2-yl)methyl)-8,16-dioxo-2,9,15,17-tetraazaicosane-14,18,20-tricarboxylic acid]

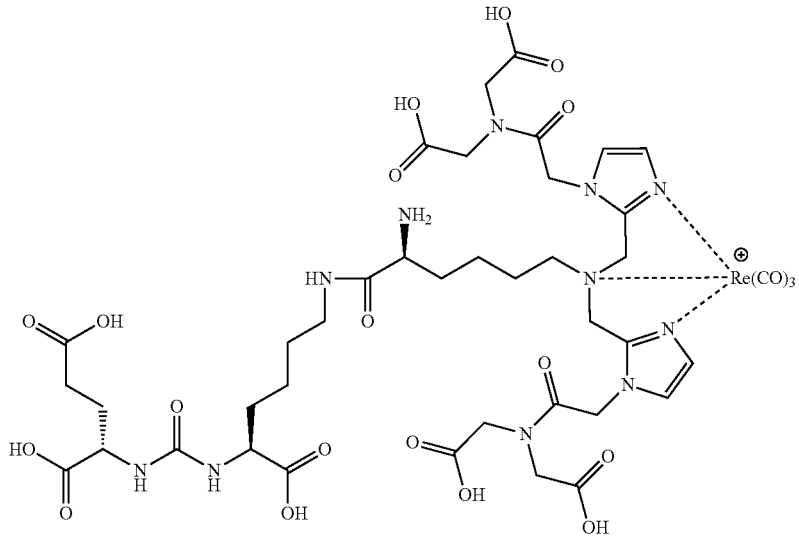

Step 1. 2-(((9H-fluoren-9-yl)methoxy)carbonylamino)-6-(bis((1-(2-(bis(2-tert-butoxy-2-oxoethyl)amino)-2-oxoethyl)-1H-imidazol-2-yl)methyl)amino)hexanoic acid

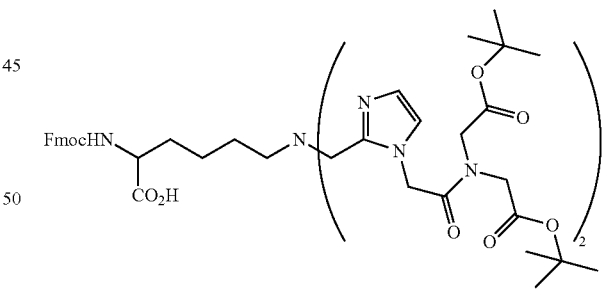

To a suspension of L-Fmoc-Lysine-OH (0.202 g, 0.50 mmol), tert-butyl 2,2'-(2-(2-formyl-1H-imidazol-1-yl)acetylazanediyl)diacetate (0.381 g, 1.00 mmol) in DCE (30 mL) was heated at 80° C. for 30 min. The reaction mixture was cooled to 0° C., and treated with NaBH(OAc)$_3$ (0.3165 g, 1.50 mmol). The reaction stirred at room temperature for 12 hours and decomposed with water. The reaction mixture was extracted with DCM. The organic layer was dried and concentrated under reduced pressure. The residue was purified by a Biotage SP4 with a gradient method of 5-25% methanol in DCM to afford 2-(((9H-fluoren-9-yl)methoxy)carbonylamino)-6-(bis((1-(2-(bis(2-tert-butoxy-2-oxoethyl)

amino)-2-oxoethyl)-1H-imidazol-2-yl)methyl)amino) hexanoic acid as a white solid (0.408 g, 74% yield). $^1$H NMR (400 MHz, CDCl$_3$) 7.74 (d, J=7.6 Hz, 2H), 7.67 (t, J=6.0 Hz, 2H), 7.38 (t, J=7.4 Hz, 2H), 7.29 (d, J=7.6 Hz, 2H), 6.92 (s, 2H), 6.29 (s, 2H), 6.19 (brs, 1H), 5.09-5.04 (m, 2H), 4.81-4.79 (m, 1H), 4.39-4.30 (m, 4H), 4.23 (t, J=7.2 Hz, 1H), 4.22-3.58 (m, 10H), 3.48 (s, 2H), 2.34-2.30 (m, 2H), 1.67-1.26 (m, 6H), 1.50 (s, 18H), 1.42 (s, 18H). ESMS m/z: 550.5 (M/2H)$^+$.

Step 2. (7S,14S,18S)-tri-tert-butyl 7-amino-1-(1-(2-(bis(2-tert-butoxy-2-oxoethyl)amino)-2-oxoethyl)-1H-imidazol-2-yl)-2-((1-(2-(bis(2-tert-butoxy-2-oxoethyl)amino)-2-oxoethyl)-1H-imidazol-2-yl)methyl)-8,16-dioxo-2,9,15,17-tetraazaicosane-14,18,20-tricarboxylate

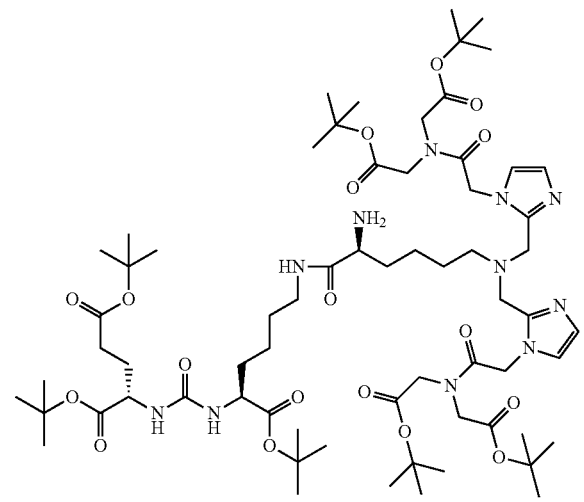 [SMILES: CC(C)(C)OC(=O)CC[C@H](NC(=O)N[C@@H](CCCCNC(=O)[C@@H](N)CCCCN(Cc1nccn1CC(=O)N(CC(=O)OC(C)(C)C)CC(=O)OC(C)(C)C)Cc1nccn1CC(=O)N(CC(=O)OC(C)(C)C)CC(=O)OC(C)(C)C)C(=O)OC(C)(C)C)C(=O)OC(C)(C)C]

A solution of (S)-di-tert-butyl 2-(3-((S)-6-amino-1-tert-butoxy-1-oxohexan-2-yl)ureido)pentanedioate (97 mg, 0.20 mmol), 2-(((9H-fluoren-9-yl)methoxy)carbonylamino)-6-(bis((1-(2-(bis(2-tert-butoxy-2-oxoethyl)amino)-2-oxoethyl)-1H-imidazol-2-yl)methyl)amino)hexanoic acid (132 mg, 0.12 mmol), EDCI (38 mg, 0.20 mmol), HOBt (26 mg, 0.20) and DIPEA (0.30 mL) in DCM (5.0 mL) was stirred at rt for 2 days. The reaction mixture was purified by biotage eluting with 1% MeOH in DCM to afford (5S,12S,16S)-tri-tert-butyl 5-(4-(bis((1-(2-(bis(2-tert-butoxy-2-oxoethyl)amino)-2-oxoethyl)-1H-imidazol-2-yl)methyl)amino)butyl)-1-(9H-fluoren-9-yl)-3,6,14-trioxo-2-oxa-4,7,13,15-tetraazaoctadecane-12,16,18-tricarboxylate (impure) as an oil.

To a solution of the above product, (5S,12S,16S)-tri-tert-butyl 5-(4-(bis((1-(2-(bis(2-tert-butoxy-2-oxoethyl)amino)-2-oxoethyl)-1H-imidazol-2-yl)methyl)amino)butyl)-1-(9H-fluoren-9-yl)-3,6,14-trioxo-2-oxa-4,7,13,15-tetraazaoctadecane-12,16,18-tricarboxylate in DMF (1.0 mL) was added piperidine (0.50 mL). The mixture was stirred at room temperature for 2 hrs. Solvent was evaporated under reduce pressure to afford a residue, which was purified by biotage eluting with 5% MeOH to 50% MeOH in DCM to afford (7S,14S,18S)-tri-tert-butyl 7-amino-1-(1-(2-(bis(2-tert-butoxy-2-oxoethyl)amino)-2-oxoethyl)-1H-imidazol-2-yl)-2-((1-(2-(bis(2-tert-butoxy-2-oxoethyl)amino)-2-oxoethyl)-1H-imidazol-2-yl)methyl)-8,16-dioxo-2,9,15,17-tetraazaicosane-14,18,20-tricarboxylate (40 mg, 25%) as a white solid. $^1$H NMR (400 MHz, CDCl$_3$) 6.96 (s, 2H), 6.83 (d, 2H), 6.37 (brs, 1H), 6.33 (brs, 1H), 5.05 (s, 4H), 4.87 (brs, 2H), 4.27-4.24 (m, 2H), 4.18 (s, 4H), 4.10 (s, 4H), 3.88 (d, J=15.2 Hz, 2H), 3.62 (d, J=15.2 Hz, 2H), 3.14-3.12 (m, 1H), 2.30-1.24 (m, 83H); MS (ESI), 674.1 (M/2+H)$^+$.

Step 3. [Re(CO)$_3$][(7S,14S,18S)-7-amino-1-(1-(2-(bis(carboxymethyl)amino)-2-oxoethyl)-1H-imidazol-2-yl)-2-((1-(2-(bis(carboxymethyl)amino)-2-oxoethyl)-1H-imidazol-2-yl)methyl)-8,16-dioxo-2,9,15,17-tetraazaicosane-14,18,20-tricarboxylic acid] (224)

A solution of (7S,14S,18S)-tri-tert-butyl 7-amino-1-(1-(2-(bis(2-tert-butoxy-2-oxoethyl)amino)-2-oxoethyl)-1H-imidazol-2-yl)-2-((1-(2-(bis(2-tert-butoxy-2-oxoethyl)amino)-2-oxoethyl)-1H-imidazol-2-yl)methyl)-8,16-dioxo-2,9,15,17-tetraazaicosane-14,18,20-tricarboxylate (19 mg, 0.014 mmol) and [NEt$_4$]$_2$[Re(CO)$_3$Br$_3$] (19 mg, 0.024 mmol) in MeOH (3 mL) at a pressure tube was stirred at 90° C. for 3 hrs. The solvent was evaporated to give a residue, which was directly used for next step. A solution of the above product in TFA (3.0 mL)/DCM (3.0 mL) was stirred at room temperature for overnight. The solvent was evaporated to give a crude product, which was purified by HPLC to give [Re(CO)$_3$][(7S,14S,18S)-7-amino-1-(1-(2-(bis(carboxymethyl)amino)-2-oxoethyl)-1H-imidazol-2-yl)-2-((1-(2-(bis(carboxymethyl)amino)-2-oxoethyl)-1H-imidazol-2-yl)methyl)-8,16-dioxo-2,9,15,17-tetraazaicosane-14,18,20-tricarboxylic acid] (14.1 mg, 82% over 2 steps) as a white solid. $^1$H NMR (400 MHz, DMSO-d$_6$) 8.43 (brs, 1H), 8.09 (brs, 3H), 7.10 (s, 2H), 7.03 (s, 2H), 6.51 (brs, 1H), 6.31 (d, J=8.0 Hz, 1H), 6.28 (d, J=8.4 Hz, 1H), 5.00 (s, 4H), 4.40-4.01 (m, 14H), 3.70-3.64 (m, 3H), 3.11-3.08 (m, 2H), 2.26-1.29 (m, 16H); MS (ESI), 612.8 (M+H)/2$^+$.

Compound 225: Re(CO)$_3$][(7S,12S,16S)-1-(1-(carboxymethyl)-1H-imidazol-2-yl)-2-((1-(carboxymethyl)-1H-imidazol-2-yl)methyl)-9,14-dioxo-2,8,13,15-tetraazaoctadecane-7,12,16,18-tetracarboxylic acid]

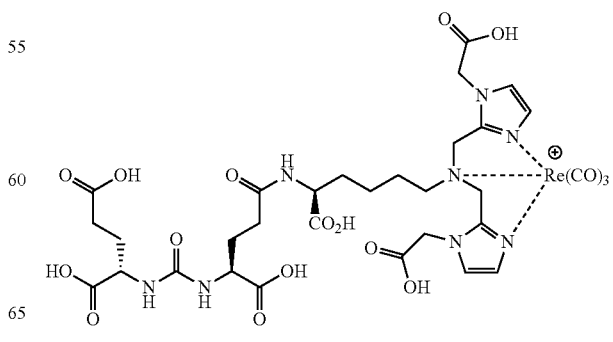

Step 1. (S)-di-tert-butyl 2-(3-((S)-1-tert-butoxy-5-(2,5-dioxopyrrolidin-1-yloxy)-1,5-dioxopentan-2-yl)ureido)pentanedioate

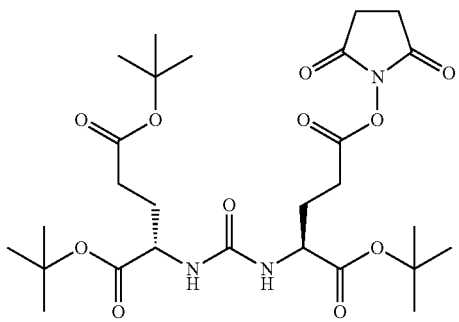 [SMILES: CC(C)(C)OC(=O)CC[C@H](NC(=O)N[C@@H](CCC(=O)ON1C(=O)CCC1=O)C(=O)OC(C)(C)C)C(=O)OC(C)(C)C]

A solution of (S)-5-tert-butoxy-4-(3-((S)-1,5-di-tert-butoxy-1,5-dioxopentan-2-yl)ureido)-5-oxopentanoic acid (Kularatne, S. A.; et. al. *Mol. Pharmaceutics*, 2009, 6, 790-800) (164 mg, 0.336 mmol), N,N'-disuccinimidyl carbonate (128 mg, 0.50 mmol) and pyridine (0.10 mL) in CH$_3$CN (5.0 mL) was stirred at rt for overnight. Solvent was removed under reduced pressure to give a residue, which was purified by biotage eluting with 10% to 70% EtOAc in hexanes to afford (S)-di-tert-butyl 2-(3-((S)-1-tert-butoxy-5-(2,5-dioxopyrrolidin-1-yloxy)-1,5-dioxopentan-2-yl)ureido)pentanedioate (190 mg, 97%) as a white solid.

Step 2. (2S,7S,11S)-2-(4-(bis((1-(2-tert-butoxy-2-oxoethyl)-1H-imidazol-2-yl)methyl)amino) butyl)-7,11-bis(tert-butoxycarbonyl)-16,16-dimethyl-4,9,14-trioxo-15-oxa-3,8,10-triazaheptadecan-1-oic acid

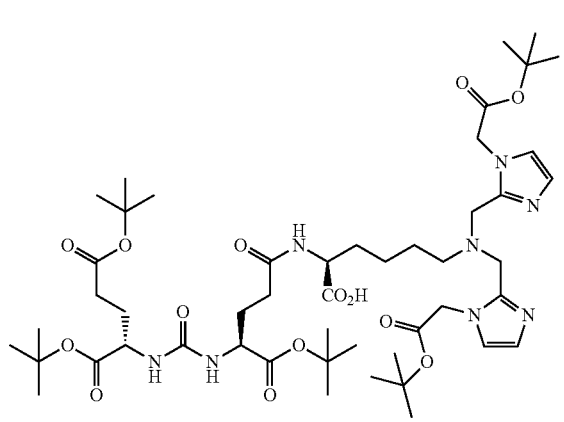 [SMILES: CC(C)(C)OC(=O)CC[C@H](NC(=O)N[C@@H](CCC(=O)N[C@@H](CCCCN(Cc1nccn1CC(=O)OC(C)(C)C)Cc1nccn1CC(=O)OC(C)(C)C)C(=O)O)C(=O)OC(C)(C)C)C(=O)OC(C)(C)C]

A solution of (S)-di-tert-butyl 2-(3-((S)-1-tert-butoxy-5-(2,5-dioxopyrrolidin-1-yloxy)-1,5-dioxopentan-2-yl)ureido)pentanedioate (138 mg, 0.236 mmol), (S)-2-amino-6-(bis((1-(2-tert-butoxy-2-oxoethyl)-1H-imidazol-2-yl)methyl)amino)hexanoic acid (127 mg, 0.237 mmol) and DIPEA (0.50 mL) in DMF (1.0 mL) was stirred at rt for overnight. The Solvent was removed under reduced pressure to give a residue, which was purified by biotage eluting with 1% to 50% MeOH in DCM to afford (2S,7S,11S)-2-(4-(bis((1-(2-tert-butoxy-2-oxoethyl)-1H-imidazol-2-yl)methyl)amino)butyl)-7,11-bis(tert-butoxycarbonyl)-16,16-dimethyl-4,9,14-trioxo-15-oxa-3,8,10-triazaheptadecan-1-oic acid (203 mg, 86%) as a white solid. $^1$H NMR (400 MHz, CDCl$_3$) 7.40 (brs, 1H), 6.99 (s, 2H), 6.79 (s, 2H), 6.12 (brs, 1H), 5.62 (brs, 1H), 4.67-4.28 (m, 7H), 3.68 (d, J=14.0 Hz, 2H), 3.62 (d, J=14.0 Hz, 2H), 2.62-2.53 (m, 2H), 2.34-2.02 (m, 8H), 1.83-1.42 (m, 51H); MS (ESI), 503.5 (M/2H)$^+$.

Step 3. [Re(CO)$_3$][(7S,12S,16S)-1-(1-(carboxymethyl)-1H-imidazol-2-yl)-2-((1-(carboxymethyl)-1H-imidazol-2-yl)methyl)-9,14-dioxo-2,8,13,15-tetraazaoctadecane-7,12,16,18-tetracarboxylic acid] (225)

A solution of ((2S,7S,11S)-2-(4-(bis((1-(2-tert-butoxy-2-oxoethyl)-1H-imidazol-2-yl)methyl)amino)butyl)-7,11-bis(tert-butoxycarbonyl)-16,16-dimethyl-4,9,14-trioxo-15-oxa-3,8,10-triazaheptadecan-1-oic acid (45 mg, 0.0448 mmol) and [NEt$_4$]$_2$[Re(CO)$_3$Br$_3$] (45 mg, 0.058 mmol) in MeOH (5 mL) at a pressure tube was stirred at 90° C. for 4 hrs. The solvent was evaporated to give a residue, which was directly used for next step. A solution of the above product in TFA (2.0 mL)/DCM (3.0 mL) was stirred at room temperature for overnight. The solvent was evaporated to give a crude product, which was purified by HPLC to give [Re(CO)$_3$][(7S,12S,16S)-1-(1-(carboxymethyl)-1H-imidazol-2-yl)-2-((1-(carboxymethyl)-1H-imidazol-2-yl)methyl)-9,14-dioxo-2,8,13,15-tetraazaoctadecane-7,12,16,18-tetracarboxylic acid] (30 mg, 67% over 2 steps) as a white solid. $^1$H NMR (400 MHz, DMSO-d$_6$) 8.14 (d, J=7.2 Hz, 1H), 7.19 (d, J=0.8 Hz, 2H), 7.05 (d, J=1.2 Hz, 2H), 6.37-6.34 (m, 2H), 4.85 (s, 4H), 4.58 (dd, J=16.4, 2.8 Hz, 2H), 4.40 (dd, J=16.0, 2.8 Hz, 2H), 4.22-4.04 (m, 3H), 3.65 (t, J=7.6 Hz, 2H), 2.25-1.32 (m, 16H); MS (ESI), 995.3 M$^+$.

Compound 226: [Re(CO)$_3$][(7S,12S,16S)-1-(1-(2-(bis(carboxymethyl) amino)-2-oxoethyl)-1H-imidazol-2-yl)-2-((1-(2-(bis(carboxymethyl)amino)-2-oxoethyl)-1H-imidazol-2-yl)methyl)-9,14-dioxo-2,8,13,15-tetraazaoctadecane-7,12,16,18-tetracarboxylic acid]

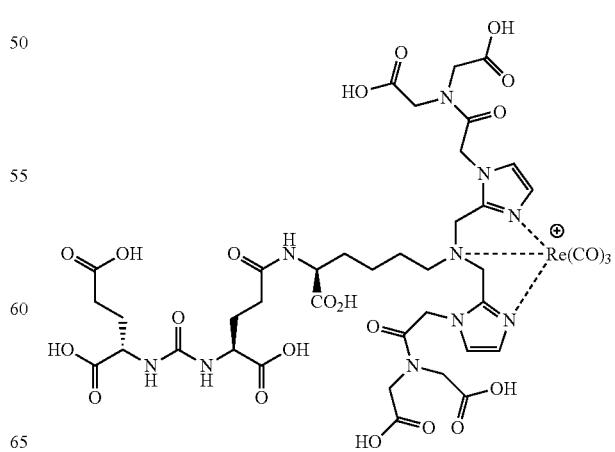

Step 1. (S)-2-amino-6-(bis((1-(2-(bis(2-tert-butoxy-2-oxoethyl)amino)-2-oxoethyl)-1H-imidazol-2-yl)methyl)amino)hexanoic acid

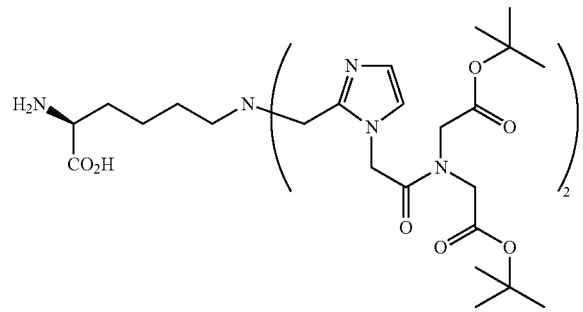

A solution of 2-(((9H-fluoren-9-yl)methoxy)carbonylamino)-6-(bis((1-(2-(bis(2-tert-butoxy-2-oxoethyl)amino)-2-oxoethyl)-1H-imidazol-2-yl)methyl)amino)hexanoic acid (190 mg, 0.173 mmol) and piperidine (0.50 mL) in DMF (0.50 mL) was stirred at room temperature for 1 hrs. The solvent was evaporated under reduced pressure to give a crude product. The crude product was purified by Biotage SP4 with a gradient method of 5-50% methanol in DCM to give (S)-2-amino-6-(bis((1-(2-(bis(2-tert-butoxy-2-oxoethyl)amino)-2-oxoethyl)-1H-imidazol-2-yl)methyl)amino)hexanoic acid (0.120 g, 79%). $^1$H NMR (400 MHz, DMSO-$d_6$) 6.92 (s, 2H), 6.76 (s, 2H), 5.01 (s, 4H), 4.32 (s, 2H), 4.31 (s, 2H), 3.92 (s, 4H), 3.44 (s, 4H), 3.01-2.99 (m, 1H), 2.30 (t, J=7.2 Hz, 2H), 1.60-1.57 (m, 2H), 1.43 (s, 18H), 1.35 (m, 18H). 1.30-1.12 (m, 4H); MS (ESI), 439.4 (M/2+H)$^+$.

Step 2. (2S,7S,11S)-2-(4-(bis((1-(2-(bis(2-tert-butoxy-2-oxoethyl)amino)-2-oxoethyl)-1H-imidazol-2-yl)methyl)amino)butyl)-7,11-bis(tert-butoxycarbonyl)-16,16-dimethyl-4,9,14-trioxo-15-oxa-3,8,10-triazaheptadecan-1-oic acid

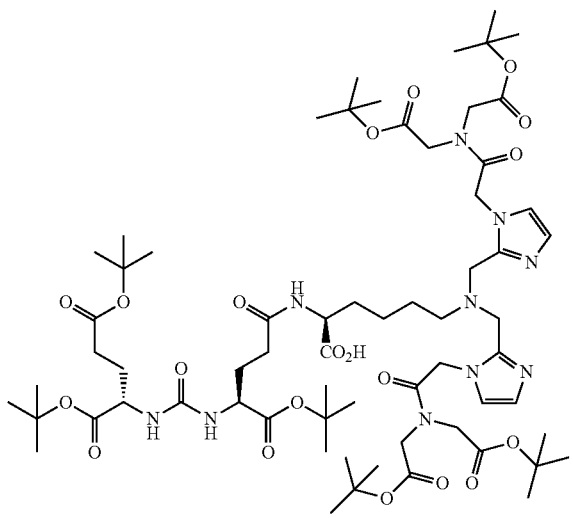 [SMILES: CC(C)(C)OC(=O)CC[C@H](NC(=O)N[C@@H](CCC(=O)N[C@@H](CCCCN(Cc1nccn1CC(=O)N(CC(=O)OC(C)(C)C)CC(=O)OC(C)(C)C)Cc1nccn1CC(=O)N(CC(=O)OC(C)(C)C)CC(=O)OC(C)(C)C)C(=O)O)C(=O)OC(C)(C)C)C(=O)OC(C)(C)C]

A solution of (S)-di-tert-butyl 2-(3-((S)-1-tert-butoxy-5-(2,5-dioxopyrrolidin-1-yloxy)-1,5-dioxopentan-2-yl)ureido)pentanedioate (82 mg, 0.14 mmol), ((S)-2-amino-6-(bis((1-(2-(bis(2-tert-butoxy-2-oxoethyl)amino)-2-oxoethyl)-1H-imidazol-2-yl)methyl)amino)hexanoic acid (98 mg, 0.11 mmol) and DIPEA (0.50 mL) in DMF (2.0 mL) was stirred at rt for overnight. The Solvent was removed under reduced pressure to give a residue, which was purified by biotage eluting with 1% to 40% MeOH in DCM to afford (2S,7S,11S)-2-(4-(bis((1-(2-(bis(2-tert-butoxy-2-oxoethyl)amino)-2-oxoethyl)-1H-imidazol-2-yl)methyl)amino)butyl)-7,11-bis(tert-butoxycarbonyl)-16,16-dimethyl-4,9,14-trioxo-15-oxa-3,8,10-triazaheptadecan-1-oic acid (125 mg, 84%) as a white solid. MS (ESI), 674.6 (M/2+H)$^+$.

Step 3. [Re(CO)$_3$][(7S,12S,16S)-1-(1-(2-(bis(carboxymethyl)amino)-2-oxoethyl)-1H-imidazol-2-yl)-2-((1-(2-(bis(carboxymethyl)amino)-2-oxoethyl)-1H-imidazol-2-yl)methyl)-9,14-dioxo-2,8,13,15-tetraazaoctadecane-7,12,16,18-tetracarboxylic acid] (226)

A solution of (2S,7S,11S)-2-(4-(bis((1-(2-(bis(2-tert-butoxy-2-oxoethyl)amino)-2-oxoethyl)-1H-imidazol-2-yl)methyl)amino)butyl)-7,11-bis(tert-butoxycarbonyl)-16,16-dimethyl-4,9,14-trioxo-15-oxa-3,8,10-triazaheptadecan-1-oic acid (54 mg, 0.040 mmol) and [NEt$_4$]$_2$[Re(CO)$_3$Br$_3$] (47 mg, 0.060 mmol) in MeOH (5 mL) at a pressure tube was stirred at 90° C. for 4 hrs. The solvent was evaporated to give a residue, which was directly used for next step. A solution of the above product in TFA (2.0 mL)/DCM (3.0 mL) was stirred at room temperature for overnight. The solvent was evaporated to give a crude product, which was purified by HPLC to give the title compound (44.8 mg, 91% over 2 steps) as a white solid. $^1$H NMR (400 MHz, DMSO-$d_6$) 8.17 (d, J=7.6 Hz, 1H), 7.11 (d, J=1.2 Hz, 2H), 7.03 (d, J=1.2 Hz, 2H), 6.37-6.33 (m, 2H), 5.02 (s, 4H), 4.40-3.98 (m, 15H), 3.65 (t, J=7.6 Hz, 2H), 2.25-1.32 (m, 14H); MS (ESI), 613.3 (M+H)/2$^+$.

Additional compounds prepared by the above methods, with appropriate reagent selection include Compounds 32-37 and 50, below.

Compound 32: (7S,22S,26S)-9,16,24-trioxo-1-(quinolin-2-yl)-2-(quinolin-2-ylmethyl)-2,8,17,23,25-pentaazaoctacosane-7,22,26,28-tetracarboxylic acid
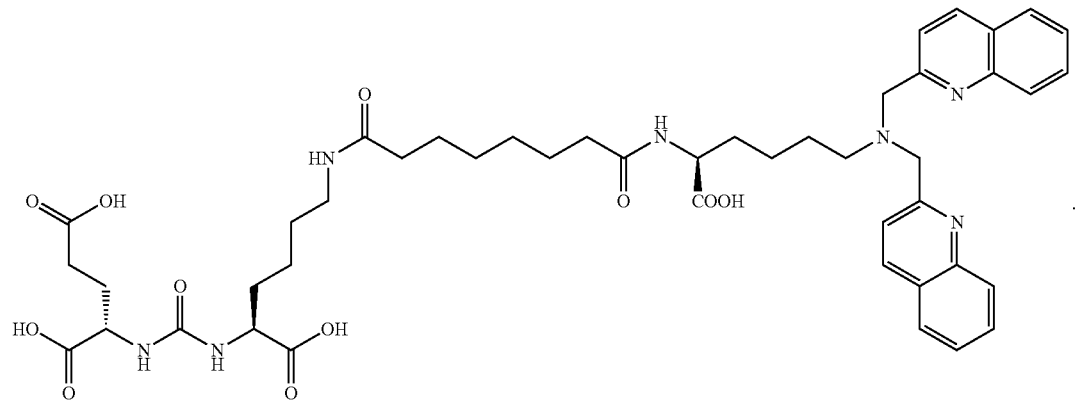 [SMILES: O=C(O)CC[C@H](NC(=O)N[C@@H](CCCCNC(=O)CCCCCCC(=O)N[C@@H](CCCCN(Cc1ccc2ccccc2n1)Cc1ccc2ccccc2n1)C(=O)O)C(=O)O)C(=O)O]
Compound 33: (7S,22S,26S)-9,16,24-trioxo-1-(pyridin-2-yl)-2-(pyridin-2-ylmethyl)-2,8,17,23,25-pentaazaoctacosane-7,22,26,28-tetracarboxylic acid
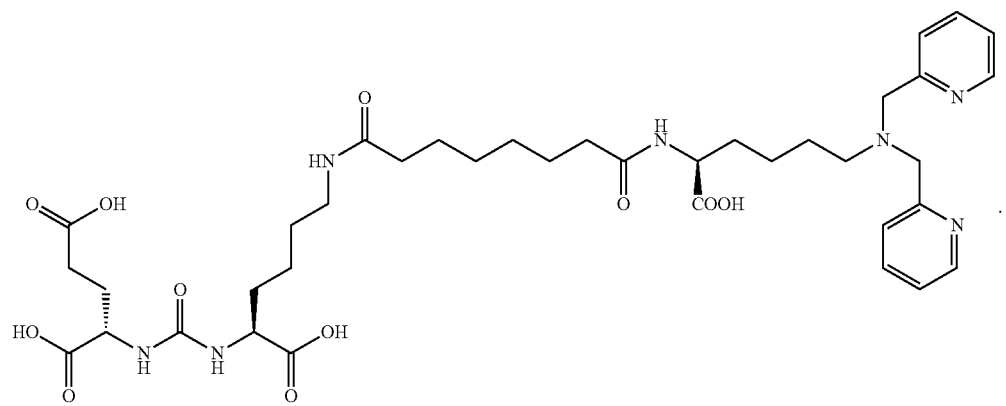 [SMILES: O=C(O)CC[C@H](NC(=O)N[C@@H](CCCCNC(=O)CCCCCCC(=O)N[C@@H](CCCCN(Cc1ccccn1)Cc1ccccn1)C(=O)O)C(=O)O)C(=O)O]

Compound 34: (22S,26S)-9,16,24-trioxo-2-(pyridin-2-ylmethyl)-2,8,17,23,25-pentaazaoctacosane-1,7,22,26,28-pentacarboxylic acid
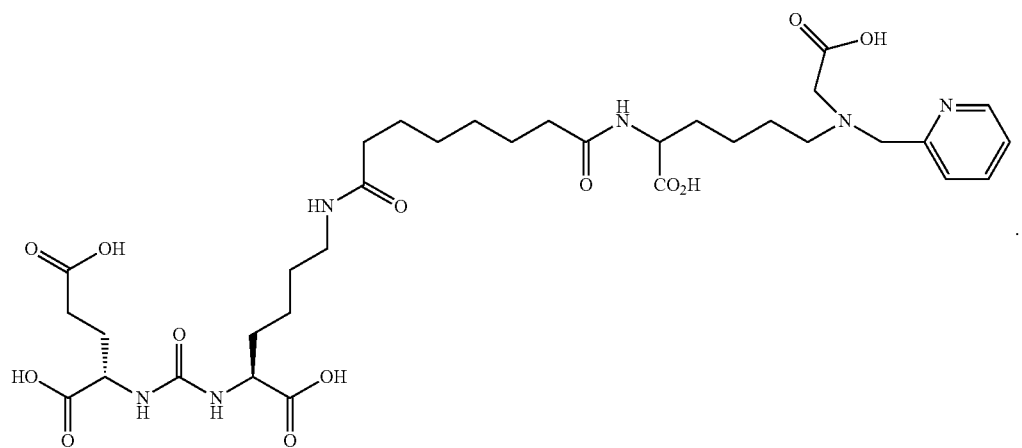 [SMILES: O=C(O)CC[C@H](NC(=O)N[C@@H](CCCCNC(=O)CCCCCCC(=O)NC(CCCCN(CC(=O)O)Cc1ccccn1)C(=O)O)C(=O)O)C(=O)O]
Compound 35: (7S,22S,26S)-1-(1-(carboxymethyl)-1H-imidazol-2-yl)-2-((3-(carboxymethyl)-3H-pyrrol-2-yl)methyl)-9,16,24-trioxo-2,8,17,23,25-pentaazaoctacosane-7,22,26,28-tetracarboxylic acid
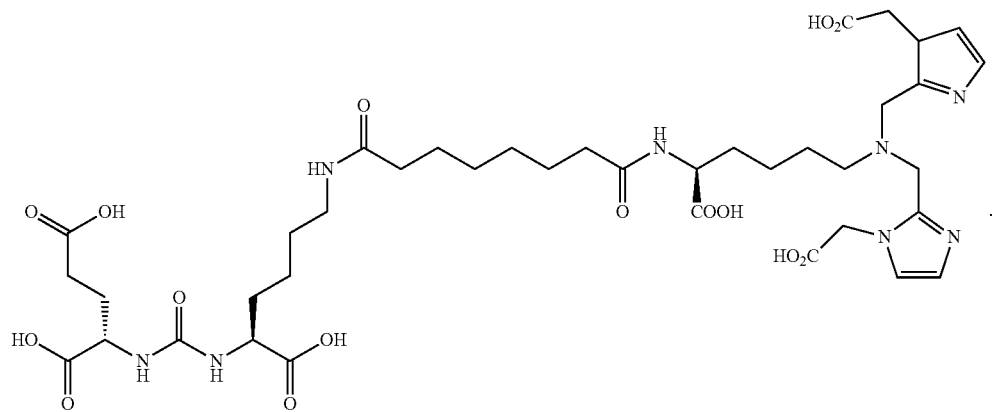 [SMILES: O=C(O)CC[C@H](NC(=O)N[C@@H](CCCCNC(=O)CCCCCCC(=O)N[C@@H](CCCCN(CC1=NC=CC1CC(=O)O)Cc1nccn1CC(=O)O)C(=O)O)C(=O)O)C(=O)O]

Compound 36: (19S,23S)-1-(1-(carboxymethyl)-1H-imidazol-2-yl)-2-((1-(carboxymethyl)-1H-imidazol-2-yl)methyl)-13,21-dioxo-2,14,20,22-tetraazapentacosane-19,23,25-tricarboxylic acid

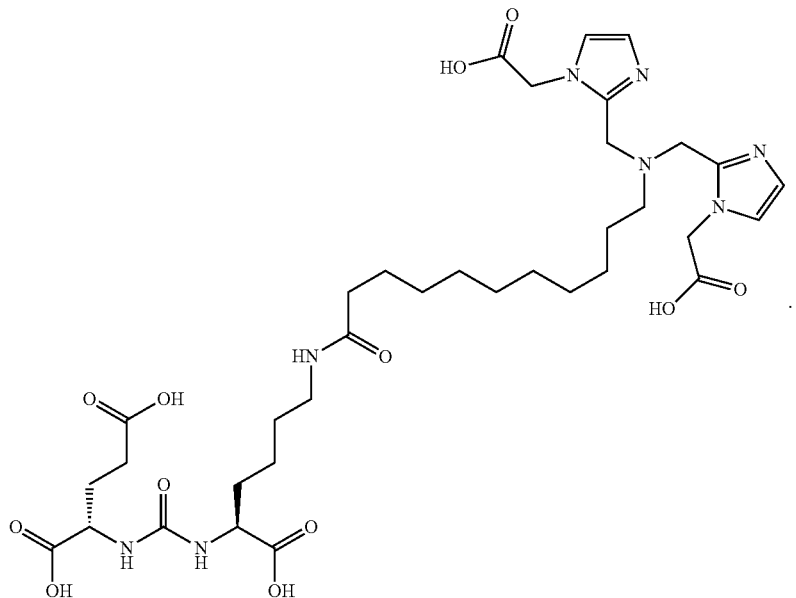 [SMILES: O=C(O)CC[C@H](NC(=O)N[C@@H](CCCCNC(=O)CCCCCCCCCCN(Cc1nccn1CC(=O)O)Cc1nccn1CC(=O)O)C(=O)O)C(=O)O]

Compound 50: (7S,11S,26S)-26-(4-(bis((1-methyl-1H-imidazol-2-yl)methyl)amino)butyl)-7,11-bis(tert-butoxycarbonyl)-2,2-dimethyl-4,9,17,24-tetraoxo-3-oxa-8,10,16,25-tetraazaheptacosan-27-oic acid

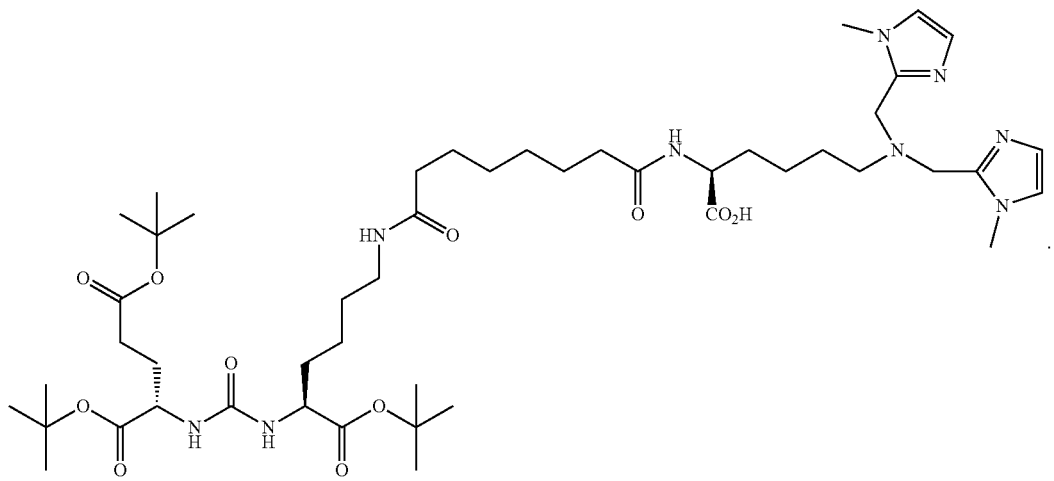 [SMILES: Cn1ccnc1CN(CCCC[C@H](NC(=O)CCCCCCC(=O)NCCCC[C@H](NC(=O)N[C@@H](CCC(=O)OC(C)(C)C)C(=O)OC(C)(C)C)C(=O)OC(C)(C)C)C(=O)O)Cc1nccn1C]

Other compounds may be prepared incorporating a chelator based upon 1,4,7,10-tetraazacyclododecane-1,4,7,10-tetraacetic acid (DOTA). Such DOTA-based chelators may be used for the cheation of a imaging metals including, but not limited to yttrium, lutetium, gallium, and indium. The DOTA-based chelators may be prepared as outlined above, exploiting one of the acid groups of DOTA to link to the other R-groups. Exemplary DOTA-based compounds include, but are not limited to, where M is Y, Lu, Ga, or In; and n is from 0 to 20:

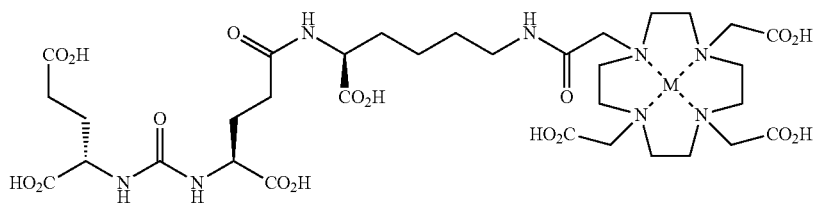

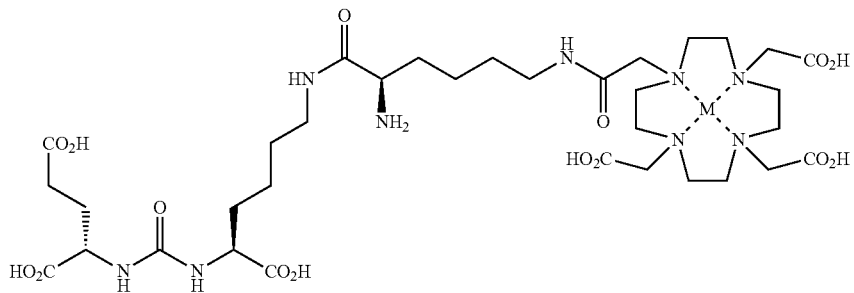

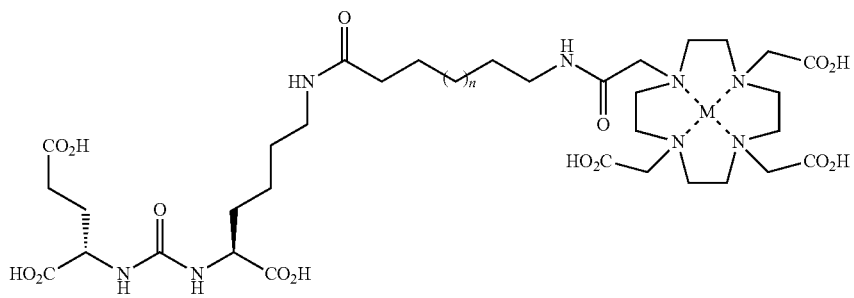

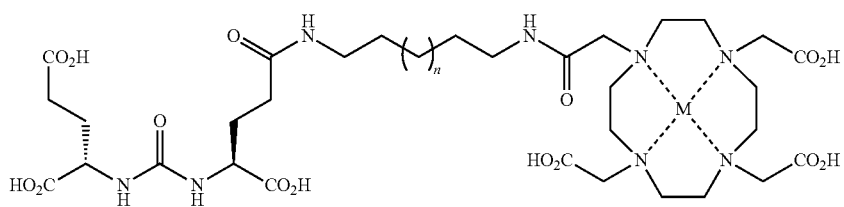

General Preparation of $^{99m}$Tc and Re Complexes.

Radiolabeling of $^{99m}$Tc-SAAC.

Radiolabeling of SAAC systems was accomplished to form complexes on either the free α-amino acids or as the appropriately N-protected amino acid derivative utilizing similar methodology, demonstrating the ease of preparation and the flexibility in the design of the SAAC systems. The $^{99m}$Tc(I)(CO)$_3^+$ radiolabeling was accomplished in two steps using the commercially available IsoLink™ kits (Covidien) to form the $[^{99m}$Tc(CO)$_3$(H$_2$O)$_3]^+$ intermediate, which was reacted with the appropriate SAAC ligand ($10^{-6}$ M-$10^{-4}$ M) in an equal volume mixture of 1:1 acetonitrile and phosphate buffer. The sealed vial was heated at 100° C. for 30 minutes. Upon cooling, the reaction was analyzed for purity via RP-HPLC. The radiochemical purity (RCP) after HPLC purification, resulting in "carrier free" products, was determined via HPLC and shown to be consistently ≥95%. Although initial results demonstrated radiolabeling at concentrations as low as $10^{-6}$ M RCY was ≤80%. To achieve a RCY>95% at 75° C., the reaction concentration needed to be increased to $10^{-4}$ M. In many cases, the corresponding Re complexes are prepared and tested as the Tc complexes in order to prepare non-radioactive analogs for testing and handling purposes. Therefore, where Re may be specifically shown, it is understood to include Tc complexes as well.

Compound 16-Re

Re(CO)$_3$ complex of the compound from example 16. A solution of tert-butyl 2,2'-(2,2'-(4-sulfamoylphenethyl-azanediyl) bis(methylene)bis(1H-imidazole-2,1-diyl))diacetate (65 mg, 0.11 mmol) and [NEt$_4$]$_2$[ReBr$_3$(CO)$_3$] (92.4 mg, 0.12 mmol) in MeOH (3.0 mL) was stirred at 95° C. for 4 hrs at a pressure tube. The reaction mixture was purified by Amberchrom eluting with MeOH/H₂O to give [Re(CO)₃][tert-butyl 2,2'-(2,2'-(4-sulfamoylphenethyl-azanediyl) bis(methylene)bis(1H-imidazole-2,1-diyl))diacetate] (51 mg, 54%) as a white solid. $^1$H NMR (400 MHz, DMSO-$d_6$) 7.81 (d, J=8.4 Hz, 2H), 7.60 (d, J=8.4 Hz, 2H), 7.31 (s, 2H), 7.26 (d, J=1.2 Hz, 2H), 7.12 (d, J=1.2 Hz, 2H), 4.95 (s, 4H), 4.74 (d, J=16.4 Hz, 2H), 4.62 (d, J=16.4 Hz, 2H), 3.90-3.86 (m, 2H), 3.16-3.14 (m, 2H), 1.45 (s, 18H); MS (ESI), 859.3 M⁺. A solution of [Re(CO)₃][tert-butyl 2,2'-(2,2'-(4-sulfamoylphenethyl-azanediyl)bis(methylene)bis(1H-imidazole-2,1-diyl))diacetate] (20 mg) in TFA (1.0 mL) and DCM (1.0 mL) was then stirred at room temperature for 4 hrs. The solvent was then removed under reduced pressure to give [Re(CO)₃][2,2'-(2,2'-(4-sulfamoylphenethylazanediyl) bis(methylene)bis(1H-imidazole-2,1-diyl))diacetic acid] (21.5 mg). $^1$H NMR (400 MHz, DMSO-$d_6$) 7.81 (d, J=8.0 Hz, 2H), 7.60 (d, J=8.4 Hz, 2H), 7.30 (s, 2H), 7.23 (d, J=1.2 Hz, 2H), 7.08 (d, J=1.2 Hz, 2H), 4.91 (s, 4H), 4.72 (s, 4H), 3.89-3.85 (m, 2H), 3.18-3.14 (m, 2H); MS (ESI), 747.2 M⁺.

Compound 17-Re

Re(CO)₃ Complex of the Compound from Example 17.

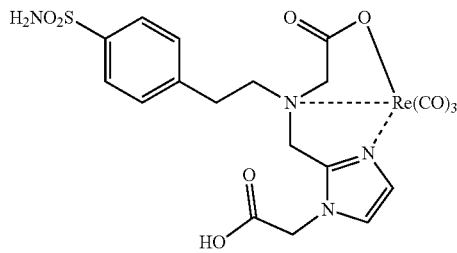

Step 1. A solution of 4-(2-aminoethyl)benzenesulfonamide (0.70 g, 3.5 mmol), AcOH (0.20 mL) and tert-butyl 2-(2-formyl-1H-imidazol-1-yl)acetate (0.735 g, 3.5 mmol) in DCE (20 mL) was heated at 80° C. for 30 min under nitrogen. The reaction mixture was cooled to 0° C., and treated sequentially with NaBH(OAc)₃ (2.25 g, 10.5 mmol) and crude tert-butyl glyoxalate (1.80 g)¹. The reaction mixture was stirred at room temperature for overnight and decomposed with water. The reaction mixture was extracted with DCM. The organic layer was dried and concentrated under reduced pressure. The residue was purified by flash chromatography over silica gel to tert-butyl 2-(((1-methyl-1H-imidazol-2-yl)methyl)(4-sulfamoylphenethyl)amino)acetate (0.63 g, 35%). %). $^1$H NMR (400 MHz, DMSO-$d_6$) 7.67 (d, J=8.4 Hz, 2H), 7.25 (s, 2H), 7.23 (d, J=8.4 Hz, 2H), 7.04 (d, J=1.2 Hz, 1H), 6.76 (d, J=1.2 Hz, 1H), 4.82 (s, 2H), 3.74 (s, 2H), 3.24 (s, 2H), 2.69-2.66 (m, 4H), 1.41 (s, 9H), 1.40 (s, 9H); MS (ESI), 509 (M+H)⁺.

Step 2. To a solution tert-butyl 2-(((1-methyl-1H-imidazol-2-yl)methyl)(4-sulfamoylphenethyl)amino)acetate (40 mg, 0.079 mmol) in DCM (2.0 mL) and TFA (2.0 mL) was stirred at room temperature for 3 hrs. Solvent was removed under reduced pressure to give 2-(2-(((carboxymethyl)(4-sulfamoylphenethyl)amino)methyl)-1H-imidazol-1-yl)acetic acid. A solution of 2-(2-(((carboxymethyl)(4-sulfamoylphenethyl)amino)methyl)-1H-imidazol-1-yl)acetic acid and [NEt₄]₂[ReBr₃(CO)₃] (70 mg, 0.09 mmol) in MeOH (2.0 mL) and H₂O (2.0 mL) was adjusted pH=9 using 2 N NaOH. The mixture was stirred at 95° C. for overnight at a pressure tube. The reaction mixture was purified by HPLC to give [Re(CO)₃][2-(2-(((carboxymethyl)(4-sulfamoylphenethyl)amino)methyl)-1H-imidazol-1-yl)acetic acid] (20 mg, 38%) as a white solid. $^1$H NMR (400 MHz, DMSO-$d_6$) 7.76 (d, J=8.0 Hz, 2H), 7.57 (d, J=8.0 Hz, 2H), 7.36 (d, J=1.6 Hz, 1H), 7.26 (s, 2H), 7.16 (d, J=1.6 Hz, 1H), 5.05 (d, J=16.4 Hz, 1H), 4.98 (d, J=16.4 Hz, 1H), 4.73 (d, J=16.0 Hz, 1H), 4.43 (d, J=16.0 Hz, 1H), 4.00 (d, J=16.8 Hz, 1H), 3.60-3.51 (m, 3H), 3.10-3.05 (m, 2H); MS (ESI), 667.2 (M+H)⁺.

Compound 23-Re

Re(CO)₃ Complex of Example 23.

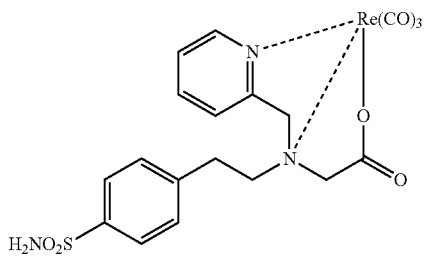

Step 1. A solution of 4-(2-aminoethyl)benzenesulfonamide (1.60 g, 8.0 mmol), AcOH (0.30 mL) and 2-pyridinecarboxaldehyde (0.76 mL, 8.0 mmol) in DCE (50 mL) was heated at 75° C. for 30 min under nitrogen. The reaction mixture was cooled to 0° C., and treated sequentially with NaBH(OAc)₃ (6.36 g, 30 mmol) and crude tert-butyl glyoxalate (2.08 g)¹. The reaction mixture was stirred at room temperature for overnight and decomposed with water. The reaction mixture was extracted with DCM. The organic layer was dried and concentrated under reduced pressure. The residue was purified by flash chromatography over silica gel to afford tert-butyl 2-((pyridin-2-ylmethyl)(4-sulfamoylphenethyl)amino)acetate (1.04 g, 32%) and tert-butyl 2,2'-(4-sulfamoylphenethylazanediyl)diacetate (0.624 g, 18%). tert-butyl 2-((pyridin-2-ylmethyl)(4-sulfamoylphenethyl)amino)acetate: $^1$H NMR (400 MHz, CD₃OD) 8.45 (d, J=4.8 Hz, 0.42H), 8.40 (d, J=4.8 Hz, 0.58H), 7.83 (t, J=6.4 Hz, 0.42H), 7.77 (d, J=8.4 Hz, 1.58H), 7.69 (t, J=8.0 Hz, 0.58H), 7.56 (d, J=7.6 Hz, 0.58H), 7.34-7.24 (m, 4H), 5.49 (s, 1H), 4.70 (s, 1H), 3.93 (s, 2H), 2.91 (t, J=6.8 Hz, 2H), 2.83 (t, J=6.8 Hz, 2H), 1.47 (s, 9H); MS (ESI), 406 (M+H)⁺; tert-butyl 2,2'-(4-sulfamoylphenethylazanediyl)diacetate: $^1$H NMR (400 MHz, CD₃Cl₃) 7.83 (d, J=8.4 Hz, 2H), 3.45 (s, 4H), 2.97 (t, J=5.6 Hz, 2H), 2.87 (t, J=6.0 Hz, 2H), 1.49 (s, 18H); MS (ESI), 429 (M+H)⁺.

Step 2. To a solution of tert-butyl 2-((pyridin-2-ylmethyl)(4-sulfamoylphenethyl)amino)acetate (150 mg, 0.37 mmol) in DCM (3.0 mL) and TFA (3.0 mL) was stirred at room temperature for overnight. Solvent was removed under reduced pressure to give 2-((pyridin-2-ylmethyl)(4-sulfamoylphenethyl)amino)acetic acid (129 mg, 100%). $^1$H NMR (400 MHz, CD₃OD) 8.73 (d, J=5.6 Hz, 0.46H), 8.58 (d, J=4.4 Hz, 1H), 8.57 (t, J=8.0 Hz, 0.46H), 8.16 (t, J=7.6 Hz, 1H), 8.01 (d, J=8.4 Hz, 0.54H), 7.96 (t, J=6.8 Hz, 0.54H), 7.79 (d, J=8.4 Hz, 2H), 7.66 (d, J=7.2 Hz, 2H), 7.35 (d, J=8.4 Hz, 2H), 4.51 (s, 2H), 4.06 (s, 2H), 3.36 (t, J=7.6 Hz, 2H), 3.05 (t, J=7.6 Hz, 2H); MS (ESI), 355 (M+H)⁺.

Step 3. A solution of 2-((pyridin-2-ylmethyl)(4-sulfamoylphenethyl) amino)acetic acid (61 mg, 0.173 mmol), [NEt₄]₂[ReBr₃(CO)₃] (192 mg, 0.25 mmol) and K₂CO₃ (30 mg) in MeOH (6.0 mL) was stirred at 100° C. for 5 hrs at a pressure tube. The reaction mixture was purified by Amberchrom (CG-161) eluting with MeOH/H₂O to give [Re(CO)₃][2-((pyridin-2-ylmethyl)(4-sulfamoylphenethyl)amino)acetic acid] (18.9 mg, 18%) as a white solid. ¹H NMR (400 MHz, DMSO-d₆) 8.77 (d, J=5.6 Hz, 1H), 8.17 (t, J=7.8 Hz, 1H), 7.79 (d, J=8.0 Hz, 2H), 7.74 (d, J=7.6 Hz, 1H), 7.59 (d, J=8.0 Hz, 2H), 7.58 (d, J=6.0 Hz, 1H), 7.29 (s, 2H), 4.92 (d, J=16.0 Hz, 1H), 4.77 (d, J=16.0 Hz, 1H), 4.10 (d, J=16.4 Hz, 1H), 3.74-3.68 (m, 1H), 3.64-3.58 (m, 1H), 3.53 (d, J=16.8 Hz, 1H), 3.14-3.08 (m, 2H); MS (ESI), 620 (M+H)⁺.

Compound 24-Re

Re(CO)₃ Complex of the Compound of Example 24.

Compound 25-Re

Re(CO)₃ Complex of Example 25.

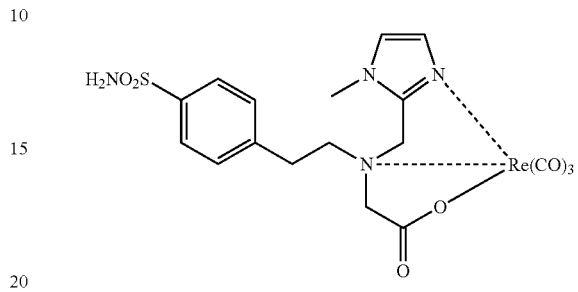

A solution of Compound 24 (230 mg, 0.477 mmol) and [NEt₄]₂[ReBr₃(CO)₃] (367 mg, 0.477 mmol) in MeOH (6.0 mL) was stirred at 100° C. for 3 hrs at a pressure tube. The reaction mixture was purified by Amberchrom eluting with MeOH/H₂O to give [Re(CO)₃][4-(2-(bis(isoquinolin-1-ylmethyl)amino)ethyl)benzenesulfonamide] (173 mg, 48%) as a yellow solid. ¹H NMR (400 MHz, DMSO-d₆) 8.69 (d, J=8.4 Hz, 2H), 8.36 (d, J=8.8 Hz, 2H), 8.12 (d, J=8.4 Hz, 2H), 7.95 (t, J=7.4 Hz, 2H), 7.82 (d, J=8.4 Hz, 2H), 7.75 (t, J=7.6 Hz, 2H), 7.70 (d, J=8.4 Hz, 2H), 7.62 (d, J=8.4 Hz, 2H), 7.34 (s, 2H), 5.46 (d, J=18.0 Hz, 2H), 5.25 (d, J=18.0 Hz, 2H), 4.07-4.03 (m, 2H), 3.32-2.99 (m, 2H); MS (ESI), 753.2 M⁺.

Step 1. A solution of 4-(2-aminoethyl)benzenesulfonamide (1.40 g, 7.0 mmol), AcOH (0.30 mL) and 1-methyl-1H-imidazole-2-carbaldehyde (0.77 g, 7.0 mmol) in DCE (40 mL) was heated at 80° C. for 30 min under nitrogen. The reaction mixture was cooled to 0° C., and treated sequentially with NaBH(OAc)₃ (4.45 g, 21 mmol) and crude tert-butyl glyoxalate (1.80 g)¹. The reaction mixture was stirred at room temperature for overnight and decomposed with water. The reaction mixture was extracted with DCM. The organic layer was dried and concentrated under reduced pressure. The residue was purified by flash chromatography over silica gel to tert-butyl 2-(((1-methyl-1H-imidazol-2-yl)methyl)(4-sulfamoylphenethyl)amino)acetate (0.63 g, 22%). ¹H NMR (400 MHz, DMSO-d₆) 7.65 (d, J=8.4 Hz, 2H), 7.26 (s, 2H), 7.21 (d, J=8.0 Hz, 2H), 6.99 (d, J=0.8 Hz, 1H), 6.73 (d, J=0.8 Hz, 1H), 3.76 (s, 2H), 3.38 (s, 3H), 3.28 (s, 2H), 2.79 (t, J=7.2 Hz, 2H), 2.69 (t, J=6.8 Hz, 2H), 1.40 (s, 9H); MS (ESI), 409 (M+H)⁺.

Step 2. To a solution tert-butyl 2-4(1-methyl-1H-imidazol-2-yl)methyl)(4-sulfamoylphenethyl)amino)acetate (110 mg, 0.27 mmol) in DCM (3.0 mL) and TFA (3.0 mL) was stirred at room temperature for overnight. Solvent was removed under reduced pressure to give 2-(((1-methyl-1H-imidazol-2-yl)methyl)(4-sulfamoylphenethyl)amino)acetic acid. A solution of 2-(((1-methyl-1H-imidazol-2-yl)methyl)(4-sulfamoylphenethyl) amino) acetic acid, [NEt₄]₂[ReBr₃(CO)₃] (270 mg, 0.35 mmol) and K₂CO₃ (78 mg) in MeOH (6.0 mL) was stirred at 90° C. for 4 hrs at a pressure tube. The reaction mixture was purified by Amberchrom (CG-161) eluting with MeOH/H₂O to give [Re(CO)₃][2-(((1-methyl-1H-imidazol-2-yl)methyl)(4-sulfamoylphenethyl)-amino)acetic acid] (105 mg, 63%) as a white solid. ¹H NMR (400 MHz, DMSO-d₆) 7.79 (d, J=8.0 Hz, 2H), 7.57 (d, J=8.0 Hz, 2H), 7.36 (d, J=0.8 Hz, 1H), 7.25 (s, 2H), 7.15 (d, J=1.2 Hz, 1H), 4.76 (d, J=16.4 Hz, 1H), 4.58 (d, J=16.0 Hz, 1H), 4.03 (d, J=16.8 Hz, 1H), 3.67 (d, J=16.8 Hz, 1H), 3.65-3.49 (m, 2H), 3.17-3.09 (m, 2H); MS (ESI), 623 (M+H)⁺.

Compound 34-Re

Re(CO)₃ Complex of the Compound of Example 34.

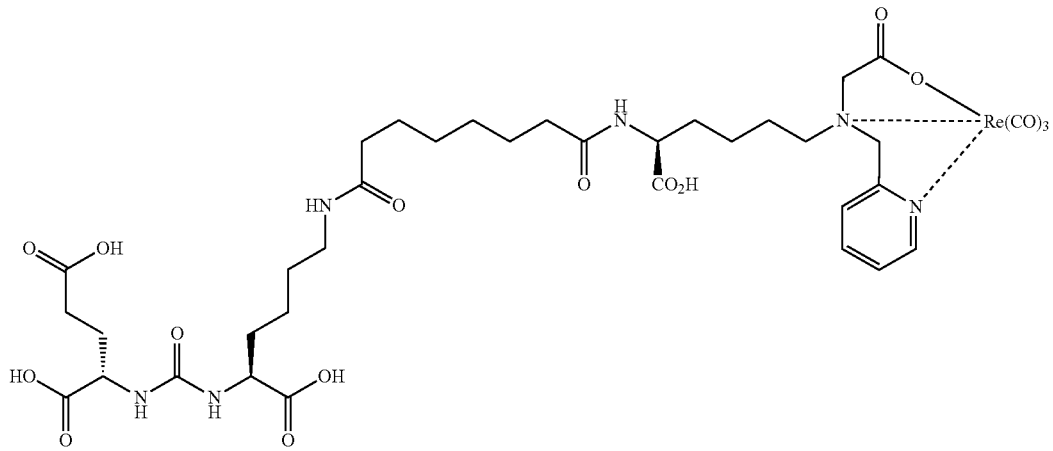

A solution of PAMA-K (0.600 g, 1.047 mmol) and piperidine (1.0 mL) in DMF (5.0 mL) was stirred at room temperature for 3 hrs. Solvent was evaporated under reduced pressure to give a residue, which was purified by Amberchrom (CG-161C) eluting with MeOH/H₂O to give (S)-2-amino-6-((2-tert-butoxy-2-oxoethyl)(pyridin-2-ylmethyl)amino)hexanoic acid (0.256 g, 70%). MS (ESI), 352 (M+H)⁺.

A solution of (S)-di-tert-butyl 2-(3-((S)-1-tert-butoxy-6-(8-(2,5-dioxopyrrolidin-1-yloxy)-8-oxooctanamido)-1-oxohexan-2-yl)ureido)pentanedioate (0.528 g, 0.712 mmol), (S)-2-amino-6-((2-tert-butoxy-2-oxoethyl)(pyridin-2-ylmethyl)amino)hexanoic acid (0.25 g, 0.712 mmol) and DIPEA (1.0 mL) in DMF (5.0 mL) was stirred at room temperature for overnight. The solvent was evaporated to give a residue, which was purified by Biotage eluting with DCM/MeOH to give (7S,11S,26S)-26-(4-((2-tert-butoxy-2-oxoethyl)(pyridin-2-ylmethyl)amino)butyl)-7,11-bis(tert-butoxycarbonyl)-2,2-dimethyl-4,9,17,24-tetraoxo-3-oxa-8,10,16,25-tetraazaheptacosan-27-oic acid (0.226 g, 32%). MS (ESI), 489.5 (M/2+H)⁺.

A solution of (7S,11S,26S)-26-(4-((2-tert-butoxy-2-oxoethyl)(pyridin-2-ylmethyl)amino)butyl)-7,11-bis(tert-butoxycarbonyl)-2,2-dimethyl-4,9,17,24-tetraoxo-3-oxa-8,10,16,25-tetraazaheptacosan-27-oic acid (56.5 mg, 0.075 mmol) in TFA (1.0 ml) and DCM (1.0 mL) was stirred at room temperature. Solvent was evaporated under reduced pressure to give a residue. A solution of the above residue in MeOH (1.0 mL) and H₂O (1.0 mL) was adjusted to pH=9 using 2 N NaOH. [NEt₄]₂[Re(CO)₃Br₃] (50 mg, 0.064 mmol) was added to the reaction mixture and was stirred at 95° C. under a pressure tube for 4 hrs. The solvent was evaporated to give a residue, which was purified by HPLC to give [Re(CO)₃][(7S,22S,26S)-9,16,24-trioxo-2-(pyridin-2-ylmethyl)-2,8,17,23,25-pentaazaoctacosane-1,7,22,26,28-pentacarboxylic acid] (13.3 mg) as a white solid. ¹H NMR (400 MHz, DMSO-d₆) 12.5 (brs, 4H), 8.74 (d, J=5.2 Hz, 1H), 8.13 (td, J=7.8, 1.2 Hz, 1H), 8.06 (d, J=8.0 Hz, 1H), 7.72-7.68 (m, 2H), 7.57 (t, J=6.6 Hz, 1H), 6.31 (d, J=8.0 Hz, 1H), 6.28 (d, J=8.4 Hz, 1H), 4.74 (d, J=16.0 Hz, 1H), 4.52 (d, J=16.0 Hz, 1H), 4.24-3.98 (m, 3H), 3.80 (d, J=16.8 Hz, 1H), 3.38 (d, J=16.8 Hz, 1H), 2.97-2.95 (m, 2H), 2.22 (q, J=7.7 Hz, 2H), 2.11 (t, J=7.4 Hz, 2H), 2.00 (t, J=7.2 Hz, 2H), 1.78-1.60 (m, 8H), 1.52-1.19 (m, 16H); MS (ESI), 512.3 (M/2H)⁺.

Compound 35-Re

Re(CO)₃ complex of the compound of example 35.

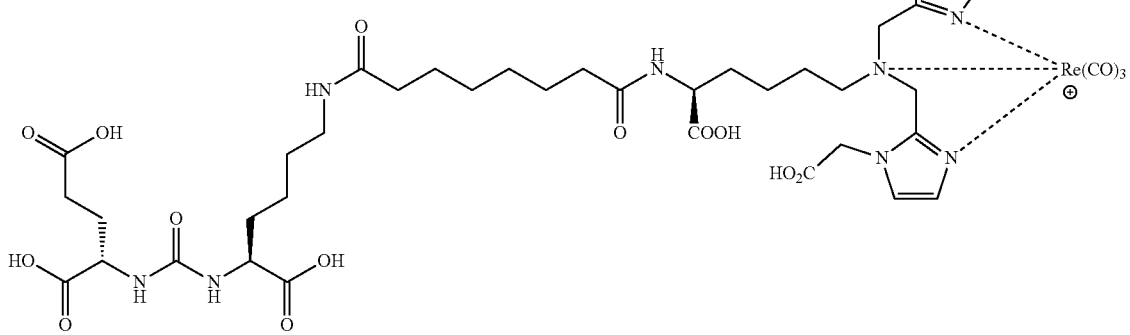

A solution of the compound of Compound 2 (300 mg, 0.396 mmol) and piperidine (0.40 mL) in DMF (2.0 mL) was stirred at room temperature for 2 hrs. The solvent was evaporated under reduced pressure to give a crude product. The crude product was purified by Amberchrom (CG-161C) eluting with H$_2$O/AcCN to give (S)-2-amino-6-(bis((1-(2-tert-butoxy-2-oxoethyl)-1H-imidazol-2-yl)methyl)amino) hexanoic acid (0.211 g, 100%). $^1$H NMR (400 MHz, DMSO-d$_6$) 7.0 (s, 2H), 6.65 (s, 2H), 4.70 (s, 4H), 4.2 (m, 4H), 3.2 (d, 2H), 2.4 (m, 2H), 1.8 (s, 2H), 1.39 (s, 18H). 1.15 (m, 2H); MS (ESI), 535.4 (M+H)$^+$.

A solution of (S)-di-tert-butyl 2-(3-((S)-6-amino-1-tert-butoxy-1-oxohexan-2-yl)ureido)pentanedioate (0.488 g, 1.0 mmol) in DMF (20 mL) was added dropwise to a solution of suberic acid bis(N-hydroxysuccinimide ester) (1.47 g, 4.0 mmol) in DMF (80 mL) via a syringe pump. After 2 h, the solvent was evaporated under reduced pressure to give a residue, which was purified by flash chromatography over silica gel eluting with AcCN/DCM to give (S)-di-tert-butyl 2-(3-((S)-1-tert-butoxy-6-(8-(2,5-dioxopyrrolidin-1-yloxy)-8-oxooctanamido)-1-oxohexan-2-yl)ureido)pentanedioate (0.54 g, 73%). MS (ESI), 741.6 (M+H)$^+$.

A solution of (S)-di-tert-butyl 2-(3-((S)-1-tert-butoxy-6-(8-(2,5-dioxopyrrolidin-1-yloxy)-8-oxooctanamido)-1-oxohexan-2-yl)ureido)pentanedioate (0.291 g, 0.45 mmol), (S)-2-amino-6-(bis((1-(2-tert-butoxy-2-oxoethyl)-1H-imidazol-2-yl)methyl) amino)hexanoic acid (0.22 g, 0.412 mmol) and DIPEA (1.0 mL) in DMF (4.0 mL) was stirred at room temperature for overnight. The solvent was evaporated to give a residue, which was purified by Biotage eluting with DCM/MeOH to give (7S,11S,26S)-26-(4-(bis((1-(2-tert-butoxy-2-oxoethyl)-1H-imidazol-2-yl)methyl)amino)butyl)-7,11-bis(tert-butoxycarbonyl)-2,2-dimethyl-4,9,17,24-tetraoxo-3-oxa-8,10,16,25-tetraazaheptacosan-27-oic acid (0.1089 g, 21%). MS (ESI), 581 (M/2+H)$^+$.

A solution of (7S,11S,26S)-26-(4-(bis((1-(2-tert-butoxy-2-oxoethyl)-1H-imidazol-2-yl)methyl)amino)butyl)-7,11-bis(tert-butoxycarbonyl)-2,2-dimethyl-4,9,17,24-tetraoxo-3-oxa-8,10,16,25-tetraazaheptacosan-27-oic acid (30 mg, 0.029 mmol) and [NEt$_4$]$_2$[Re(CO)$_3$Br$_3$] (30 mg, 0.039 mmol) in MeOH (4 mL) at a pressure tube was stirred at 95° C. for 4 hrs. The solvent was evaporated to give a residue, which was directly used for next step. A solution of the above product in TFA/DCM was stirred at room temperature for 5 hrs. The solvent was evaporated to give a crude product, which was purified by HPLC to give [Re(CO)$_3$][(22S,26S)-1-(1-(carboxymethyl)-1H-imidazol-2-yl)-2-((1-(carboxymethyl)-1H-imidazol-2-yl)methyl)-9,16,24-trioxo-2,8,17,23,25-pentaazaoctacosane-7,22,26,28-tetracarboxylic acid] (2.2 mg) as a white solid. $^1$H NMR (400 MHz, DMSO-d$_6$) 8.06 (d, J=8.0 Hz, 1H), 7.71 (d, J=5.6 Hz, 1H), 7.17 (d, J=1.2 Hz, 2H), 7.04 (d, J=1.2 Hz, 2H), 6.30 (d, J=8.4 Hz, 1H), 6.27 (d, J=8.0 Hz, 1H), 4.84 (s, 4H), 4.56 (d, J=16.8 Hz, 2H), 4.38 (d, J=16.4 Hz, 2H), 4.30-4.18 (m, 1H), 4.01-3.98 (m, 2H), 3.60-3.58 (m, 2H), 2.97-2.92 (m, 2H), 2.24-2.11 (m, 2H), 2.07 (t, J=8.0 Hz, 2H), 1.99 (t, J=7.6 Hz, 2H), 1.80-1.19 (m, 22H); MS (ESI), 575.9 (M/2+H)$^+$.

Compound 49-Tc

Radiolabelled Compound 49. Compound 49 was radiolabeled with Tc-99m, by complexation of Tc(CO)$_3$ with the bis-imidazole compound complexed as the t-butyl protected diacid, which was subsequently deprotected with TFA to afford the desired complex as depicted below.

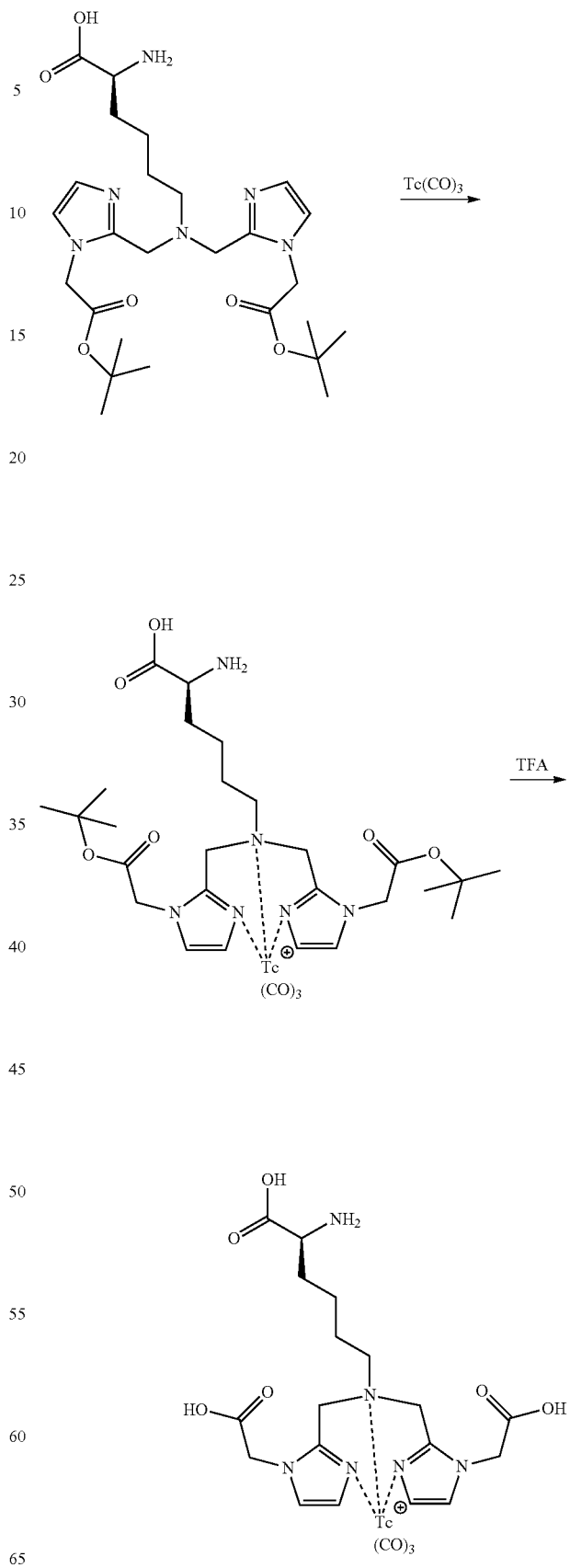

Compound 50-Re

Re(CO)₃ Complex of the Compound of Example 50.

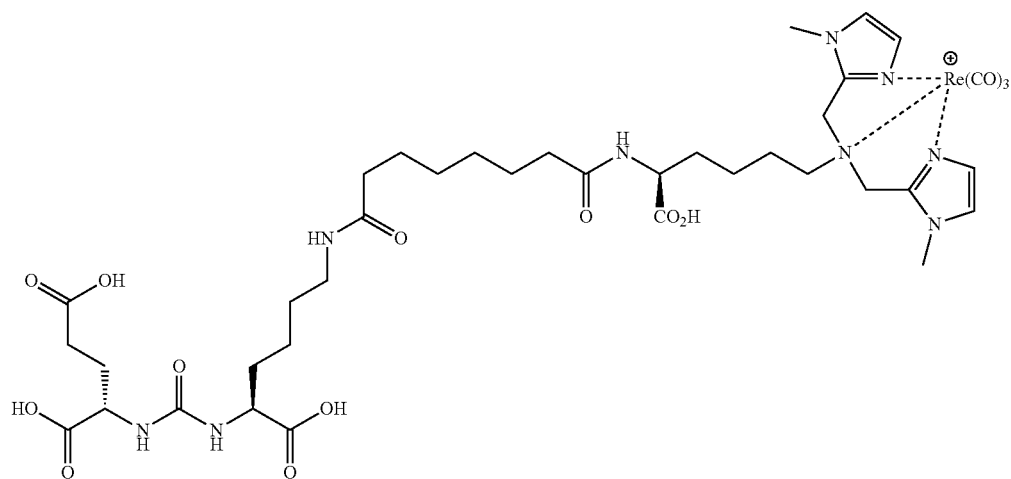

A solution of (S)-di-tert-butyl 2-(3-((S)-1-tert-butoxy-6-(8-(2,5-dioxopyrrolidin-1-yloxy)-8-oxooctanamido)-1-oxohexan-2-yl)ureido)pentanedioate (0.356 g, 0.48 mmol), the compound of Compound 13 (0.16 g, 0.48 mmol) and DIPEA (1.0 mL) in DMF (5.0 mL) was stirred at room temperature for overnight. The solvent was evaporated to give a residue, which was purified by Biotage eluting with DCM/MeOH to give (7S,11S,26S)-26-(4-(bis((1-methyl-1H-imidazol-2-yl)methyl)amino)butyl)-7,11-bis(tert-butoxycarbonyl)-2,2-dimethyl-4,9,17,24-tetraoxo-3-oxa-8,10,16,25-tetraazaheptacosan-27-oic acid (81 mg, 18%). MS (ESI), 481 (M/2+H)⁺.

A solution of (7S,11S,26S)-26-(4-(bis((1-methyl-1H-imidazol-2-yl)methyl)amino)butyl)-7,11-bis(tert-butoxycarbonyl)-2,2-dimethyl-4,9,17,24-tetraoxo-3-oxa-8,10,16,25-tetraazaheptacosan-27-oic acid (72 mg, 0.075 mmol) and [NEt₄]₂[Re(CO)₃Br₃] (72 mg, 0.094 mmol) in MeOH (4 mL) at a pressure tube was stirred at 95° C. for 4 hrs. The solvent was evaporated to give a residue, which was directly used for next step. A solution of the above product in TFA/DCM was stirred at room temperature for overnight. The solvent was evaporated to give a crude product, which was purified by HPLC to give [Re(CO)₃][(7S,22S,26S)-1-(1-methyl-1H-imidazol-2-yl)-2-(1-methyl-1H-imidazol-2-yl)methyl)-9,16,24-trioxo-2,8,17,23,25-pentaazaoctacosane-7,22,26,28-tetracarboxylic acid] (4.0 mg) as a white solid. ¹H NMR (400 MHz, DMSO-d₆) 8.08 (d, J=8.0 Hz, 1H), 7.72 (t, J=5.4 Hz, 1H), 7.24 (d, J=1.2 Hz, 2H), 7.05 (d, J=1.2 Hz, 2H), 6.31 (d, J=8.4 Hz, 1H), 6.28 (d, J=8.0 Hz, 1H), 4.69 (d, J=16.8 Hz, 2H), 4.54 (d, J=16.8 Hz, 2H), 4.28-4.23 (m, 1H), 4.11-4.03 (m, 2H), 3.78 (s, 6H), 2.97-2.92 (m, 2H), 2.26-2.20 (m, 2H), 2.11 (t, J=7.2 Hz, 2H), 1.99 (t, J=7.6 Hz, 2H), 1.90-1.20 (m, 24H); MS (ESI), 531.8 (M/2H)⁺.

Other Compounds of rhenium-labelled, technetium-labelled or other metal-labelled compounds may be prepared by the above exemplified methods. Compounds that have been prepared, include compounds such as those listed in Table 2. Due to the lanthanide contraction, rhenium and technetium have a similar size and reactivity, however, rhenium has a number of stable isotopes that are not radioactive, and therefore the rhenium compounds make good synthetic and testing models for the behavior of the corresponding radioactive technetium compounds. Therefore, each of the compounds in Table 2 may also be prepared as a Tc analog, however, it may not have been actually prepared in view of safety considerations for the handlers of the material.

TABLE 2

Illustrative Re- and Tc-chelated compounds.

| Ex. Compd. | Compound Structure |
|---|---|
| 16-Re | (structure) |
| 17-Re | (structure) |
| 18-Tc | (structure) |
| 21-Re | (structure) |
| 22-Re | (structure) |

131 132
TABLE 2-continued
Illustrative Re- and Tc-chelated compounds.
| Ex. Compd. | Compound Structure |
|---|---|
| 23-Re | 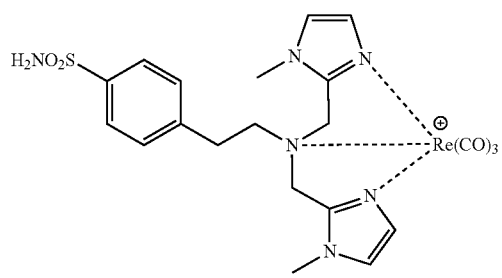 |
| 24-Re | 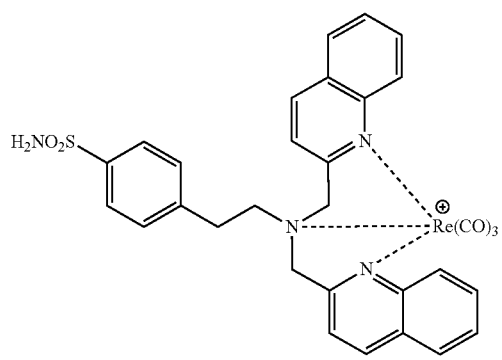 |
| 26-Re | 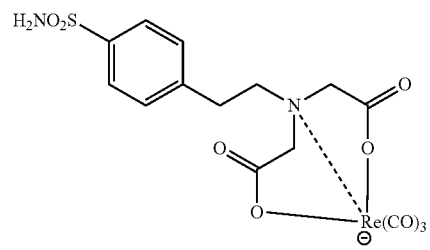 |
| 27-Re | 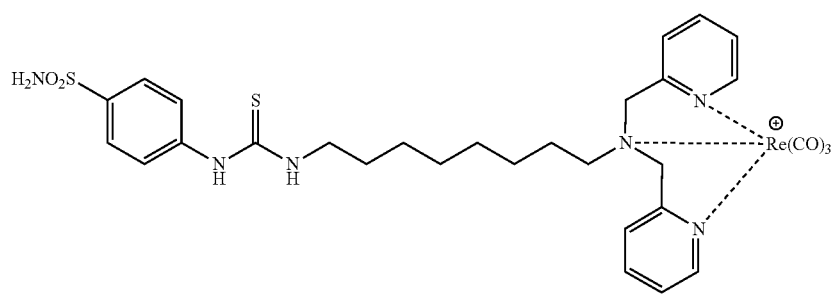 |
| 28-Re | 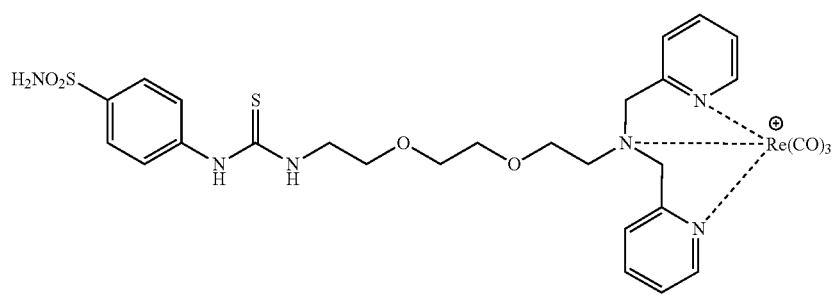 |

TABLE 2-continued

Illustrative Re- and Tc-chelated compounds.

| Ex. Compd. | Compound Structure |
|---|---|
| 29-Re | 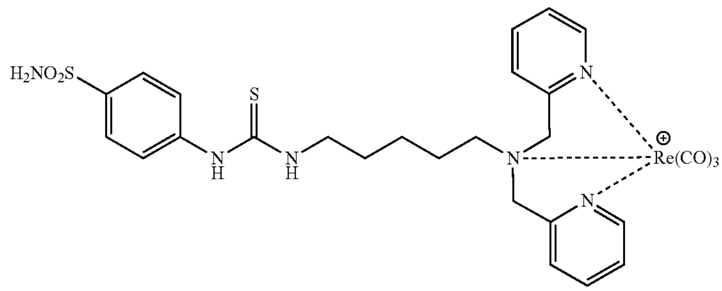 |
| 30-Re | 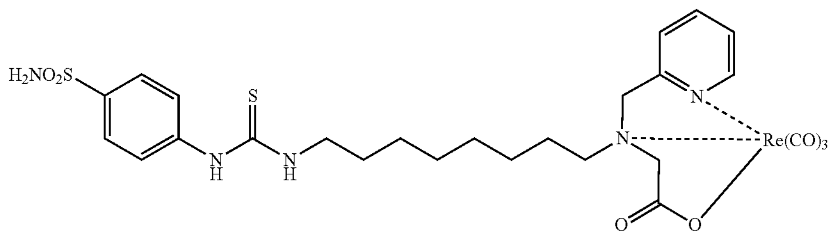 |
| 31-Re | 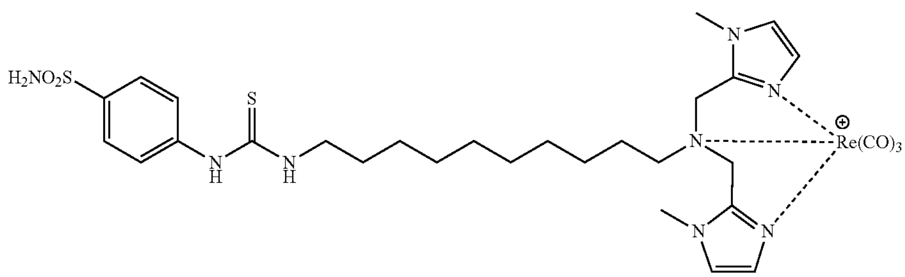 |
| 32-Re | 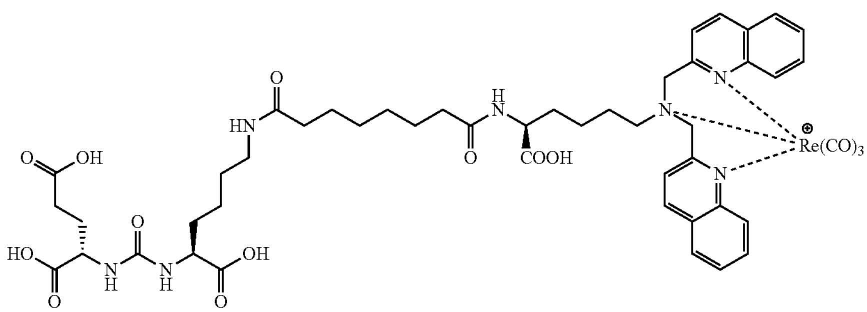 |
| 33-Re | 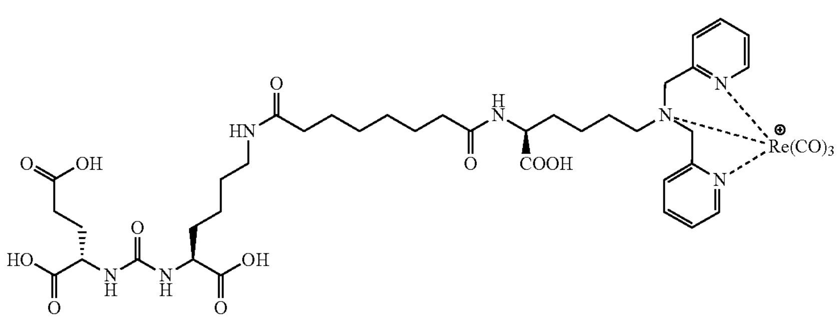 |

TABLE 2-continued
Illustrative Re- and Tc-chelated compounds.
| Ex. Compd. | Compound Structure |
|---|---|
| 36-Re | 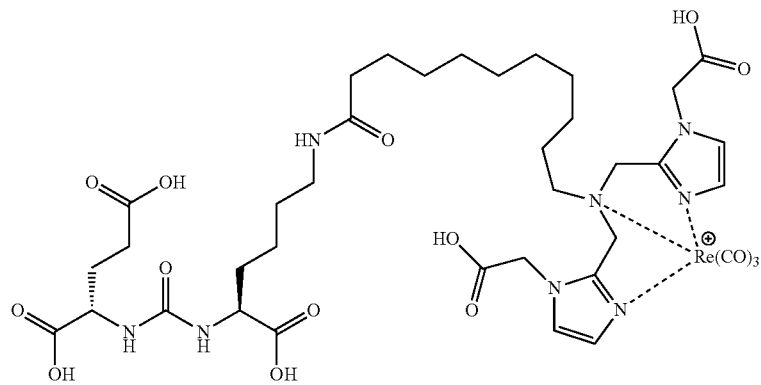 |
| 37-Re | 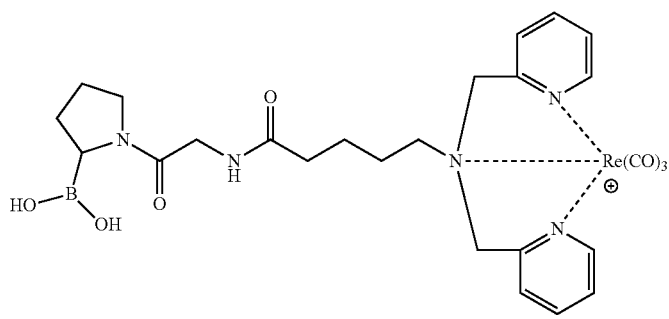 |
| 38-Re | 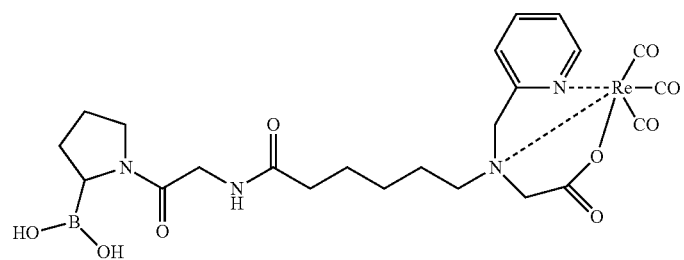 |
| 39-Re | 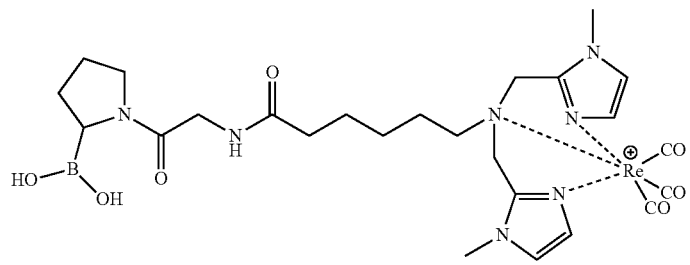 |
| 40-Re | 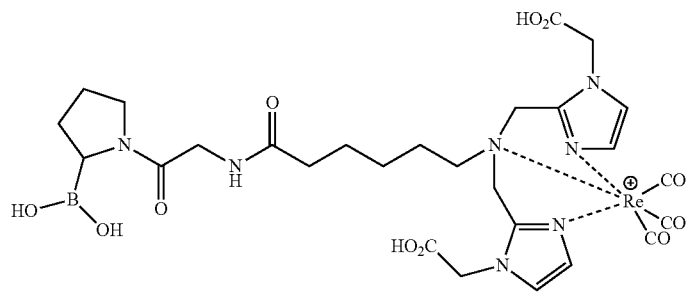 |

TABLE 2-continued
Illustrative Re- and Tc-chelated compounds.
| Ex. Compd. | Compound Structure |
|---|---|
| 44-Re | 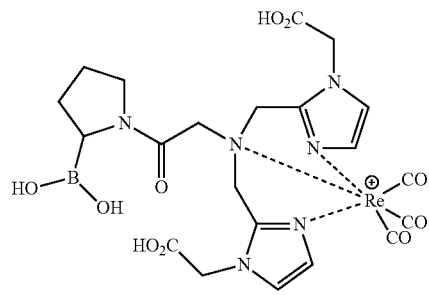 |
| 45-Re | 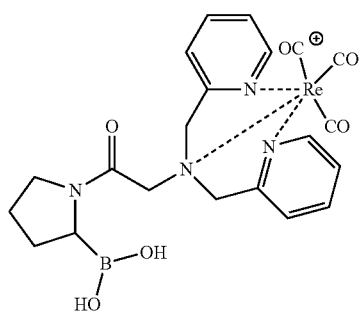 |
| 48-Re | 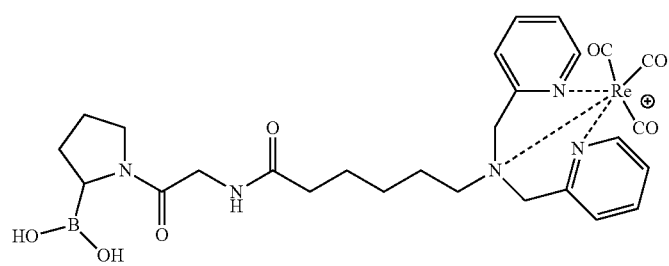 |
| 49-Re | 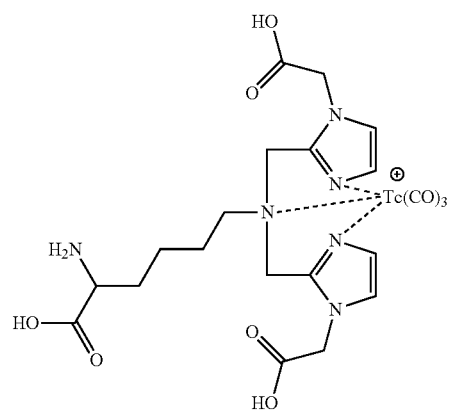 |

139 140
TABLE 2-continued
Illustrative Re- and Tc-chelated compounds.
| Ex. Compd. | Compound Structure |
|---|---|
| 50-Re | 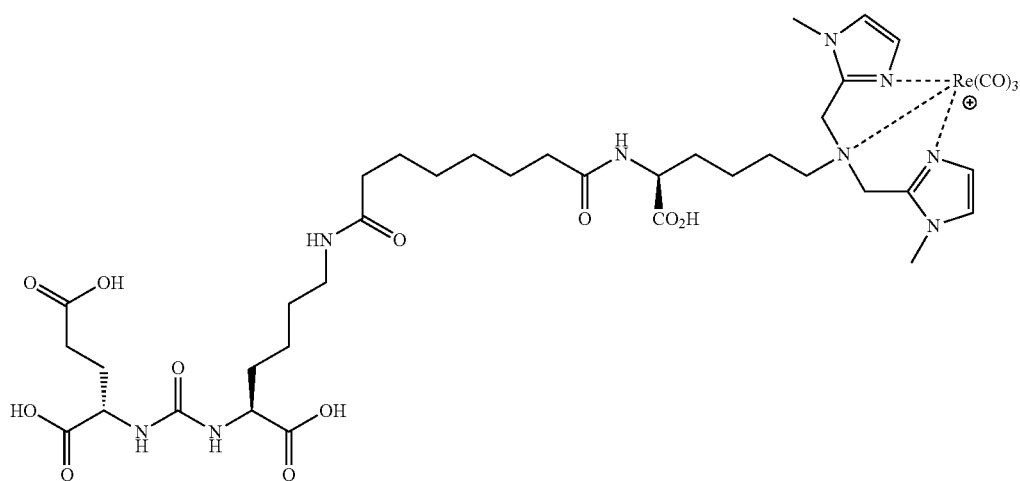 |
| 69-Re | 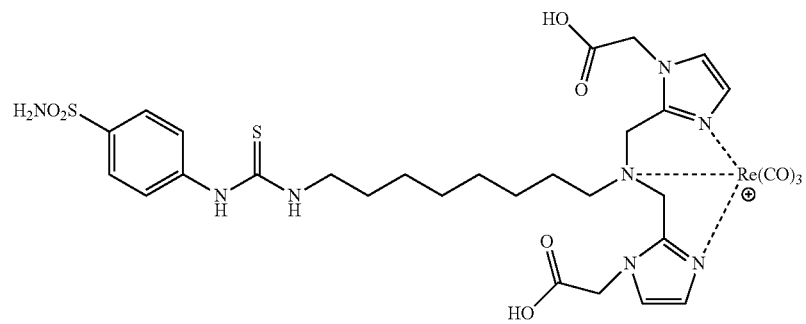 |
| 70-Re | 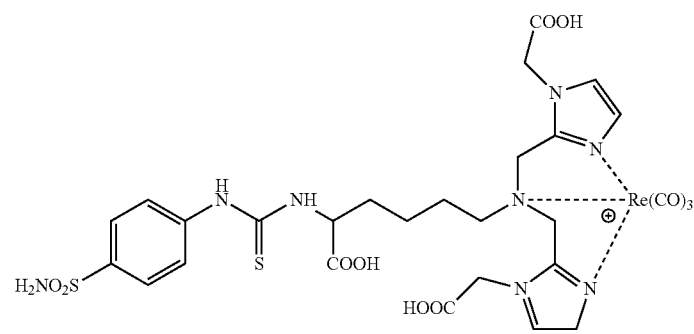 |
| 71-Re | 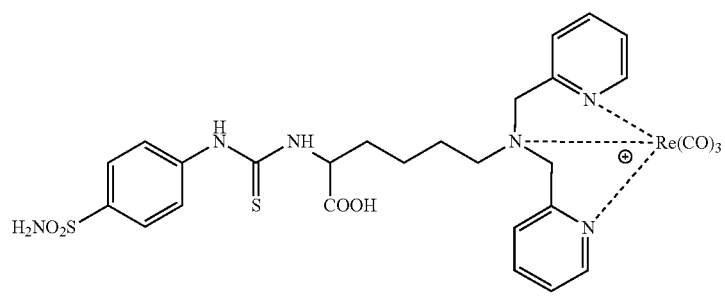 |

TABLE 2-continued
Illustrative Re- and Tc-chelated compounds.
Ex.
Compd.    Compound Structure
73-Re
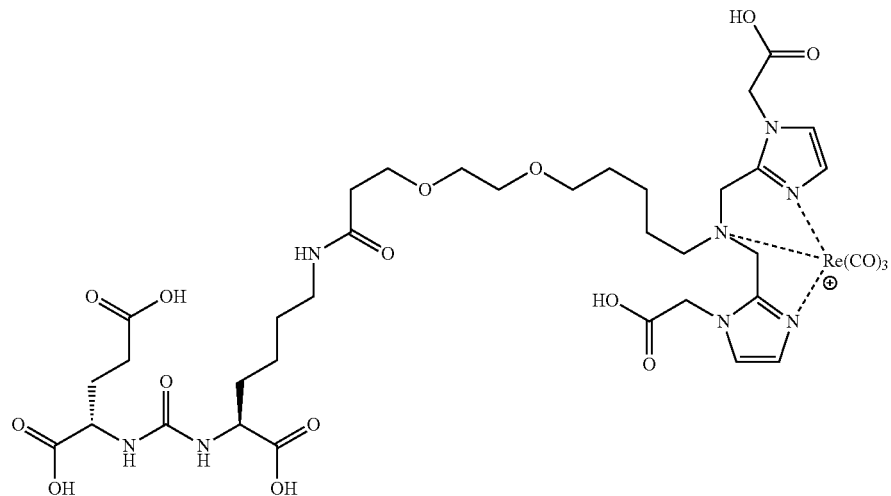
74-Re
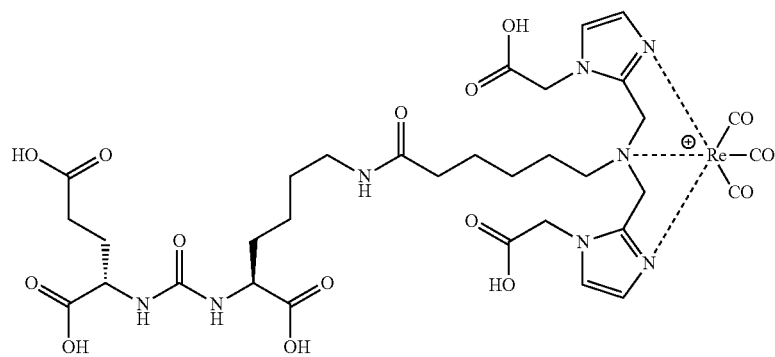
75-Re
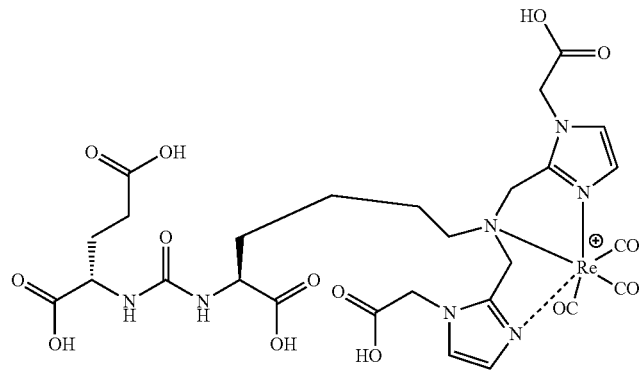

US 9,433,594 B2
143                             144
TABLE 2-continued
Illustrative Re- and Tc-chelated compounds.
| Ex. Compd. | Compound Structure |
|---|---|
| 76-Re | 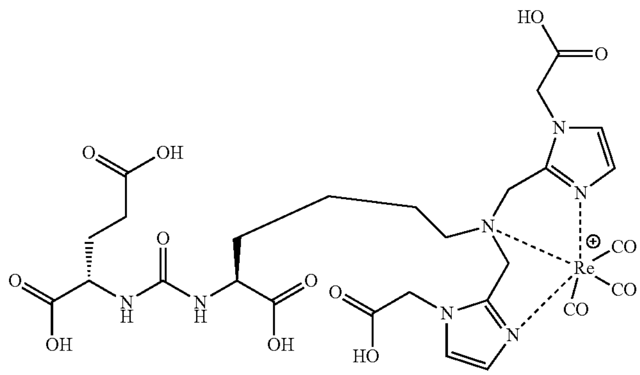 |
| 77-Re | 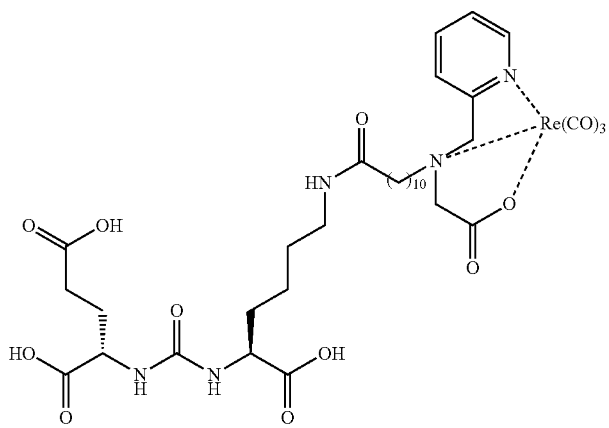 |
| 78-Re | 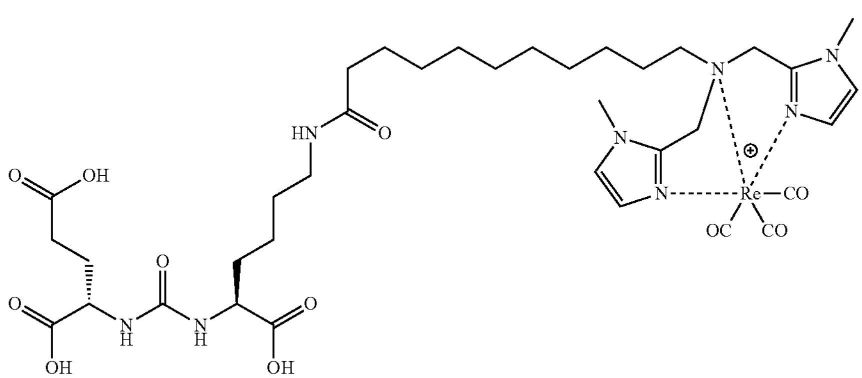 |
| 200-Re | 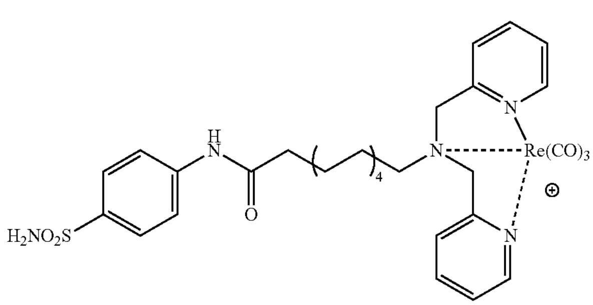 |
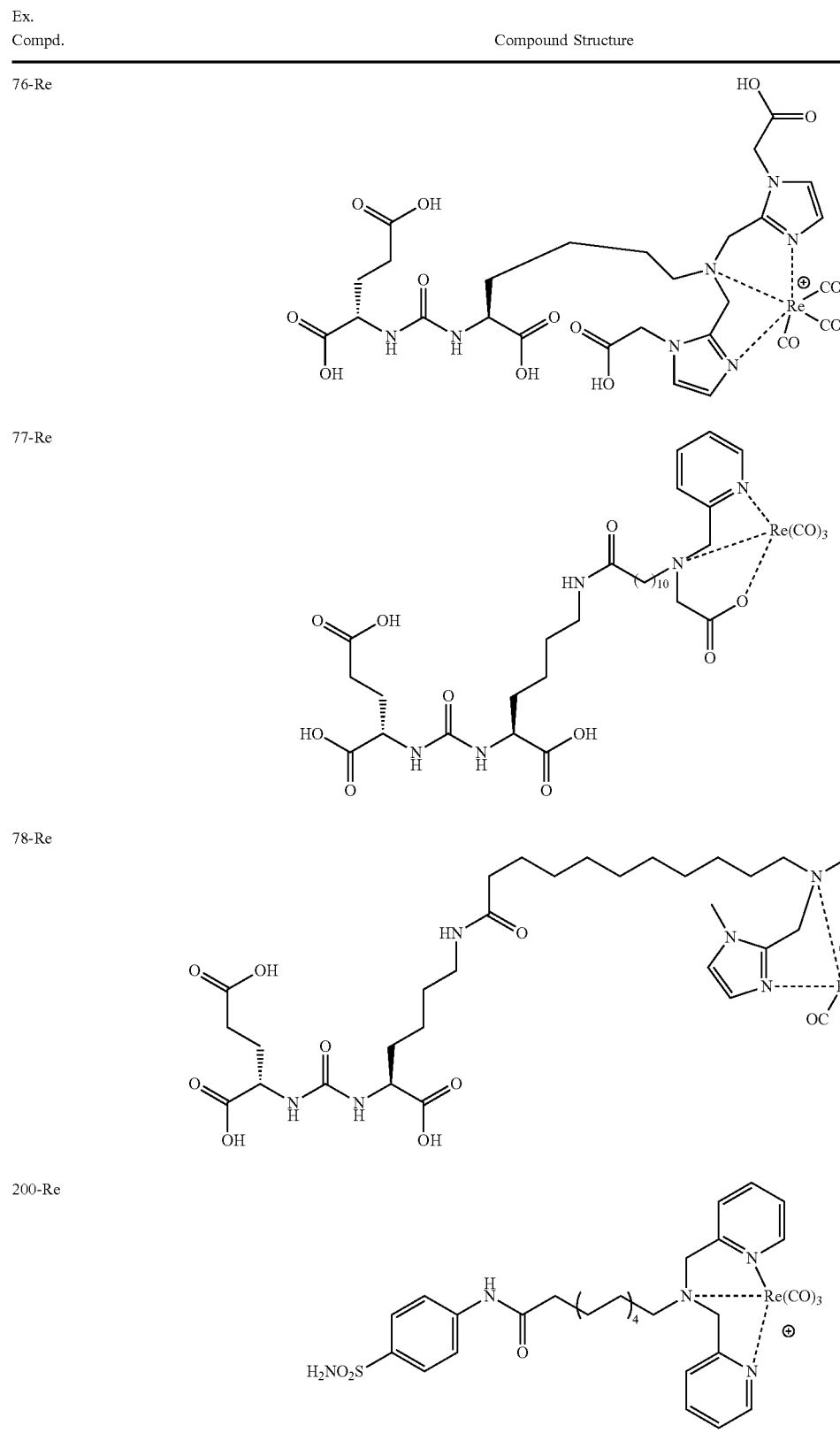

TABLE 2-continued
Illustrative Re- and Tc-chelated compounds.
| Ex. Compd. | Compound Structure |
|---|---|
| 201-Re | 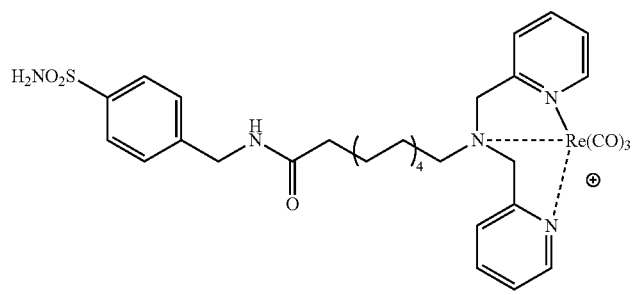 |
| 202-Re | 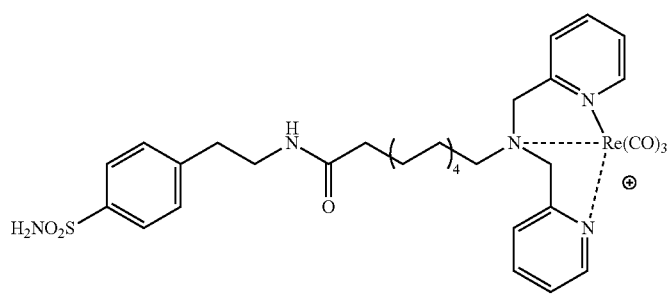 |
| 203-Re | 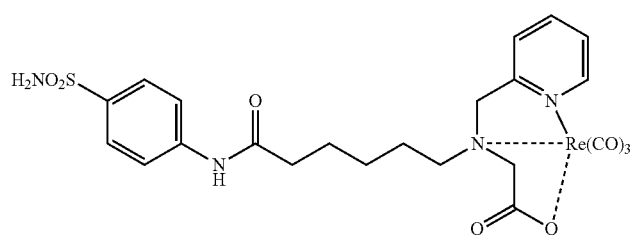 |
| 204-Re | 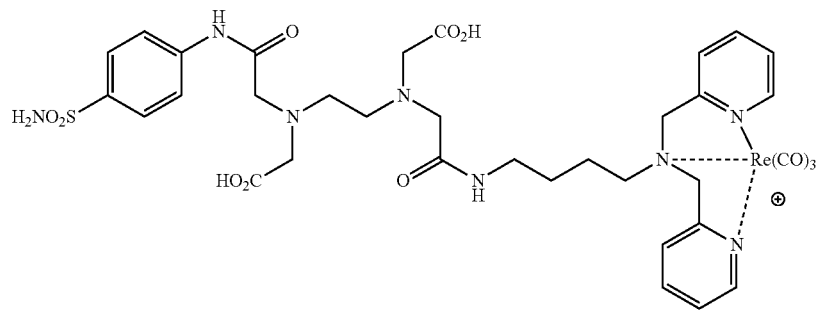 |
| 205-Re | 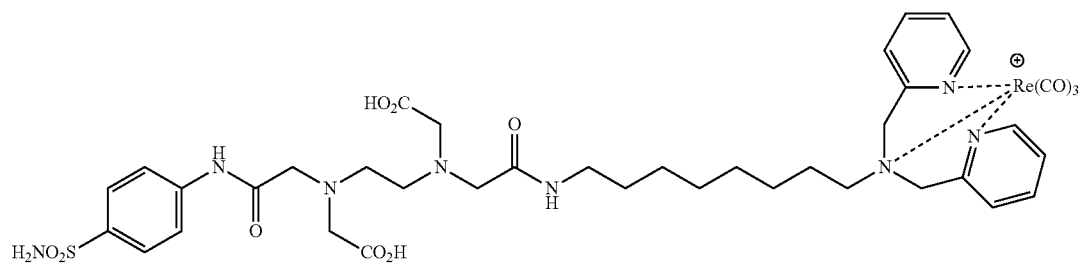 |

TABLE 2-continued
Illustrative Re- and Tc-chelated compounds.
| Ex. Compd. | Compound Structure |
|---|---|
| 206-Re | 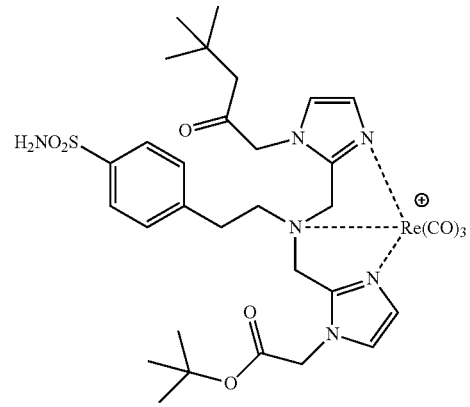 |
| 207-Re | 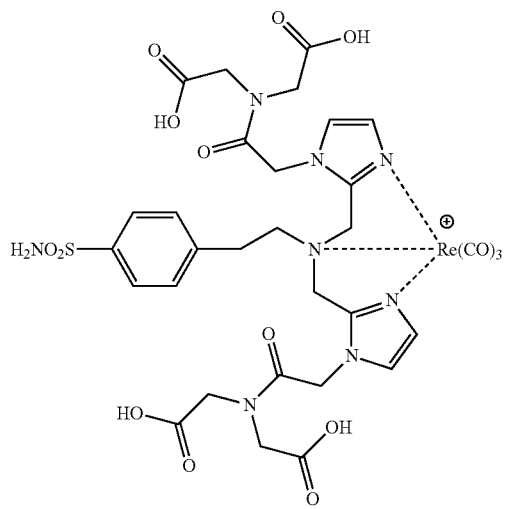 |
| 209-Re | 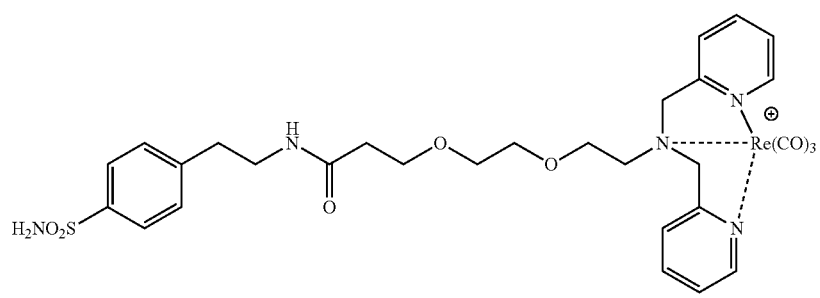 |
| 210-Re | 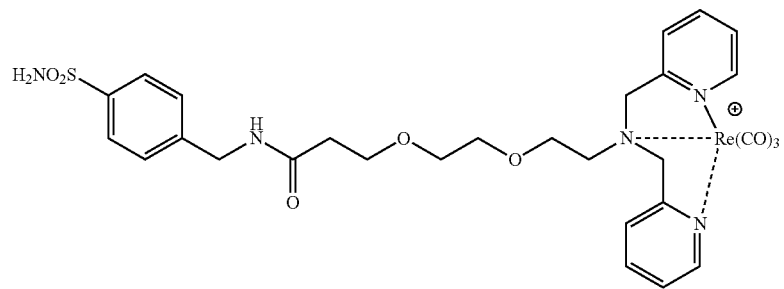 |

TABLE 2-continued

Illustrative Re- and Tc-chelated compounds.

| Ex. Compd. | Compound Structure |
|---|---|
| 211-Re | 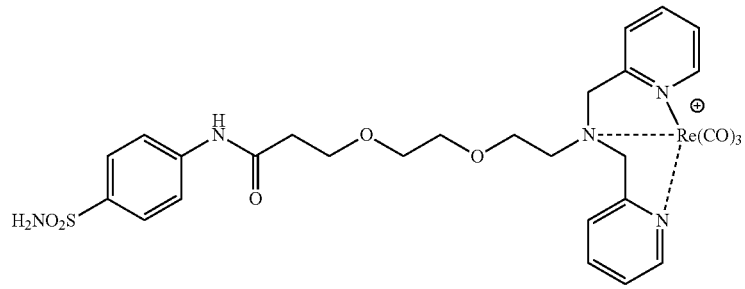 |
| 212-Re | 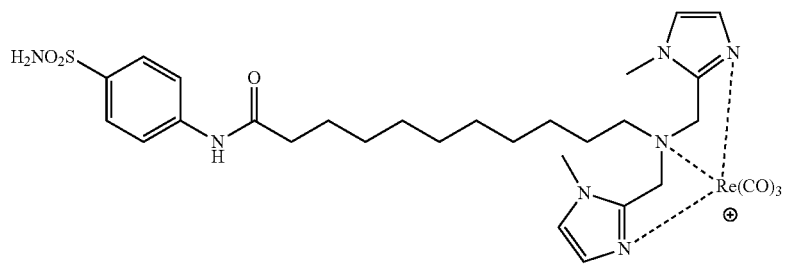 |
| 213-Re | 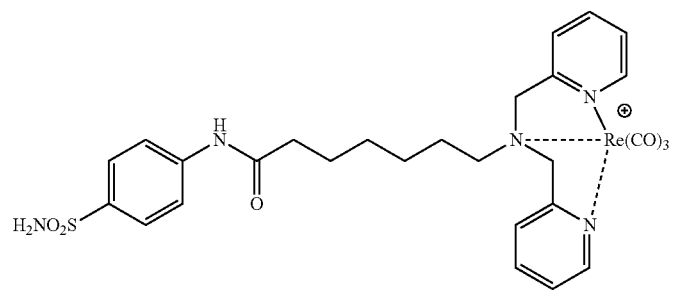 |

Example 1

Determination of Log P Values

The Log P values of the $^{99m}$Tc(I)-complexes were determined as follows. The $^{99m}$Tc-SAAC complexes were prepared and purified by RP-HPLC. The desired peak was collected and the sample was evaporated under a stream of nitrogen. The residue was dissolved in 25 µL of saline and placed in an equal volume of n-octanol (3 mL) and 25 mM pH=7.4 phosphate buffer (3 mL). The samples were mixed under vortex for 20 min, centrifuged at 8000 rpm for 5 min and three 100 µL aliquots were removed from both the aqueous and the organic layers for analysis on a gamma counter (Wallac 1282). Subsequently, 1 mL of the phosphate buffer-Tc-complex solution was removed and the process was repeated with fresh n-octanol, for a total number of six extractions to ensure full extraction of all the organic components. The partition coefficients were calculated using the equation: P=(activity concentration in n-octanol)/(activity concentration in aqueous layer). The Log P values reported were calculated from the average of the different measurements.

TABLE 3

Comparisons of the partition coefficients (Log P) and HPLC retention times for the $^{99m}$Tc-SAAC complexes.

| 99mTc-Complex | HPLC Rt [min] | Log P |
|---|---|---|
| DpK | 14.0 | −1.89 |
| DtK | 12.5 | −2.40 |
| PAMA-K | 14.0 | −1.80 |
| Diphenol-K | 17.2 | n.d. |
| Compound 79-Tc | 18.4 | −0.42 |
| Compound 4-Tc | 18.9 | −1.10 |
| Compound 6-Tc | 17.8 | −1.72 |
| Compound 42-Tc | 14.4 | n.d. |
| Compound 13-Tc | 16.9 | −2.0 |
| Compound 2-Tc | 16.7 | −2.33 |
| Compound 18-Tc | 14.4 | −1.84 |
| Compound 7-Tc | 11.8 | −2.20 |
| DTPA | 11.1 | n.d. |
| Histidine | 10.2 | n.d. | n.d. = not determined

Example 2

Rat Tissue Distribution Studies

The distribution and pharmacokinetics of selected $^{99m}$Tc-SAAC complexes were evaluated in normal male Sprague Dawley rats (180-200 grams) administered via the tail vein as a bolus injection (approximately 10 μCi/rat) in a constant volume of 0.1 ml. The animals (n=5 per time point) were euthanized by asphyxiation with carbon dioxide at 5, 30, 60, and 120 min post injection. Tissues (blood, heart, lungs, liver, spleen, kidneys, adrenals, stomach, intestines (with contents), testes, skeletal muscle, bone and brain) were dissected, excised, weighed wet, and counted in an automated γ-counter (LKB Model 1282, Wallac Oy, Finland). Tissue time-radioactivity levels expressed as percent injected dose per gram of tissue (% ID/g) was determined.

Example 3

The preparation of Compound 51 and Tc-99m Labelling Studies

Step 1. [ε-{N,N-di(pyridyl-2-methyl)}α-(fmoc)lysine] (Fmoc-DpK)

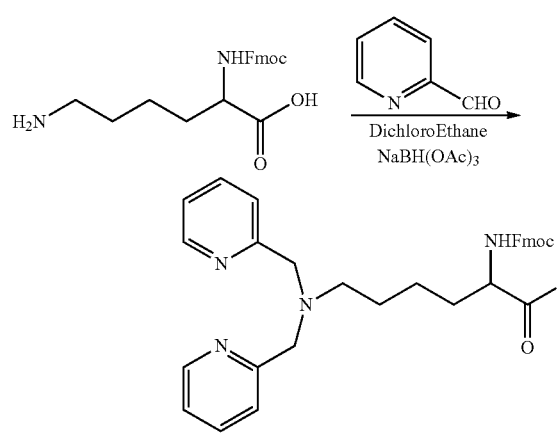

The fmoc-lysine, 2-pyridinecarboxaldehyde and sodium triacetoxyborohydride were mixed in 1,2-dichloroethane. The suspension was stirred at ambient temperature under an argon atmosphere for 1 hr. The reaction mixture was portioned between chloroform and water. The residue was purified through a pad of silica gel using methanol-chloroform to provide the product in 85% yield. Fmoc-deprotection employed stirring 4-dimethylaminopyridine in DMF/methanol at 25° C. for 12 hrs. Structural confirmation was performed by $^1$H and $^{13}$C NMR. $^1$H NMR (CDCl$_3$): δ 10.85 (bs, 1H, CO$_2$H), 8.50 (d, J=5.10 Hz, 2H, PyH), 7.70 (d, J=7.24 Hz, 2H, FlH), 7.55 (m, 4H, PyH, FlH), 7.46 (d, J=7.24 Hz, 2H, FlH), 7.32 (t, J=7.72, 2H, Py), 7.22 (t, J=7.52, 2H, Py), 7.09 (t, J=6.20, 2H, FlH), 6.0 (d, J=9.31, 1H, NH), 4.29 (m, 3H, OCH$_2$, NCHCO$_2$), 4.17 (t, J=6.20, 1H, CH), 3.86 (s, 4H, PyCH$_2$), 2.57 (t, 2H, NCH$_2$), 1.90-1.20 (m, 6H, CH$_2$). $^{13}$C NMR (CDCl$_3$): δ 175.96 (C, CO$_2$H), 157.74 (2C, Py), 156.15 (C, CONH), 148.29 (2CH, Py), 144.12 (2C, Fl), 141.27 (2C, Fl), 137.38 (2CH, Py), 127.68 (2CH, Py), 127.08 (2CH, Fl), 125.26 (2CH, Fl), 123.92 (2CH, Fl), 122.64 (2CH, Fl), 119.96 (2CH, Fl), 66.81 (1C, OCH$_2$), 59.03 (2C, PyCH$_2$), 54.48 (C, NCHCO$_2$), 53.87 (C, NCH$_2$), 47.24 (C, Fl), 32.54 (C, CH$_2$), 26.04 (C, CH$_2$), 22.86 (C, CH$_2$).

Step 2. [Re(CO)$_3${η$^3$-ε-[(N,N-di(pyridyl-2-methyl)] α(fmoc) lysine}][Br]

Compound 51

To a stirred solution of [NEt$_4$]$_2$[Re(CO)$_3$Br$_3$] (1.12 g, 1.45 mmol) in methanol (20 mL) was added [ε-{N,N-di(pyridyl-2-methyl)}α-(fmoc)lysine] (0.8 g, 1.45 mmol) in 2 mL methanol, whereupon the solution was refluxed for 5 hr and concentrated. The residue was dissolved in chloroform, washed with water, dried (NaSO$_4$) and evaporated to dryness to give a colorless product (1.04 g, 80%). $^1$H NMR (MeOH-d$_4$): δ 8.88 (d, J=5.29, 2H), 8.02-7.37 (m, 14H), 5.05 (d, J=17.64 Hz, 2H, PyCH$_2$), 4.82 (d, J=17.64 Hz, 2H, PyCH$_2$), 4.44-4.35 (m, 4H), 3.88 (m, 2H), 2.20-1.50 (m, 6H, CH$_2$). $^{13}$C NMR (MeOH-d$_4$): δ 197.47, 196.44 (fac-Re—CO$_3$), 175.42 (C, CO$_2$H), 161.82 (2C, Py), 158.30 (C, CONH), 152.87 (2CH, Py), 145.13 (2C, FlH), 142.29 (2C, FlH), 141.48 (2CH, Py), 129.07 (2CH, Py), 128.46 (2CH, Py), 126.94 (2CH, FlH), 126.58 (2CH, FlH), 124.83 (2CH, FlH), 121.23 (2CH, FlH), 71.66 (NCH$_2$), 68.72 (2C, PyCH$_2$), 67.70 (C, OCH$_2$), 55.27 (NCHCO$_2$), 32.15 (C, CH$_2$), 25.71 (2C, CH$_2$), 24.39 (C, CH$_2$).

3. Tc-99m Labeling.

[$^{99m}$Tc(CO)$_3$(H$_2$O)$_3$]$^+$ was heated with [ε-{N,N-di(pyridyl-2-methyl)}α-(fmoc)lysine] (DpK) in 0.5 mL (1 mg/mL) of methanol at 100° C. for 30 minutes. Purity, analyzed via C18 HPLC, showed >99% RCY. In challenge experiments the HPLC purified product demonstrated no degradation in either 100 mM Cysteine or Histidine in PBS pH 7.2 at 37° C. for 18 hrs. Labeling yields of >50% RCY, were achievable at levels as low as 2 μg/mL.

TABLE 4

Labeling results of Tc99m-DpK Complexes.

| Ligand Amounts (μg) | % Labeled Fmoc-DpK | % Labeled DpK |
|---|---|---|
| 500 | 100 | 100 |
| 100 | 100 | 47 |
| 10 | 93.9 | 32 |
| 1 | 52 | 16 |
| 0.1 | 7 | 5 |

Example 4

Labeling DPMA Analogs with Tc-99m Using Labeling Methods Based on the Tc(V)-Oxo and Tc(I)(CO)$_3$L$_3$ Cores (a) Tc(V)-Oxo Core:

Preparation of the Tc-99m-labeled DPMA derivatives was achieved by adding 10 mCi of TcO$_4^-$ to a 0.9% saline solution of the DPMA derivative (200 mg/3 mL). The mixture was heated at 80° C. for 30 min. Depending on the biological ligand, the solution was used as needed or the mixture was extracted with ethyl acetate (3, 1 mL portions), dried over sodium sulfate, and dried under N$_2$. The residue was then re-dissolved in ethanol (400 uL) and purity checked via HPLC by a Vydac C18 (5 mm, 25 cm) column using methanol to elute the reaction products.

(b) Tc(I)(CO)$_3^+$ Core:

The Tc(I) carbonyl chemistry allows for the possibility of an alternative route to form stable $^{99m}$Tc-DPMA complexes. To explore this labeling method we began by placing Na$_2$CO$_3$ (0.004 g, 0.038 mmol), NaBH$_4$ (0.005 g, 0.13 mmol), and 2 mg of the DPMA derivative in a vial. Next, the vial was sealed and flushed with CO for 10 min. To the vial was added 1 mL of Na $^{99m}TcO_4^-$ in saline. Finally the solution was heated to 100° C. for 30 minutes. After cooling, the reaction was then checked for purity via HPLC by a Vydac C18 (5 mm, 25 cm) column using methanol to elute the reaction products.

Alternatively, a 'two pot' synthesis could be performed, where the DPMA derivative was added after the formation of $[^{99m}Tc(OH_2)_3(CO)_3]^+$. After cooling, 0.3 mL of 1 M PBS solution was added (pH 7.4), resulting in the stable formation of $[^{99m}TC(OH_2)_3(CO)_3]$ This Tc(I) tricarbonyl species was then heated at 75° C. for 30 minutes with the DPMA derivative to form the $^{99m}$Tc-DPMA complex. The reaction was then checked for purity via HPLC by a Vydac C18 (5 mm, 25 cm) column using methanol to elute the reaction products. The versatility of the reaction allows for the reaction of a variety of sensitive biological DPMA derivatized ligands to be kept under idealized conditions.

Example 5

Preparation of SAAC Ligands

The chemistry utilized to prepare SAAC ligands was based on the use of the reductive alkylation reaction, as noted above. The compounds can be purified by column chromatography to afford the pure prototype SAAC systems, (dipyridyl)lysine (DpK), (dithiazole)lysine (DTK), (pyridylamine)monoacetic acid lysine (PAMAK), and Diphenol lysine (Diphenol K). Incorporation of SAAC into a peptide sequence or conjugation to a small molecule is accomplished by standard amide bond coupling to either the carboxylic acid or the amine functional group of the SAAC.

Example 6

Radiolabeling of SAAC ($^{99m}$Tc-SAAC Complexes)

Radiolabeling of SAAC ligands can be effected on either the free amino acids or as the appropriately N-protected amino acid derivatives utilizing similar methodologies, demonstrating the ease of preparation and the flexibility in the design of the SAAC ligands. The $^{99m}Tc(I)(CO)_3^+$ radiolabeling was accomplished in two steps using the commercially available IsoLink™ kits (Mallinckrodt) to form the $[^{99m}Tc(CO)_3(H_2O)_3]^+$ intermediate, which was reacted with the appropriate SAAC ($1\times10^{-4}$M) in 0.5 mL of acetonitrile. The sealed vial was heated at 75° C. for 30 minutes. Upon cooling, the reaction was analyzed for purity via HPLC using a Vydac C18 (4.6 mm, 25 cm) column. The radiochemical purity (RCP) was determined via C18 high pressure liquid chromatography (HPLC) and shown to be 85%. Although initial results demonstrated radiolabeling at concentrations as low as $10^{-6}$M in certain instances, the radiochemical yields (RCY) were only modest at best≤55%.

Example 7

Complex Stability: $^{99m}$Tc Challenge Experiments

The complexes were analyzed by HPLC for stability against cysteine and histidine challenge over time. The products (carrier free) demonstrated no degradation by HPLC analysis after incubation with 100 mM cysteine or 100 mM histidine in phosphate buffer solution (PBS), pH=7.2 at 37° C. for 18 h. The $^{99m}$Tc-SAAC complexes were stable to excess histidine and cysteine challenges for more than 18 hours at 37° C. for the DpK, DTK, and PAMAK chelators, however the anionic complex $^{99m}$Tc-DiphenolK was much less stable.

Example 8

Peptide Synthesis and Characterization

Peptides are prepared on an Advanced ChemTech 348Ω Peptide Synthesizer using p-benzotriazole-N,N,N',N'-tetramethyluronium hexafluorophosphate (HBTU) as the coupling agent. An Fmoc protected chelate, or its organometallic complex as the bromide salt, is dissolved in DMF and coupled to the growing peptide chain using about a 4-fold excess of ligand. The duration of the coupling steps to afford complete conversion is determined by exposing samples of resin taken from the reaction mixtures to a solution containing ninhydrin. The time to complete conversion of the amine to the amide in both cases is identical to the conditions used for natural amino acid derivatives. As a result, modification of standard peptide coupling protocols is not necessary. Peptides are cleaved from the resin using a TFA solution containing ethanedithiol (EDT, 2%), water (2%), and triisopropylsilane (TIS, 2%). Because of the presence of methionine, exclusion of oxygen and the use of freshly distilled EDT is necessary to avoid oxidation of the thioether to the sulfoxide. Precipitation of the peptide TFA salts is brought about by trituration with cold ether. The resulting solids are collected by centrifugation and washed with cold ether. Following dissolution in distilled water and lyophilization, compounds are collected as solids.

Example 9

Normal Rat Tissue Distribution Studies

Normal rat tissue distribution studies were performed with $[^{99m}Tc(CO)_3\{\eta^3\text{-}(DpK)\}]$, $[Tc(CO)_3\{\eta^3\text{-}(DTK)\}]$ and $[Tc(CO)_3\{\eta^3\text{-}(PAMAK)\}]$ in groups of male Sprague Dawley rats (n=4/group, 180-200 grams each) at 5, 30, 60, and 120 minutes post injection. The compounds were injected via the tail vein in saline (10 μCi/100 μl). The clearance from selected tissues is shown in Table 5. Each of the three SAAC ligands, $[^{99m}Tc(CO)_3\{\eta^3\text{-}(DPK)\}]$, $[Tc(CO)_3\{\eta^3\text{-}(DTK)\}]$, and $[Tc(CO)_3\{\eta^3\text{-}(PAMAK)\}]$, exhibited significantly different pharmacokinetic profiles and clearance patterns in the kidneys and liver. $[Tc(CO)_3\{\eta^3\text{-}(DTK)\}]$ cleared more slowly from the blood than either $[^{99m}Tc(CO)_3\{\eta^3\text{-}(DPK)\}]$ or $[Tc(CO)_3\{\eta^3\text{-}(PAMAK)\}]$. All three SAAC ligands had very high accumulation and retention in the gastrointestinal (GI) tract. These data demonstrate that, in general, the SAAC ligands with lipophilic substitutions, exhibit high hepatobiliary excretion. The design of hydrophilic SAAC ligands may alter the pharmacokinetics by mitigating the lipophilicity of the complex and potentially favoring renal, over liver and GI clearance. Such a result may facilitate the development of clinically relevant molecular imaging radiopharmaceuticals with desirable pharmacokinetic properties.

TABLE 5

Selected tissue distribution results of $^{99m}$Tc-SAAC complexes, expressed as average % ID/g ± (SEM)

| | 5 Min | 30 Min. | 60 Min. | 120 Min |
|---|---|---|---|---|
| [$^{99m}$Tc(CO)$_3$(DPK)] | | | | |
| Blood | 7.01 ± 1.38 | 1.12 ± 0.31 | 0.39 ± 0.16 | 0.18 ± 0.01 |
| Liver | 16.28 ± 5.12 | 26.03 ± 1.50 | 22.71 ± 1.14 | 14.44 ± 2.75 |
| Kidney | 8.88 ± 3.20 | 9.72 ± 0.68 | 9.47 ± 1.23 | 7.08 ± 1.58 |
| GI | 4.65 ± 1.78 | 15.01 ± 1.82 | 24.46 ± 6.20 | 38.90 ± 5.94 |
| [$^{99m}$Tc(CO)$_3$(DTK)] | | | | |
| Blood | 44.78 ± 11.26 | 31.50 ± 1.37 | 19.28 ± 1.21 | 10.55 ± 1.06 |
| Liver | 14.11 ± 3.94 | 17.49 ± 1.10 | 20.30 ± 2.46 | 22.98 ± 3.60 |
| Kidney | 5.81 ± 1.35 | 8.19 ± 1.06 | 8.25 ± 0.41 | 8.79 ± 0.45 |
| GI | 4.55 ± 1.91 | 8.61 ± 1.42 | 11.59 ± 4.60 | 13.13 ± 2.34 |
| [$^{99m}$Tc(CO)$_3$(PAMAK)] | | | | |
| Blood | 9.77 ± 1.79 | 3.19 ± 0.43 | 1.16 ± 0.07 | 0.59 ± 0.18 |
| Liver | 10.93 ± 2.64 | 11.84 ± 1.38 | 4.69 ± 0.87 | 1.67 ± 0.26 |
| Kidney | 11.47 ± 2.52 | 6.79 ± 0.49 | 2.34 ± 0.26 | 0.86 ± 0.14 |
| GI | 2.95 ± 0.47 | 22.13 ± 5.61 | 33.40 ± 5.46 | 39.39 ± 15.73 |

Example 10

Evaluation of the Pharmacokinetic Properties of SAAC and DOTA Somatostatins in AR42J Tumor-Bearing Mice SAAC DpK has been incorporated onto the N-terminus of Tyr-3-Octreotide, a somatostatin receptor II (SSTRII) selective peptide agonist. The SAAC DpK has been compared to $^{111}$In-DOTA-Tyr-3-Octreotide, an imaging agent for carcinoid and other neurodenocrine tumor detection, with regard to tissue distribution, tumor uptake and retention, clearance, and route of excretion in mice bearing AR42J xenografts. The results are shown in FIG. 1. While both $^{99m}$Tc-DpK-Tyr-3-Octreotide and $^{111}$In-DOTA-Tyr-3-Octreotide demonstrate uptake and retention in target tissues, such as the tumor and pancreas, the liver and GI uptake of $^{99m}$Tc-DpK-Tyr-3-Octreotide is significantly greater than $^{111}$In-DOTA-Tyr-3-Octreotide. This result is similar to the data obtained with the chelator alone in rats, thereby highlighting the necessity of developing SAAC ligands with a pharmacokinetic profile that favors renal clearance.

Example 11

$^{99m}$Tc Complexes of Various Example Ligands in Sprague-Dawley Rats

The data is presented in Table 6:

TABLE 6

| Compd. | Tissue | 5 min | 30 min |
|---|---|---|---|
| 4 | Blood | 0.83 ± 0.09 | 0.09 ± 0.02 |
| | Liver | 1.61 ± 0.32 | 0.35 ± 0.08 |
| | Kidney | 6.86 ± 0.86 | 12.13 ± 2.36 |
| | GI | 0.57 ± 0.13 | 2.33 ± 0.61 |
| | Sk. Muscle | 0.13 ± 0.02 | 0.02 ± 0.01 |
| 42 | Blood | 0.94 ± 0.19 | 0.22 ± 0.06 |
| | Liver | 1.16 ± 0.09 | 1.06 ± 0.35 |
| | Kidney | 10.84 ± 1.25 | 9.07 ± 0.66 |
| | GI | 0.16 ± 0.03 | 1.16 ± 0.4 |
| | Sk. Muscle | 0.21 ± 0.03 | 0.05 ± 0.01 |
| 79 | Blood | 0.36 ± 0.06 | 0.09 ± 0.02 |
| | Liver | 3.55 ± 0.38 | 0.94 ± 0.28 |
| | Kidney | 4.56 ± 0.79 | 4.34 ± 1.07 |
| | GI | 1.63 ± 0.26 | 2.95 ± 1.27 |
| | Sk. Muscle | 0.1 ± 0.01 | 0.02 ± 0 |
| 18 | Blood | 1.03 ± 0.14 | 0.45 ± 0.1 |
| | Liver | 0.95 ± 0.14 | 3.02 ± 0.59 |
| | Kidney | 10.79 ± 1.97 | 17.05 ± 3.17 |
| | GI | 0.16 ± 0.01 | 1.96 ± 0.49 |
| | Sk. Muscle | 0.21 ± 0.05 | 0.09 ± 0.02 |
| DPK | Blood | 0.58 ± 0.05 | 0.07 ± 0.01 |
| | Liver | 3.36 ± 0.44 | 2.75 ± .011 |
| | Kidney | 6.05 ± 1.03 | 4.94 ± 0.11 |
| | GI | 0.49 ± 0.08 | 0.89 ± 0.07 |
| | Sk. Muscle | 0.18 ± 0.02 | 0.03 ± 0.00 |
| 6 | Blood | 1.46 ± 0.21 | 0.47 ± 0.05 |
| | Liver | 1.06 ± 0.34 | 0.45 ± 0.04 |
| | Kidney | 13.82 ± 2.81 | 34.1 ± 5.59 |
| | GI | 0.34 ± 0.12 | 1.05 ± 0.2 |
| | Sk. Muscle | 0.3 ± 0.04 | 0.1 ± 0.01 |
| 13 | Blood | 1.18 ± 0.18 | 0.28 ± 0.03 |
| | Liver | 0.8 ± 0.28 | 1.03 ± 0.21 |
| | Kidney | 6.65 ± 2.06 | 22.2 ± 3.9 |
| | GI | 0.15 ± 0.02 | 0.45 ± 0.11 |
| | Sk. Muscle | 0.22 ± 0.03 | 0.06 ± 0.02 |
| 2 | Blood | 1.33 ± 0.2 | 1.14 ± 0.23 |
| | Liver | 0.52 ± 0.07 | 0.55 ± 0.07 |
| | Kidney | 6.85 ± 1.85 | 10.7 ± 2.3 |
| | GI | 0.15 ± 0.02 | 0.44 ± 0.08 |
| | Sk. Muscle | 0.29 ± 0.04 | 0.21 ± 0.06 |
| PAMAK | Blood | 0.63 ± 0.12 | 0.19 ± 0.03 |
| | Liver | 1.26 ± 0.27 | 1.34 ± 0.29 |
| | Kidney | 6.4 ± 1.4 | 3.55 ± 0.49 |
| | GI | 0.18 ± 0.04 | 1.22 ± 0.34 |
| | Sk. Muscle | 0.15 ± 0.07 | 0.05 ± 0 |
| DTK | Blood | 3.32 ± 0.82 | 2.33 ± 0.26 |
| | Liver | 1.7 ± 0.42 | 1.93 ± 0.15 |
| | Kidney | 3.26 ± 1.04 | 4.71 ± 0.41 |
| | GI | 0.3 ± 0.15 | 0.59 ± 0.13 |
| | Sk. Muscle | 0.16 ± 0.05 | 0.16 ± 0.01 |

| Compd. | Tissue | 60 min | 120 min |
|---|---|---|---|
| 4 | Blood | 0.02 ± 0 | 0.01 ± 0 |
| | Liver | 0.28 ± 0.07 | 0.14 ± 0.02 |
| | Kidney | 12.54 ± 1 | 12.54 ± 0.81 |
| | GI | 3.62 ± 0.3 | 2.96 ± 0.44 |
| | Sk. Muscle | 0.01 ± 0 | 0.01 ± 0 |
| 42 | Blood | 0.09 ± 0 | 0.03 ± 0.01 |
| | Liver | 1.04 ± 0.18 | 0.72 ± 0.16 |
| | Kidney | 4.19 ± 0.57 | 1.63 ± 0.51 |
| | GI | 1.93 ± 0.37 | 2.27 ± 0.59 |
| | Sk. Muscle | 0.02 ± 0 | 0.01 ± 0 |
| 79 | Blood | 0.07 ± 0.02 | 0.05 ± 0.01 |
| | Liver | 0.88 ± 0.15 | 0.51 ± 0.08 |
| | Kidney | 3.36 ± 0.46 | 3.57 ± 0.96 |
| | GI | 4.03 ± 1.01 | 4.67 ± 1.18 |
| | Sk. Muscle | 0.02 ± 0 | 0.01 ± 0 |
| 18 | Blood | 0.22 ± 0.02 | 0.09 ± 0.01 |
| | Liver | 0.98 ± 0.22 | 0.44 ± 0.14 |
| | Kidney | 9.52 ± 2.54 | 3.94 ± 0.43 |
| | GI | 1.64 ± 0.64 | 2.53 ± 0.7 |
| | Sk. Muscle | 0.05 ± 0.01 | 0.02 ± 0 |
| DPK | Blood | 0.03 ± 0.01 | 0.01 ± 0.00 |
| | Liver | 2.59 ± 0.08 | 2.20 ± 0.06 |
| | Kidney | 4.93 ± 0.43 | 3.89 ± .042 |
| | GI | 1.46 ± 0.09 | 2.73 ± 0.57 |
| | Sk. Muscle | 0.03 ± 0.01 | 0.01 ± 0.00 |
| 6 | Blood | 0.14 ± 0.04 | 0.04 ± 0.01 |
| | Liver | 0.24 ± 0.04 | 0.16 ± 0.02 |
| | Kidney | 40.25 ± 5.17 | 33.18 ± 2.75 |
| | GI | 1.39 ± 0.24 | 1.21 ± 0.27 |
| | Sk. Muscle | 0.04 ± 0.01 | 0.01 ± 0 |
| 13 | Blood | 0.11 ± 0.02 | 0.03 ± 0.01 |
| | Liver | 0.86 ± 0.16 | 0.74 ± 0.14 |
| | Kidney | 25.4 ± 1.7 | 25.5 ± 3.4 |
| | GI | 0.84 ± 0.1 | 1.12 ± 0.37 |
| | Sk. Muscle | 0.03 ± 0.01 | 0.01 ± 0 |
| 2 | Blood | 0.86 ± 0.17 | 0.72 ± 0.12 |
| | Liver | 0.42 ± 0.08 | 0.39 ± 0.07 |
| | Kidney | 16.8 ± 4.8 | 10.2 ± 2.5 |

TABLE 6-continued

| | | | |
|---|---|---|---|
| | GI | 0.76 ± 0.31 | 1.22 ± 0.27 |
| | Sk. Muscle | 0.16 ± 0.03 | 0.14 ± 0.02 |
| PAMAK | Blood | 0.07 ± 0.00 | 0.03 ± 0.01 |
| | Liver | 0.56 ± 0.1 | 0.2 ± 0.06 |
| | Kidney | 1.14 ± 0.27 | 0.47 ± 0.09 |
| | GI | 1.82 ± 0.35 | 2.44 ± 1.18 |
| | Sk. Muscle | 0.02 ± 0.00 | 0.02 ± 0.01 |
| DTK | Blood | 1.4 ± 0.07 | 0.76 ± 0.12 |
| | Liver | 2.05 ± .041 | 2.61 ± 0.31 |
| | Kidney | 4.78 ± 0.14 | 4.83 ± 0.41 |
| | GI | 0.73 ± 0.29 | 0.87 ± 0.2 |
| | Sk. Muscle | 0.15 ± 0.02 | 0.12 ± 0.01 |

Example 12

Selective Inhibition of Carbonic Anhydrase Enzyme Activity

Compounds were tested for their ability to inhibit carbonic anhydrase isozymes II and IX in vitro. Purified human enzymes were from R&D Systems (Minneapolis, Minn.). The inhibition constants ($K_i$) for CA-II and CA-IX were determined by the method of Pocker and Stone. Initial rates of 4-nitrophenyl acetate hydrolysis catalyzed by the different carbonic anhydrase isozymes were measured spectrophotometrically at 400 nm. Solutions of substrate ($1 \times 10^{-2}$ to $1 \times 10^{-6}$ M) were prepared in anhydrous acetonitrile. A molar extinction coefficient of 18,000 $M^{-1} \cdot cm^{-1}$ was used for the 4-nitrophenolate formed by hydrolysis under the conditions of the experiment (9 mM Tris-HCl, 81 mM NaCl, pH 7.4, 25° C.). The enzyme concentrations were 100 nM for CA-IX and 30 nM for CA-II. Non-enzymatic hydrolysis rates, determined in the absence of added enzyme, were subtracted from the observed rates. Stock solutions of inhibitor were made up in deionized water with 10-20% DMSO (which does not inhibit the enzymatic activity). Dilutions of inhibitor were added to enzyme solutions and preincubated for 10 min to allow for the formation of the E-I complex prior to the addition of substrate. Acetazolamide was included in all assays as positive controls. The results for several examples are presented in Table 7.

TABLE 7

CA-IX Assay Summary

| Compd. | CA-IX IC$_{50}$ (nM) | CA-II IC$_{50}$ (nM) |
|---|---|---|
| 21-Re | 40 | 445 |
| 22-Re | 23 | 170 |
| 23-Re | 564 | 652 |
| 27-Re | 42 | 140 |
| 28-Re | 305 | 2159 |
| 29-Re | 260 | 770 |
| 30-Re | 189 | 405 |
| 31-Re | 130 | 669 |

Example 13

Tissue Distribution Studies on Compound 22

Figure 2:
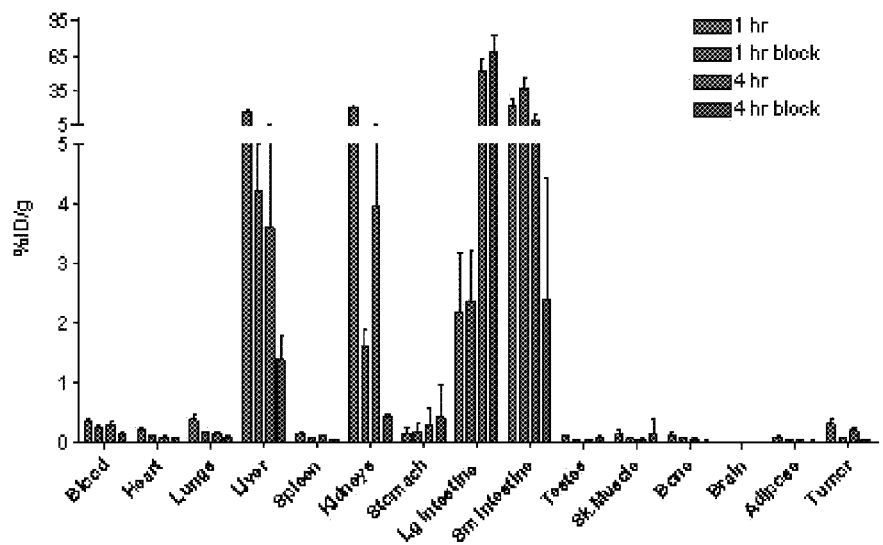
FIG. 2 is a graph of the tissue biodistribution of a $^{99m}$Tc complex of Compound 22, in HeLa xenographs expressed as % ID/g±(SEM).

Tissue distribution data was generated with a $^{99m}$Tc analog chelate of Compound 22-Re in HeLa Xenograft mice. The data are presented in FIG. 2.

Example 14

Tissue Distributions Studies with Compound 16

Figure 9:
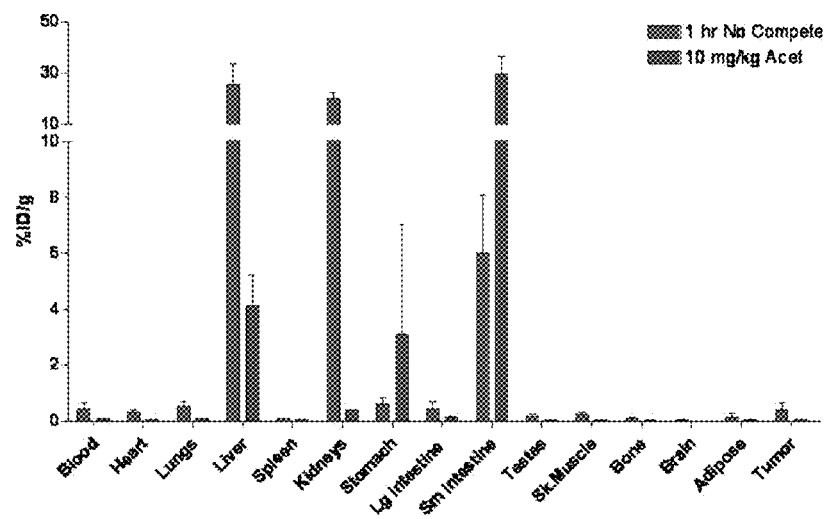
FIG. 9 is a table of tissue distribution for a $^{99m}$Tc complex of Compound 16A in HeLa Xenograft mice in % ID/g.

Tissue distribution data was generated with a $^{99m}$Tc chelate analog Compound 16-Re in HeLa Xenograft mice. The data are presented in FIG. 9.

Example 15

Figure 4:
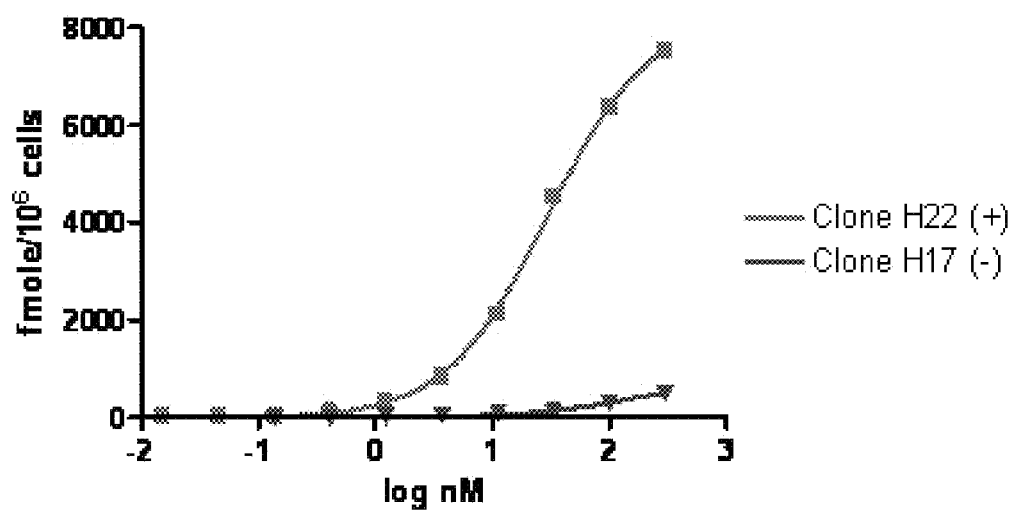
FIG. 4 is graph of saturation binding experiments for the saturation binding of Compound 80 and 48A to seprase+/− cells.
Figure 4:
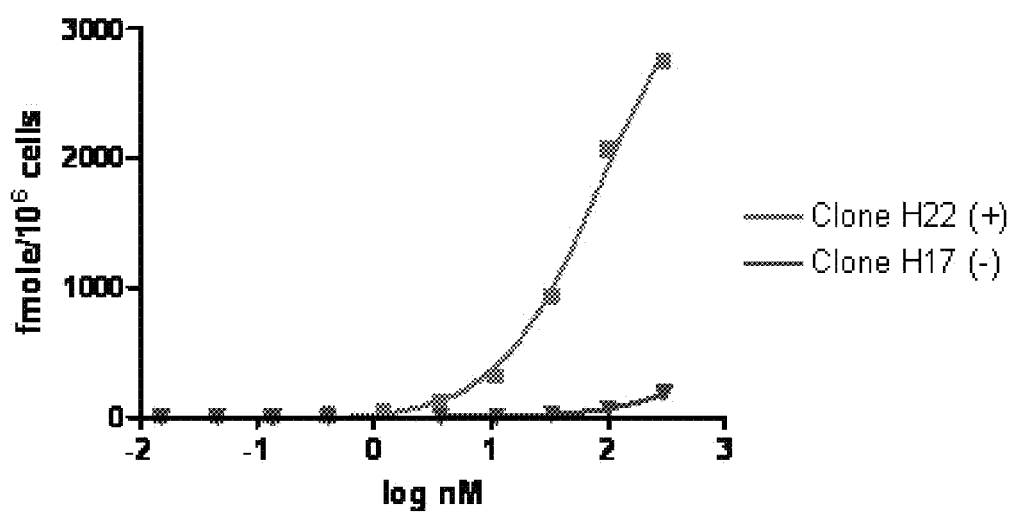

Saturation binding experiments were conducted for the saturation binding of Compound 80 and Compound 48-Re to seprase+/− cells. The results are graphically presented in FIG. 4. $^{123}$I-Labelled Compound 80 has the following structure:

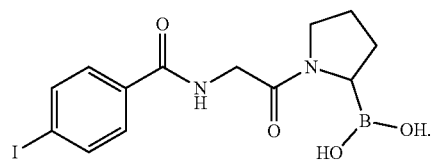 [SMILES: O=C(NCC(=O)N1CCCC1B(O)O)c1ccc(I)cc1]

Example 16

Seprase enzymes were assayed and the results for several compounds are presented in Table 8.

TABLE 8

| Compd. | Description | FAP (IC$_{50}$ nM) | POP (IC$_{50}$ nM) | DPPIV (IC$_{50}$ nM) |
|---|---|---|---|---|
| 48-Re | Re-DP-C5-Gly-Pro-Boro | 21 | 102 | 25,400 |
| 38-Re | Re-PAMA-C5-Gly-Pro-Boro | 3,533 | 11,400 | 19,620 |
| 39-Re | Re-di-methyl imidazole-Gly-Pro-Boro | 20 | 59 | 12,380 |

Example 17

Figure 3:
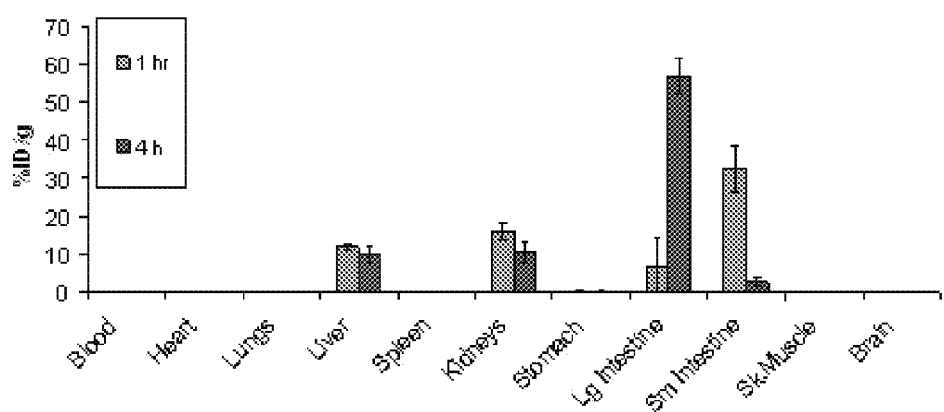
FIG. 3 is a graph of the tissue biodistribution in normal mice of a $^{99m}$Tc complex of Compound 48, expressed as % ID/g±(SEM).

Tissue distribution data was generated with a Tc chelate analog of Compound 48-Re in normal mice. The results are provided in FIG. 3.

Example 18

Figure 5:
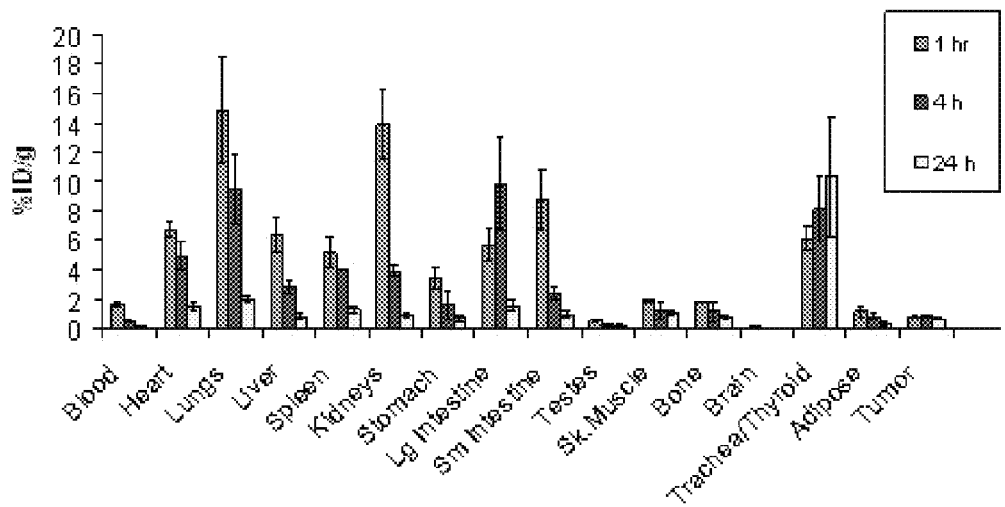
FIG. 5 is a graph of tissue distribution for the compound of Compound 80 in FaDu Xenograft mice (% ID/g).

Tissue distribution data was generated for $^{123}$I-Compound 80 in FaDu Xenograft mice expressed as (% ID/g). The results are provided in FIG. 5.

Example 19

Figure 6:
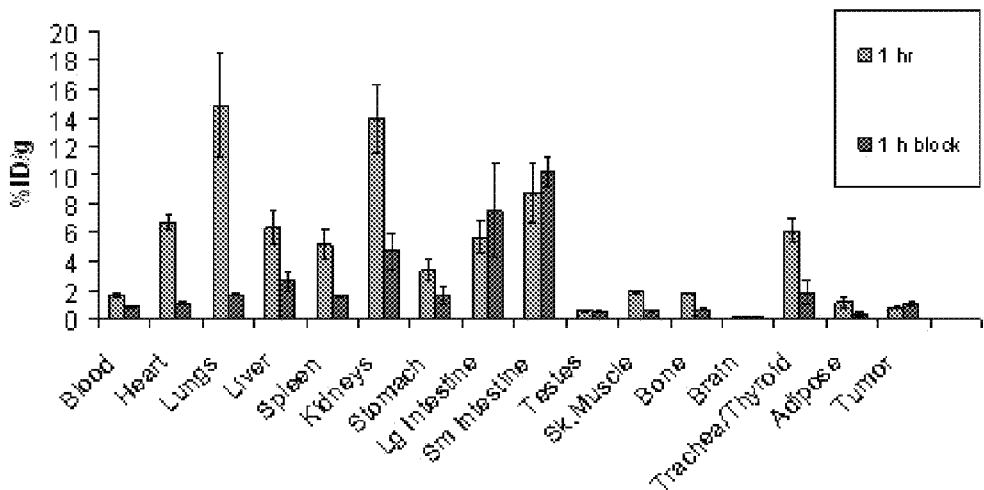
FIGS. 6, 7, and 8 are graphs of tissue distribution for a compound of Compound 80 in FaDu, H22(+), and H17(−) Xenograft mice expressed as (% ID/g), respectively.
Figure 7:
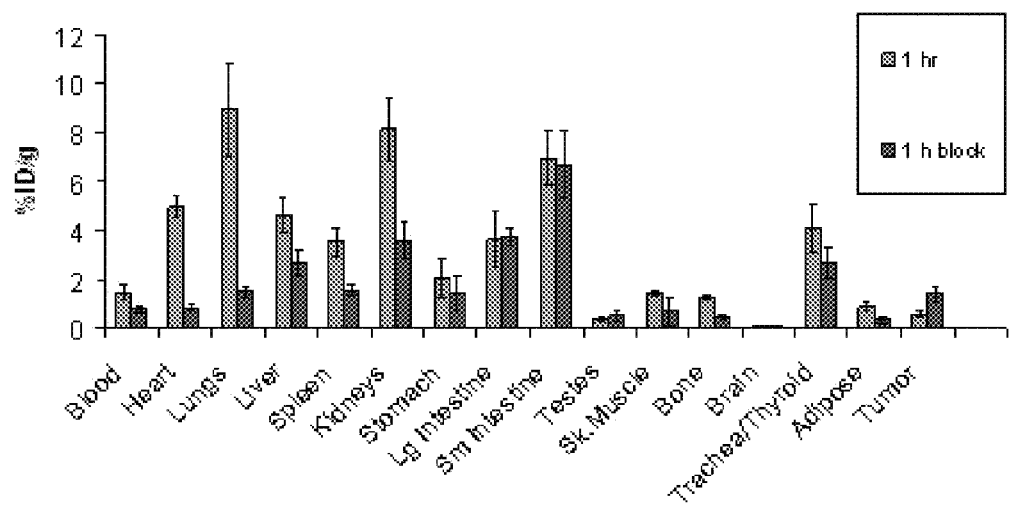
Figure 8:
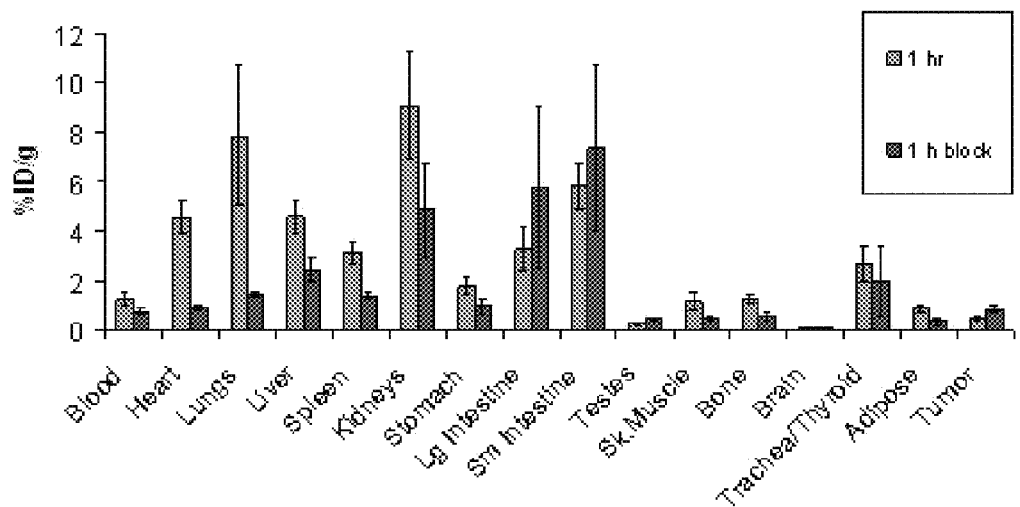

Tissue distribution data comparisons for $^{123}$I-Compound 80 in FaDu, H22(+), and H17(−) Xenograft mice (% ID/g), are presented in FIGS. 6, 7, and 8, respectively. The data were generated at 1 hr with blocking.

Example 20

Figure 10:
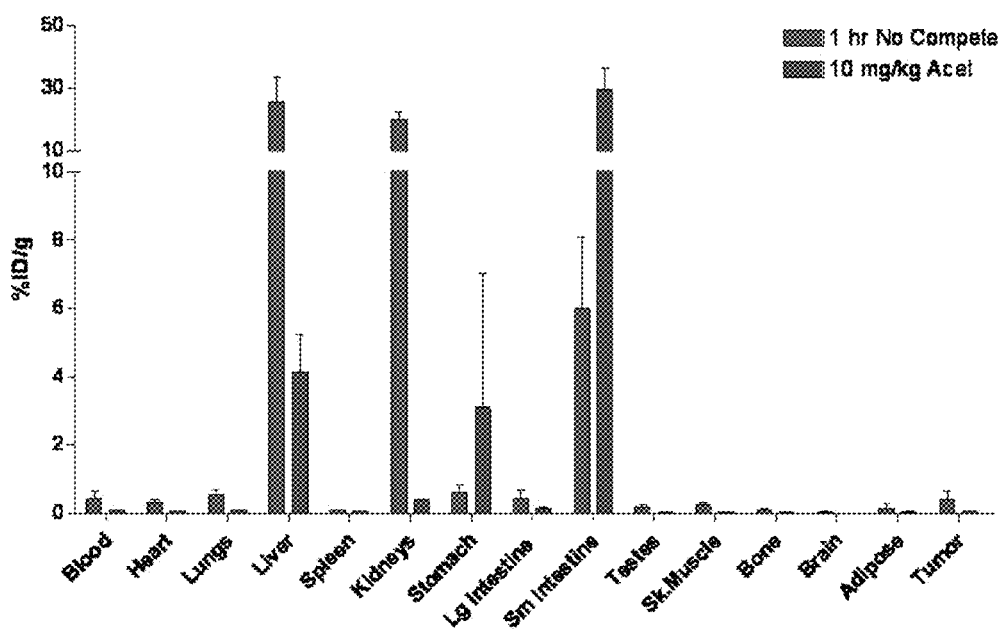
FIG. 10 is a graph of tissue distribution for a $^{99m}$Tc complex of compound of Compound 26 in HeLa Xenograft mice in % ID/g.
Figure 11:
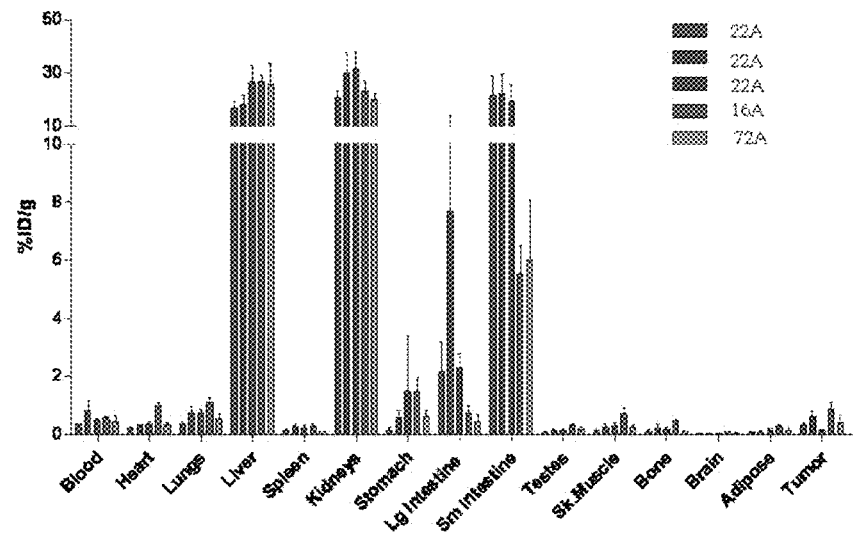
FIG. 11 is a graph of tissue distribution for complexes of various compounds in HeLa Xenograft mice in % ID/g.

Tissue distribution data was generated with a $^{99m}$Tc chelate analog of Compound 26-Re (i.e. 26-Tc) in HeLa Xenograft mice. The data are presented in FIG. 10.

Example 21

IC$_{50}$ values were determined for a number of the free ligand examples for Tc-PSMA complexes and are presented in Table 9.

TABLE 9

IC$_{50}$ Values.

| Compd./Complex | IC$_{50}$ Value (Free Ligand) |
|---|---|
| Glu-urea-Lys-DP-Re | >2000 (98) |
| Glu-urea-Lys-PAMA-Re | >2000 (31) |
| Glu-urea-Lys-DIMK | 600 |
| Glu-urea-Glu-C4-DP-Re | 580 (1700) |
| Glu-urea-Lys-PEG2DP-Re | 215 |
| Glu-urea-Lys-PEG4DP-Re | 866 |
| Glu-urea-Lys-PEG8DP-Re | 1747 |
| Compound 76-Re | 113 |
| Compound 77-Re | 696 |
| Compound 78-Re | 180 |
| Compound 36-Re | 25 |
| Compound 74-Re | 57 |
| Compound 75-Re | >2000 |
| Compound 73-Re | >2000 |
| Glu-ures-Lys-C14-DpK-Re | 106 (23) |
| Glu-ures-Lys-C14(suberate)-DqK-Re | 25 |
| Glu-urea-Lys-C14-PAMA-Re | 37 |
| Glu-urea-Lys-C14-DP-Re | 279 (246) |
| Glu-urea-Lys-suberate-PAMA-K-Re | 26 |
| Compound 35-Re | 111 |
| Glu-urea-Lys-suberate-Lys-NMI-Re | 126 |

Example 22

Figure 12:
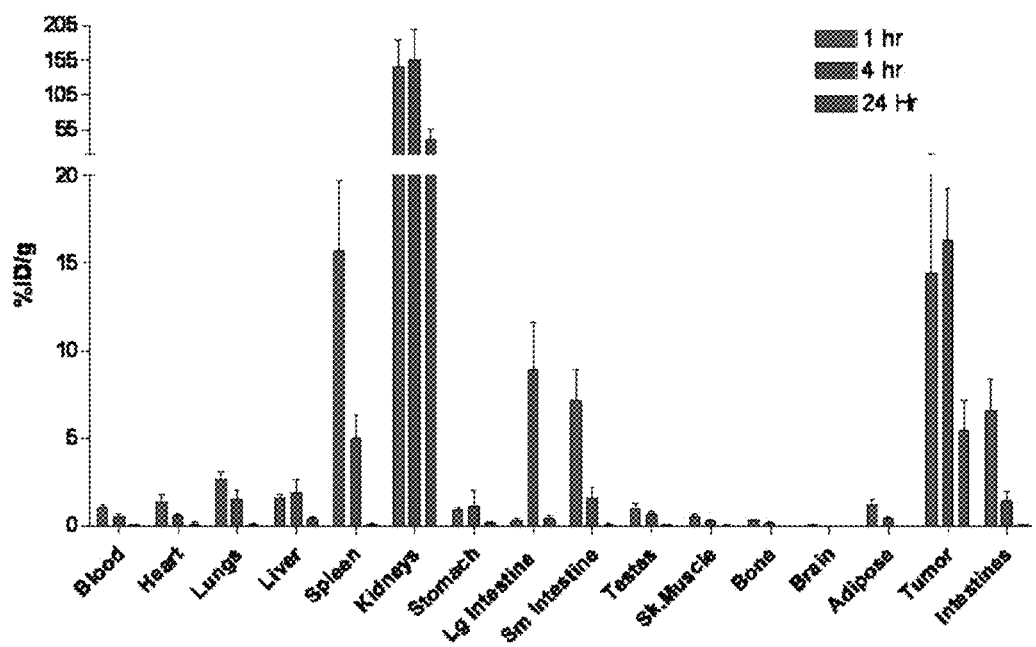
FIG. 12 is a graph of the tissue distribution for a $^{99m}$Tc complex of the compound of Compound 36 in LNCaP Xenograft mice in % ID/g.

Tissue distribution data comparisons for Compound 36 in LNCaP Xenograft mice expressed as % ID/g are presented in FIG. 12.

Example 23

Figure 13:
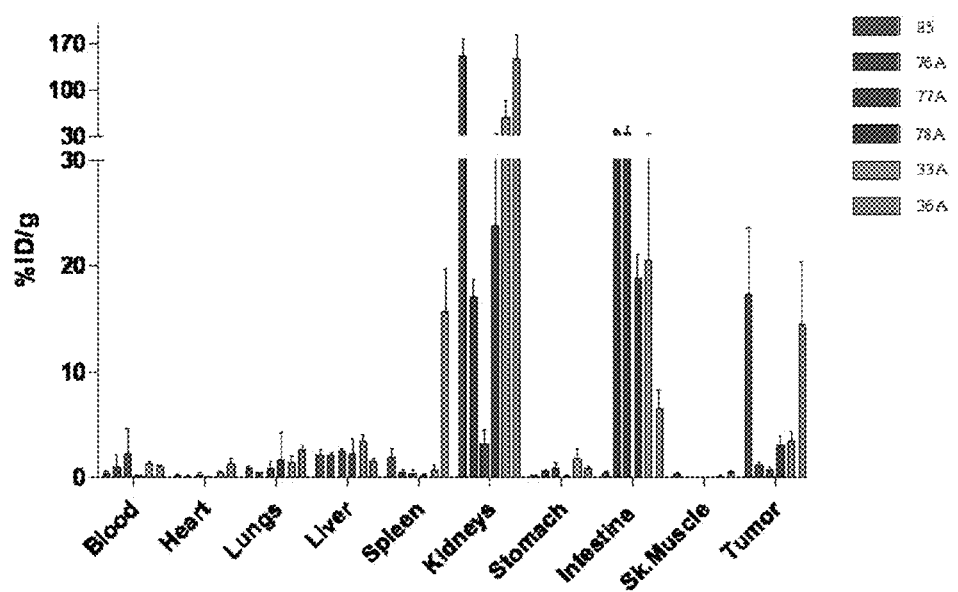
FIG. 13 is a graph of tissue distribution for complexes of various compounds in LNCaP Xenograft mice in % ID/g.

Tissue distribution data comparisons for Compounds 85, 76-Re, 77-Re, 78-Re, 33-Re, and 36-Re in LNCaP Xenograft mice, are presented in FIG. 13. $^{123}$I-Labelled Compound 85 is 2-{3-[1-Carboxy-5-(4-iodo-benzylamino)-pentyl]-ureido}-pentanedioic acid:

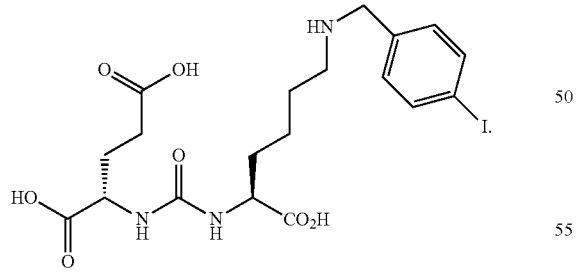

The following table (Table 10) is a listing of compounds of Formula VII, VIII, IX, and X may generally be made using the methods described above. It is expected that these compounds will exhibit properties and activities similar to those exemplified above.

Table 10.

Compounds of Formulas VIII, IX, X, XI, and XIII whereby R$_{100}$, R$_{101}$, R$_{102}$ and X are interchangeable as exemplified below whereby n is equal to 1-12.

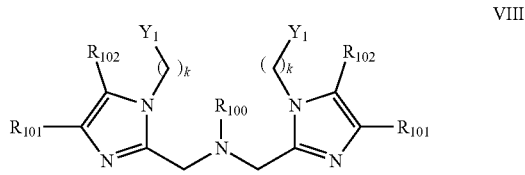
VIII

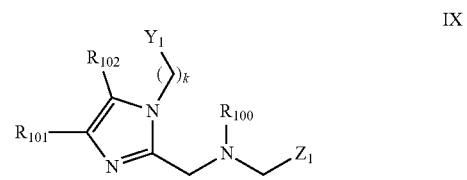
IX

X

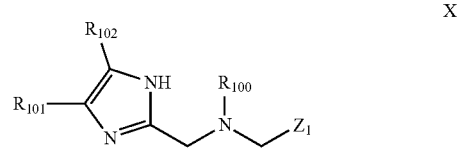

XI

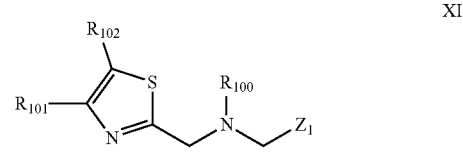

XII

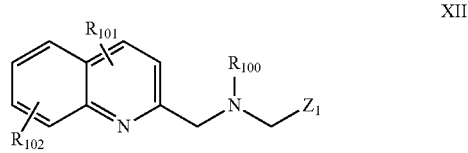

| Compd.# | R$_{100}$ | R$_{101}$ | R$_{102}$ | Y$_1$ | Z$_1$ |
|---|---|---|---|---|---|
| 100 | (CH$_2$)$_4$CH—(NH$_2$)CO$_2$H | H | H | H | N/A |
| 101 | (CH$_2$)$_3$CH—(NH$_2$)CO$_2$H | CH$_3$ | CH$_3$ | CH$_3$ | N/A |
| 102 | (CH$_2$)$_2$CH—(NH$_2$)CO$_2$H | (CH$_2$)$_n$CO$_2$H | (CH$_2$)$_n$CO$_2$H | (CH$_2$)$_n$CO$_2$H | N/A |
| 103 | C(O)CH$_2$(CH)—NH$_2$CO$_2$H | (CH$_2$)$_n$(CO$_2$H)$_2$ | (CH$_2$)$_n$(CO$_2$H)$_2$ | (CH$_2$)$_n$(CO$_2$H)$_2$ | N/A |

-continued

| Compd.# | R₁₀₀ | R₁₀₁ | R₁₀₂ | Y₁ | Z₁ |
|---|---|---|---|---|---|
| 104 | C(O)(CH₂)₂—(CH)NH₂CO₂H | CH₂CH₂OCH₂CH₃ | CH₂CH₂OCH₂CH₃ | CH₂CH₂OCH₂CH₃ | N/A |
| 105 | (CH₂)nCO₂H | CH₂C(OCH₃)₂ | CH₂C(OCH₃)₂ | CH₂C(OCH₃)₂ | N/A |
| 106 | (CC)(CH₂)₂CH—(NH₂)CO₂H | (CH₂CH₂O)ₙ—CH₂CH₃ | (CH₂CH₂O)ₙ—CH₂CH₃ | (CH₂CH₂O)ₙ—CH₂CH₃ | N/A |
| 107 | (CHCH)(CH₂)₂—CHNH₂CO₂H | (CH₂)ₙNH₂ | (CH₂)ₙNH₂ | (CH₂)ₙNH₂ | N/A |
| 108 | (CH₂)₂(CHOH)—(CH₂)CHNH₂CO₂H | CH₂CH₂C(O)NH₂ | CH₂CH₂C(O)NH₂ | CH₂CH₂C(O)NH₂ | N/A |
| 109 | (CH₂)(CHOH)—(CH₂)₂CHNH₂CO₂H | (CH₂)ₙN(CH₃)₂ | (CH₂)ₙN(CH₃)₂ | (CH₂)ₙN(CH₃)₂ | N/A |
| 110 | (CH2)ₙNHCH₂NH₂ | CH₂CH₂OH | CH₂CH₂OH | CH₂CH₂OH | N/A |
| 111 | (CH2)ₙNHCH₂CO₂H | (CH₂)ₙC(CO₂H)₂ | (CH₂)ₙC(CO₂H)₂ | (CH₂)ₙC(CO₂H)₂ | N/A |
| 112 | (CH2)ₙOCH₂NH₂ | (CH₂)ₙP(O)OH₂ | (CH₂)ₙP(O)(OH)₂ | (CH₂)ₙP(O)(OH)₂ | N/A |
| 113 | (CH2)ₙOCH₂CO₂H | (CH₂)ₙB(OH)₃ | (CH₂)ₙB(OH)₂ | (CH₂)ₙB(OH)₂ | N/A |
| 114 | (CH₂)ₙPh(SO₂NH₂) | CH₂(15-Crown-5) | CH₂(15-Crown-5) | CH₂(15-Crown-5) | N/A |
| 115 | (CH₂)ₙCH(CO₂H)(NHC(S)NH)Ph(SO₂NH₂) | CH₂(18-Crown-6) | CH₂(18-Crown-6) | CH₂(18-Crown-6) | N/A |
| 116 | (CH₂)₄CH(NH₂)CO₂H | (CH₂)ₙ(tetrazole) | (CH₂)ₙ(tetrazole) | (CH₂)ₙ(tetrazole) | N/A |
| 117 | (CH₂)₃CH(NH₂)CO₂H | (CH₂)ₙ(oxazole) | (CH₂)ₙ(oxazole) | (CH₂)ₙ(oxazole) | N/A |
| 118 | (CH₂)₂CH(NH₂)CO₂H | (CH₂)ₙ(aziridine) | (CH₂)ₙ(aziridine) | (CH₂)ₙ(aziridine) | N/A |
| 119 | C(O)CH₂(CH)—NH₂CO2H | (CH₂)ₙ(triazole) | (CH₂)ₙ(triazole) | (CH₂)ₙ(triazole) | N/A |
| 120 | C(O)(CH₂)₂—(CH)NH₂CO2H | (CH₂)ₙ(imidazole) | (CH₂)ₙ(imidazole) | (CH₂)ₙ(imidazole) | N/A |
| 121 | (CH₂)ₙCO₂H | (CH₂)ₙ(pyrazole) | (CH₂)ₙ(pyrazole) | (CH₂)ₙ(pyrazole) | N/A |
| 122 | (CC)(CH₂)₂CH—(NH₂)CO₂H | (CH₂)ₙ(thiazole) | (CH₂)ₙ(thiazole) | (CH₂)ₙ(thiazole) | N/A |
| 123 | (CHCH)(CH₂)₂—CHNH₂CO₂H | (CH₂)ₙ-(hydroxamicacid) | (CH₂)ₙ-(hydroxamicacid) | (CH₂)ₙ-(hydroxamicacid) | N/A |
| 124 | (CH₂)₂(CHOH)—(CH₂)CHNH₂CO₂H | (CH₂)ₙ-(phosphonate) | (CH₂)ₙ-(phosphonate) | (CH₂)ₙ-(phosphonate) | N/A |
| 125 | (CH₂)(CHOH)—(CH₂)₂CHNH₂CO₂H | (CH₂)ₙ-(phosphinate) | (CH₂)ₙ-(phosphinate) | (CH₂)ₙ-(phosphinate) | N/A |
| 126 | (CH2)ₙNHCH₂NH₂ | (CH₂)ₙ(thiol) | (CH₂)ₙ(thiol) | (CH₂)ₙ(thiol) | N/A |
| 127 | (CH₂)ₙNHCH₂CO₂H | (CH₂)ₙ(thioether) | (CH₂)ₙ(thioether) | (CH₂)ₙ(thioether) | N/A |
| 128 | (CH2)ₙOCH₂NH₂ | (CH₂)ₙ-(polysacharride) | (CH₂)ₙ-(polysacharride) | (CH₂)ₙ-(polysacharride) | N/A |
| 129 | (CH₂)ₙOCH₂CO₂H | (CH₂)ₙ(sacharride) | (CH₂)ₙ(sacharride) | (CH₂)ₙ(sacharride) | N/A |
| 130 | (CH₂)ₙPh(SO₂NH₂) | (CH₂)ₙ(nucleotide) | (CH₂)ₙ(nucleotide) | (CH₂)ₙ(nucleotide) | N/A |
| 131 | (CH₂)ₙCH(CO₂H)(NH)—CS(NH)Ph(SO₂NH₂) | (CH₂)ₙ(oligonucleotide) | (CH₂)ₙ(oligonucleotide) | (CH₂)ₙ(oligonucleotide) | N/A |
| 132 | (CH₂)₄CH—(NH₂)CO₂H | H | H | H | CO₂H |
| 133 | (CH₂)₃CH—(NH₂)CO₂H | CH₃ | CH₃ | CH₃ | (CH₂)nCO₂H |
| 134 | (CH₂)₂CH—(NH₂)CO₂H | (CH₂)ₙCO₂H | (CH₂)ₙCO₂H | (CH₂)ₙCO₂H | (CO₂H)₂ |
| 135 | C(O)CH₂(CH)—NH₂CO₂H | (CH₂)ₙ(CO₂H)₂ | (CH₂)ₙ(CO₂H)₂ | (CH₂)ₙ(CO₂H)₂ | (CH₂)nNH₂ |
| 136 | C(O)(CH₂)₂—(CH)NH₂CO₂H | CH₂CH₂OCH₂CH₃ | CH₂CH₂OCH₂CH₃ | CH₂CH₂OCH₂CH₃ | (CH₂)nOH |
| 137 | (CH₂)nCO₂H | CH₂C(OCH₃)₂ | CH₂C(OCH₃)₂ | CH₂C(OCH₃)₂ | (CH₂)nSH |
| 138 | (CC)(CH₂)₂CH—(NH₂)CO₂H | (CH₂CH₂O)ₙ—CH₂CH₃ | (CH₂CH₂O)ₙ—CH₂CH₃ | (CH₂CH₂O)ₙ—CH₂CH₃ | Aminoacid |
| 139 | (CHCH)(CH₂)₂—CHNH₂CO₂H | (CH₂)ₙNH₂ | (CH₂)ₙNH₂ | (CH₂)ₙNH₂ | Pyridine |
| 140 | (CH₂)₂(CHOH)—(CH₂)CHNH₂CO₂H | CH₂CH₂C(O)NH₂ | CH₂CH₂C(O)NH₂ | CH₂CH₂C(O)NH₂ | CO₂H |
| 141 | (CH₂)(CHOH)—(CH₂)₂CHNH₂CO₂H | (CH₂)ₙN(CH₃)₂ | (CH₂)ₙN(CH₃)₂ | (CH₂)ₙN(CH₃)₂ | (CH₂)nCO₂H |
| 142 | (CH₂)ₙNHCH₂NH₂ | CH₂CH₂OH | CH₂CH₂OH | CH₂CH₂OH | (CO₂H)₂ |
| 143 | (CH2)ₙNHCH₂CO₂H | (CH₂)ₙC(CO₂H)₂ | (CH₂)ₙC(CO₂H)₂ | (CH₂)ₙC(CO₂H)₂ | (CH₂)nNH₂ |
| 144 | (CH2)ₙOCH₂NH₂ | (CH₂)ₙP(O)OH₂ | (CH₂)ₙP(O)(OH)₂ | (CH₂)ₙP(O)(OH)₂ | (CH₂)nOH |
| 145 | (CH2)ₙOCH₂CO₂H | (CH₂)ₙB(OH)₃ | (CH₂)ₙB(OH)₂ | (CH₂)ₙB(OH)₂ | (CH₂)nSH |
| 146 | (CH₂)ₙPh(SO₂NH₂) | CH₂(15-Crown-5) | CH₂(15-Crown-5) | CH₂(15-Crown-5) | Aminoacid |
| 147 | (CH₂)ₙCH(CO₂H)(NH)—CS(NH)Ph(SO₂NH₂) | CH₂(18-Crown-6) | CH₂(18-Crown-6) | CH₂(18-Crown-6) | Pyridine |
| 148 | (CH₂)₄CH(NH₂)CO₂H | (CH₂)ₙ(tetrazole) | (CH₂)ₙ(tetrazole) | (CH₂)ₙ(tetrazole) | CO₂H |
| 149 | (CH₂)₃CH(NH₂)CO₂H | (CH₂)ₙ(oxazole) | (CH₂)ₙ(oxazole) | (CH₂)ₙ(oxazole) | (CH₂)nCO₂H |
| 150 | (CH₂)₂CH(NH₂)CO₂H | (CH₂)ₙ(aziridine) | (CH₂)ₙ(aziridine) | (CH₂)ₙ(aziridine) | (CO₂H)₂ |
| 151 | C(O)CH₂(CH)—NH₂CO2H | (CH₂)ₙ(triazole) | (CH₂)ₙ(triazole) | (CH₂)ₙ(triazole) | (CH₂)nNH₂ |
| 152 | C(O)(CH₂)₂—(CH)NH₂CO2H | (CH₂)ₙ(imidazole) | (CH₂)ₙ(imidazole) | (CH₂)ₙ(imidazole) | (CH₂)nOH |
| 153 | (CH₂)ₙCO₂H | (CH₂)ₙ(pyrazole) | (CH₂)ₙ(pyrazole) | (CH₂)ₙ(pyrazole) | (CH₂)nSH |
| 154 | (CC)(CH₂)₂CH—(NH₂)CO₂H | (CH₂)ₙ(thiazole) | (CH₂)ₙ(thiazole) | (CH₂)ₙ(thiazole) | Aminoacid |
| 155 | (CHCH)(CH₂)₂—CHNH₂CO₂H | (CH₂)ₙ-(hydroxamicacid) | (CH₂)ₙ-(hydroxamicacid) | (CH₂)ₙ-(hydroxamicacid) | Pyridine |
| 156 | (CH₂)₂(CHOH)—(CH₂)CHNH₂CO₂H | (CH₂)ₙ-(phosphonate) | (CH₂)ₙ-(phosphonate) | (CH₂)ₙ-(phosphonate) | CO₂H |
| 157 | (CH₂)(CHOH)—(CH₂)₂CHNH₂CO₂H | (CH₂)ₙ-(phosphinate) | (CH₂)ₙ-(phosphinate) | (CH₂)ₙ-(phosphinate) | (CH₂)nCO₂H |

-continued

| Compd.# | R$_{100}$ | R$_{101}$ | R$_{102}$ | Y$_1$ | Z$_1$ |
|---|---|---|---|---|---|
| 158 | (CH2)$_n$NHCH$_2$NH$_2$ | (CH$_2$)$_n$(thiol) | (CH$_2$)$_n$(thiol) | (CH$_2$)$_n$(thiol) | (CO$_2$H)$_2$ |
| 159 | (CH$_2$)$_n$NHCH$_2$CO$_2$H | (CH$_2$)$_n$(thioether) | (CH$_2$)$_n$(thioether) | (CH$_2$)$_n$(thioether) | (CH$_2$)$n$NH$_2$ |
| 160 | (CH2)$_n$OCH$_2$NH$_2$ | (CH$_2$)$_n$-(polysacharride) | (CH$_2$)$_n$-(polysacharride) | (CH$_2$)$_n$-(polysacharride) | (CH$_2$)$n$OH |
| 161 | (CH2)$_n$OCH$_2$CO$_2$H | (CH$_2$)$_n$(sacharride) | (CH$_2$)$_n$(sacharride) | (CH$_2$)$_n$(sacharride) | (CH$_2$)$n$SH |
| 162 | (CH$_2$)$_n$Ph(SO$_2$NH$_2$) | (CH$_2$)$_n$(nucleotide) | (CH$_2$)$_n$(nucleotide) | (CH$_2$)$_n$(nucleotide) | Aminoacid |
| 163 | (CH$_2$)$_n$CH(CO$_2$H)(NH)—CS(NH)Ph(SO$_2$NH$_2$) | (CH$_2$)$_n$(oligonucleotide) | (CH$_2$)$_n$(oligonucleotide) | (CH$_2$)$_n$(oligonucleotide) | Pyridine |

EQUIVALENTS

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A complex represented by any of the following formulae:

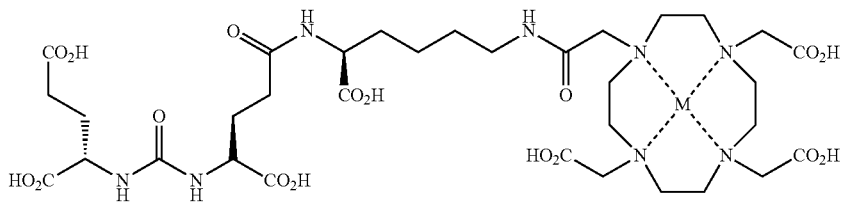

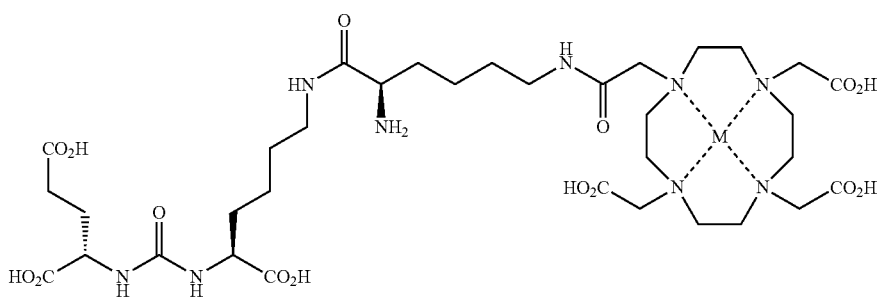

-continued
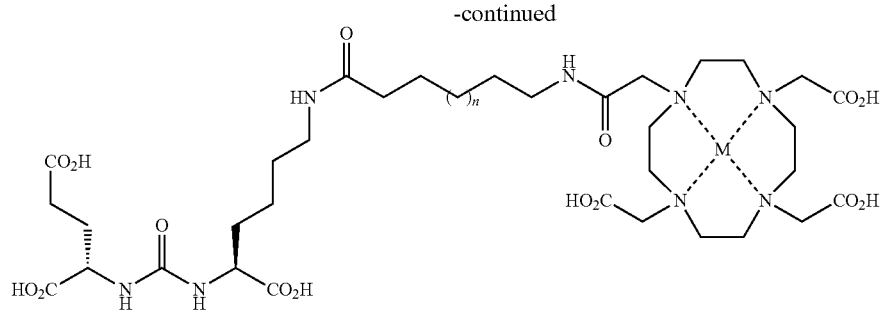
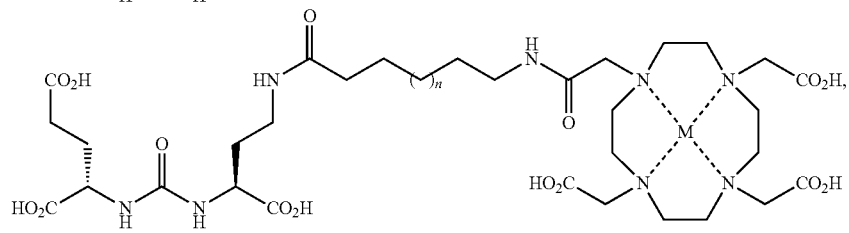
wherein n is 0 to 20, and M is a metal.
2. The complex of claim 1, wherein the metal is a radionuclide.
3. The complex of claim 1, where in the metal is yttrium, lutetium, gallium, or indium.
4. A pharmaceutical formulation comprising the complex of claim 1 and a pharmaceutically acceptable excipient.
5. A complex which is:
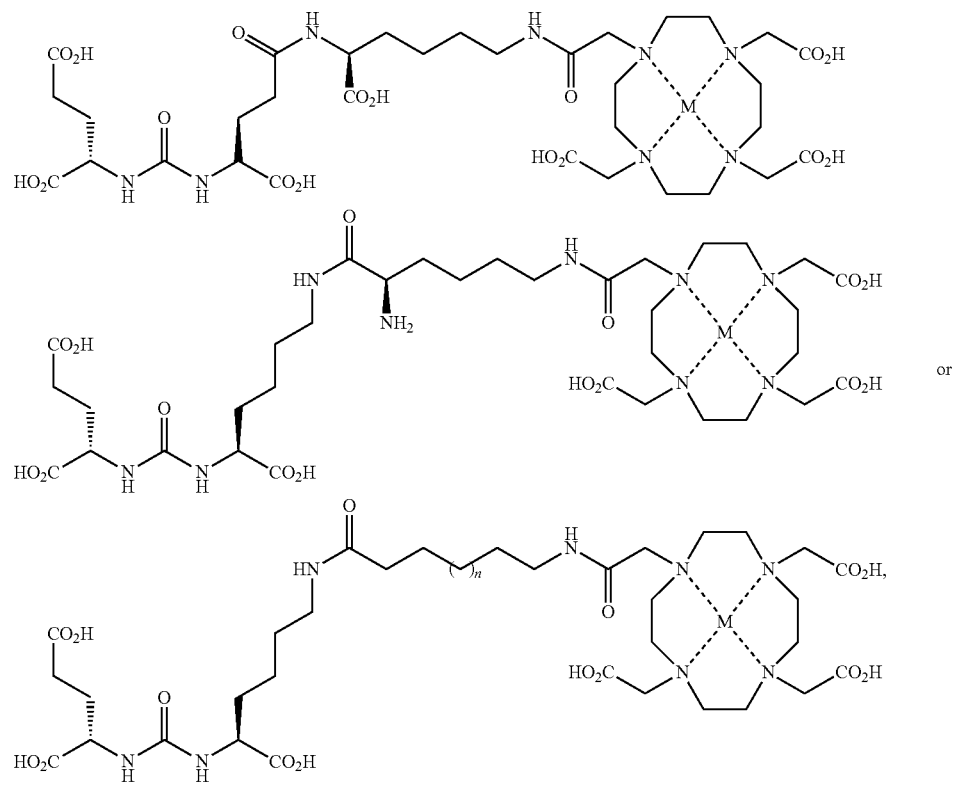
wherein n is 0 to 20, and M is yttrium, lutetium, gallium, or indium.
* * * * *